(12) United States Patent
Agnew et al.

(10) Patent No.: US 11,719,705 B2
(45) Date of Patent: *Aug. 8, 2023

(54) IL-17F AND IL-17A-SPECIFIC CAPTURE AGENTS, COMPOSITIONS, AND METHODS OF USING AND MAKING

(71) Applicants: Indi Molecular, Inc., Culver City, CA (US); California Institute of Technology, Pasadena, CA (US)

(72) Inventors: Heather Agnew, Culver City, CA (US); Bert Tsunyin Lai, Culver City, CA (US); Suresh Mark Pitram, La Jolla, CA (US); Blake Farrow, Pasadena, CA (US); James R. Heath, South Pasadena, CA (US); David Bunck, Pasadena, CA (US); Jingxin Liang, Pasadena, CA (US); Arundhati Nag, Pasadena, CA (US); Samir Das, Pasadena, CA (US)

(73) Assignees: INDI MOLECULAR, INC., Culver City, CA (US); CALIFORNIA INSTITUTE OF TECHNOLOGY, Pasadena, CA (US)

(*) Notice: Subject to any disclaimer, the term of this patent is extended or adjusted under 35 U.S.C. 154(b) by 680 days.

This patent is subject to a terminal disclaimer.

(21) Appl. No.: 16/010,347

(22) Filed: Jun. 15, 2018

(65) Prior Publication Data
US 2018/0364253 A1 Dec. 20, 2018

Related U.S. Application Data

(60) Provisional application No. 62/617,944, filed on Jan. 16, 2018, provisional application No. 62/520,307, filed on Jun. 15, 2017.

(51) Int. Cl.
*G01N 33/68* (2006.01)
*C07K 7/06* (2006.01)
*C07K 14/54* (2006.01)

(52) U.S. Cl.
CPC .......... *G01N 33/6869* (2013.01); *C07K 7/06* (2013.01); *C07K 14/54* (2013.01)

(58) Field of Classification Search
CPC . C07K 7/64; C07K 14/54; C07K 7/06; C07K 2319/00; G01N 33/6869; G01N 2333/54
See application file for complete search history.

(56) References Cited

U.S. PATENT DOCUMENTS

| | | |
|---|---|---|
| 4,899,755 A | 2/1990 | Lauffer |
| 5,021,556 A | 6/1991 | Srinivasan |
| 5,075,099 A | 12/1991 | Srinivasan |
| 5,118,797 A | 6/1992 | Jurisson |
| 5,183,653 A | 2/1993 | Linder |
| 5,364,613 A | 11/1994 | Sieving |
| 5,367,080 A | 11/1994 | Toner |
| 5,387,409 A | 2/1995 | Nunn |
| 5,474,756 A | 12/1995 | Tweedle |
| 5,547,668 A | 8/1996 | Kranz |
| 5,608,110 A | 3/1997 | Ramalingam |
| 5,656,254 A | 8/1997 | Ramalingam |
| 5,662,885 A | 9/1997 | Pollak |
| 5,665,329 A | 9/1997 | Ramalingam |
| 5,688,487 A | 11/1997 | Linder |
| 5,720,934 A | 2/1998 | Dean |
| 5,780,006 A | 7/1998 | Pollak |
| 5,846,519 A | 12/1998 | Tweedle |
| 5,886,142 A | 3/1999 | Thakur |
| 5,976,495 A | 11/1999 | Pollak |
| 6,093,382 A | 7/2000 | Wedeking |
| 6,143,274 A | 11/2000 | Tweedle |
| 6,566,088 B1 | 5/2003 | McKnight |
| 8,710,180 B2 | 4/2014 | Pitram |
| 8,841,083 B2 | 9/2014 | Heath |
| 8,906,830 B2 | 12/2014 | Agnew |
| 9,188,584 B2 | 11/2015 | Agnew |
| 9,221,889 B2 | 12/2015 | Pitram |
| 9,239,332 B2 | 1/2016 | Heath |
| 9,913,875 B2 | 3/2018 | Farrow |
| 10,017,540 B2 | 7/2018 | Henning |
| 10,598,671 B2 * | 3/2020 | Heath ............ C07K 7/64 |
| 10,913,774 B2 | 2/2021 | Henning |
| 11,007,245 B2 | 5/2021 | Farrow |
| 2006/0153839 A1 | 7/2006 | Mohamed |
| 2010/0009896 A1 | 1/2010 | Agnew |
| 2011/0263515 A1 | 10/2011 | Agnew |

(Continued)

FOREIGN PATENT DOCUMENTS

| | | |
|---|---|---|
| EP | 2719706 | 4/2014 |
| WO | 1986006605 | 11/1986 |

(Continued)

OTHER PUBLICATIONS

Mabry et al. Engineering of stable bispecific antibodies targeting IL-17A and IL-23. Protein Engineering, Design & Selection. 2010, vol. 23, No. 3, pp. 115-127 (Year: 2010).*

Dieck et al. Development of bispecific molecules for the in situ detection of protein-protein interactions and protein phosphorylation. Cell & Biology 2014, vol. 21, pp. 357-368. (Year: 2014).*

Chan et al. Dual-targeting anti-angiogenic cyclic peptides as potential drug leads for cancer therapy. Scientific Reports 2016, Article No. 35247, pp. 1-13. (Year: 2016).*

Agnew, et al., "Iterative in situ click chemistry creates antibody-like protein-capture agents", Angew. Chemie Int Ed., 48(27):4944-4948 (2009).

(Continued)

*Primary Examiner* — Shafiqul Haq
(74) *Attorney, Agent, or Firm* — Pabst Patent Group LLP

(57) ABSTRACT

The present application provides stable peptide-based IL-17F and IL-17A capture agents and methods of use as detection agents. The application further provides methods of manufacturing IL-17F capture agents.

40 Claims, 4 Drawing Sheets

Specification includes a Sequence Listing.

(56) References Cited

U.S. PATENT DOCUMENTS

| | | |
|---|---|---|
| 2012/0202219 A1 | 8/2012 | Agnew |
| 2012/0252071 A1 | 10/2012 | Greif |
| 2014/0302998 A1 | 10/2014 | Heath |
| 2015/0099658 A1 | 4/2015 | Pfeilsticker |
| 2015/0132314 A1 | 5/2015 | Masternak |
| 2015/0344523 A1 | 12/2015 | Deyle |
| 2016/0264627 A1 | 9/2016 | Henning |
| 2016/0331800 A1 | 11/2016 | Farrow |
| 2017/0319722 A1 | 11/2017 | Agnew |
| 2018/0364253 A1 | 12/2018 | Agnew |
| 2020/0407712 A1 | 12/2020 | Boyd |
| 2022/0211648 A1 | 7/2022 | Agnew |

FOREIGN PATENT DOCUMENTS

| | | |
|---|---|---|
| WO | 1991003200 | 3/1991 |
| WO | 1995003280 | 2/1995 |
| WO | 1995006633 | 3/1995 |
| WO | 1995028179 | 10/1995 |
| WO | 1995028967 | 11/1995 |
| WO | 1996003427 | 2/1996 |
| WO | 1996023526 | 8/1996 |
| WO | 1997036619 | 10/1997 |
| WO | 1998018496 | 5/1998 |
| WO | 1998018497 | 5/1998 |
| WO | 1998046612 | 10/1998 |
| WO | 1998052618 | 11/1998 |
| WO | 1999017809 | 4/1999 |
| WO | 9921576 | 5/1999 |
| WO | 02083064 | 10/2002 |
| WO | 03006620 | 1/2003 |
| WO | 2005113762 | 12/2005 |
| WO | 2007050963 | 5/2007 |
| WO | 2009051555 | 4/2009 |
| WO | 2009105746 | 8/2009 |
| WO | 2009155420 | 12/2009 |
| WO | 20091554201 | 12/2009 |
| WO | 2010135431 | 11/2010 |
| WO | 2011057347 | 5/2011 |
| WO | 2012106651 | 8/2012 |
| WO | 2012106671 | 8/2012 |
| WO | 2013009869 | 1/2013 |
| WO | 2013033561 | 3/2013 |
| WO | 2013034982 | 3/2013 |
| WO | 2014056813 | 4/2014 |
| WO | 2014074907 | 5/2014 |
| WO | 2014205317 | 12/2014 |
| WO | 2017011769 | 1/2017 |
| WO | 2017176769 | 10/2017 |
| WO | 2018064597 | 4/2018 |
| WO | 2018111580 | 6/2018 |
| WO | 2018170096 | 9/2018 |
| WO | 2018200551 | 11/2018 |
| WO | 2020127227 | 6/2020 |

OTHER PUBLICATIONS

Alexander, et al., "Intracranial black-blood MR angiography with high-resolution 3D fast spin echo", Magn. Reson. Med., 40:298-310 (1998).

Altschul, et al., "Gapped BLAST and PSI-BLAST: a new generation of protein database search programs", Nucleic Acids Res., 25:3389-402 (1997).

Beringer, et al., "IL-17 in Chronic Inflammation: From Discovery to Targeting", Trends Mol. Med., 22:230-241 (2016).

Claverie, "Information enhancement methods for large scale sequence analysis", Comput. Chem., 17:191-201 (1993).

Das, et al., "A General Synthetic Approach for Designing Epitope Targeted Macrocyclic Peptide Ligands", Angew. Chemie Int. Ed., 54(45):13219-24 (2015).

Edelman, et al., "Extracranial carotid arteries: evaluation with "black blood" MR angiography", Radiology, 177:45-50 (1990).

Ely, et al., "Structural basis of receptor sharing by interleukin 17 cytokines", Nat. Immunol, 10:1245-51 (2009).

Farrow, et al., "Epitope targeting of tertiary protein structure enables target-guided synthesis of a potent in-cell inhibitor of botulinum neurotoxin", Angew. Chemie Int. Ed., 54(24):7114-9 (2015).
Genovese, et al., "LY2439821, a humanized anti-interleukin-17 monoclonal antibody, in the treatment of patients with rheumatoid arthritis: A phase I randomized, double-blind, placebo-controlled, proof-of-concept study", Arthritis Rheum, 62:929-939 (2010).
Goodrich, et al., "A quantitative study of ramped radio frequency, magnetization transfer, and slab thickness in three-dimensional time-of-flight magnetic resonance angiography in a patient population", Invest. Radia, 31:323-32 (1996).
Ho, et al., "IL-17RC is required for immune signaling via an extended SEF/IL-17R signaling domain in the cytoplasmic tail", J. Immunol., 185:1063-70 (2010).
Hu, et al., "IL-17RC is required for IL-17A- and IL-17F-dependent signaling and the pathogenesis of experimental autoimmune encephalomyelitis", J. Immunol., 184:4307-16 (2010).
Hueber, et al., "Effects of AIN457, a fully human antibody to interleukin-17A, on psoriasis, rheumatoid arthritis, and uveitis", Sci. Transl. Med., 2:52ra72 (2010).
Hurst, et al., "New IL-17 family members promote Th1 or Th2 responses in the lung: in vivo function of the novel cytokine IL-25", J. Immunol, 169:443-453 (2002).
Hymowitz, et al., "IL-17s adopt a cystine knot fold: structure and activity of a novel cytokine, IL-17F, and implications for receptor binding", EMBO J., 20:5332-5341 (2001).
Iwakura, et al., "Functional specialization of interleukin-17 family members", Immunity, 34:149-162 (2011).
Iwata, et al., "A new, convenient method for the preparation of 4-[18F]fluorobenzyl halides", Appl Radia Isot, 52:87-92 (2000).
Kawaguchi, et al., "Identification of a novel cytokine, ML-1, and its expression in subjects with asthma", J. Immunol., 167:4430-5 (2001).
Kolls, "Interleukin-17 Family Members Review and Inflammation", Immunity, 21:467-76 (2004).
Leonardi, et al., "Anti-interleukin-17 monoclonal antibody ixekizumab in chronic plaque psoriasis", N. Engl. J. Med, 366:1190-9 (2012).
Liese, et al., "Influence of length and flexibility of spacers on the binding affinity of divalent ligands", Org. Chem., 11:804-816 (2015).
Liu and Edwards, "99mTc-Labeled Small Peptides as Diagnostic Radiopharmaceuticals", Chem. Rev., 99:2235-68 (1999).
Manolitsas, et al., "The expression of intercellular adhesion molecule-1 and the beta 1-integrins in asthma", Eur. Respir. J., 7:1439-44 (1994).
Meyers and Miller, "Optimal alignments in linear space", Computer Applic. Biol. Sci., 4(1):11-17 (1988).
Mossec and Kolls, "Targeting IL-17 and TH17 cells in chronic inflammation", Nat. Rev. Drug Discov., 11:763-776 (2012).
Oda, et al., "Interleukin-17F induces pulmonary neutrophilia and amplifies antigen-induced allergic response", Am. J. Respir. Crit. Care Med., 171:12-18 (2005).
Park, et al., "A distinct lineage of CD4 T cells regulates tissue inflammation by producing interleukin 17", Nat. Immunol., 6:1133-41 (2005).
Poethko, et al., "wo-step methodology for high-yield routine radiohalogenation of peptides: (18)F-labeled RGD and octreotide analogs", J Nucl Med, 45:892-902 (2004).
Schottelius, et al., "First (18)F-labeled tracer suitable for routine clinical imaging of sst receptor-expressing tumors using positron emission tomography", Clin Can Res, 10:3593-3606 (2004).
Silacci, et al., "Linker length matters, fynomer-Fc fusion with an optimized linker displaying picomolar IL-17A inhibition potency", J. Biol. Chem., 289:14392-98 (2014).
Toy, et al., "Cutting edge: interleukin 17 signals through a heteromeric receptor complex", J. Immunol., 177:36-9 (2006).
Wei, et al., "Interleukin-6 promotes cervical tumor growth by VEGF-dependent angiogenesis via a STAT3 pathway", Oncogene, 22:1517-27 (2003).

(56) References Cited

OTHER PUBLICATIONS

Wilson, et al., "Reductive amination of [18F]fluorobenzaldehydes: Radiosyntheses of [2☐18F]☐ and [4☐18F]fluorodexetimides", J Labeled Compounds and Radiopharmaceuticals, 28(10): 1189-99 (1990).
Wong, et al., "Interleukin-6 modulates production of T lymphocyte-derived cytokines in antigen-induced arthritis and drives inflammation-induced osteoclastogenesis", Arthritis Rheum, 54:158-168 (2006).
Wootton and Federhen, "Statistics of Local Complexity in Amino Acid Sequences and Sequence Databases", Comput. Chem., 17(2):149-63 (1993).
Wright, et al., "Identification of an interleukin 17F/17A heterodimer in activated human CD4+ T cells", J. Biol. Chem., 282:13447-13455 (2007).
Wright, et al., "The human IL-17F/IL-17A heterodimeric cytokine signals through the IL-17RA/IL-17RC receptor complex", J. Immunol., 181:2799-2805 (2008).
Yang, et al., "Regulation of inflammatory responses by IL-17F", J. Exp. Med., 205:1063-1075 (2008).
Agnew, et al., "Protein-Catalyzed Capture Agents", Chemical Reviews, 119(17): 9950-9970 (2019).
Artali, et al., "A molecular dynamics study of human serum albumin binding sites", II Farmaco, 60:485-495 (2005).
Bianchi et al., "Vaccination with peptide mimetics of the gp41 prehairpin fusion intermediate yields neutralizing antisera against HIV-1 isolates", PNAS, 107(23): 10655-10660 (2010).
Boersma, "Gaining knowledge of single carbon chains", Theory of condensed matter, Radboud Univ. Nijmegen, 18 pages (2011).
Chan, et al., "Dual-targeting anti-angiogenic cyclic peptides as potential drug leads for cancer therapy", Scientific Reports, 6:35247, 13 pages (2016).
Chattopadhyay, et al., "Techniques to improve the direct ex vivo detection of low frequency antigen-specific CD8+ T cells with peptide-major histocompatibility complex class I tetramers", Cytometry Part A, 73(11): 1001-1009 (2008).
Chauhan, et al. "The Taming of the Cell Penetrating Domain of the HIV Tat: Myths and Realities", J. Control Release, 117(2): 148-162 (2007).
Chen, et al., "Fusion protein linkers: property, design and functionality", Adv. Drug Deliv. Rev., 65(10): 1357-1369 (2013).
Cheong, et al., "A patent review of IDO1 inhibitors for cancer", Expert Opinion on Therapeutic Patents, 28(4):317-330 (2018).
Choksi, et al., "ACD8 DE loop peptide analog prevents graft-versus-host disease in a multiple minor histocompatibility antigen-mismatched bone marrow transplantation model", Biology of Blood and Marrow Transplantation, 10(10):669-680 (2004).
Coppock, et al., "Peptide-based protein capture agents with high affinity, selectivity, and stability as antibody replacements in biodetection assays", Proc. of SPIE, 9107:910711-1 (2014).
Dieck, et al., "Development of bispecific molecules for the in situ detection of protein-protein interactions and protein phosphorylation", Cell & Biology, 21:357-368 (2014).
Eiber, et al., "Prostate-Specific Membrane Antigen Ligands for Imaging and Therapy", The Journal of Nuclear Medicine, 58(Supplement 2):67S-76S (2017).
Fisher, et al, "Trivalent Gd-DOTA reagents for modification of proteins", RSC Adv., 5: 96194-96200 (2015).
Fitzer-Attas, et al., "Harnessing Syk family tyrosine kinases as signaling domains for chimeric single chain of the Variable Domain recept", J. Immunol., 160(1):145-154 (1998).
Gao, et al., "Crystal structure of the complex between human CD8alpha(alpha) and HLA-A2", Nature, 387:630-4 (1997).
Gen Bank: AAH25715.1 , "CD8a molecule [*Homo sapiens*]" retrived from the internet Jun. 17, 2022.
Glaven, et al., "Linking single domain antibodies that recognize different epitopes on the same target", Biosensors, 2:43-56 (2012).
Handl, et al., "Hitting multiple targets with multimeric ligands", Expert Opin. Ther. Targets, 8(6):565-586 (2004).
Hill, et al., "Constraining Cyclic Peptides to Mimic Protein Structure Motifs", Angewandte Chemie, 53(48):13020-13041 (2014).

Hirai, et al., "MK-2206, an Allosteric Akt Inhibitor, Enhances Antitumor Efficacy by Standard Chemotherapeutic Agents or Molecular Targeted Drugs In vitro and In vivo", Molecular Cancer Therapeutics, 9(7): 1956-1967 (2010).
Hudson, et al, "Multiplex epitope mapping using bacterial surface display reveals both linear and conformational epitopes", Scientific Reports, 2(706):1-9 (2012).
Josan, et al., "Cell-specific targeting by heterobivalent ligands", Bioconjug Chem., 22(7): 1270-1278 (2011).
Koonin, et al., "Sequence—Evolution—Function: Computational Approaches in Comparative Genomics", Boston: Kluwer Academic; 2003, Chapter 2 Evolutionary Concept in Genetics and Genomics (2003).
Lai, et al., "Epitope-Targeted Macrocyclic Peptide Ligand with Picomolar Cooperative Binding to Interleukin-17F", Chemistry, 24(15):3760-3767 (2018).
Li, et al., "Identification of the CD8 DE loop as a surface functional epitope. Implications for major histocompatibility complex class I binding and CD8 inhibitor design", Journal of Biological Chemistry, 273(26): 16442-16445 (1998).
Lin, et al., "Inhibition of HIV-1 Tat-mediated transcription by a coumarin derivative, BPRHIV001, through the Akt pathway", Journal of Virology, 85(17): 9114-9126 (2011).
Lindlsey, et al., "The P13K/Akt Pathway: Recent Progress in the Development of ATP-Competitive and Allosteric Akt Kinase Inhibitors", Current Cancer Drug Targets, 8: 7-18 (2008).
Ma, et al., "Acyclic peptide-polymer probe for the detection of Clostridium botulinum neurotoxin serotype A", Toxicon., 47(8):901-908 (2006).
Mabry, et al., "Engineering of stable bispecific antibodies targeting IL-17 A and IL-23", Protein Engineering, Design & Selection, 23(3):115-127 (2010).
MacRaild et al., "Antibody Recognition of Disordered Antigens", Structure 24:148-157, (2016).
MacRaild et al., "Conformational Dynamics and Antigenicity in the Disordered Malaria Antigen Merozoite Surface Protein 2", PLOS ONE, 13 pages (2015).
Mamidyala et al., In situ click chemistry: probing the binding landscapes of biological molecules, Chemical Society Reviews, 39(4):1252-1261 (2010).
Manea, et al., "Antibody Recognition and Conformational Flexibility of a Plaque-Specific-Amyloid Epitope Modulated by Non-native Peptide Flanking Regions", J. Med. Chem., 51(5):1150-1161 (2008).
Matsuura, "Identification of conformational neutralizing epitopes on the capsid protein of canine calicivirus", Journal of General Virology, 82:1695-1702 (2001).
Melenhorst et el., "Detection of low avidity CD8(+) T cell populations with coreceptor-enhanced peptide-major histocompatibility complex class I tetramers", J Immunol Methods, 338(1-2): 31-39 (2008).
Merriam-Webster online definition of "correspond" downloaded Jun. 29, 2020 from internet, https://www.merriam-webster.com/dictionary/correspond (Year: 2020).
Millward, et al., "In situ click chemistry: from small molecule discovery to synthetic antibodies", Integr. Biol (Camb)., 5(1): 87-95 (2013).
Millward, et al., "Iterative in situ click chemistry assembles a branched capture agent and allosteric inhibitor for Akt1", JACS, 133(45):18280-18288 (2011).
Miossec, "Update on interleukin-17: a role in the pathogenesis of inflammatory arthritis and implication for clinical practice", RMD Open, 3(1):e000284 (2017).
Mor, et al., Mimicking the Structure of the V3 Epitope Bound to HIV-1 Neutralizing Antibodies, Biochemistry, 48(15):3288-3303 (2009).
Muller, et al., "DOTA Conjugate with an Albumin-Binding Entity Enables the First Folic Acid-Targeted 177Lu-Radionuclide Tumor Therapy in Mice", The Jour. of Nucl. Med., 54(11):124-131.
Muller, et al., "Folic acid conjugates for nuclear imaging of folate receptor-positive cancer", J. Nucl. Med., 52(1): 1-4 (2011).
Nag et al., "A chemical epitope-targeting strategy for protein capture agents: the serine 474 epitope of the kinase Akt2", Angewandte Chemie International Edition, 52:13975-13979 (2013).

(56) References Cited

OTHER PUBLICATIONS

O'Shannessy, et al., "Characterization of the human folate receptor alpha via novel antibody-based probes", Oncotarget, 2(12):1227-1243 (2011).

Pansca, et al., "Structural disorder in eukaryotes", PLoS ONE, www.plosone.org Apr. 1, 2012, 7(4): e34687, 10 pages (2012).

Pfeilsticker, et al., "A cocktail of thermally stable, chemically synthesized capture agents forthe efficient detection of anti-gp41 antibodies from human sera", PloS One, 8(10):Article No. e76224, 5 pages (2013).

Reeck, et al., "'Homolgy' in Proteins and Nucleic Acids: A Terminology Muddle and a Way out of it", Cell, 50:667 (1987).

Saito, et al., "Identification of anti-CD98 antibody mimotopes for inducing antibodies with antitumor activity by mimotope immunization", Cancer Science, 105(4): 396-401 (2014).

Sarbassov, et al., "Phosphorylation and regulation of Akt/PKB by the rictor-mTOR complex", Science, American Association for the Advancement of Science, 307(5712): 1098-1101 (2005).

Schweinsberg, et al., "Novel glycated [99mTc(CO)3]-labeled bombesin analogues for improved targeting of gastrin-releasing peptide receptor-positive tumors", Bioconjugate Chem., 19(12):2432-2439 (2008).

Smith, et al., "Zinc Mediated Azide-Alkyne Ligation to 1,5- and 1,4,5-Substituted 1,2,3-Triazoles", Org. Lett., 15(18):4826-4829 (2013).

Son, et al., "New Cyclic Lipopeptides of the Inturin Class Produced by Saltern-Derived *Bacillus* sp. KCB14S006", Marine Drugs, 14(4):72 (2016).

Sormanni, et al., "Rational design of antibodies targeting specific epitopes within intrinsically disordered proteins", PNAS, 112(32):9902-9907 (2015).

Subramanyam, et al., "Inhibition of Protein Kinase Akt1 by Apoptosis Signal-regulating Kinase-1 (ASK1) Is Involved in Apoptotic Inhibition of Regulatory Volume Increase", Journal of Biological Chemistry, 285(9): 6109-6117(2010).

Tang et al., "Chimeric molecules facilitate the degradation of androgen receptors and repress the growth of LNCaP cells", Asian Journal of Andrology, 11(1): 119-126 (2009).

Tao, et al., "Expression, purification and identification of an immunogenic fragment in the ectodomain of prostate-specific membrane antigen", Experimental And Therapeutic Medicine, 11(3): 747-752 (2016).

Testa, et al., "CD 123 is a membrane biomarker and a therapeutic target in hematologic malignancies", Biomarker Research, 2:4 (2014).

Todorova, et al., "Biochemical nature and mapping of PSMA epitopes recognized by human antibodies induces after immunization with gene-based vaccines", Anticancer Research, 25: 4727-4732 (2005).

Torres, et al., "A revolutionary therapeutic approach for psoriasis: bi specific biological agents", Expert Opinion on Investigational Drugs, 25(7): 751-754 (2016).

Wang, et al., "Epitope Mapping Using Phage-Display Random Fragment Libraries", Epitope Mapping Protocols, Methods in Molecular Biology, 524: 315-332 (2009). Abstract Only.

Wang, et al., "Radioligand Therapy of Prostate Cancer with a Long-Lasting Prostate-Specific Membrane Antigen Targeting Agent Y-DOTA-EB-MCG", Bioconjug. Chem., 29(7):2309-2315 (2018).

Wooldridge, et al., "Tricks with tetramers: how to get the most from multimeric peptide-MHC", Immunology, 126:147-164 2009 (2009).

Zhang, et al., "Structure and function of interleukin-17 family cytokines", Protein & Cell, 2(1): 26-40 (2011).

\* cited by examiner

IL-17F AND IL-17A-SPECIFIC CAPTURE AGENTS, COMPOSITIONS, AND METHODS OF USING AND MAKING

CROSS-REFERENCE TO RELATED APPLICATIONS

This application claims benefit of and priority to U.S. Provisional Application No. 62/617,944, filed Jan. 16, 2018, and U.S. Provisional Application No. 62/520,307, filed Jun. 15, 2017, are hereby incorporated herein by reference in their entirety.

STATEMENT REGARDING FEDERALLY SPONSORED RESEARCH

This invention was made with Government support under Grant No. W911NF-09-D-0001 awarded by U.S. Army. The Government has certain rights in the invention.

REFERENCE TO SEQUENCE LISTING

The Sequence Listing submitted Jun. 15, 2018, as a text file named "INDI_32_1_US_ST25.txt," created on Jun. 15, 2018, and having a size of 22,461 bytes is hereby incorporated by reference pursuant to 37 C.F.R. § 1.52(e)(5).

FIELD OF THE INVENTION

The disclosed invention is generally in the field of capture agents and specifically in the area of IL-17F and IL-17A capture agents and methods of making and using such capture agents.

BACKGROUND OF THE INVENTION

Human interleukin-17 (IL-17A) is a pro-inflammatory cytokine secreted by immune cells. There are six different homodimeric cytokines (IL-17A-F) and the heterodimer IL-17A/F in the IL-17 cytokine family (J. K. Kolls, A. Lindén, Immunity 2004, 21, 467-476; J. F. Wright, et al., J. Immunol. 2008, 181, 2799-2805; J. F. Wright, et al., J. Biol. Chem. 2007, 282, 13447-13455). IL-17A and IL-17F are viewed as the most important drug targets, and are also the most similar). IL-17F is the closest homologue to IL-17A and is 50% identical in sequence (Y. Iwakura, et al., Immunity 2011, 34, 149-162). IL-17A and IL-17F are secreted both as disulfide-linked homodimers (32-38 kDa) and as the IL-17A/F covalent heterodimer (40-45 kDa), exhibiting related functions. Like IL-17A, IL-17F activates immune and non-immune cells to induce pro-inflammatory mediators. These mediators can induce neutrophil recruitment at inflammatory sites (X. O. Yang, et al., J. Exp. Med. 2008, 205, 1063-1075; H. Park, et al. Nat. Immunol. 2005, 6, 1133-1141; S. D. Hurst, et al., J. Immunol. 2002, 169, 443-453; N. Oda, et al., Am. J. Respir. Crit. Care Med. 2005, 171, 12-18), promote local tissue destruction, induce neovascularization in tumors (L.-H. Wei, et al., Oncogene 2003, 22, 1517-1527), enhance osteoclastogenesis (P. K. K. Wong, et al., Arthritis Rheum. 2006, 54, 158-168), and protect from pathogen infection, resulting in disease development and host protection(Y. Iwakura, et al., Immunity 2011, 34, 149-162).

IL-17 cytokine family members mediate their effects through binding to the IL-17 receptor family, of which there are five related members (IL-17RA-IL-17RE). Both IL-17A and IL-17F bind as homodimers or heterodimers to the heterodimeric receptor complex formed between IL-17RA and IL-17RC (J. F. Wright, et al., J. Immunol. 2008, 181, 2799-2805; J. F. Wright, et al., J. Biol. Chem. 2007, 282, 13447-13455; S. Liese, et al., Org. Chem. 2015, 11, 804-816). However, IL-17A and IL-17F exhibit differences in receptor binding affinities (S. G. Hymowitz, et al., EMBO J. 2001, 20, 5332-5341; L. K. Ely, et al., Nat. Immunol. 2009, 10, 1245-1251; A. W. Ho, et al., J. Immunol. 2010, 185, 1063-1070; Y. Hu, et al., J. Immunol. 2010, 184, 4307-4316; D. Toy, et al., J. Immunol. 2006, 177, 36-39). Resulting functional differences including the pathogenesis of chronic obstructive pulmonary disease (COPD) have been linked to IL-17F signaling (C. Doe, et al., Chest 2010, 138, 1140-1147; A. Eustace, et al., Chest 2011, 139, 1089-1100. Further, the expression of intracellular adhesion molecule-1 (ICAM-1), which is associated with airway inflammation in bronchial asthma patients, may be induced by IL-17F (M. Kawaguchi, et al., J. Immunol. 2001, 167, 4430-4435; N. Manolitsas, et al., Eur. Respir. J. 1994, 7, 1439-1444). On the other hand, high tissue expression of IL-17A has been found in patients with chronic inflammatory diseases such as psoriasis, and psoriatic and rheumatoid arthritis (P. Miossec, J. K. Kolls, Nat. Rev. Drug Discov. 2012, 11, 763-776).

One approach to drug-targeting these proteins is to block IL-17A/IL-17R interactions by neutralizing circulating IL-17A using monoclonal antibodies (mAbs) and fragments thereof (M. Silacci, et al., J. Biol. Chem. 2014, 289, 14392-14398; M. C. Genovese, et al., Arthritis Rheum. 2010, 62, 929-939; W. Hueber, et al., Sci. Transl. Med. 2010, 2, 52ra72; C. Leonardi, et al., N. Engl. J. Med. 2012, 366, 1190-1199. Bispecific molecules that target IL-17A and tumor necrosis factor alpha (TNFα), or IL-17A and IL-17F, seek to harness the common synergistic interactions between these cytokines (A. Beringer, et al., Trends Mol. Med. 2016, 22, 230-241). The very low natural abundance of circulating IL-17A and IL-17A/F has been a challenge for detecting these biomarkers by traditional sandwich immunoassays. Highly sensitive detection of the circulating levels of each homodimer (IL17A, IL-17F), as well as the IL-17A/F heterodimer, would be informative for understanding the involvement of each cytokine over the course of disease and treatment.

BRIEF SUMMARY OF THE INVENTION

Disclosed are compositions and methods that involve capture agents that bind IL-17A, IL-17F, or both IL-17A and IL-17F. For example, disclosed are methods of using the disclosed capture agents to detect 17A, IL-17F, or both IL-17A and IL-17F. For example, the present disclosure relates to chemically synthesized capture agents (called protein-catalyzed capture agents, or PCC Agents) that are designed to bind to detect interleukin 17A (IL-17A) and interleukin 17F (IL-17F), methods for making said capture agents using iterative in situ click chemistry, methods for using said capture agents to detect IL-17A and IL-17F, and assays employing said methods.

In one aspect, provided herein is a stable, synthetic capture agent that specifically binds IL-17A, wherein the capture agent comprises a ligand having affinity for an epitope on IL-17A. In certain embodiments the capture agent is selective over for IL-17A over IL-17F.

According to certain embodiments, the epitope comprises the amino acid sequence PNSEDKNFPRTVMVNL[Az4] (SEQ ID NO:43). In certain embodiments, the ligand comprises an amino acid sequence 80-100% identical to an amino acid sequence selected from the group consisting of: (a) rhfrl (SEQ ID NO:44), (b) nrfff (SEQ ID NO:45); and (c) rkhyh (SEQ ID NO:46).

According to certain embodiments, the ligand is cyclic. In certain embodiments the ligand comprises a 1,4-substituted-1,2,3-triazole residue (Tz4) or a 1,5-substituted-1,2,3-triazole residue (Tz5). In certain embodiments, the triazole residue is a 1,4-substituted-1,2,3-triazole (Tz4) residue.

According to certain embodiments, the capture agent is labeled with a detectable moiety. In certain embodiments, the detectable moiety is selected from the group consisting of biotin, copper-DOTA, biotin-PEG$_3$, aminooxyacetate, $^{19}$FB, $^{18}$FB and FITC-PEG$_3$. In certain embodiments, the detectable moiety is selected from the group consisting of $^{64}$Cu DOTA, $^{68}$Ga DOTA, $^{68}$Ga NOTA, $^{18}$F, Al$^{18}$F NOTA, $^{64}$Cu, $^{68}$Ga, $^{89}$Zr, $^{124}$I, $^{86}$Y, $^{94m}$Tc, $^{110m}$In, $^{11}$C and $^{76}$Br.

According to certain embodiments, the capture agent has the structure tuted-1,2,3-triazole residue (Tz5). In certain embodiments, the triazole residue is a 1,4-substituted-1,2,3-triazole (Tz4) residue.

According to certain embodiments, the linker is divalent. In certain embodiments, the length of the linker corresponds to distance between the first epitope and the second epitope. In certain embodiments, the length of the linker is from ~4.4 Å to ~26.4 Å, from ~8.8 Å to ~26.4 Å or from ~7 Å to ~15 Å. In certain embodiments, the length of the linker is ~15 Å. In certain embodiments, the linker comprises one or more repeat units of ethylene glycol. In certain embodiments, the linker comprises a peptide. In certain embodiments, the linker is glycine. In certain embodiments, the linker is PEG$_1$. In certain embodiments, the linker is PEG$_2$. In certain embodiments, the linker is PEG$_3$. In certain embodiments, the linker is PEG$_4$. In certain embodiments, the linker is PEG$_5$.

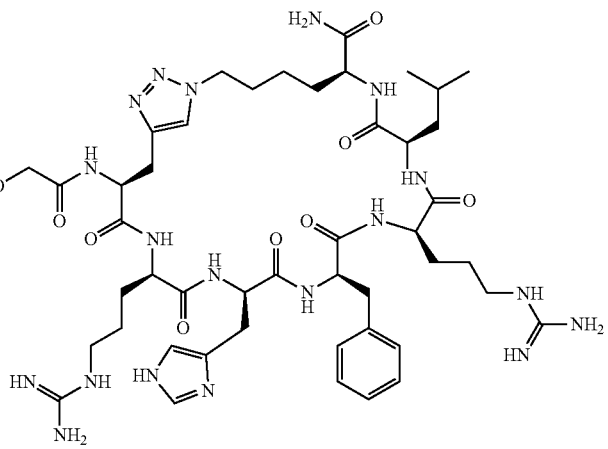

In an aspect, provided herein is a method for detecting IL-17A in a biological sample, comprising the step of contacting the biological sample with one or more of the IL-17A capture agents described herein. In certain embodiments, the method further comprises the steps of binding IL-17A to the one or more capture agents, and detecting the detectable moiety linked to the one or more capture agents.

According to certain embodiments, the IL-17A is in the form of a homodimer, or a heterodimer with IL-17F.

In an aspect, provided herein is a stable, synthetic capture agent that specifically binds IL-17A, wherein the capture agent comprises a first ligand having affinity for a first epitope on IL-17A, a second ligand having affinity for a second epitope on IL-17A, and a linker covalently connecting the first ligand to the second ligand. In certain embodiments, the capture agent is selective for IL-17A over IL-17F.

According to certain embodiments, the first epitope comprises the amino acid sequence PNSEDKNFPRTVMVNL [Az4] (SEQ ID NO:43).

According to certain embodiments, the first ligand comprises an amino acid sequence 80-100% identical to an amino acid sequence selected from the group consisting of (a) rhfrl (SEQ ID NO:44); (b) nrfff (SEQ ID NO:45); and (c) rkhyh (SEQ ID NO:46).

According to certain embodiments, the first ligand is cyclic. In certain embodiments, the first ligand comprises a 1,4-substituted-1,2,3-triazole residue (Tz4) or a 1,5-substi- According to certain embodiments, the capture agent is labeled with a detectable moiety. In certain embodiments, the detectable moiety is selected from the group consisting of biotin, copper-DOTA, biotin-PEG$_3$, aminooxyacetate, $^{19}$FB, $^{18}$FB and FITC-PEG$_3$. In certain embodiments, the detectable moiety is selected from the group consisting of $^{64}$Cu DOTA, $^{68}$Ga DOTA, $^{68}$Ga NOTA, $^{18}$F, Al$^{18}$F NOTA, $^{64}$Cu, $^{68}$Ga, $^{89}$Zr, $^{124}$I, $^{86}$Y, $^{94m}$Tc, $^{110m}$In, $^{11}$C and $^{76}$Br.

In another aspect, provided herein is a method for detecting IL-17A in a biological sample, comprising the step of contacting the biological sample with one or more of the capture agents. In certain embodiments, the capture agent is labeled with a detectable moiety.

According to certain embodiments, the method further comprises binding IL-17A to the one or more capture agents, and detecting the detectable moiety linked to the one or more capture agents.

According to certain embodiments, the IL-17A is in the form of a homodimer, or a heterodimer with IL-17F.

In another aspect, provided herein, is a stable, synthetic capture agent that specifically binds IL-17F, wherein the capture agent comprises a first ligand having affinity for a first epitope on IL-17F, a second ligand having affinity for a second epitope on IL-17F, and a linker covalently connecting the first ligand to the second ligand, wherein at least two amino acids of each of the first and the second ligands are D-amino acids.

According to certain embodiments, the capture agent is selective for IL-17F over IL-17A.

According to certain embodiments, the D-amino acids are D-arginine and D-lysine.

According to certain embodiments, the first epitope comprises the amino acid sequence FFQKPES (SEQ ID NO:1). In certain embodiments, the first epitope comprises the amino acid sequence FFQKPESCPPVPGG (SEQ ID NO:2). In certain embodiments, the second epitope comprises the amino acid sequence NENQRVS (SEQ ID NO:3). In certain embodiments, the second epitope comprises the amino acid sequence GIINENQRVS (SEQ ID NO:4).

According to certain embodiments, the first ligand comprises an amino acid sequence 80-100% identical to an amino acid sequence selected from the group consisting of: (a) rrATS (SEQ ID NO:47); (b) rrAQS (SEQ ID NO:48); (c) rrats (SEQ ID NO:49); and (d) rraqs (SEQ ID NO:50).

According to certain embodiments, the first ligand is cyclic. In certain embodiments, the first ligand comprises a 1,4-substituted-1,2,3-triazole residue (Tz4) or a 1,5-substituted-1,2,3-triazole residue (Tz5). In certain embodiments, the triazole residue is a 1,4-substituted-1,2,3-triazole (Tz4) residue.

According to certain embodiments, the second ligand comprises an amino acid sequence 80-100% identical to an amino acid sequence selected from the group consisting of (a) kYGEV (SEQ ID NO:51); VHkSG (SEQ ID NO:52); QkHGP (SEQ ID NO:53); TkHGP (SEQ ID NO:54); YDLQr (SEQ ID NO:55); YDLTr (SEQ ID NO:56); YDkQr (SEQ ID NO:57); YDkTr (SEQ ID NO:58); kkGWP (SEQ ID NO:59); kLGWP (SEQ ID NO:60); LkGWP (SEQ ID NO:61); rSYNL (SEQ ID NO:62); rSYNk (SEQ ID NO:63); kygev (SEQ ID NO:64); vhksg (SEQ ID NO:65); qkhgp (SEQ ID NO:66); tkhgp (SEQ ID NO:67); ydlqr (SEQ ID NO:68); ydltr (SEQ ID NO:69); ydkqr (SEQ ID NO:70); ydktr (SEQ ID NO:71); kkgwp (SEQ ID NO:72); klgwp (SEQ ID NO:73); lkgwp (SEQ ID NO:74); rsynl (SEQ ID NO:75); and rsynk (SEQ ID NO:76).

According to certain embodiments, the second ligand is cyclic. In certain embodiments the second ligand comprises a 1,4-substituted-1,2,3-triazole residue (Tz4) or a 1,5-substituted-1,2,3-triazole residue (Tz5). In certain embodiments, the triazole residue is a 1,4-substituted-1,2,3-triazole residue (Tz4).

According to certain embodiments, the linker is divalent. In certain embodiments, the length of the linker corresponds to distance between the first epitope and the second epitope. In certain embodiments, the length of the linker is from ~4.4 Å to ~26.4 Å, from ~8.8 Å to ~26.4 Å or from ~7 Å to ~15 Å. In certain embodiments, the length of the linker is ~15 Å.

According to certain embodiments, the linker comprises one or more repeat units of ethylene glycol. In certain embodiments, the linker comprises a peptide.

According to certain embodiments, the first ligand comprises the sequence rrATS (SEQ ID NO:47) and the second ligand comprises the sequence rSYNK (SEQ ID NO: 63). In certain embodiments, first ligand comprises the sequence rrats (SEQ ID NO:49) and the second ligand comprises the sequence rsynk (SEQ ID NO:76).

According to certain embodiments, the first and second ligands are cyclic and comprise a Tz4 residue. In certain embodiments, the linker is glycine. In certain embodiments, the linker is $PEG_1$. In certain embodiments, the linker is $PEG_2$. In certain embodiments, the linker is $PEG_5$. In certain embodiments, the linker is $PEG_4$. In certain embodiments, the linker is $PEG_5$.

According to certain embodiments, the capture agent is labeled with a detectable moiety. In certain embodiments, the detectable moiety is selected from the group consisting of biotin, copper-DOTA, biotin-$PEG_3$, aminooxyacetate, $^{19}FB$, $^{18}FB$ and FITC-$PEG_3$. In certain embodiments, the detectable moiety is selected from the group consisting of $^{64}Cu$ DOTA, $^{68}Ga$ DOTA, $^{68}Ga$ NOTA, $^{18}F$, $Al^{18}F$ NOTA, $^{64}Cu$, $^{68}Ga$, $^{89}Zr$, $^{124}I$, $^{86}Y$, $^{94m}Tc$, $^{110m}In$, $^{11}C$ and $^{76}Br$.

According to certain embodiments, the capture agent has a structure selected from the group consisting of:

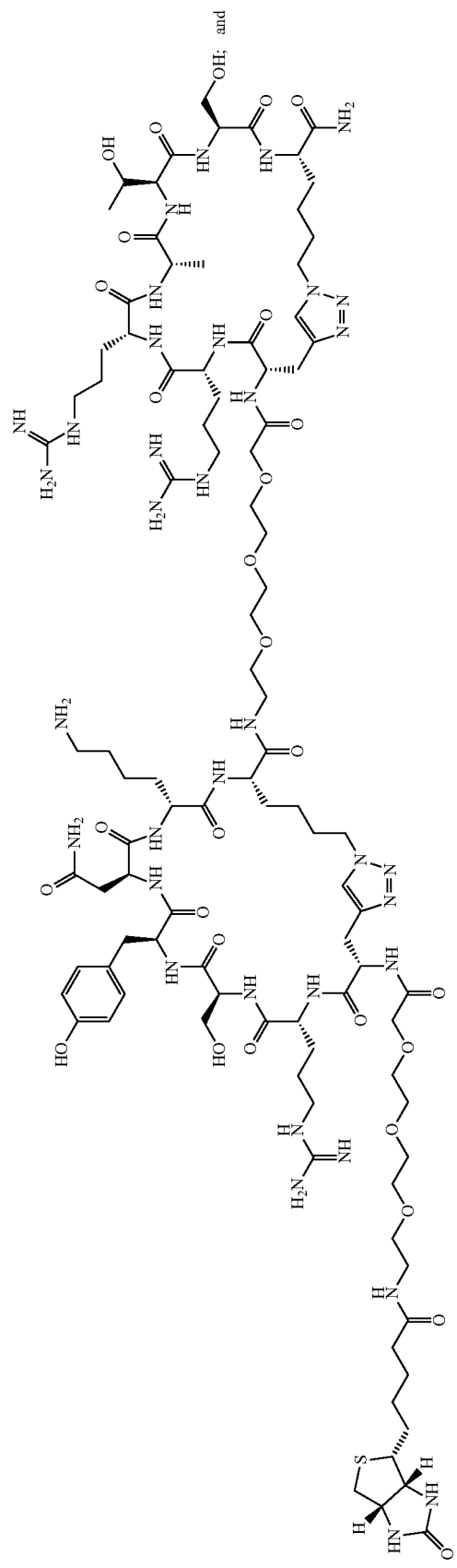
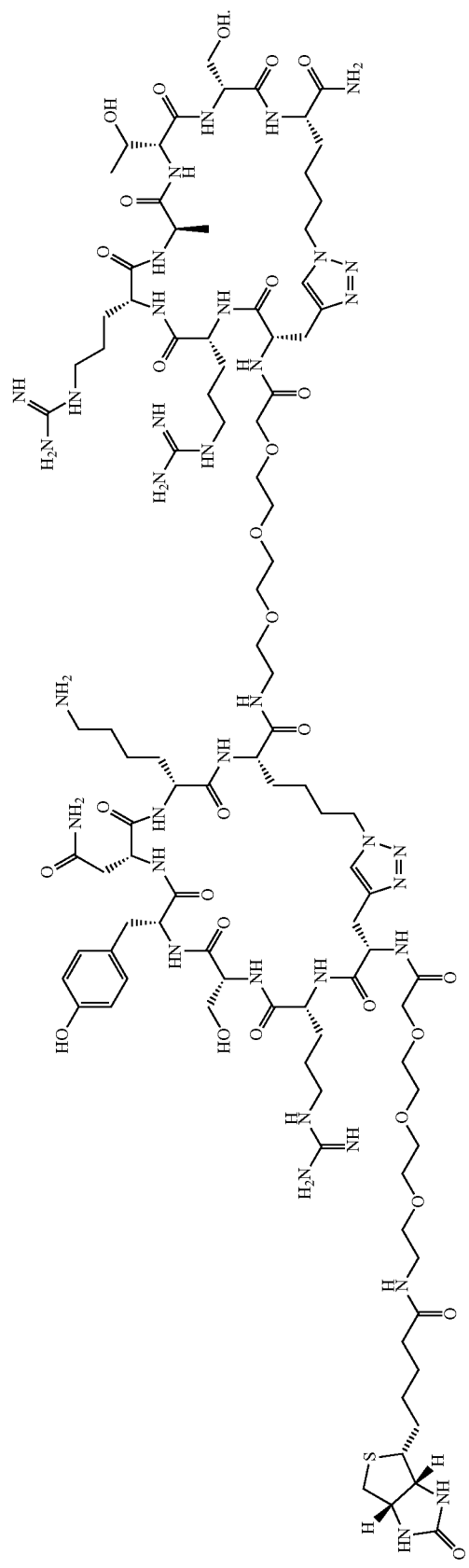

Also disclosed are capture agents for targets, where the capture agent comprises two or more ligands covalently linked to each other, where the ligands specifically bind to one of two or more distinct epitopes of a target that are in different locations on the target. In some forms, the capture agent comprises a first of the ligands has affinity for a first of the epitopes, a second of the ligands has affinity for a second of the epitopes, and a linker covalently connecting the first ligand to the second ligand. In some forms, the capture agent binds IL-17A, IL-17F, or both IL-17A and IL-17F.

In some forms, the first epitope is an epitope on IL-17A, where the first ligand has affinity for the epitope on IL-17A. In some forms, the second epitope is an epitope on IL-17A, where the second ligand has affinity for the epitope on IL-17A. In some forms, the capture agent specifically binds IL-17A. In some forms, the capture agent is selective for IL-17A over IL-17F.

In some forms, the first epitope comprises the amino acid sequence PNSEDKNFPRTVMVNL (SEQ ID NO:43). In some forms, the first ligand comprises an amino acid sequence 80-100% identical to an amino acid sequence selected from the group consisting of: (a) rhfrl (SEQ ID NO:44); (b) nrfff (SEQ ID NO:45); and (c) rkhyh (SEQ ID NO:46).

In some forms, the first ligand has structure

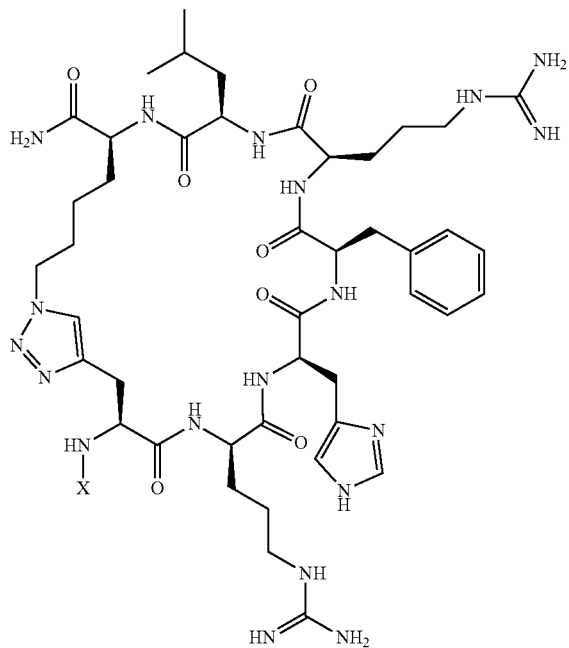

where X represents the rest of the capture agent.

In some forms, the first epitope is an epitope on IL-17F, where the first ligand has affinity for the epitope on IL-17F. In some forms, the second epitope is an epitope on IL-17F, where the second ligand has affinity for the epitope on IL-17F. In some forms, the capture agent specifically binds IL-17F. In some forms, the capture agent is selective for IL-17F over IL-17A.

In some forms, the first epitope comprises the amino acid sequence FFQKPES (SEQ ID NO:1). In some forms, the first epitope comprises the amino acid sequence FFQKPESCPPVPGG (SEQ ID NO:2). In some forms, the second epitope comprises the amino acid sequence NENQRVS (SEQ ID NO:3). In some forms, the second epitope comprises the amino acid sequence GIINENQRVS (SEQ ID NO:4).

In some forms, the first ligand comprises an amino acid sequence 80-100% identical to an amino acid sequence selected from the group consisting of: (a) FYKTH (SEQ ID NO:5); (b) FYKQH (SEQ ID NO:6); (c) FYLTH (SEQ ID NO:7); (d) FYLQH (SEQ ID NO:8); (e) RRATS (SEQ ID NO:9); (f) RRAQS (SEQ ID NO:10); (g) rrATS (SEQ ID NO:47); (h) rrAQS (SEQ ID NO:48); (i) rrats (SEQ ID NO:49); and (j) rraqs (SEQ ID NO:50). In some forms, the second ligand comprises an amino acid sequence 80-100% identical to an amino acid sequence selected from the group consisting of: (a) KYGEV (SEQ ID NO:11); (b) LYGEV (SEQ ID NO:12); (c) VHKSG (SEQ ID NO:13); (d) VHLSG (SEQ ID NO:14); (e) QKHGP (SEQ ID NO:15); (f) TKHGP (SEQ ID NO:16); (g) QLHGP (SEQ ID NO:17); (h) TLHGP (SEQ ID NO:18); (i) YDLQR (SEQ ID NO:19); (j) YDLTR (SEQ ID NO:20); (k) YDKQR (SEQ ID NO:21); (l) YDKTR (SEQ ID NO:22); (m) KKGWP (SEQ ID NO:23); (n) KLGWP (SEQ ID NO:24); (o) LKGWP (SEQ ID NO:25); (p) LLGWP (SEQ ID NO:26); (q) RSYNL (SEQ ID NO:27); (r) RSYNK (SEQ ID NO:28); (s) kYGEV (SEQ ID NO:51); (t) VHkSG (SEQ ID NO:52); (u) QkHGP (SEQ ID NO:53); (v) TkHGP (SEQ ID NO:54); (w) YDLQr (SEQ ID NO:55); (x) YDLTr (SEQ ID NO:56); (y) YDkQr (SEQ ID NO:57); (z) YDkTr (SEQ ID NO:58); (aa) kkGWP (SEQ ID NO:59); (bb) kLGWP (SEQ ID NO:60); (cc) LkGWP (SEQ ID NO:61); (dd) rSYNL (SEQ ID NO:62); (ee) rSYNk (SEQ ID NO:63); (ff) kygev (SEQ ID NO:64) (gg) vhksg (SEQ ID NO:65); (hh) qkhgp (SEQ ID NO:66); (ii) tkhgp (SEQ ID NO:67); (jj) ydlqr (SEQ ID NO:68); (kk) ydltr (SEQ ID NO:69); (ll) ydkqr (SEQ ID NO:70); (mm) ydktr (SEQ ID NO:71); (nn) kkgwp (SEQ ID NO:72); (oo) klgwp (SEQ ID NO:73); (pp) lkgwp (SEQ ID NO:74); (qq) rsynl (SEQ ID NO:75); and (rr) rsynk (SEQ ID NO:76).

In some forms, the first ligand comprises the sequence RRATS (SEQ ID NO:9) and the second ligand comprises the sequence QKHGP (SEQ ID NO:15). In some forms, the first ligand comprises the sequence RRATS (SEQ ID NO:9) and the second ligand comprises the sequence RSYNK (SEQ ID NO:28). In some forms, the first ligand comprises the sequence rrATS (SEQ ID NO:47) and the second ligand comprises the sequence rSYNK (SEQ ID NO: 63). In some forms, the first ligand comprises the sequence rrats (SEQ ID NO:49) and the second ligand comprises the sequence rsynk (SEQ ID NO:76).

In some forms, the capture agent has a structure selected from the group consisting of:

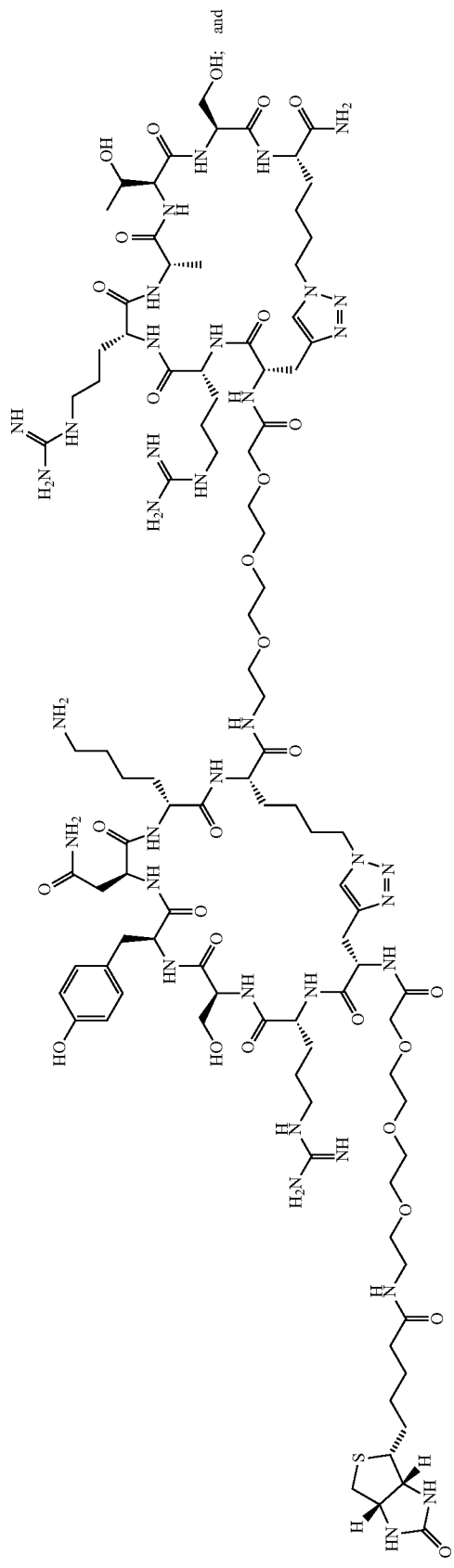
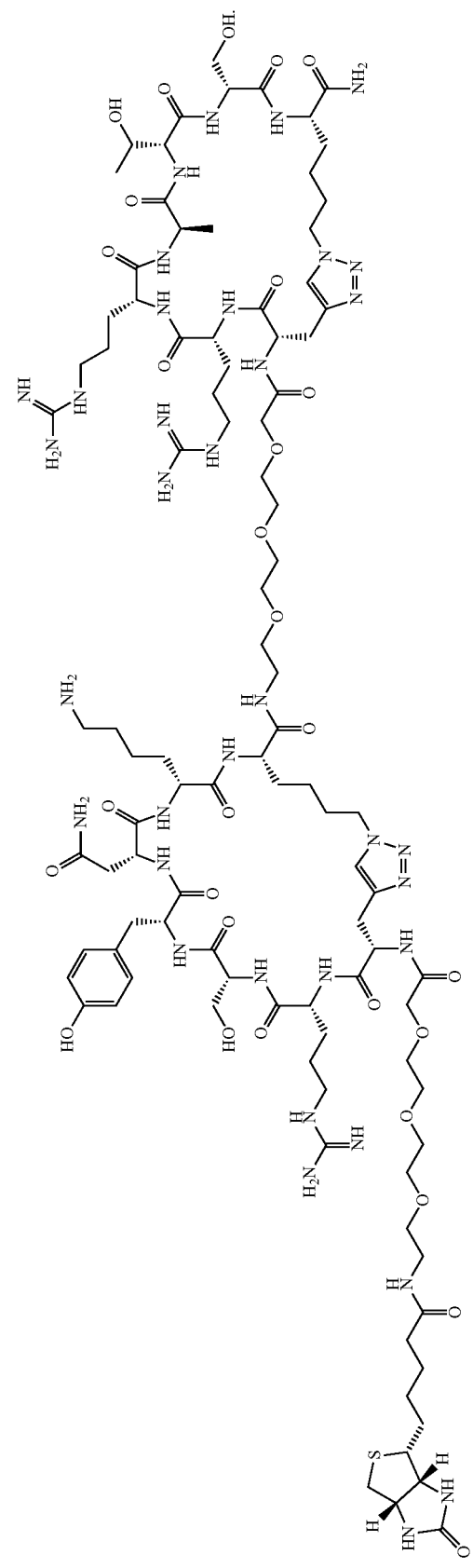

In some forms, the first epitope is an epitope on IL-17A, where the first ligand has affinity for the epitope on IL-17A, where the second epitope is an epitope on IL-17F, where the second ligand has affinity for the epitope on IL-17F. In some forms, the capture agent specifically binds IL-17A/F heterodimer. In some forms, the capture agent is selective for IL-17A/F heterodimer over IL-17F and over IL-17A. In some forms, the first epitope comprises the amino acid sequence PNSEDKNFPRTVMVNL (SEQ ID NO:43).

In some forms, the first ligand comprises an amino acid sequence 80-100% identical to an amino acid sequence selected from the group consisting of: (a) rhfrl (SEQ ID NO:44); (b) nrfff (SEQ ID NO:45); and (c) rkhyh (SEQ ID NO:46).

In some forms, the first ligand has structure

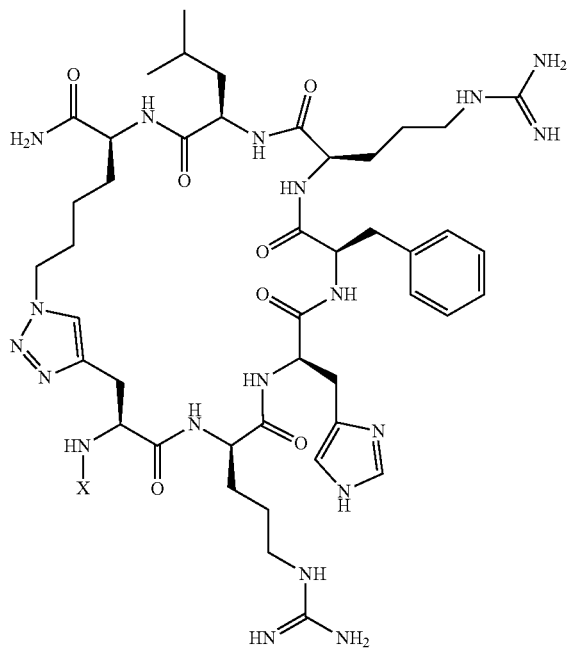

where X represents the rest of the capture agent.

In some forms, the second epitope comprises the amino acid sequence NENQRVS (SEQ ID NO:3). In some forms, the second epitope comprises the amino acid sequence GIINENQRVS (SEQ ID NO:4). In some forms, the second ligand comprises an amino acid sequence 80-100% identical to an amino acid sequence selected from the group consisting of: (a) KYGEV (SEQ ID NO:11); (b) LYGEV (SEQ ID NO:12); (c) VHKSG (SEQ ID NO:13); (d) VHLSG (SEQ ID NO:14); (e) QKHGP (SEQ ID NO:15); (f) TKHGP (SEQ ID NO:16); (g) QLHGP (SEQ ID NO:17); (h) TLHGP (SEQ ID NO:18); (i) YDLQR (SEQ ID NO:19); (j) YDLTR (SEQ ID NO:20); (k) YDKQR (SEQ ID NO:21); (l) YDKTR (SEQ ID NO:22); (m) KKGWP (SEQ ID NO:23); (n) KLGWP (SEQ ID NO:24); (o) LKGWP (SEQ ID NO:25); (p) LLGWP (SEQ ID NO:26); (q) RSYNL (SEQ ID NO:27); (r) RSYNK (SEQ ID NO:28); (s) kYGEV (SEQ ID NO:51); (t) VHkSG (SEQ ID NO:52); (u) QkHGP (SEQ ID NO:53); (v) TkHGP (SEQ ID NO:54); (w) YDLQr (SEQ ID NO:55); (x) YDLTr (SEQ ID NO:56); (y) YDkQr (SEQ ID NO:57); (z) YDkTr (SEQ ID NO:58); (aa) kkGWP (SEQ ID NO:59); (bb) kLGWP (SEQ ID NO:60); (cc) LkGWP (SEQ ID NO:61); (dd) rSYNL (SEQ ID NO:62); (ee) rSYNk (SEQ ID NO:63); (ff) kygev (SEQ ID NO:64) (gg) vhksg (SEQ ID NO:65); (hh) qkhgp (SEQ ID NO:66); (ii) tkhgp (SEQ ID NO:67); (jj) ydlqr (SEQ ID NO:68); (kk) ydltr (SEQ ID NO:69); (ll) ydkqr (SEQ ID NO:70); (mm) ydktr (SEQ ID NO:71); (nn) kkgwp (SEQ ID NO:72); (oo) klgwp (SEQ ID NO:73); (pp) lkgwp (SEQ ID NO:74); (qq) rsynl (SEQ ID NO:75); and (rr) rsynk (SEQ ID NO:76).

In some forms, the first ligand comprises the sequence rhfrl (SEQ ID NO:44) and the second ligand comprises the sequence QKHGP (SEQ ID NO:15). In some forms, the first ligand comprises the sequence rhfrl (SEQ ID NO:44) and the second ligand comprises the sequence RSYNK (SEQ ID NO:28). In some forms, the first ligand comprises the sequence rhfrl (SEQ ID NO:44) and the second ligand comprises the sequence rSYNK (SEQ ID NO: 63). In some forms, the first ligand comprises the sequence rhfrl (SEQ ID NO:44) and the second ligand comprises the sequence rsynk (SEQ ID NO:76).

In some forms, the first ligand is cyclic. In some forms, the first ligand comprises a 1,4-substituted-1,2,3-triazole residue (Tz4) or a 1,5-substituted-1,2,3-triazole residue (Tz5). In some forms, the first ligand comprises a 1,4-substituted-1,2,3-triazole residue (Tz4).

In some forms, the first ligand comprises a 1,5-substituted-1,2,3-triazole residue (Tz5). In some forms, the second ligand is cyclic. In some forms, the second ligand comprises a 1,4-substituted-1,2,3-triazole residue (Tz4) or a 1,5-substituted-1,2,3-triazole residue (Tz5). In some forms, the second ligand comprises a 1,4-substituted-1,2,3-triazole residue (Tz4). In some forms, the second ligand comprises a 1,5-substituted-1,2,3-triazole residue (Tz5).

In some forms, the capture agent is labeled with a detectable moiety. In some forms, the detectable moiety is selected from the group consisting of biotin, copper-DOTA, biotin-PEG$_3$, aminooxyacetate, $^{19}$FB, $^{18}$FB and FITC-PEG$_3$. In some forms, the detectable moiety is selected from the group consisting of $^{64}$Cu DOTA, $^{68}$Ga DOTA, $^{68}$Ga NOTA, $^{18}$F, Al$^{18}$F NOTA, $^{64}$Cu, $^{68}$Ga, $^{89}$Zr, $^{124}$I, $^{86}$Y, $^{94m}$Tc, $^{110m}$In, $_{11}$C, and $^{76}$Br.

In some forms, the linker is divalent. In some forms, the length of the linker corresponds to distance between the first epitope and the second epitope. In some forms, the length of the linker is from ~4.4 Å to ~26.4 Å, from ~8.8 Å to ~26.4 Å or from ~7 Å to ~15 Å. In some forms, the length of the linker is ~15 Å.

In some forms, the linker comprises one or more repeat units of ethylene glycol. In some forms, the linker is selected from the group consisting of PEG$_1$, PEG$_2$, PEG$_3$, PEG$_4$ and PEG$_5$. In some forms, the linker comprises a peptide. In some forms, the linker is glycine.

Also disclosed are method for detecting IL-17A, IL-17F, or both IL-17A and IL-17F in a biological sample. In some forms, the method comprises the step of contacting the biological sample with one or more of the disclosed capture agents.

In some forms, at least one of the capture agents specifically binds IL-17A. In some forms, IL-17A is detected. In some forms, at least one of the capture agents specifically binds IL-17F. In some forms, IL-17F is detected. In some forms, at least one of the capture agents specifically binds IL-17A/F heterodimer. In some forms, IL-17A/F heterodimer is detected. In some forms, one or more of the capture agents are labeled with a detectable moiety.

In some forms, the method further comprises the steps of binding IL-17A, IL-17F, or both IL-17A and IL-17F to the one or more capture agents, and detecting the detectable moiety linked to the one or more capture agents. In some forms, the IL-17A is in the form of a homodimer or a heterodimer with IL-17F. In some forms, the IL-17F is in the form of a homodimer or a heterodimer with IL-17A. In some forms, the method further comprises the steps of binding IL-17A, IL-17F, or both IL-17A and IL-17F to the one or more capture agents, and detecting the detectable moiety linked to the one or more capture agents.

Also disclosed are capture agents for a target, where the capture agent comprises two or more ligands covalently linked to each other, where the ligands specifically bind to two distinct, epitopes of a target that are in different locations on the target. In some forms, the capture agent binds IL-17A. For example, disclosed are stable, synthetic capture agents that specifically bind IL-17A, where the capture agent comprises a ligand having affinity for an epitope on IL-17A. In some forms, the capture agent is selective for IL-17A over IL-17F. In some forms, the epitope comprises the amino acid sequence PNSEDKNFPRTVMVNL[Az4] (SEQ ID NO:43).

In some forms, the ligand comprises an amino acid sequence 80-100% identical to an amino acid sequence selected from the group consisting of rhfrl (SEQ ID NO:44), nrfff (SEQ ID NO:45), and rkhyh (SEQ ID NO:46). In some forms, the ligand is cyclic. In some forms, the ligand comprises a 1,4-substituted-1,2,3-triazole residue (Tz4) or a 1,5-substituted-1,2,3-triazole residue (Tz5). In some forms, the triazole residue is a 1,4-substituted-1,2,3-triazole (Tz4) residue.

In some forms, the capture agent is labeled with a detectable moiety. In some forms, the detectable moiety is selected from the group consisting of biotin, copper-DOTA, biotin-PEG$_3$, aminooxyacetate, $^{19}$FB, $^{18}$FB and FITC-PEG$_3$. In some forms, the detectable moiety is selected from the group consisting of $^{64}$Cu DOTA, $^{68}$Ga DOTA, $^{68}$Ga NOTA, $^{18}$F, Al$^{18}$F NOTA, $^{64}$Cu, $^{68}$Ga, $^{89}$Zr, $^{124}$I, $^{86}$Y, $^{94m}$Tc, $^{110m}$In, $^{11}$C and $^{76}$Br.

In some forms, the capture agent has the structure nrfff (SEQ ID NO:45), and rkhyh (SEQ ID NO:46). In some forms, the first ligand is cyclic. In some forms, the first ligand comprises a 1,4-substituted-1,2,3-triazole residue (Tz4) or a 1,5-substituted-1,2,3-triazole residue (Tz5). In some forms, the triazole residue is a 1,4-substituted-1,2,3-triazole (Tz4) residue.

In some forms, the linker is divalent. In some forms, the length of the linker corresponds to distance between the first epitope and the second epitope. In some forms, the length of the linker is from ~4.4 Å to ~26.4 Å, from ~8.8 Å to ~26.4 Å or from ~7 Å to ~15 Å. In some forms, the length of the linker is ~15 Å. In some forms, the linker comprises one or more repeat units of ethylene glycol. In some forms, the linker comprises a peptide. In some forms, the linker is glycine. In some forms, the linker is selected from the group consisting of PEG$_1$, PEG$_2$, PEG$_3$, PEG$_4$ and PEG$_5$.

In some forms, the capture agent is labeled with a detectable moiety. In some forms, the detectable moiety is selected from the group consisting of biotin, copper-DOTA, biotin-PEG$_3$, aminooxyacetate, $^{19}$FB, $^{18}$FB and FITC-PEG$_3$. In some forms, the detectable moiety is selected from the group consisting of $^{64}$Cu DOTA, $^{68}$Ga DOTA, $^{68}$Ga NOTA, $^{18}$F, Al$^{18}$F NOTA, $^{64}$Cu, $^{68}$Ga, $^{89}$Zr, $^{124}$I, $^{94m}$Tc, $^{110m}$In, $^{11}$C and $^{76}$Br.

Also disclosed are methods for using the disclosed capture agents. For example, disclosed are methods for detecting IL-17A in a biological sample, comprising the step of contacting the biological sample with one or more of the disclosed capture agents. In some forms, the capture agent is labeled with a detectable moiety. In some forms, the method further comprises the steps of binding IL-17A to the one or more capture agents, and detecting the detectable moiety linked to the one or more capture agents. In some forms, the IL-17A is in the form of a homodimer, or a heterodimer with IL-17F.

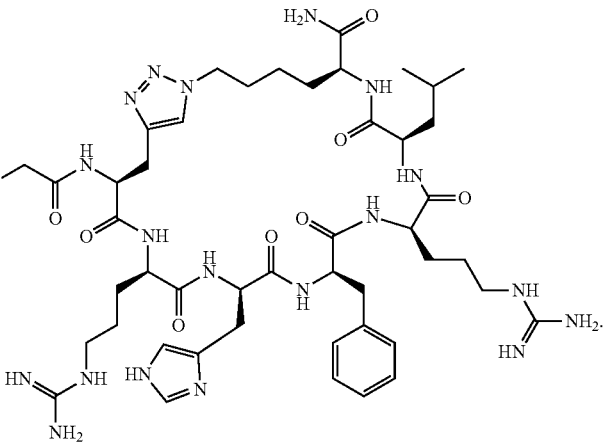

In some forms, the capture agent comprises a first ligand having affinity for a first epitope on IL-17A, a second ligand having affinity for a second epitope on IL-17A, and a linker covalently connecting the first ligand to the second ligand. In some forms, the capture agent is selective for IL-17A over IL-17F. In some forms, the first epitope comprises the amino acid sequence PNSEDKNFPRTVMVNL[Az4] (SEQ ID NO:43).

In some forms, the first ligand comprises an amino acid sequence 80-100% identical to an amino acid sequence selected from the group consisting of rhfrl (SEQ ID NO:44), In some forms, the IL-17A (to be detected, to which the capture agents binds, or both) is in the form of a homodimer or a heterodimer with IL-17F.

Also disclosed are stable, synthetic capture agents that specifically binds IL-17F, where the capture agent comprises a first ligand having affinity for a first epitope on IL-17F, a second ligand having affinity for a second epitope on IL-17F, and a linker covalently connecting the first ligand to the second ligand. In some forms, the capture agent is selective for IL-17F over IL-17A. In some forms, the first epitope comprises the amino acid sequence FFQKPES (SEQ ID NO:1). In some forms, the first epitope comprises the amino acid sequence FFQKPESCPPVPGG (SEQ ID NO:2). In some forms, the second epitope comprises the amino acid sequence NENQRVS (SEQ ID NO:3). In some forms, the second epitope comprises the amino acid sequence GII-NENQRVS (SEQ ID NO:4).

In some forms, the first ligand comprises an amino acid sequence 80-100% identical to an amino acid sequence selected from the group consisting of FYKTH (SEQ ID NO:5), FYKQH (SEQ ID NO:6), FYLTH (SEQ ID NO:7), FYLQH (SEQ ID NO:8), RRATS (SEQ ID NO:9), RRAQS (SEQ ID NO:10), rrATS (SEQ ID NO:47), rrAQS (SEQ ID NO:48), rrats (SEQ ID NO:49), and rraqs (SEQ ID NO:50). In some forms, the first ligand is cyclic. In some forms, the first ligand comprises a 1,4-substituted-1,2,3-triazole residue (Tz4) or a 1,5-substituted-1,2,3-triazole residue (Tz5). In some forms, the triazole residue is a 1,4-substituted-1,2,3-triazole (Tz4) residue.

In some forms, the second ligand comprises an amino acid sequence 80-100% identical to an amino acid sequence selected from the group consisting of KYGEV (SEQ ID NO:11), LYGEV (SEQ ID NO:12), VHKSG (SEQ ID NO:13), VHLSG (SEQ ID NO:14), QKHGP (SEQ ID NO:15), TKHGP (SEQ ID NO:16), QLHGP (SEQ ID NO:17), TLHGP (SEQ ID NO:18), YDLQR (SEQ ID NO:19), YDLTR (SEQ ID NO:20), YDKQR (SEQ ID NO:21), YDKTR (SEQ ID NO:22), KKGWP (SEQ ID NO:23), KLGWP (SEQ ID NO:24), LKGWP (SEQ ID NO:25), LLGWP (SEQ ID NO:26), RSYNL (SEQ ID NO:27), RSYNK (SEQ ID NO:28), kYGEV (SEQ ID NO:51), VHkSG (SEQ ID NO:52), QkHGP (SEQ ID NO:53), TkHGP (SEQ ID NO:54), YDLQr (SEQ ID NO:55), YDLTr (SEQ ID NO:56), YDkQr (SEQ ID NO:57), YDkTr (SEQ ID NO:58), kkGWP (SEQ ID NO:59), kLGWP (SEQ ID NO:60), LkGWP (SEQ ID NO:61), rSYNL (SEQ ID NO:62), rSYNk (SEQ ID NO:63), kygev (SEQ ID NO:64), vhksg (SEQ ID NO:65), qkhgp (SEQ ID NO:66), tkhgp (SEQ ID NO:67), ydlqr (SEQ ID NO:68), ydltr (SEQ ID NO:69), ydkqr (SEQ ID NO:70), ydktr (SEQ ID NO:71), kkgwp (SEQ ID NO:72), klgwp (SEQ ID NO:73), lkgwp (SEQ ID NO:74), rsynl (SEQ ID NO:75), and rsynk (SEQ ID NO:76).

In some forms, the second ligand is cyclic. In some forms, the second ligand comprises a 1,4-substituted-1,2,3-triazole residue (Tz4) or a 1,5-substituted-1,2,3-triazole residue (Tz5). In some forms, the triazole residue is a 1,4-substituted-1,2,3-triazole residue (Tz4).

In some forms, the linker is divalent. In some forms, the length of the linker corresponds to distance between the first epitope and the second epitope. In some forms, the length of the linker is from ~4.4 Å to ~26.4 Å, from ~8.8 Å to ~26.4 Å or from ~7 Å to ~15 Å. In some forms, the length of the linker is ~15 Å. In some forms, the linker comprises one or more repeat units of ethylene glycol. In some forms, the linker comprises a peptide.

In some forms, the first ligand comprises the sequence RRATS (SEQ ID NO:9) and the second ligand comprises the sequence QKHGP (SEQ ID NO:15). In some forms, the first ligand comprises the sequence RRATS (SEQ ID NO:9) and the second ligand comprises the sequence RSYNK (SEQ ID NO:28). In some forms, the first ligand comprises the sequence rrATS (SEQ ID NO:47) and the second ligand comprises the sequence rSYNK (SEQ ID NO: 63). In some forms, the first ligand comprises the sequence rrats (SEQ ID NO:49) and the second ligand comprises the sequence rsynk (SEQ ID NO:76). In some forms, the first and second ligands are cyclic and comprise a Tz4 residue. In some forms, the linker is glycine. In some forms, the linker is selected from the group consisting of $PEG_1$, $PEG_2$, $PEG_3$, $PEG_4$ and $PEG_5$.

In some forms, the capture agent is labeled with a detectable moiety. In some forms, the detectable moiety is selected from the group consisting of biotin, copper-DOTA, biotin-$PEG_3$, aminooxyacetate, $^{19}FB$, $^{18}FB$ and FITC-$PEG_3$. In some forms, the detectable moiety is selected from the group consisting of $^{64}Cu$ DOTA, $^{68}Ga$ DOTA, $^{68}Ga$ NOTA, $^{18}F$, $Al^{18}F$ NOTA, $^{46}Cu$, $^{68}Ga$, $^{89}Zr$, $^{124}I$, $^{94m}Tc$, $^{110m}In$, $^{11}C$ and $^{76}Br$.

In some forms, the capture agent has a structure selected from the group consisting of:

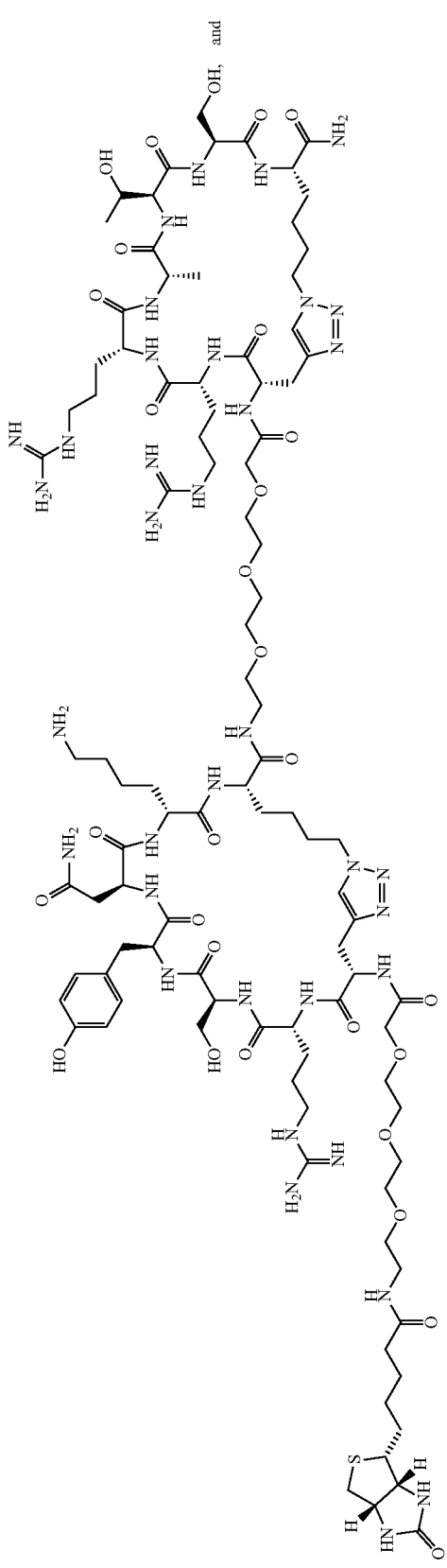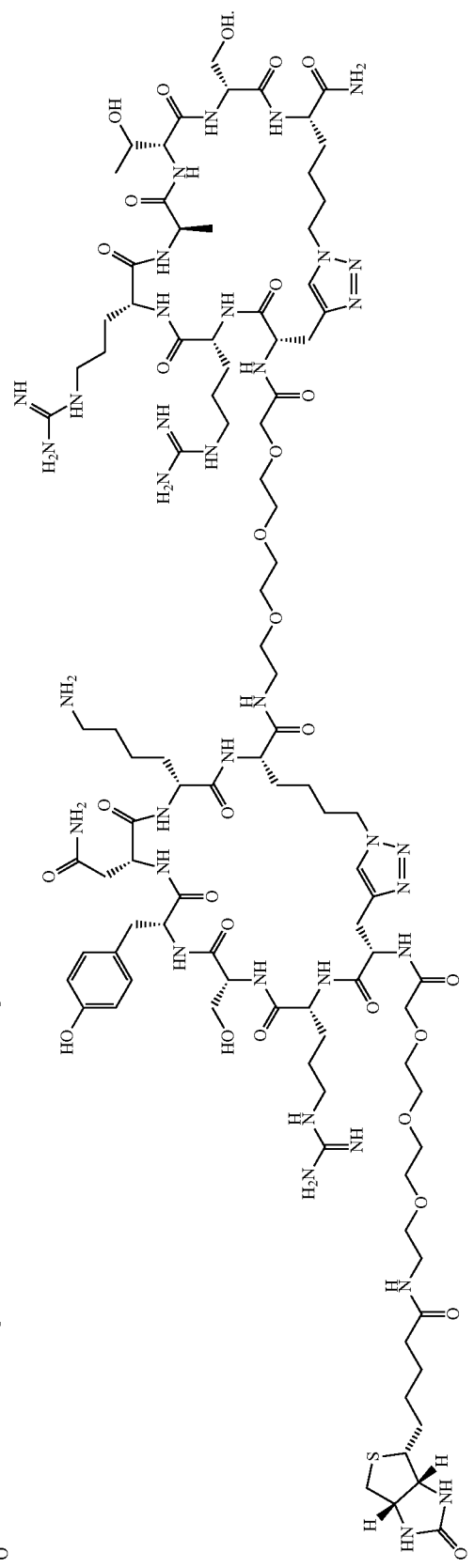

In another aspect, provided herein is a stable, synthetic capture agent that specifically binds IL-17F, wherein the capture agent comprises one or more designed anchor ligands. In certain embodiments, the capture agent comprises two anchor ligands joined by a linker. In another aspect, provided herein is a composition comprising one or more synthetic capture agents, as described herein, that specifically bind IL-17F. According to certain embodiments, the capture agent binds IL-17F with a greater affinity than IL-17A. According to certain embodiments, the capture agent binds IL-17F with at least 0.25, 0.5, 1, 2, 3, 4, 5, 6, 7, 8, 9, 10, 100 or 1000 greater affinity than IL-17A.

In another aspect, provided herein is a stable, synthetic capture agent that specifically binds IL-17F, wherein the capture agent comprises a first ligand having affinity for a first epitope on IL-17F, a second ligand having affinity for a second epitope on IL-17F, and a linker covalently connecting the first ligand to the second ligand. Particularly, the first ligand binds the first epitope (or a synthetic version thereof) in isolation and the second ligand binds the second epitope (or a synthetic version thereof) in isolation. In the capture agent, the first ligand and the second ligand cooperatively bind the first and second epitopes of IL-17F, respectively.

In another aspect, provided herein is a method for detecting IL-17F in a biological sample, comprising the step of treating the biological sample with one or more capture agents described herein.

Anchor Ligand

In one embodiment of the capture agent, the capture agent comprises two ligands that specifically bind IL-17F at two distinct epitopes. These anchor ligands (sometimes referred to herein as simply "ligands") can then be bound to each other by a linker that provides increased affinity for IL-17F. In certain embodiments, there is a first ligand and a second ligand that bind to a first epitope and a second epitope, respectively.

According to certain embodiments, the first epitope comprises the amino acid sequence of FFQKPES (SEQ ID NO:1) or FFQKPESCPPVPGG (SEQ ID NO:2). In certain embodiments, the first epitope is between 5 and 20 amino acids long. In other embodiments, the first epitope is between 7 and 13 amino acids long. In other embodiments, the first epitope is at most, 5, 6, 7, 8, 9, 10, 11, 12, 13, 14, 15, 16, 17, 18, 19 or 20 amino acids long.

According to certain embodiments, the first epitope comprises the amino acid sequence of NENQRVS (SEQ ID NO:3) or GIINENQRVS (SEQ ID NO:4). In certain embodiments, the first epitope is between 5 and 20 amino acids long. In other embodiments, the first epitope is between 7 and 10 amino acids long. In other embodiments, the first epitope is at most, 5, 6, 7, 8, 9, 10, 11, 12, 13, 14, 15, 16, 17, 18, 19 or 20 amino acids long.

According to certain embodiments, the first ligand comprises an amino acid sequence selected from FYKTH (SEQ ID NO:5), FYKQH (SEQ ID NO:6), FYLTH (SEQ ID NO:7), FYLQH (SEQ ID NO:8), RRATS (SEQ ID NO:9) and RRAQS (SEQ ID NO:10). According to certain embodiments, the first ligand comprises an amino acid sequence selected from RRATS (SEQ ID NO:9) and RRAQS (SEQ ID NO:10). In certain embodiments, the first ligand is cyclic. In certain embodiments, the first ligand comprises a 1,4-substituted-1,2,3-triazole residue (Tz4) or a 1,5-substituted-1,2,3-triazole residue (Tz5).

According to certain embodiments, the first ligand comprises an amino acid sequence selected from KYGEV (SEQ ID NO:11), LYGEV (SEQ ID NO:12), VHKSG (SEQ ID NO:13), VHLSG (SEQ ID NO:14), QKHGP (SEQ ID NO:15), TKHGP (SEQ ID NO:16), QLHGP (SEQ ID NO:17), TLHGP (SEQ ID NO:18), YDLQR (SEQ ID NO:19), YDLTR (SEQ ID NO:20), YDKQR (SEQ ID NO:21), YDKTR (SEQ ID NO:22), KKGWP (SEQ ID NO:23), KLGWP (SEQ ID NO:24), LKGWP (SEQ ID NO:25), LLGWP (SEQ ID NO:26), RSYNL (SEQ ID NO:27), and RSYNK (SEQ ID NO:28). According to certain embodiments, the first ligand comprises an amino acid sequence selected from TKHGP (SEQ ID NO:16), QKHGP (SEQ ID NO:15), KKGWP (SEQ ID NO:23) and RSYNK (SEQ ID NO:28). In certain embodiments, the first ligand is cyclic. In certain embodiments, the first ligand comprises a 1,4-substituted-1,2,3-triazole residue (Tz4) or a 1,5-substituted-1,2,3-triazole residue (Tz5).

According to certain embodiments, the first ligand comprises the sequence RRATS (SEQ ID NO:9) and the second ligand comprises the sequence QKHGP (SEQ ID NO:15). In other embodiments, the first ligand comprises the sequence RRATS (SEQ ID NO:9) and the second ligand comprises the sequence RSYNK (SEQ ID NO:28). In other embodiments, the first and second ligands are cyclic and comprise a Tz4 residue.

Linker

According to certain embodiments, the capture agent further comprises a linker that binds both the first and second ligand. According to certain embodiments, the length of the linker corresponds to distance between the first epitope and the second epitope. The length of the linker must be at least the distance between the first and second epitopes. In certain embodiments, the linker is longer than the distance between the first and second epitopes. According to certain embodiments, the linker is 1, 2, 3, 4, 5, 6, 7, 8, 9, 10, 20, 30, 40, 50, 60, 70, 80, 90 or 100% longer than the distance between the first and second epitopes.

According to certain embodiments, the linker is ~4.4 Å to ~26.4 Å, ~8.8 Å to ~26.4 Å or ~7 Å to ~15 Å in length. In certain embodiments, the length of the linker is ~15 Å.

In other embodiments, the linker comprises one or more repeat units of ethylene glycol. In some embodiments, the linker is $PEG_1$, $PEG_2$, $PEG_3$, $PEG_4$, or $PEG_5$. In other embodiments, the linker comprises a peptide. In other embodiments, the linker comprises an amino acid. In a particular embodiment, the linker is glycine. In other embodiments, the linker comprises an alkylene moiety, wherein the alkylene moiety is optionally substituted with one or more moieties provided herein.

Triazole Linkage

In one embodiment of the capture agent, the anchor ligand and secondary ligand are linked together via a 1,4-substituted-1,2,3-triazole residue (Tz4). In another embodiment, the secondary ligand and the tertiary ligand are linked together via a 1,4-substituted-1,2,3-triazole residue (Tz4). In yet another embodiment, the tertiary ligand and the quaternary ligand are linked together via a 1,4-substituted-1,2,3-triazole residue (Tz4). In yet another embodiment, the anchor ligand and secondary ligand are linked together via a 1,4-substituted-1,2,3-triazole residue, and the secondary ligand and the tertiary ligand are linked together via a 1,4-substituted-1,2,3-triazole residue. In yet another embodiment, the anchor ligand and secondary ligand are linked together via a 1,4-substituted-1,2,3-triazole residue, the secondary ligand and the tertiary ligand are linked together via a 1,4-substituted-1,2,3-triazole residue and the tertiary ligand and the quaternary ligand are linked together via a 1,4-substituted-1,2,3-triazole residue.

Capture Agents

According to certain embodiments, the capture agent has a structure selected from the following:

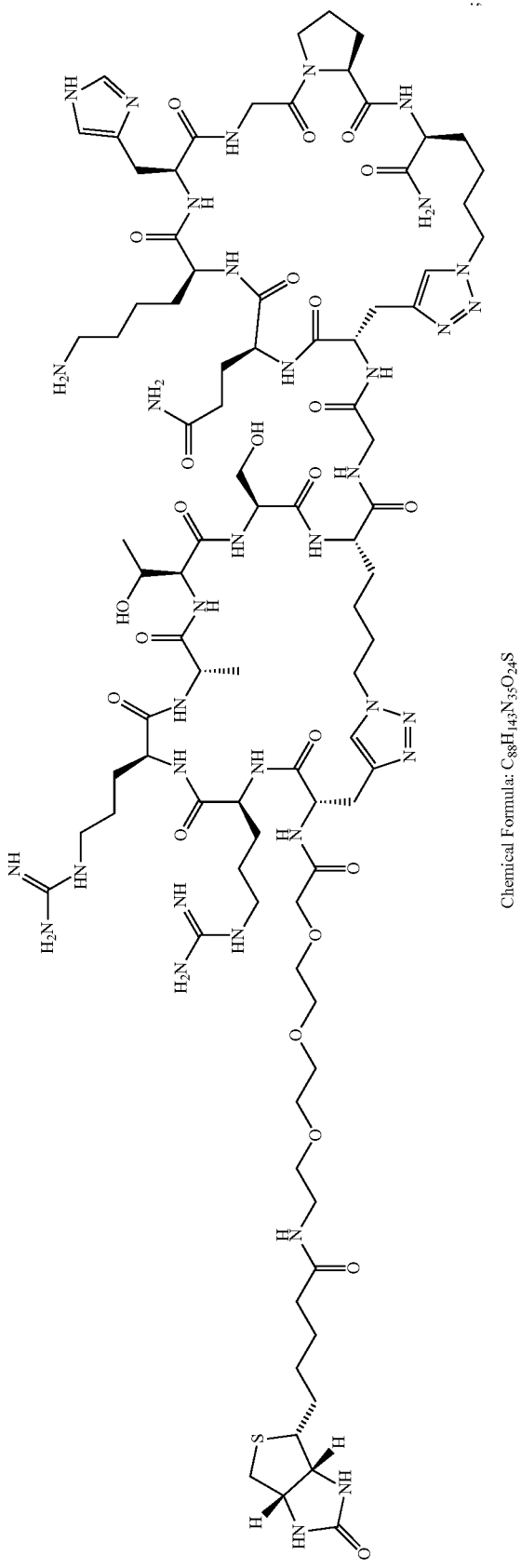

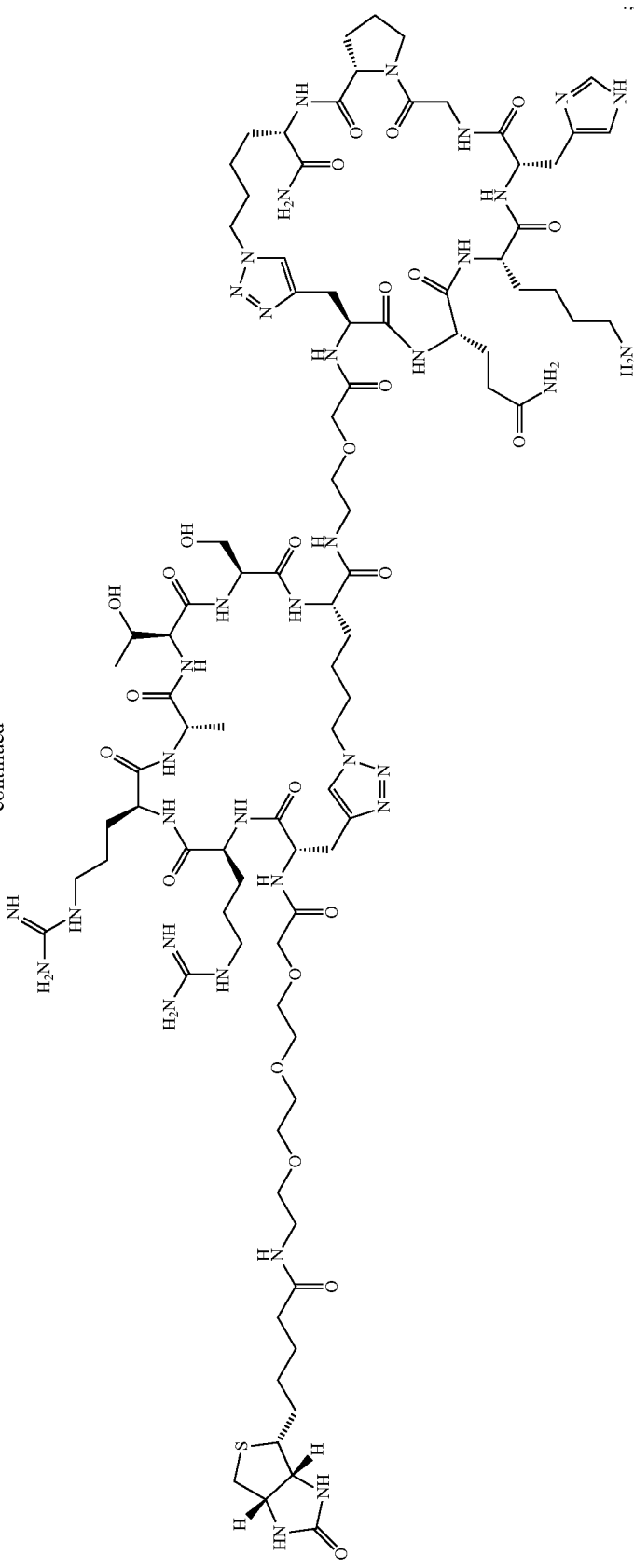
Chemical Formula: C₉₀H₁₄₇N₃₅O₂₅S
Exact Mass: 2150.10
Molecular Weight: 2151.41

-continued
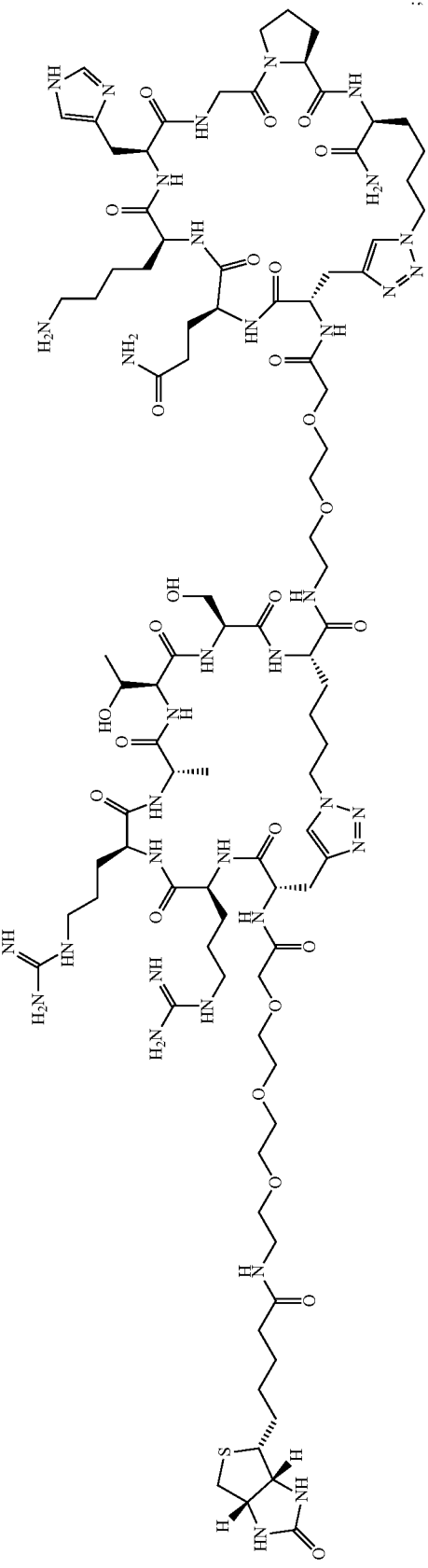
Chemical Formula: $C_{92}H_{151}N_{35}O_{26}S$
Exact Mass: 2194.13
Molecular Weight: 2195.47

-continued
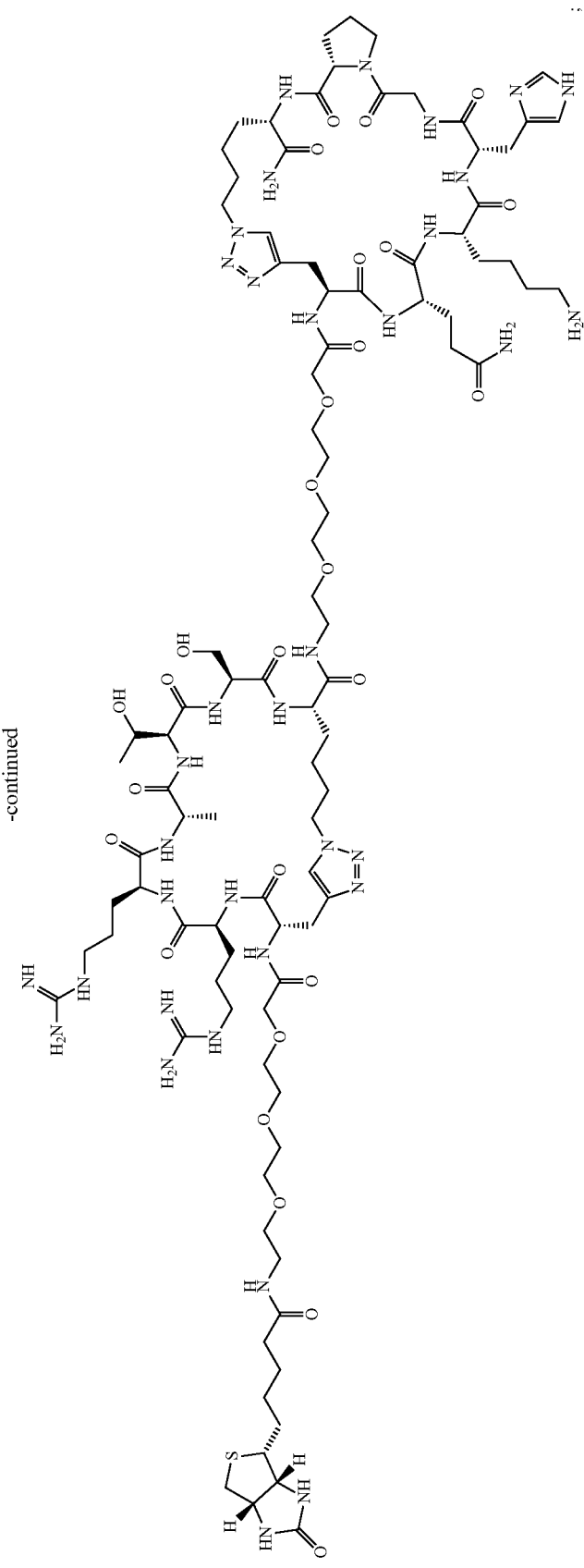
Chemical Formula: $C_{94}H_{155}N_{35}O_{27}S$
Exact Mass: 2238.16
Molecular Weight: 2239.52

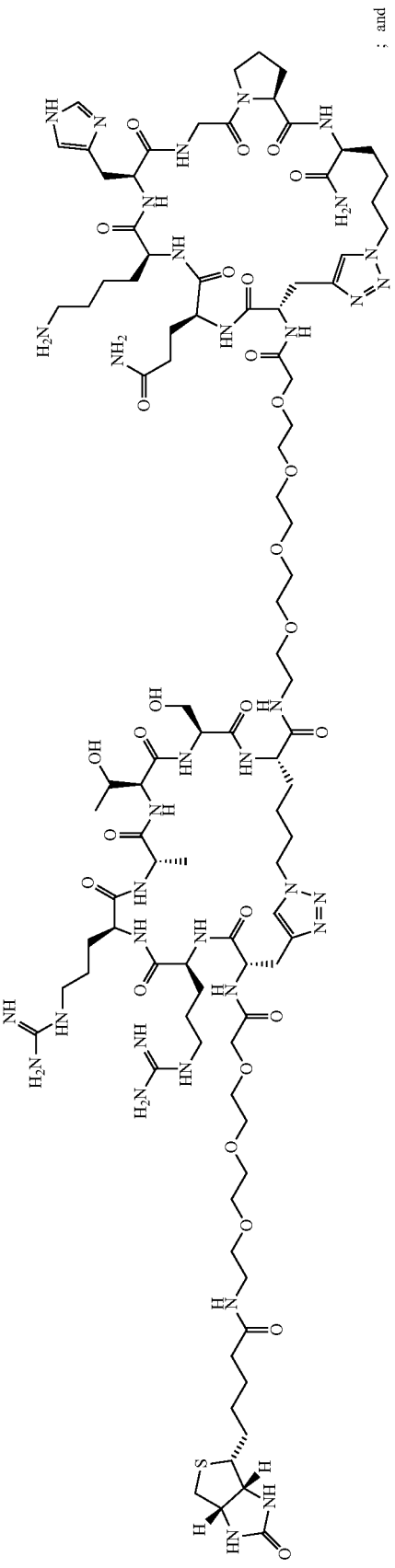
Chemical Formula: $C_{96}H_{159}N_{35}O_{28}S$
Exact Mass: 2282.18
Molecular Weight: 2283.57
; and -continued
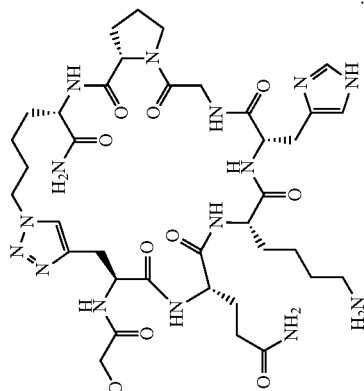
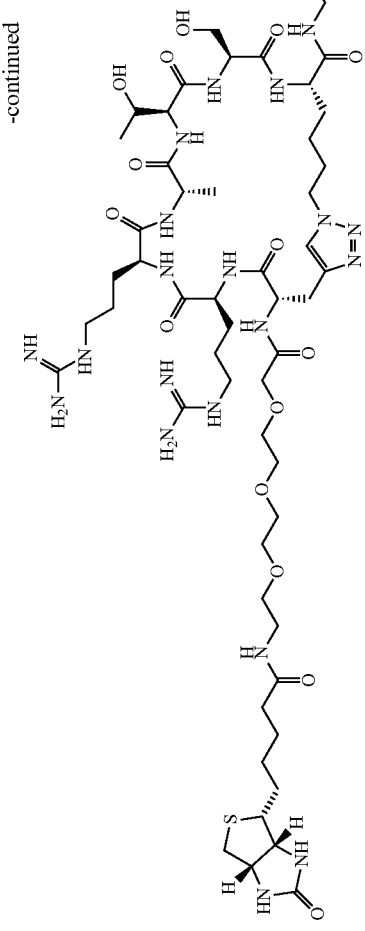
Chemical Formula: $C_{98}H_{163}N_{35}O_{29}S$
Exact Mass: 2326.21
Molecular Weight: 2327.62

According to other embodiments, the capture agent has a structure selected from the following:

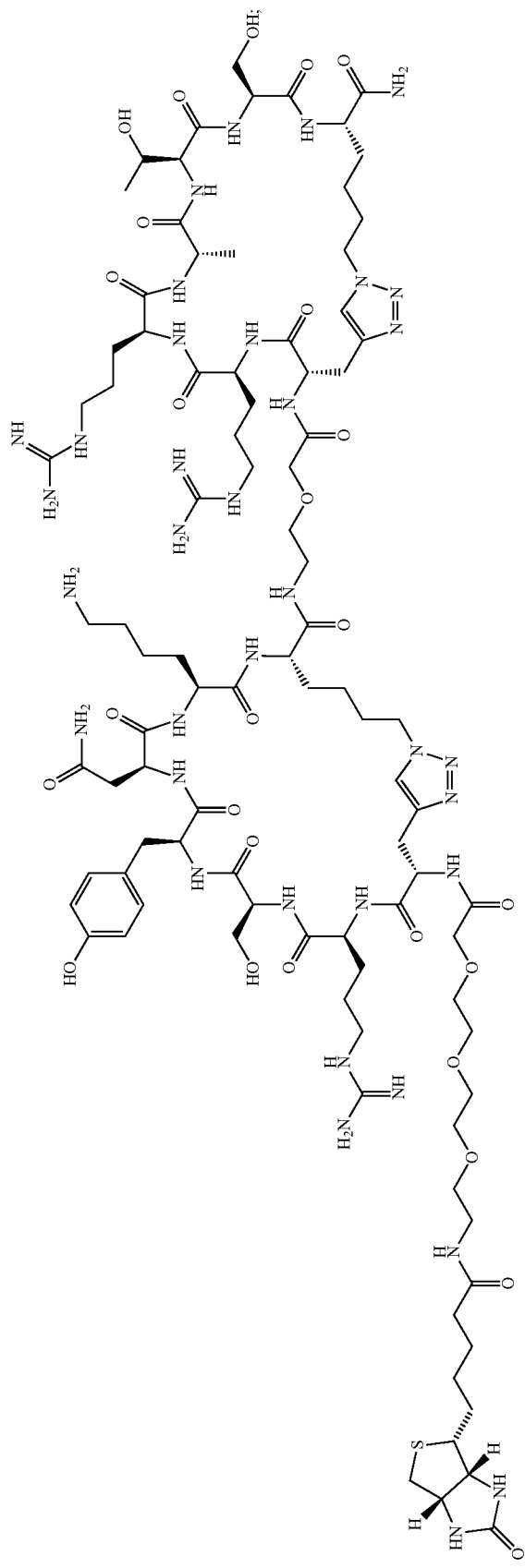

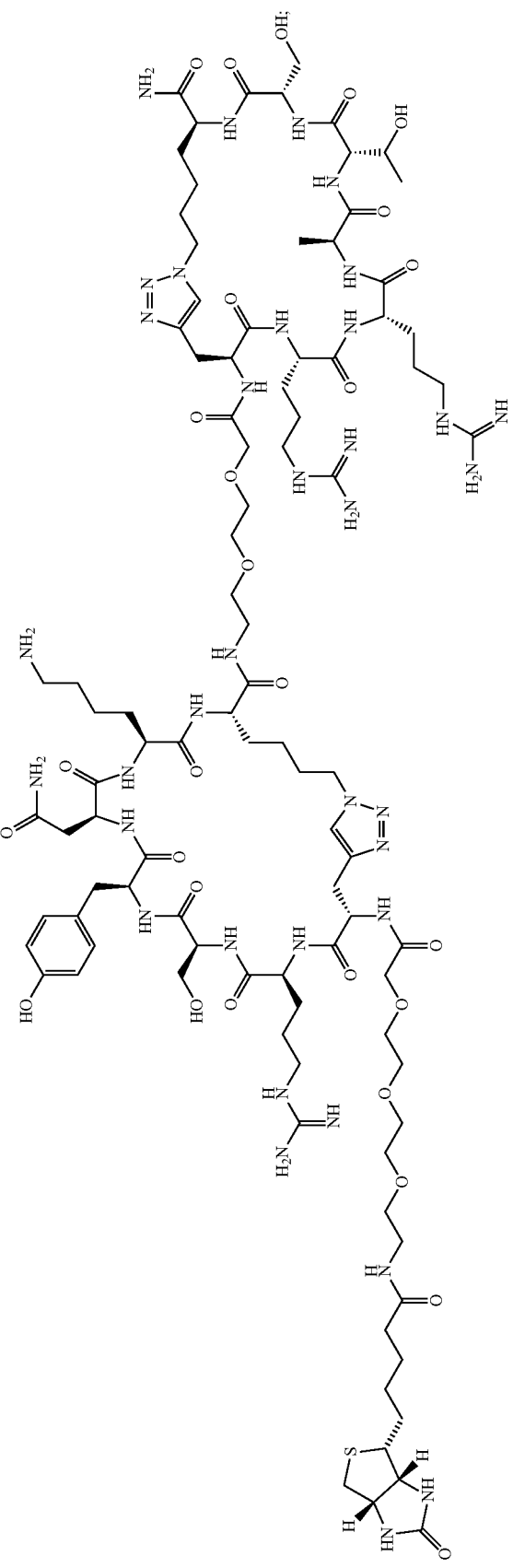

-continued
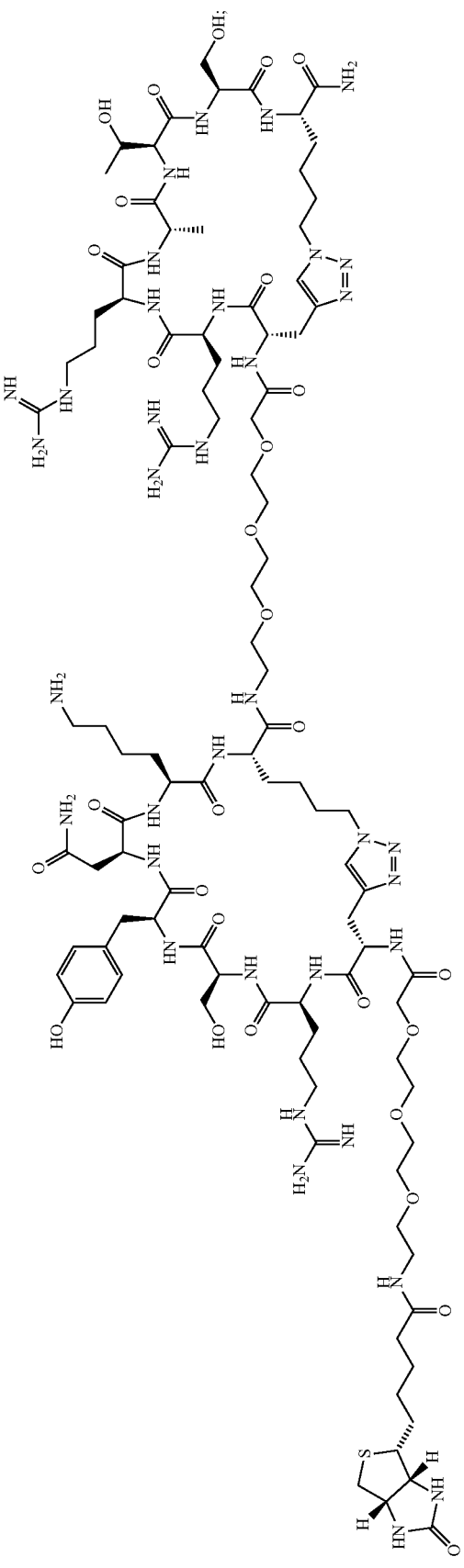
Chemical Formula: $C_{98}H_{162}N_{36}O_{29}S$
Exact Mass: 2339.20
Molecular Weight: 2340.62
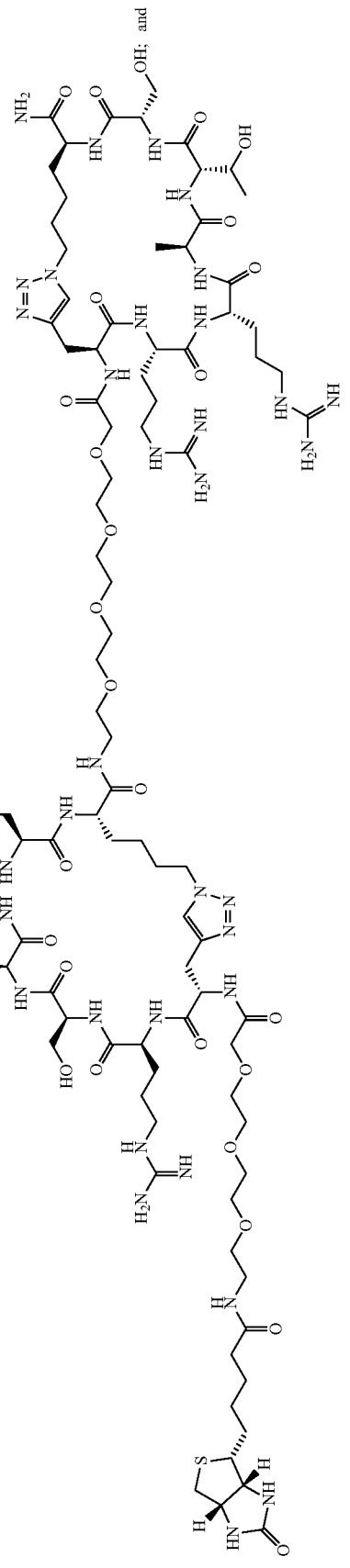
Chemical Formula: $C_{100}H_{166}N_{36}O_{30}S$
Exact Mass: 2383.23
Molecular Weight: 2384.68

-continued
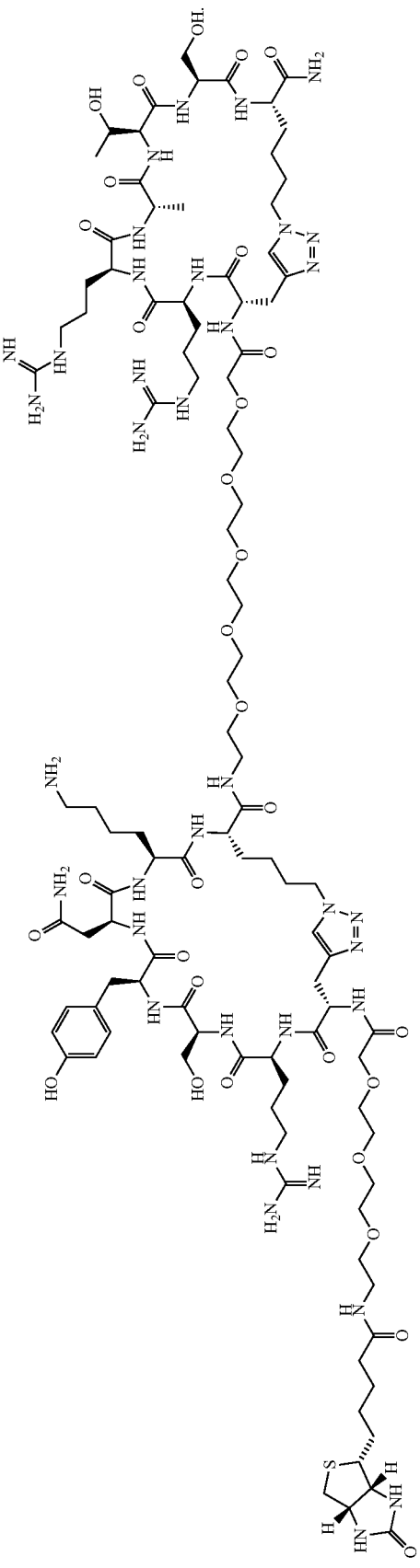
Chemical Formula: $C_{102}H_{170}N_{36}O_{31}S$
Exact Mass: 2427.26
Molecular Weight: 2428.73

Properties

In certain embodiments, the IL-17F capture agents provided herein are stable across a wide range of temperatures, pH values, storage times, storage conditions, and reaction conditions, and in certain embodiments the capture agents are more stable than a comparable antibody or biologic. In certain embodiments, the capture agents are stable in storage as a lyophilized powder. In certain embodiment, the capture agents are stable in storage at a temperature of about −80° C. to about 60° C. In certain embodiments, the capture agents are stable at room temperature. In certain embodiments, the capture agents are stable in human serum for at least 24 hours. In certain embodiments, the capture agents are stable at a pH in the range of about 3 to about 12. In certain embodiments, the capture agents are stable as a powder for two months at a temperature of about 60° C.

Detectable Labels

In some embodiments, the capture agent is labeled with a label selected from the group consisting of biotin, copper-DOTA, biotin-PEG3, aminooxyacetate, $^{19}$FB, $^{18}$FB and FITC-PEG3. In other embodiments, the capture agent is labeled with the detectable moiety consisting of $^{64}$Cu DOTA, $^{68}$Ga DOTA, $^{18}$F, $^{64}$Cu, $^{89}$Zr, $^{124}$I, $^{86}$Y, $^{94m}$Tc, $^{110m}$In, $^{11}$C and $^{76}$Br. In other embodiments, the label is a fluorescent label. In a particular embodiment, the detectable label is $^{18}$F.

Methods and Uses

As used herein, the terms "capture agent of the invention", or "capture agents of the invention" refer to synthetic protein-catalyzed capture agents which bind IL-17F, as described herein.

Also provided is a method of detecting IL-17F in a subject, comprising the step of contacting a biological sample from the subject with one or more capture agents of the invention. Also provided is the use of one or more capture agents of the invention for the detection of IL-17F in a subject.

Also provided is a method of detecting IL-17F in a biological sample using an immunoassay, wherein the immunoassay utilizes a capture agent as described herein, and wherein said capture agent replaces an antibody or its equivalent in the immunoassay. In certain embodiments, methods are provided for identifying, detecting, quantifying, or separating IL-17F in a biological sample using the capture agents as described herein. In one embodiment of the method, the immunoassay is selected from the group of Western blot, pull-down assay, dot blot, and ELISA.

Also provided is a method of detecting the presence of IL-17F in a human or mammalian subject, the method comprising the steps of:
a) administering to a biological sample from the subject one or more capture agents of the invention, wherein each capture agent is linked to a detectable moiety; and
b) detecting the moiety linked to each capture agent in the subject; wherein detection of the moiety indicates the presence of IL-17F in the subject.

Also provided herein is a method of detecting IL-17F in a sample comprising:
a) exposing the sample to one or more capture agents of the invention, wherein each capture agent is linked to a detectable moiety;
b) binding IL-17F in the biological sample to a capture agent and
c) detecting the moiety linked to each capture agent on the substrate; wherein detection of the moiety on the substrate detects IL-17F in the sample.

Kits

Provided herein in certain embodiments are kits comprising one or more capture agents of the invention. In certain embodiments, these kits may be used for identifying, detecting, quantifying, and/or separating IL-17F, and in certain embodiments the kits may be used in the diagnosis and/or staging of a condition associated with the presence of IL-17F. In certain embodiments, a kit as provided herein comprises: (a) a substrate comprising an adsorbent thereon, wherein the adsorbent is suitable for binding IL-17F, and (b) a washing solution or instructions for making a washing solution, wherein the combination of the adsorbent and the washing solution allows detection of IL-17F. In other embodiments, the kits provided herein may be used in the treatment of a condition associated with the presence of IL-17F.

In certain embodiments, a kit may further comprise instructions for suitable operational parameters in the form of a label or a separate insert. For example, the kit may have standard instructions informing a consumer/kit user how to wash the probe after a sample of plasma or other tissue sample is contacted on the probe.

In certain embodiments, a kit comprises (a) one or more capture agents that specifically bind IL-17F; and (b) a detection reagent. Such kits can be prepared from the materials described herein.

The kits provided herein may optionally comprise a standard or control information, and/or a control amount of material, so that the test sample can be compared with the control information standard and/or control amount to determine if the test amount of IL-17F detected in a sample is an amount consistent with a diagnosis of a particular condition.

Synthesis of Capture Agents

Provided herein are methods for making (i.e., synthesizing) IL-17F-specific capture agents of the invention. In one embodiment, the method comprises the steps of:
a. selecting a first ligand that binds to a first epitope on the target protein,
b. selecting a second ligand that binds to a second epitope on the target protein,
c. selecting a linker that has a length that allows the linker to bind both the first ligand and the second ligand when both the first and the second ligands are specifically binding the first and second epitopes, respectively, and
d. binding the linker to the first and second ligands, thereby producing the synthetic capture agent that specifically binds to the target protein.

In certain embodiments the ligands are identified using the following steps:
1) a pre-clear to eliminate non-specific binders,
2) a product screen to identify hits resulting from epitope-templated in situ click chemistry,
3) a target screen against His-tagged IL-17F protein, and
4) another target screen against His-tagged IL-17F protein in 2% (v/v) human serum to identify peptides whose binding to IL-17F is unperturbed by serum proteins.

In certain embodiments, the first epitope and the second epitope are ~4.4 Å to ~26.4 Å, ~8.8 Å to ~26.4 Å or ~7 Å to ~15 Å or ~15 Å distant from each other. In some embodiments, the linker is longer than the distance between the first and second epitope. Optionally, the linker is 10-50%, 5-25% or 1-10% longer than the distance between the first and second epitope.

In certain embodiments, the capture agent has a binding affinity for the target protein greater than either of the ligands. In some embodiments, the capture agent has a binding affinity that is at least 50, 75 or 90% of the binding affinity of a full cooperative binder. In other embodiments, the capture agent has a binding affinity that is at least 1, 2, 3, 4, 5, 6, 7, 8, 9, 10, 20, 30, 40, 50, 60, 70, 80, 90, or 100% of the binding affinity of a full cooperative binder.

In certain embodiments, the target protein is a synthetic epitope, wherein the synthetic epitope comprises at least a 20 amino acid sequence of a full length protein, wherein at least one amino acid of the synthetic epitope comprises an azide or an acetylene group. In some embodiments, the synthetic epitope is at least 10, 20, 30, 40, 50, 60, 70, 80, 90, 100, 110, 120, 150, 200, 250 or 300 amino acid sequence of a full length protein. In some embodiments, at least two amino acids of the synthetic epitope comprise an azide or an acetylene group. In other embodiments, at least 3, 4, 5, 6, 7, 8, 9 or 10 amino acids of the synthetic epitope comprise an azide or an acetylene group.

According to certain embodiments, the full length protein is a naturally occurring protein. According to other embodiments, the naturally occurring protein is IL-17.

According to certain embodiments, the capture agent binds the synthetic epitope and the full length protein with a binding affinity that is at least 50% of the binding affinity of a full cooperative binder. According to certain embodiments, the capture agent binds the synthetic epitope and the full length protein with a binding affinity that is at least 1, 2, 3, 4, 5, 6, 7, 8, 9, 10, 20, 30, 40, 50, 60, 70, 80, 90, or 100% of the binding affinity of a full cooperative binder.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

DETAILED DESCRIPTION OF THE INVENTION

Figure 1:
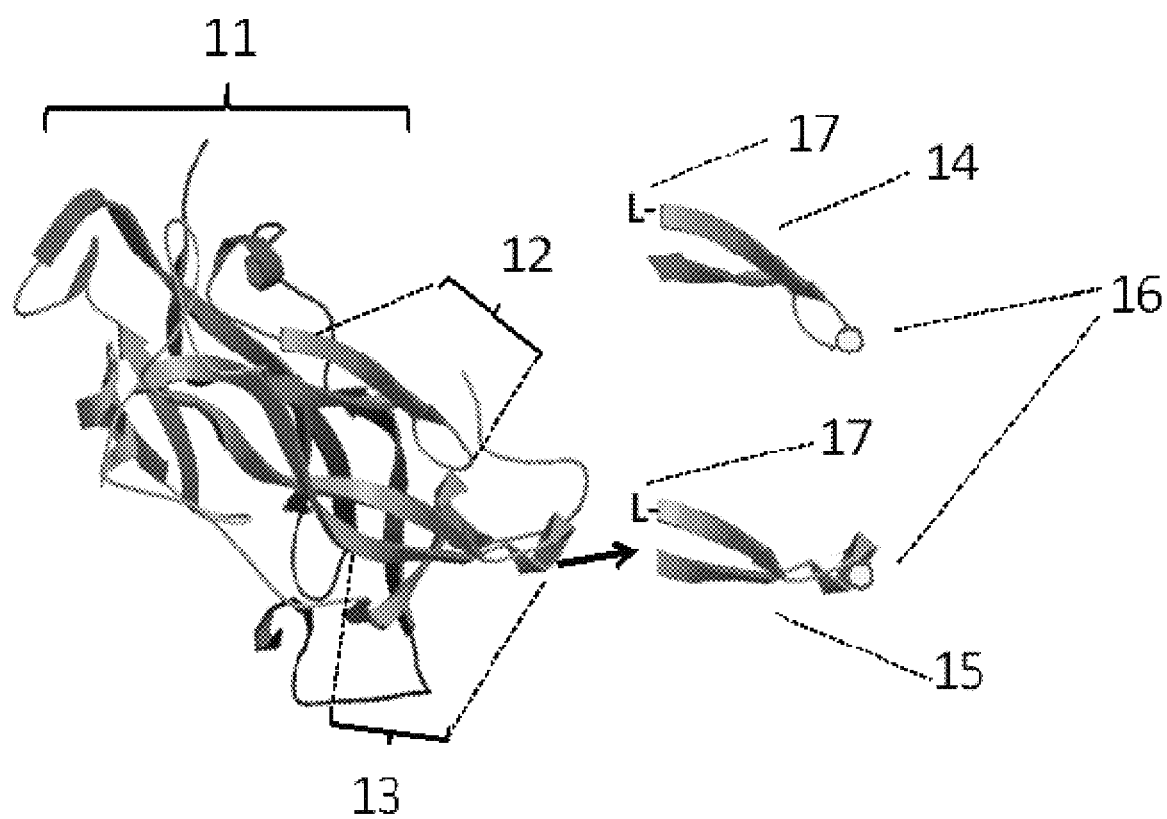
FIG. 1: Starting point for developing a set of PCC binders against a protein target. The initial goal is to identify one or more PCCs that bind to one epitope on the protein target (12), and one or more different PCCs binding to a second epitope (13). Additional PCCs that bind to a third, fourth, etc., epitope may be useful as well. The epitope targeted PCC method teaches that this may be accomplished by screening peptide libraries against synthetic epitopes (SynEps) (14, 15). A SynEp is a polypeptide that has the sequence of the naturally occurring target epitope, except that one position contains an artificial amino acid that presents an azide or acetylene chemical group (16), called a click handle. The SynEp is further modified to contain an assay handle, such as a biotin group, at the N or C-terminus (17). The screening procedure has been described previously (Das, S. et al., A General Synthetic Approach for Designing Epitope Targeted Macrocyclic Peptide Ligands. Angew. Chem. Int. Ed. Engl. 2015, incorporated herein by reference in its entirety). Using that procedure, one identifies at least one unique peptide binder to each of at least two epitopes on the target. Those peptide binders are validated via carrying out binding assays against the full protein target (11) as well as against the SynEps. For those binding assays, the SynEps are prepared with the naturally occurring residue in place of the click handle (16). Ideally, the different regions of the target protein to which the different ligands bind will be relatively close together (a few nanometers or less) in the tertiary protein structure. For even a single SynEp, a screen can produce PCCs that bind to two different sites.

The disclosed method and compositions may be understood more readily by reference to the following detailed description of particular embodiments and the Example included therein and to the Figures and their previous and following description.

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

Unless the context requires otherwise, throughout the present specification and claims, the word "comprise" and variations thereof, such as, "comprises" and "comprising" are to be construed in an open, inclusive sense—that is as "including, but not limited to."

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Definitions

"Amino" refers to the —NH$_2$ radical.

"Cyano" refers to the —CN radical.

"Hydroxy" or "hydroxyl" refers to the —OH radical.

"Imino" refers to the =NH substituent.

"Nitro" refers to the —NO$_2$ radical.

"Oxo" refers to the =O substituent.

"Thioxo" refers to the =S substituent.

"Alkyl" refers to a straight or branched hydrocarbon chain radical consisting solely of carbon and hydrogen atoms, which is saturated or unsaturated (i.e., contains one or more double and/or triple bonds), having from one to twelve carbon atoms ($C_1$-$C_{12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n propyl, 1 methylethyl (isopropyl), n-butyl, n-pentyl, 1,1 dimethylethyl (t-butyl), 3 methylhexyl, 2 methylhexyl, ethenyl, prop-1-enyl, but-1-enyl, pent-1-enyl, penta 1,4 dienyl, ethynyl, propynyl, butynyl, pentynyl, hexynyl, and the like. Unless stated otherwise specifically in the specification, an alkyl group may be optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond.

The points of attachment of the alkylene chain to the rest of the molecule and to the radical group can be through one carbon or any two carbons within the chain. Unless stated otherwise specifically in the specification, an alkylene chain may be optionally substituted.

"Alkoxy" refers to a radical of the formula —OR$_a$ where R$_a$ is an alkyl radical as defined above containing one to twelve carbon atoms. Unless stated otherwise specifically in the specification, an alkoxy group may be optionally substituted.

"Aminocarbonyl" refers to a radical of the formula —C(=O)NR$_a$R$_a$, where each R$_a$ is independently H, alkyl or a linker moiety.

"α-amino carbonyl" refers to a radical of the formula —C(=O)CR$_b$(NR$_a$R$_a$), where each R$_a$ is independently H, alkyl or a linker moiety and R$_b$ is H or alkyl. In some embodiments, an alpha amino carbonyl is part of a cyclic moiety (e.g., peptide) where the carbonyl is within the ring and the amino (NR$_a$R$_a$) is exocyclic. For example, in certain embodiments an alpha aminocarbonyl is useful for Edman degradation of cyclic peptides.

α-amido carbonyl" refers to a radical of the formula —C(=O)CR$_b$(N(C=O)R$_a$R$_a$), where each R$_a$ is independently H, alkyl or a linker moiety and R$_b$ is H or alkyl. In some embodiments, an alpha amido carbonyl is part of a cyclic moiety (e.g., peptide) where the carbonyl is within the ring and the amido (N(C=O)R$_a$R$_a$) is exocyclic.

"Alkylamino" refers to a radical of the formula —NHR$_a$ or —NR$_a$R$_a$ where each R$_a$ is, independently, an alkyl radical as defined above containing one to twelve carbon atoms. Unless stated otherwise specifically in the specification, an alkylamino group may be optionally substituted.

"Thioalkyl" refers to a radical of the formula —SR$_a$ where R$_a$ is an alkyl radical as defined above containing one to twelve carbon atoms. Unless stated otherwise specifically in the specification, a thioalkyl group may be optionally substituted.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —R$_b$—R$_c$ where R$_b$ is an alkylene chain as defined above and R$_c$ is one or more aryl radicals as defined above, for example, benzyl, diphenylmethyl and the like. Unless stated otherwise specifically in the specification, an aralkyl group may be optionally substituted.

"Cycloalkyl" or "carbocyclic ring" refers to a stable non aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7 dimethyl bicyclo[2.2.1]heptanyl, and the like. Unless otherwise stated specifically in the specification, a cycloalkyl group may be optionally substituted.

"Cycloalkylalkyl" refers to a radical of the formula —R$_b$R$_d$ where R$_b$ is an alkylene chain as defined above and R$_d$ is a cycloalkyl radical as defined above. Unless stated otherwise specifically in the specification, a cycloalkylalkyl group may be optionally substituted.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2 trifluoroethyl, 1,2 difluoroethyl, 3 bromo 2 fluoropropyl, 1,2 dibromoethyl, and the like. Unless stated otherwise specifically in the specification, a haloalkyl group may be optionally substituted.

"Heterocyclyl" or "heterocyclic ring" refers to a stable 3 to 18 membered non aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2 oxopiperazinyl, 2 oxopiperidinyl, 2 oxopyrrolidinyl, oxazolidinyl, piperidinyl, piperazinyl, 4 piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1 oxo thiomorpholinyl, and 1,1 dioxo thiomorpholinyl. Unless stated otherwise specifically in the specification, a heterocyclyl group may be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, an N-heterocyclyl group may be optionally substituted.

"Heterocyclylalkyl" refers to a radical of the formula —RbRe where Rb is an alkylene chain as defined above and Re is a heterocyclyl radical as defined above, and if the heterocyclyl is a nitrogen containing heterocyclyl, the heterocyclyl may be attached to the alkyl radical at the nitrogen atom. Unless stated otherwise specifically in the specification, a heterocyclylalkyl group may be optionally substituted.

"Heteroaryl" refers to a 5 to 14 membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4 benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2 oxoazepinyl, oxazolyl, oxiranyl, 1-oxidopyridinyl, 1 oxidopyrimidinyl, 1-oxidopyrazinyl, 1-oxidopyridazinyl, 1 phenyl 1H pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group may be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group may be optionally substituted.

"Heteroarylalkyl" refers to a radical of the formula —R$_b$R$_f$ where Rb is an alkylene chain as defined above and Rf is a heteroaryl radical as defined above. Unless stated otherwise specifically in the specification, a heteroarylalkyl group may be optionally substituted.

The term "substituted" used herein means any of the above groups (e.g., alkyl, alkylene, alkoxy, alkylamino, aminocarbonyl, α-aminocarbonyl, α-amidocarbonyl, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —NR$_g$R$_h$, —NR$_g$C(=O)R$_h$, —NR$_g$C(=O)NR$_g$R$_h$, —NR$_g$C(=O)OR$_h$, —NR$_g$SO2R$_h$, —OC(=O)NR$_g$R$_h$, —OR$_g$, —SR$_g$, —SOR$_g$, —SO$_2$R$_g$, —OSO$_2$R$_g$, —SO$_2$OR$_g$, =NSO$_2$R$_g$, and —SO$_2$NR$_g$R$_h$. "Substituted" also means any of the above groups in which one or more hydrogen atoms are replaced with —C(=O)R$_g$, —C(=O)OR$_g$, —C(=O)NR$_g$R$_h$, —CH$_2$SO$_2$R$_g$, —CH$_2$SO$_2$NR$_g$R$_h$. In the foregoing, R$_g$ and R$_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

"Prodrug" is meant to indicate a compound that may be converted under physiological conditions or by solvolysis to a biologically active compound of the invention (i.e., a disclosed capture agent). Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7 9, 21 24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the invention and the like.

The invention disclosed herein is also meant to encompass all pharmaceutically acceptable disclosed capture agents being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabeled compounds could be useful to help determine or measure the effectiveness of the compounds, by characterizing, for example, the site or mode of action, or binding affinity to pharmacologically important site of action. Certain isotopically-labeled disclosed capture agents, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled capture agents can generally be prepared by conventional techniques known to those skilled in the art or by processes analogous to those described in the Preparations and Examples as set out below using an appropriate isotopically-labeled reagent in place of the non-labeled reagent previously employed.

The invention disclosed herein is also meant to encompass the in vivo metabolic products of the disclosed capture agents. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabeled compound of the invention in a detectable dose to an animal, such as rat, mouse, guinea pig, monkey, or to human, allowing sufficient time for metabolism to occur, and isolating its conversion products from the urine, blood or other biological samples.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2 dimethylaminoethanol, 2 diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N ethylpiperidine, polyamine resins and the like. Particularly preferred organic bases are isopropylamine, diethylamine, ethanolamine, trimethylamine, dicyclohexylamine, choline and caffeine.

The compounds (capture agents) of the invention, or their pharmaceutically acceptable salts may contain one or more asymmetric centers and may thus give rise to enantiomers, diastereomers, and other stereoisomeric forms that may be defined, in terms of absolute stereochemistry, as (R) or (S) or, as (D) or (L) for amino acids. The present invention is meant to include all such possible isomers, as well as their racemic and optically pure forms. Optically active (+) and ( ) (R) and (S), or (D) and (L) isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included. (D)-amino acids (also referred to as D-amino acids) are referred to herein in lower case letters (e.g. D-valine is referred to as "v"), while (L)-amino acids (also referred to herein as L-amino acids) are referred to in upper case letters (e.g. L-valine or valine is referred to as "V"). Glycine is non-chiral and is referred to as "G".

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

The term "capture agent" as used herein refers to a composition that comprises two or more target-binding moieties and which specifically binds to a target protein via those target-binding moieties. Each target-binding moiety exhibits binding affinity for the target protein, either individually or in combination with other target-binding moieties. In certain embodiments, each target-binding moiety binds to the target protein via one or more non-covalent interactions, including for example hydrogen bonds, hydrophobic interactions, and van der Waals interactions. A capture agent may comprise one or more organic molecules, including for example polypeptides, peptides, polynucleotides, and other non-polymeric molecules. In some aspects a capture agent is a protein catalyzed capture agent (PCC).

The term "epitope" as used herein refers to a distinct molecular surface of a protein (e.g., IL-17A or IL-17F). Typically, the epitope is a polypeptide and it can act on its own as a finite sequence of 10-40 amino acids.

The terms "polypeptide," "peptide," and "protein" are used interchangeably herein to refer to an amino acid sequence comprising a polymer of amino acid residues. The terms apply to amino acid polymers in which one or more amino acid residues is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids, and isomers thereof. Naturally occurring amino acids are those encoded by the genetic code, as well as those amino acids that are later modified, e.g., hydroxyproline, carboxyglutamate, O-phosphoserine, and isomers thereof. The term "amino acid analogs" refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. The term "amino acid mimetics" refers to chemical compounds that have a structure that is different from the general chemical structure of an amino acid, but that functions in a manner similar to a naturally occurring amino acid Amino acids may be referred to herein by either their commonly known three letter symbols or by the one-letter symbols recommended by the IUPAC-IUB Biochemical Nomenclature Commission.

The term "non-natural amino acid" as used herein refers to an amino acid that is different from the twenty naturally occurring amino acids (alanine, arginine, glycine, asparagine, aspartic acid, cysteine, glutamine, glutamic acid, serine, threonine, histidine, lysine, methionine, proline, valine, isoleucine, leucine, tyrosine, tryptophan, phenylalanine) in its side chain functionality. The non-natural amino acid can be a close analog of one of the twenty natural amino acids, or it can introduce a completely new functionality and chemistry, as long as the hydrophobicity of the non-natural amino acid is either equivalent to or greater than that of the natural amino acid. The non-natural amino acid can either replace an existing amino acid in a protein (substitution), or be an addition to the wild type sequence (insertion). The incorporation of non-natural amino acids can be accomplished by known chemical methods including solid-phase peptide synthesis or native chemical ligation, or by biological methods.

The terms "specific binding," "selective binding," "selectively binds," or "specifically binds" as used herein refer to capture agent binding to an epitope on a predetermined antigen. Typically, the capture agent binds with an affinity ($K_D$) of approximately less than $10^{-7}$ M, such as approximately less than $10^{-8}$ M, $10^{-9}$ M or $10^{-10}$ M or even lower.

The term "$K_D$" as used herein refers to the dissociation equilibrium constant of a particular capture agent-antigen interaction. Typically, the capture agents of the invention bind to IL-17 with a dissociation equilibrium constant ($K_D$) of less than approximately $10^{-6}$ M, $10^{-7}$ M, such as less than approximately $10^{-8}$ M, $10^{-9}$ M or $10^{-9}$ M or even lower, for example, as determined using surface plasmon resonance (SPR) technology in a Biacore instrument using the antigen as the ligand and the capture agent as the analyte, and binds to the predetermined antigen with an affinity corresponding to a $K_D$ that is at least ten-fold lower, such as at least 100 fold lower, for instance at least 1000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the $K_D$ of the capture agent, so that when the $K_D$ of the capture agent is very low (that is, the capture agent is highly specific), then the amount with which the affinity for the antigen is lower than the affinity for a non-specific antigen may be at least 10,000 fold.

The term "$d_d$" ($sec^{-1}$) as used herein refers to the dissociation rate constant of a particular capture agent-antigen interaction. Said value is also referred to as the $k_{off}$ value.

The term "$k_a$" ($M^{-1} \times sec^{-1}$) as used herein refers to the association rate constant of a particular capture agent-antigen interaction.

The term "$K_D$" (M) as used herein refers to the dissociation equilibrium constant of a particular capture agent-antigen interaction.

The term "$K_A$" ($M^{-1}$) as used herein refers to the association equilibrium constant of a particular capture agent-antigen interaction and is obtained by dividing the $k_a$ by the $k_d$.

A "pharmaceutical composition" refers to a formulation of a compound of the invention and a medium generally accepted in the art for the delivery of the biologically active compound to mammals, e.g., humans Such a medium includes all pharmaceutically acceptable carriers, diluents or excipients therefor.

The term "condition" as used herein refers generally to a disease, event, or a change in health status. A change in health status may be associated with a particular disease or event, in which case the change may occur simultaneously with or in advance of the disease or event. In those cases where the change in health status occurs in advance of a disease or event, the change in health status may serve as a predictor of the disease or event. For example, a change in health status may be an alteration in the expression level of a particular gene associated with a disease or event. Alternatively, a change in health status may not be associated with a particular disease or event.

The terms "treat," "treating," or "treatment" as used herein generally refer to preventing a condition or event, slowing the onset or rate of development of a condition or delaying the occurrence of an event, reducing the risk of developing a condition or experiencing an event, preventing or delaying the development of symptoms associated with a condition or event, reducing or ending symptoms associated with a condition or event, generating a complete or partial regression of a condition, lessening the severity of a condition or event, or some combination thereof.

An "effective amount" or "therapeutically effective amount" as used herein refers to an amount effective, at dosages and for periods of time necessary, to achieve a desired therapeutic result. A therapeutically effective amount of a disclosed capture agent may vary according to factors such as the disease state, age, sex, and weight of the individual, and the ability of the capture agent to elicit a desired response in the individual.

The term "stable" as used herein with regard to a capture agent protein catalyzed capture agent or pharmaceutical formulation thereof refers to the agent or formulation retaining structural and functional integrity for a sufficient period of time to be utilized in the methods described herein.

The term "synthetic" as used herein with regard to a protein catalyzed capture agent or capture agent refers to the capture agent has been generated by chemical rather than biological means.

Unless otherwise stated, sequence identity/similarity values provided herein refer to the value obtained using the BLAST 2.0 suite of programs using default parameters (Altschul, et al., (1997) Nucleic Acids Res. 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) Comput. Chem. 17:149-63) and XNU (Claverie and States, (1993) Comput. Chem. 17:191-201) low-complexity filters can be employed alone or in combination.

As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) Computer Applic. Biol. Sci. 4:11-17, e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" or "substantially identical" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 55%, preferably at least 60%, more preferably at least 70%, 80%, 90% and most preferably at least 95%.

In certain embodiments, the term "IL-17F" as used herein refers to human IL-17F. In some embodiments, IL-17F comprises the following amino acid sequence or an amino acid sequence substantially identical to it.

```
                                                             (SEQ ID NO: 31)
  1 MTVKTLHGPA MVKYLLLSIL GLAFLSEAAA RKIPKVGHTF FQKPESCPPV PGGSMKLDIG

61 IINENQRVSM SRNIESRSTS PWNYTVTWDP NRYPSEVVQA QCRNLGCINA QGKEDISMNS

121 VPIQQETLVV RRKHQGCSVS FQLEKVLVTV GCTCVTPVIH RVQ
```

In other embodiments, IL-17F is a protein encoded by the gene represented by Entrez Gene ID Number 112744.

In certain embodiments, the term "IL-17A" as used herein refers to human IL-17A. In some embodiments, IL-17A comprises the following amino acid sequence or an amino acid sequence substantially identical to it.

```
                                                             (SEQ ID NO: 34)
  1 MTPGKTSLVS LLLLLSLEAI VKAGITIPRN PGCPNSEDKN FPRTVMVNLN IHNRNTNTNP

61 KRSSDYYNRS TSPWNLHRNE DPERYPSVIW EAKCRHLGCI NADGNVDYHM NSVPIQQEIL

121 VLRREPPHCP NSFRLEKILV SVGCTCVTPI VHHVA
```

In other embodiments, IL-17A is a protein encoded by the gene represented by Entrez Gene ID Number 3605.

Development of IL-17A and IL-17F Capture Agents

Antibodies are currently the default detection agent for use in diagnostic platforms. However, antibodies possess several disadvantages, including high cost, poor stability, and, in many cases, lack of proper characterization and high specificity. The ideal replacement for use in diagnostic assays should be synthetic, stable to a range of thermal and chemical conditions, and display high affinity and specificity for the target of interest.

A high quality monoclonal antibody possesses low-nanomolar affinity and high target specificity. Interestingly, structural and genetic analyses of the antigen recognition surface have shown that the majority of the molecular diversity of the variable loops is contained in a single highly variable loop (CDR-H3). In humans, this loop ranges in size from 1-35 residues (15 on average), can adopt a wide range of structural conformations, and is responsible for most of the interactions with the antigen. The other five loops are significantly less diverse and adopt only a handful of conformations. This suggests that a carefully selected "anchor" peptide can dominate the mode and strength of the interaction between a capture agent and its target protein. It also suggests that other peptide components, while providing only modest contributions to the total interaction energy, can supply important scaffolding features and specificity elements.

In situ click chemistry is a technique in which a small molecule enzymatic inhibitor is separated into two moieties, each of which is then expanded into a small library—one containing acetylene functionalities, and the other containing azide groups. The enzyme itself then assembles the 'best fit' inhibitor from these library components by selectively promoting 1,3-dipolar cycloaddition between the acetylene and azide groups to form a triazole linkage (the 'click' reaction). The protein effectively plays the role of an extremely selective variant of the Cu(I) catalyst that is commonly used for such couplings. The enzyme promotes the click reaction only between those library components that bind to the protein in the right orientation. The resultant inhibitor can exhibit far superior affinity characteristics relative to the initial inhibitor that formed the basis of the two libraries.

Sequential in situ click chemistry extends the in situ click chemistry concept to enable the discovery of multiligand capture agents (see: U.S. Application Publication No. 20100009896, incorporated herein by reference). This process was used previously to produce a triligand capture agent against the model protein carbonic anhydrase II (CAII). Sequential in situ click chemistry has several advantages. First, structural information about the protein target is replaced by the ability to sample a very large chemical space to identify the ligand components of the capture agent. For example, an initial ligand may be identified by screening the protein against a large (>106 element) one-bead-one-compound (OBOC) peptide library, where the peptides themselves may be comprised of natural, non-natural, and/or artificial amino acids. The resultant anchor ligand is then utilized in an in situ click screen, again using a large OBOC library, to identify a biligand binder. A second advantage is that the process can be repeated, so that the biligand is used as an anchor to identify a triligand, and so forth. The final capture agent can then be scaled up using relatively simple and largely automated chemistries, and it can be developed with a label, such as a biotin group, as an intrinsic part of its structure. This approach permits the exploration of branched, cyclic, and linear capture agent architectures. While many strategies for protein-directed multiligand assembly have been described, most require detailed structural information on the target to guide the screening strategy, and most (such as the original in situ click approach), are optimized for low-diversity small molecule libraries.

The present embodiment further generalizes the in situ click application to naively find an anchor ligand using in situ click. In previous approaches, a known binder was necessary to begin the ligand. This method provides a mechanism to find an anchor ligand de novo.

As described herein, an iterative in situ click chemistry approach was utilized to synthesize a biligand capture agent that specifically binds IL-17F. This in situ click chemistry approach comprised two steps. First, two "anchor" ligands were found that bound IL-17F at distinct but relatively close sites. Second, a linker of an appropriate size was found that bound the two ligands producing a capture agent with higher affinity for IL-17F.

The capture agents generated by the methods disclosed herein were found to display binding affinity for IL-17F. The capture agents were shown to function as both capture and detection agents in ELISA assays and efficiently immunoprecipitate IL-17F.

IL-17A and IL-17F Capture Agents

In one aspect, provided herein is a stable, synthetic capture agent that specifically binds IL-17A or IL-17F, wherein the capture agent comprises two or more "anchor" ligands (also referred to as simply "ligands" herein) and a linker and wherein the ligands selectively bind IL-17A or IL-17F.

In certain embodiments, a ligand comprises one or more polypeptides or peptides. In certain of these embodiments, a target-binding moiety comprises one or more peptides comprising D-amino acids, L-amino acids, and/or amino acids substituted with functional groups selected from the group consisting of substituted and unsubstituted alkyl, substituted and unsubstituted azido, substituted and unsubstituted alkynyl, substituted and unsubstituted biotinyl, substituted and unsubstituted azioalkyl, substituted and unsubstituted polyethyleneglycolyl, and substituted and unsubstituted 1,2,3-triazole.

In certain embodiments, the ligands are linked to one another via a covalent linkage through a linker. In certain of these embodiments, the ligand and linker are linked to one another via an amide bond or a 1,4-disubstituted-1,2,3-triazole linkage as shown below:

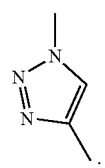

1,4-disubstituted-
1,2,3-triazole linkage

In those embodiments where the ligands and linker are linked to one another via a 1,4-disubstituted-1,2,3-triazole linkage, the 1,4-disubstituted-1,2,3-triazole linkage may be formed by Cu-Catalyzed Azide/Alkyne Cycloaddition (CuAAC).

In certain embodiments, the ligands and linker are linked to one another by a Tz4 linkage having the following structure:

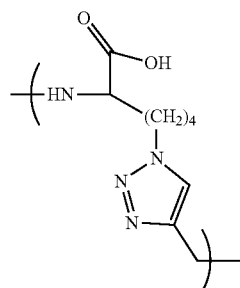

In certain embodiments, the ligands and linker are linked to one another by a Tz5 linkage having the following structure:

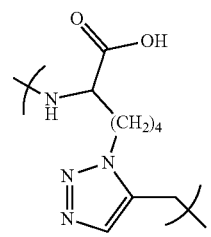

In those embodiments wherein one or more of the ligands and linker are linked to one another via amide bonds, the amide bond may be formed by coupling a carboxylic acid group and an amine group in the presence of a coupling agent (e.g., 0-(7-azabenzotriazol-1-yl)-N,N,N',N'-tetramethyluronium hexafluorophosphate (HATU), N-hydroxy-7-aza-benzotriazole (HOAt), or diisopropylethylamine (DIEA) in DMF).

In certain embodiments, the capture agents provided herein are stable across a range of reaction conditions and/or storage times. A capture agent that is "stable" as used herein maintains the ability to specifically bind to a target protein. In certain embodiments, the capture agents provided herein are more stable than an antibody binding to the same target protein under one or more reaction and/or storage conditions. For example, in certain embodiments the capture agents provided herein are more resistant to proteolytic degradation than an antibody binding to the same target protein.

In certain embodiments, the capture agents provided herein have a shelf-life of greater than six months, meaning that they are stable in storage for greater than six months. In certain of these embodiments, the capture agents have a shelf-life of one year or greater, two years or greater, or more than three years. In certain of these embodiments, the capture agents are stored as a lyophilized powder. In certain embodiments, the capture agents provided herein have a longer shelf-life than an antibody binding to the same target protein.

In certain embodiments, the capture agents provided herein are stable at temperatures ranging from about −80° to about 120° C. In certain of these embodiments, the capture agents are stable within a temperature range of −80° to −40° C.; −40° to −20° C.; −20° to 0° C.; 0° to 20° C.; 20° to 40° C.; 40° to 60° C.; 60° to 80° C.; and/or 80° to 120° C. In certain embodiments, the capture agents provided herein are stable across a wider range of temperatures than an antibody binding to the same target protein, and/or remain stable at a specific temperature for a longer time period than an antibody binding to the same target protein.

In certain embodiments, the capture agents provided herein are stable at a pH range from about 3.0 to about 8.0. In certain embodiments, the range is about 4.0 to about 7.0. In certain embodiments, the range is about 7.0 to about 8.0.

In certain embodiments, the capture agents provided herein are stable in human serum for more than 12 hours. In certain of these embodiments, the capture agents are stable in human serum for more than 18 hours, more than 24 hours, more than 36 hours, or more than 48 hours. In certain embodiments, the capture agents provided herein are stable for a longer period of time in human serum than an antibody binding to the same target protein. In certain embodiments, the capture agents are stable as a powder for two months at a temperature of about 60° C.

In certain embodiments, the capture agents provided herein may comprise one or more detection labels, including for example biotin, copper-1,4,7,10-tetraazacyclododecane-1,4,7,10-tetraacetic acid (copper-DOTA), $^{64}$Cu DOTA, $^{68}$Ga DOTA, $^{18}$F, $^{64}$Cu, $^{68}$Ga, $^{89}$Zr, $^{124}$I, $^{86}$Y, $^{94m}$Tc, $^{110m}$In, 11C, $^{76}$Br, $^{123}$I, $^{131}$I, $^{67}$Ga, $^{111}$In and $^{99m}$Tc, or other radiolabeled products that may include gamma emitters, proton emitters, positron emitters, tritium, or covered tags detectable by other methods (i.e., gadolinium) among others. In a particular embodiment, the detection label is $^{18}$F. In certain embodiments, the capture agents may be modified to be used as imaging agents. The imaging agents may be used as diagnostic agents.

In certain embodiments, the capture agents provided herein may be modified to obtain a desired chemical or biological activity. Examples of desired chemical or biological activities include, without limitation, improved solubility, stability, bioavailability, detectability, or reactivity. Examples of specific modifications that may be introduced to a capture agent include, but are not limited to, cyclizing the capture agent through formation of a disulfide bond; modifying the capture agent with other functional groups or molecules. Similarly, a capture agent may be synthesized to bind to non-canonical or non-biological epitopes on proteins, thereby increasing their versatility. In certain embodiments, the capture agent may be modified by modifying the synthesis blocks of the target-binding moieties before the coupling reaction.

In certain embodiments, increased IL17A is associated with several chronic inflammatory diseases including rheumatoid arthritis, tendon inflammation, psoriasis and multiple sclerosis. The capture agent of the invention may be used as both a therapeutic and an imaging agent.

Methods of Making/Screening Capture Agents

Provided herein in certain embodiments are methods of screening target-binding moieties and/or making capture agents that comprise these target-binding moieties. Methods for screening target-binding moieties and/or making capture agents that comprise these target-binding moieties can also be found in International Publication Nos. WO 2012/106671, WO 2013/033561, WO 2013/009869 and WO 2014/074907, each of which is incorporated by reference, herein, in their entireties.

In certain embodiments, two separately-identified ligands that bind to two different regions of the same protein (the target) are chemically linked together to form a biligand. By optimizing a linker of the two ligands, the biligand formed by the ligands and linker can exhibit a binding affinity that is far superior to either of the individual ligands. This enhanced binding effect is called binding cooperativity. For an ideal cooperative binder, the thermodynamic binding energies of the individual ligands to the target will sum to yield the binding energy of the linked biligand. This means that the binding affinity constant ($K_D$) of the linked biligand will be the product of the binding affinity of the individual ligands (i.e. $K_D=K_{D1}\times K_{D2}$, where the subscripts 1 and 2 refer to the two ligands). In practice, full cooperative binding is rarely, if ever, achieved. Thus, a comparison of the properties of a linked biligand against those of a fully cooperative binder provides a measurement of how optimally the two ligands were linked.

If the protein target has a known and well-defined tertiary (folded) structure, then key aspects of this targeting method involve strategies for identifying ligands that bind to preferred regions of the protein, followed by approaches for identifying an optimized linker. If the protein does not have a well-defined tertiary structure, the disclosure describes strategies designed to still achieve a significant measure of cooperative binding from a biligand.

FIG. 1 describes the starting point for developing a set of PCC binders against a protein target (11). The initial goal is to identify one or more PCCs that bind to one epitope on the protein target (12), and one or more different PCCs binding to a second epitope (13). Additional PCCs that bind to a third, fourth, etc., epitope may be useful as well. The epitope targeted PCC method teaches that this may be accomplished by screening peptide libraries against synthetic epitopes (SynEps, also referred to as "Epitopes" herein, e.g. Epitope1, Epitope2 and Epitope3) such as those shown in FIG. 1 (14, 15). A SynEp is a polypeptide that has the sequence of the naturally occurring target epitope, except that one position contains an artificial amino acid that presents an azide or acetylene chemical group (16), called a click handle. The SynEp is further modified to contain an assay handle, such as a biotin group, at the N or C-terminus (17). The screening procedure can be done using any procedure disclosed herein or known in the art. By screening, one identifies at least one unique peptide binder to each of at least two epitopes on the target. Those peptide binders are validated via carrying out binding assays against the full protein target (11) as well as against the SynEps. For those binding assays, the SynEps are prepared with the naturally occurring residue in place of the click handle (16).

Figure 2:
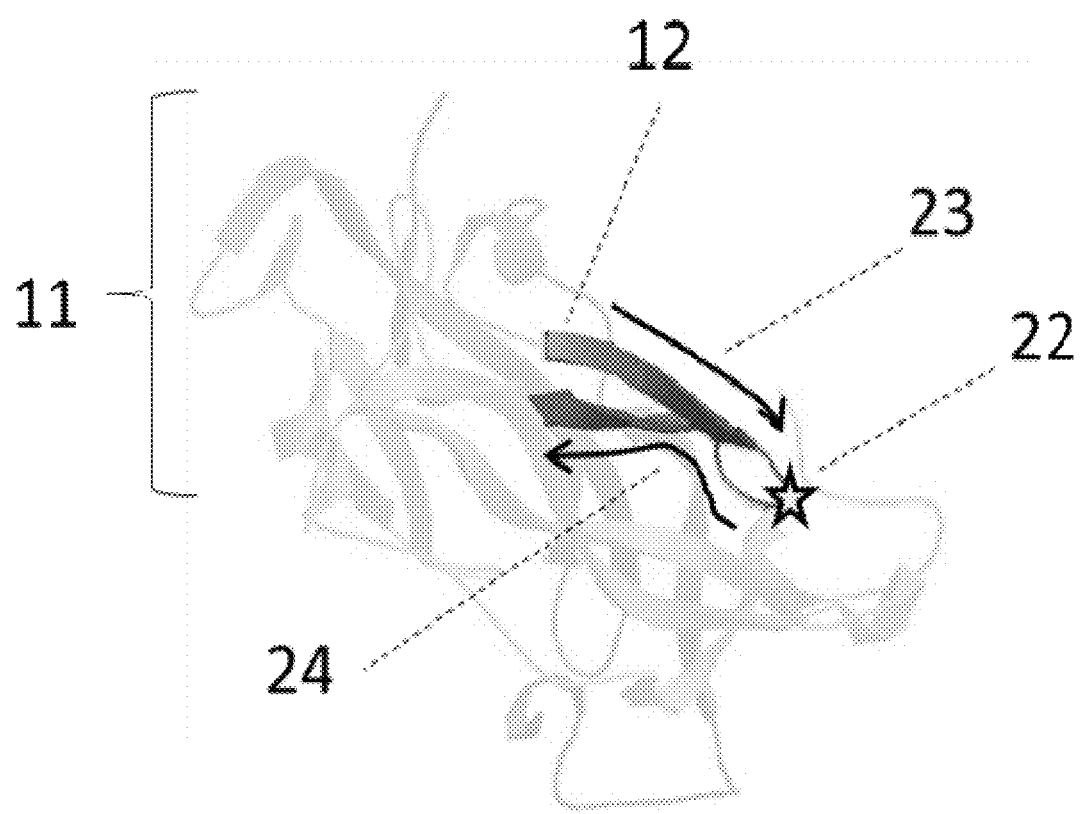
FIG. 2: PCC that binds to two different sites. The region representing the epitope of interest (12) is highlighted against a dimmer background of the full protein (11). The amino acid residue that was substituted for a click handle in the SynEp structure is indicated by a star (22). During the SynEp screening steps, PCCs that bind to the N-terminal side of the epitope (23) or the C-terminal side (24) may both be identified.

Ideally, the different regions of the target protein to which the different ligands bind will be relatively close together (a few nanometers or less) in the tertiary protein structure. For even a single SynEp, a screen can produce PCCs that bind to two different sites. In FIG. 2, the region representing the epitope of interest (12) is highlighted against a dimmer background of the full protein (11). The amino acid residue that was substituted for a click handle in the SynEp structure is indicated by a star (22). During the SynEp screening steps, PCCs that bind to the N-terminal side of the epitope (23) or the C-terminal side (24) may both be identified.

Once the epitope targeted PCCs are identified, there are several methods for selecting a linker.

Figure 3A:
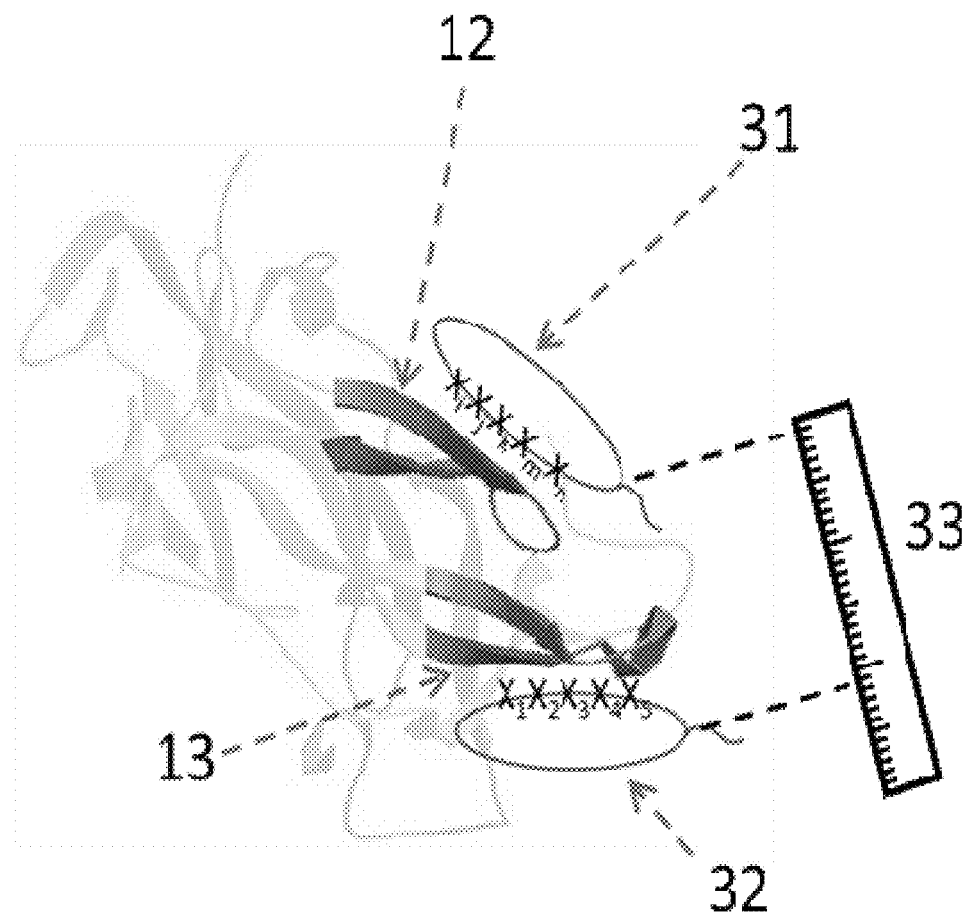
FIGS. 3A and 3B: Estimation of optimal linker length. A first PCC (31) that binds to the N-side of one epitope (12) and a second PCC (32) binding to the C-side of a second epitope (13) are shown. Analysis of this binding arrangement, together with the structure of the protein from, for example, the Protein Database, permits an estimate of the length of an optimized linker (33). Such an estimate can narrow down the choice of candidate linkers to a very small number. One example might be to use such a length estimate to select one or two length-marched polyethylene glycol oligomers for testing. The best linker (34) is the one that brings the biligand affinity closest to that of a fully cooperative binder.
Figure 3B:
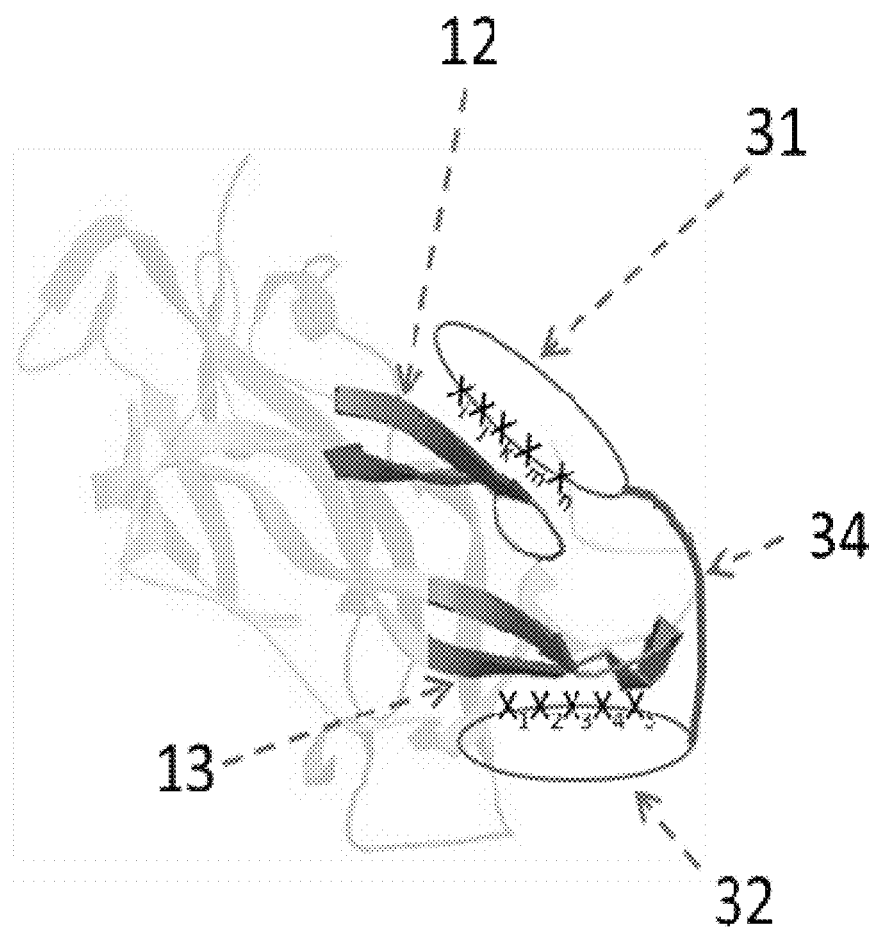

In a first embodiment, if the folded structure of the protein is known, and if the PCCs bind to that folded structure, then one can use that information, plus knowledge of which PCCs bind to which epitopes, to estimate an optimal linker length. This is illustrated in FIGS. 3A and 3B. These figures show one PCC (31) that binds to the N-side of one epitope (12) and a second PCC (32) binding to the C-side of a second epitope (13). Analysis of this binding arrangement, together with the structure of the protein from, for example, the Protein Database, permits an estimate of the length of an optimized linker (33). Such an estimate can narrow down the choice of candidate linkers to a very small number. One example might be to use such a length estimate to select one or two length-matched polyethylene glycol oligomers for testing. The best linker (34) is the one that brings the biligand affinity closest to that of a fully cooperative binder.

In a second embodiment, if the folded structure of the protein is not known, or if the protein simply does not have a well-defined folded structure, then one uses as much information as is available to determine the composition of a library of candidate linker molecules. That library is then screened to identify a best linker.

In a third embodiment, if the folded structure of the protein is not known or if the protein simply does not have a well-defined folded structure, then, using what knowledge about the protein does exist, simply select a linker to append the two PCCs. Even if an optimized, fully cooperative binder is not identified in this way, the linked biligand will almost certainly outperform either of the two monoligands because of cooperativity effects.

In Vitro

For detection of IL-17A or IL-17F in solution, a capture agent of the invention can be detectably labeled, then contacted with the solution, and thereafter formation of a complex between the capture agent and the IL-17A or IL-17F target can be detected. As an example, a fluorescently labeled capture agent can be used for in vitro IL-17A or IL-17F detection assays, wherein the capture agent is added to a solution to be tested for IL-17A or IL-17F under conditions allowing binding to occur. The complex between the fluorescently labeled capture agent and the IL-17A or IL-17F target can be detected and quantified by, for example, measuring the increased fluorescence polarization arising from the complex-bound peptide relative to that of the free peptide.

Alternatively, a sandwich-type "ELISA" assay can be used, wherein a capture agent is immobilized on a solid support such as a plastic tube or well, then the solution suspected of containing IL-17A or IL-17F is contacted with the immobilized binding moiety, non-binding materials are washed away, and complexed polypeptide is detected using a suitable detection reagent for recognizing IL-17A or IL-17F.

For detection or purification of soluble IL-17A or IL-17F from a solution, capture agents of the invention can be immobilized on a solid substrate such as a chromatographic support or other matrix material, then the immobilized binder can be loaded or contacted with the solution under conditions suitable for formation of a capture agent/IL-17A or IL-17F complex. The non-binding portion of the solution can be removed and the complex can be detected, for example, using an anti-IL-17F antibody, or an anti-binding polypeptide antibody, or the IL-17A or IL-17F can be released from the binding moiety at appropriate elution conditions.

In Vivo Diagnostic Imaging

A particularly preferred use for the capture agents of the invention is for creating visually readable images of IL-17A or IL-17F or IL-17A or IL-17F-expressing cells in a biological fluid, such as, for example, in human serum. The IL-17A or IL-17F capture agents disclosed herein can be converted to imaging reagents by conjugating the capture agents with a label appropriate for diagnostic detection. Preferably, a capture agent exhibiting much greater specificity for IL-17A or IL-17F than for other serum proteins is conjugated or linked to a label appropriate for the detection methodology to be employed. For example, the capture agent can be conjugated with or without a linker to a paramagnetic chelate suitable for Magnetic Resonance Imaging (MRI), with a radiolabel suitable for x-ray, Positron Emission Tomography (PET), Single Photon Emission Computed Tomography (SPECT) or scintigraphic imaging (including a chelator for a radioactive metal), with an ultrasound contrast agent (e.g., a stabilized microbubble, a microballoon, a microsphere or what has been referred to as a gas filled "liposome") suitable for ultrasound detection, or with an optical imaging dye.

In another embodiment, rather than directly labeling a capture agent with a detectable label or radiotherapeutic construct, one or more peptides or constructs of the invention can be conjugated with for example, avidin, biotin, or an antibody or antibody fragment that will bind the detectable label or radiotherapeutic.

A. Magnetic Resonance Imaging

The IL-17A or IL-17F capture agents described herein can advantageously be conjugated with a paramagnetic metal chelate in order to form a contrast agent for use in MRI.

Preferred paramagnetic metal ions have atomic numbers 21-29, 42, 44, or 57-83. This includes ions of the transition metal or lanthanide series which have one, and more preferably five or more, unpaired electrons and a magnetic moment of at least 1.7 Bohr magneton. Preferred paramagnetic metals include, but are not limited to, chromium (III), manganese (II), manganese (III), iron (II), iron (III), cobalt (II), nickel (II), copper (II), praseodymium (III), neodymium (III), samarium (III), gadolinium (III), terbium (III), dysprosium (III), holmium (III), erbium (III), europium (III) and ytterbium (III), chromium (III), iron (III), and gadolinium (III). The trivalent cation, Gd3+, is particularly preferred for MRI contrast agents, due to its high relaxivity and low toxicity, with the further advantage that it exists in only one biologically accessible oxidation state, which minimizes undesired metabolism of the metal by a patient. Another useful metal is Cr3+, which is relatively inexpensive. Gd(III) chelates have been used for clinical and radiologic MR applications since 1988, and approximately 30% of MRI exams currently employ a gadolinium-based contrast agent.

The paramagnetic metal chelator is a molecule having one or more polar groups that act as a ligand for, and complex with, a paramagnetic metal. Suitable chelators are known in the art and include acids with methylene phosphonic acid groups, methylene carbohydroxamine acid groups, carboxyethylidene groups, or carboxymethylene groups. Examples of chelators include, but are not limited to, diethylenetriaminepentaacetic acid (DTPA), 1,4,7,10-tetraazacyclo-tetradecane-1,4,7,10-tetraacetic acid (DOTA), 1-substituted 1,4,7,-tricarboxymethyl-1,4,7,10-teraazacyclododecane (DO3A), ethylenediaminetetraacetic acid (EDTA), and 1,4,8,11-tetra-azacyclotetradecane-1,4,8,11-tetraacetic acid (TETA). Additional chelating ligands are ethylene bis-(2-hydroxy-phenylglycine) (EHPG), and derivatives thereof, including 5-Cl-EHPG, 5-Br-EHPG, 5-Me-EHPG, 5-t-Bu-EHPG, and 5-sec-Bu-EHPG; benzodiethylenetriamine pentaacetic acid (benzo-DTPA) and derivatives thereof, including dibenzo-DTPA, phenyl-DTPA, diphenyl-DTPA, benzyl-DTPA, and dibenzyl DTPA; bis-2 (hydroxybenzyl)-ethylene-diaminediacetic acid (HBED) and derivatives thereof; the class of macrocyclic compounds which contain at least 3 carbon atoms, more preferably at least 6, and at least two heteroatoms (O and/or N), which macrocyclic compounds can consist of one ring, or two or three rings joined together at the hetero ring elements, e.g., benzo-DOTA, dibenzo-DOTA, and benzo-NOTA, where NOTA is 1,4,7-triazacyclononane N,N',N''-triacetic acid, benzo-TETA, benzo-DOTMA, where DOTMA is 1,4,7,10-tetraazacyclotetradecane-1,4,7,10-tetra(methyl tetraacetic acid), and benzo-TETMA, where TETMA is 1,4,8,11-tetraazacyclotetradecane-1,4,8,11-(methyl tetraacetic acid); derivatives of 1,3-propylene-diaminetetraacetic acid (PDTA) and triethylenetetraaminehexaacetic acid (TTNA); derivatives of 1,5,10-N,N',N''-tris(2,3-dihydroxybenzoyl)-tricatecholate (LICAM); and 1,3,5-N,N',N''-tris(2,3-dihydroxybenzoyl)aminomethylbenzene (MECAM). A preferred chelator for use in the present invention is DTPA, and the use of DO3A is particularly preferred. Examples of representative chelators and chelating groups contemplated by the present invention are described in WO 98/18496, WO 86/06605, WO 91/03200, WO 95/28179, WO 96/23526, WO 97/36619, PCT/US98/01473, PCT/US98/20182, and U.S. Pat. Nos. 4,899,755, 5,474,756, 5,846,519, 6,143,274, all of which are hereby incorporated by reference.

In accordance with the present invention, the chelator of the MRI contrast agent is coupled to the IL-17A or IL-17F capture agent. The positioning of the chelate should be selected so as not to interfere with the binding affinity or specificity of the IL-17A or IL-17F capture agent. The chelate also can be attached anywhere on the capture agent.

In general, the IL-17A or IL-17F capture agent can be bound directly or covalently to the metal chelator (or other detectable label), or it can be coupled or conjugated to the metal chelator using a linker, which can be, without limitation, amide, urea, acetal, ketal, double ester, carbonyl, carbamate, thiourea, sulfone, thioester, ester, ether, disulfide, lactone, imine, phosphoryl, or phosphodiester linkages; substituted or unsubstituted saturated or unsaturated alkyl chains; linear, branched, or cyclic amino acid chains of a single amino acid or different amino acids (e.g., extensions of the N- or C-terminus of the IL-17A or IL-17F binding moiety); derivatized or underivatized polyethylene glycols (PEGs), polyoxyethylene, or polyvinylpyridine chains; substituted or unsubstituted polyamide chains; derivatized or underivatized polyamine, polyester, polyethylenimine, polyacrylate, poly(vinyl alcohol), polyglycerol, or oligosaccharide (e.g., dextran) chains; alternating block copolymers; malonic, succinic, glutaric, adipic and pimelic acids; caproic acid; simple diamines and dialcohols; any of the other linkers disclosed herein; or any other simple polymeric linkers known in the art (see, for example, WO 98/18497 and WO 98/18496). Preferably the molecular weight of the linker can be tightly controlled. The molecular weights can range in size from less than 100 to greater than 1000. Preferably the molecular weight of the linker is less than 100. In addition, it can be desirable to utilize a linker that is biodegradable in vivo to provide efficient routes of excretion for the imaging reagents of the present invention. Depending on their location within the linker, such biodegradable functionalities can include ester, double ester, amide, phosphoester, ether, acetal, and ketal functionalities.

In general, known methods can be used to couple the metal chelate and the IL-17A or IL-17F capture agent using such linkers (WO 95/28967, WO 98/18496, WO 98/18497 and discussion therein). The IL-17A or IL-17F binding moiety can be linked through an N- or C-terminus via an amide bond, for example, to a metal coordinating backbone nitrogen of a metal chelate or to an acetate arm of the metal chelate itself. The present disclosure contemplates linking of the chelate on any position, provided the metal chelate retains the ability to bind the metal tightly in order to minimize toxicity. MRI contrast reagents prepared according to the disclosures herein can be used in the same manner as conventional MRI contrast reagents. Certain MR techniques and pulse sequences can be preferred to enhance the contrast of the site to the background blood and tissues. These techniques include (but are not limited to), for example, black blood angiography sequences that seek to make blood dark, such as fast spin echo sequences (Alexander, A. et al., 1998. Magn. Reson. Med., 40: 298-310) and flow-spoiled gradient echo sequences (Edelman, R. et al., 1990. Radiology, 177: 45-50). These methods also include flow independent techniques that enhance the difference in contrast, such as inversion-recovery prepared or saturation-recovery prepared sequences that will increase the contrast between IL-17A or IL-17F-expressing tissue and background tissues. Finally, magnetization transfer preparations also can improve contrast with these agents (Goodrich, K. et al., 1996. Invest. Radia, 31: 323-32).

The labeled reagent is administered to the patient in the form of an injectable composition. The method of administering the MRI contrast agent is preferably parenterally, meaning intravenously, intraarterially, intrathecally, interstitially, or intracavitarilly. For imaging IL-17A or IL-17F-expressing tissues, such as tumors, intravenous or intraarterial administration is preferred. For MRI, it is contemplated that the subject will receive a dosage of contrast agent sufficient to enhance the MR signal at the site IL-17A or IL-17F expression by at least 10%. After injection with the IL-17A or IL-17F capture agent containing MRI reagent, the patient is scanned in the MRI machine to determine the location of any sites of IL-17A or IL-17F expression. In therapeutic settings, upon identification of a site of IL-17A or IL-17F expression (e.g., fluid or tissue), an anti-cancer agent (e.g., inhibitors of IL-17A or IL-17F) can be immediately administered, if necessary, and the patient can be subsequently scanned to visualize viral load.

B. Nuclear Imaging (Radionuclide Imaging) and Radiotherapy

The IL-17A or IL-17F capture agents of the invention can be conjugated with a radionuclide reporter appropriate for scintigraphy, SPECT, or PET imaging and/or with a radionuclide appropriate for radiotherapy. Constructs in which the IL-17A or IL-17F capture agents are conjugated with both a chelator for a radionuclide useful for diagnostic imaging and a chelator useful for radiotherapy are within the scope of the invention.

For use as a PET agent a disclosed capture agent may be complexed with one of the various positron emitting metal ions, such as $^{51}$Mn, $^{52}$Fe, $^{60}$Cu, $^{68}$Ga, $^{72}$As, $^{94m}$Tc, or $^{110}$In. The binding moieties of the invention can also be labeled by halogenation using radionuclides such as $^{18}$F, $^{124}$I, $^{125}$I, $^{131}$I, $^{123}$I, $^{77}$Br, and $^{76}$Br. Preferred metal radionuclides for scintigraphy or radiotherapy include $^{99m}$Tc, $^{51}$Cr, $^{67}$Ga, $^{68}$Ga, $^{47}$Sc, $^{51}$Cr, $^{167}$Tm, $^{141}$Ce, $^{111}$In, $^{168}$Yb, $^{175}$Yb, $^{140}$La, $^{90}$Y, $^{88}$Y, $^{153}$Sm, $^{166}$Ho, $^{165}$Dy, $^{166}$Dy, $^{62}$Cu, $^{64}$Cu, $^{67}$Cu, $^{97}$Ru, $^{103}$Ru, $^{186}$Re, $^{188}$Re, $^{203}$Pb, $^{211}$Bi, $^{212}$Bi, $^{213}$Bi, $^{214}$Bi, $^{105}$Rh, $^{109}$Pd, $^{117m}$Sn, $^{149}$Pm, $^{161}$Tb, $^{177}$Lu, $^{198}$Au and $^{199}$Au. The choice of metal will be determined based on the desired therapeutic or diagnostic application. For example, for diagnostic purposes the preferred radionuclides include $^{64}$Cu, $^{67}$Ga, $^{68}$Ga, $^{99m}$Tc, and $^{111}$In. For therapeutic purposes, the preferred radionuclides include $^{46}$Cu, $^{90}$Y, $^{105}$Rh, $^{111}$In, $^{117m}$Sn, $^{149}$Pm, $^{153}$Sm, $^{161}$Tb, $^{166}$Tb, $^{166}$Dy, $^{166}$Ho, $^{175}$Yb, $^{177}$Ln, $^{186/188}$Re, and $^{199}$Au. $^{99m}$Tc is useful for diagnostic applications because of its low cost, availability, imaging properties, and high specific activity. The nuclear and radioactive properties of 99mTc make this isotope an ideal scintigraphic imaging agent. This isotope has a single photon energy of 140 keV and a radioactive half-life of about 6 hours, and is readily available from a $^{99}$Mo-$^{99m}$Tc generator. $^{18}$F, 4-[$^{18}$F]fluorobenzaldehyde ($^{18}$FB), Al[$^{18}$F]-NOTA, $^{68}$Ga-DOTA, and $^{68}$Ga-NOTA are typical radionuclides for conjugation to IL-17A or IL-17F capture agents for diagnostic imaging.

The metal radionuclides may be chelated by, for example, linear, macrocyclic, terpyridine, and $N_3S$, $N_2S_2$, or $N_4$ chelants (see also, U.S. Pat. Nos. 5,367,080, 5,364,613, 5,021,556, 5,075,099, 5,886,142), and other chelators known in the art including, but not limited to, HYNIC, DTPA, EDTA, DOTA, DO3A, TETA, NOTA and bisamino bisthiol (BAT) chelators (see also U.S. Pat. No. 5,720,934). For example, N.sub.4 chelators are described in U.S. Pat. Nos. 6,143,274, 6,093,382, 5,608,110, 5,665,329, 5,656, 254, 5,688,487. Certain N.sub.35 chelators are described in PCT/CA94/00395, PCT/CA94/00479, PCT/CA95/00249 and in U.S. Pat. Nos. 5,662,885, 5,976,495, 5,780,006. The chelator also can include derivatives of the chelating ligand mercapto-acetyl-acetyl-glycyl-glycine (MAG3), which contains an $N_3S$, and $N_2S_2$ systems such as MAMA (monoamidemonoaminedithiols), DADS ($N_2S$ diaminedithiols), CODADS and the like. These ligand systems and a variety of others are described in, for example, Liu, S, and Edwards, D., 1999. Chem. Rev., 99:2235-2268, and references therein.

The chelator also can include complexes containing ligand atoms that are not donated to the metal in a tetradentate array. These include the boronic acid adducts of technetium and rhenium dioximes, such as are described in U.S. Pat. Nos. 5,183,653, 5,387,409, 5,118,797, the disclosures of which are incorporated by reference herein, in their entirety.

The chelators can be covalently linked directly to the IL-17A or IL-17F capture agent via a linker, as described previously, and then directly labeled with the radioactive metal of choice (see, WO 98/52618, U.S. Pat. Nos. 5,879, 658, 5,849,261).

IL-17A or IL-17F capture agents comprising $^{18}$F, 4-[$^{18}$F] fluorobenzaldehyde ($^{18}$FB), Al[$^{18}$F]-NOTA, $^{68}$Ga-DOTA, and $^{68}$Ga-NOTA are of preferred interest for diagnostic imaging. Complexes of radioactive technetium are also useful for diagnostic imaging, and complexes of radioactive rhenium are particularly useful for radiotherapy. In forming a complex of radioactive technetium with the reagents of this invention, the technetium complex, preferably a salt of $^{99m}$Tc pertechnetate, is reacted with the reagent in the presence of a reducing agent. Preferred reducing agents are dithionite, stannous and ferrous ions; the most preferred reducing agent is stannous chloride. Means for preparing such complexes are conveniently provided in a kit form comprising a sealed vial containing a predetermined quantity of a reagent of the invention to be labeled and a sufficient amount of reducing agent to label the reagent with $^{99m}$Tc. Alternatively, the complex can be formed by reacting a peptide of this invention conjugated with an appropriate chelator with a pre-formed labile complex of technetium and another compound known as a transfer ligand. This process is known as ligand exchange and is well known to those skilled in the art. The labile complex can be formed using such transfer ligands as tartrate, citrate, gluconate or mannitol, for example. Among the $^{99m}$Tc pertechnetate salts useful with the present invention are included the alkali metal salts such as the sodium salt, or ammonium salts or lower alkyl ammonium salts.

Preparation of the complexes of the present invention where the metal is radioactive rhenium can be accomplished using rhenium starting materials in the +5 or +7 oxidation state. Examples of compounds in which rhenium is in the Re(VII) state are $NH_4ReO_4$ or $KReO_4$. Re(V) is available as, for example, [$ReOCl_4$](NBu$_4$), [$ReOCl_4$](AsPh$_4$), $ReOCl_3$ (PPh$_3$)$_2$ and as $ReO_2$(pyridine)$^{4+}$, where Ph is phenyl and Bu is n-butyl. Other rhenium reagents capable of forming a rhenium complex also can be used.

Radioactively labeled PET, SPECT, or scintigraphic imaging agents provided by the present invention are encompassed having a suitable amount of radioactivity. Generally, the unit dose to be administered has a radioactivity of about 0.01 mCi to about 100 mCi, preferably 1 mCi to 20 mCi. The solution to be injected at unit dosage is from about 0.01 mL to about 10 mL. It is generally preferred to form radioactive complexes in solutions containing radioactivity at concentrations of from about 0.01 mCi to 100 mCi per mL.

Typical doses of a radionuclide-labeled IL-17A or IL-17F capture agent according to the invention provide 10-20 mCi. After injection of the radionuclide-labeled IL-17A or IL-17F capture agents into the patient, a gamma camera calibrated for the gamma ray energy of the nuclide incorporated in the imaging agent is used to image areas of uptake of the agent and quantify the amount of radioactivity present in the site. Imaging of the site in vivo can take place in a matter of a few minutes. However, imaging can take place, if desired, in hours or even longer, after the radiolabeled peptide is injected into a patient. In most instances, a sufficient amount of the administered dose will accumulate in the area to be imaged within about 0.1 of an hour to permit the taking of scintiphotos.

Proper dose schedules for the radiotherapeutic compounds of the present invention are known to those skilled in the art. The compounds can be administered using many methods including, but not limited to, a single or multiple IV or IP injections, using a quantity of radioactivity that is sufficient to cause damage or ablation of the targeted IL-17A or IL-17F-expressing tissue, but not so much that substantive damage is caused to non-target (normal tissue). The quantity and dose required is different for different constructs, depending on the energy and half-life of the isotope used, the degree of uptake and clearance of the agent from the body and the mass of the IL-17A or IL-17F-expressing tissue. In general, doses can range from a single dose of about 30-50 mCi to a cumulative dose of up to about 3 Ci.

The radiotherapeutic compositions of the invention can include physiologically acceptable buffers, and can require radiation stabilizers to prevent radiolytic damage to the compound prior to injection. Radiation stabilizers are known to those skilled in the art, and can include, for example, para-aminobenzoic acid, ascorbic acid, gentistic acid and the like.

A single, or multi-vial kit that contains all of the components needed to prepare the complexes of this invention, other than the radionuclide, is an integral part of this invention.

A single-vial kit preferably contains a chelating ligand, a source of stannous salt, or other pharmaceutically acceptable reducing agent, and is appropriately buffered with pharmaceutically acceptable acid or base to adjust the pH to a value of about 3 to about 9. The quantity and type of reducing agent used would depend on the nature of the exchange complex to be formed. The proper conditions are well known to those that are skilled in the art. It is preferred that the kit contents be in lyophilized form. Such a single vial kit can optionally contain labile or exchange ligands such as glucoheptonate, gluconate, mannitol, malate, citric or tartaric acid and can also contain reaction modifiers such as diethylenetriamine-pentaacetic acid (DPTA), ethylenediamine tetraacetic acid (EDTA), or α, β, or γ cyclodextrin that serve to improve the radiochemical purity and stability of the final product. The kit also can contain stabilizers, bulking agents such as mannitol, that are designed to aid in the freeze-drying process, and other additives known to those skilled in the art.

A multi-vial kit preferably contains the same general components but employs more than one vial in reconstituting the radiopharmaceutical. For example, one vial can contain all of the ingredients that are required to form a labile Tc(V) complex on addition of pertechnetate (e.g., the stannous source or other reducing agent). Pertechnetate is added to this vial, and after waiting an appropriate period of time, the contents of this vial are added to a second vial that contains the ligand, as well as buffers appropriate to adjust the pH to its optimal value. After a reaction time of about 5 to 60 minutes, the complexes of the present invention are formed. It is advantageous that the contents of both vials of this multi-vial kit be lyophilized. As above, reaction modifiers, exchange ligands, stabilizers, bulking agents, etc. can be present in either or both vials.

Also provided herein is a method to incorporate an 18F radiolabeled prosthetic group onto an IL-17A or IL-17F capture agent. In one embodiment, 4-[$^{18}$F]fluorobenzaldehyde ($^{18}$FB) is conjugated onto a capture agent bearing an aminooxy moiety, resulting in oxime formation. In another embodiment, [$^{18}$F]fluorobenzaldehyde is conjugated onto a capture agent bearing an acyl hydrazide moiety, resulting in a hydrazone adduct. 4-Fluorobenzaldehyde, can be prepared in $^8$F form by displacement of a leaving group, using $^8$F ion, by known methods.

$^{18}$F-labeled capture agents can also be prepared from capture agents possessing thiosemicarbazide moieties under conditions that promote formation of a thiosemicarbozone, or by use of a $^{18}$F-labeled aldehyde bisulfite addition complex.

The above methods are particularly amenable to the labeling of capture agents, e.g., the capture agents described herein, which can be modified during synthesis to contain a nucleophilic hydroxylamine, thiosemicarbazide or hydrazine (or acyl hydrazide) moiety that can be used to react with the labeled aldehyde. The methods can be used for any capture agent that can accommodate a suitable nucleophilic moiety. Typically the nucleophilic moiety is appended to the N-terminus of the peptide, but the skilled artisan will recognize that the nucleophile also can be linked to an amino acid side chain or to the peptide C-terminus. Methods of synthesizing a radiolabeled peptide sequence are provided in which 4-[$^{18}$F]fluorobenzaldehyde is reacted with a peptide sequence comprising either a hydroxylamine, a thiosemicarbazide or a hydrazine (or acyl hydrazide) group, thereby forming the corresponding oximes, thiosemicarbazones or hydrazones, respectively. The 4-[$^{18}$F]fluorobenzaldehyde typically is generated in situ by the acid-catalyzed decomposition of the addition complex of 4-[$^{18}$F]fluorobenzaldehyde and sodium bisulfite. The use of the bisulfite addition complex enhances the speed of purification since, unlike the aldehyde, the complex can be concentrated to dryness. Formation of the complex is also reversible under acidic and basic conditions. In particular, when the complex is contacted with a peptide containing a hydroxylamine, a thiosemicarbazide or a hydrazine (or acyl hydrazide) group in acidic medium, the reactive free 4-[$^{18}$F]fluorobenzaldehyde is consumed as it is formed in situ, resulting in the corresponding $^{18}$F radiolabeled peptide sequence.

In the instances when the oxime, thiosemicarbazone or hydrazone linkages present in vivo instability, an additional reduction step may be employed to reduce the double bond connecting the peptide to the $^{18}$F bearing substrate. The corresponding reduced peptide linkage would enhance the stability. One of skill in the art would appreciate the variety of methods available to carry out such a reduction step. Reductive amination steps as described in Wilson et al., Journal of Labeled Compounds and Radiopharmaceuticals, XXVIII (10), 1189-1199, 1990 may also be used to form a Schiff's base involving a peptide and 4-[$^{18}$F]fluorobenzaldehyde and directly reducing the Schiff's base using reducing agents such as sodium cyanoborohydride.

The 4-[$^{18}$F]fluorobenzaldehyde may be prepared as described in Wilson et al., Journal of Labeled Compounds and Radiopharmaceuticals, XXVIII (10), 1189-1199, 1990; Iwata et al., Applied radiation and isotopes, 52, 87-92, 2000; Poethko et al., The Journal of Nuclear Medicine, 45, 892-902, 2004; and Schottelius et al., Clinical Cancer Research, 10, 3593-3606, 2004. The Na18F in water may be added to a mixture of kryptofix and K$_2$CO$_3$. Anhydrous acetonitrile may be added and the solution is evaporated in a heating block under a stream of argon. Additional portions of acetonitrile may be added and evaporated to completely dry the sample. The 4-trimethylammoniumbenzaldehyde triflate may be dissolved in DMSO and added to the dried F-18. The solution may then be heated in the heating block. The solution may be cooled briefly, diluted with water and filtered through a Waters®. Oasis HLB LP extraction cartridge. The cartridge may be washed with 9:1 water:acetonitrile and water to remove unbound $^{18}$F and unreacted 4-trimethylammoniumbenzaldehyde triflate. The 4-[$^{18}$F]fluorobenzaldehyde may then be eluted from the cartridge with methanol in fractions.

Therapeutic Applications

Provided herein in certain embodiments are methods of using the IL-17A or IL-17F capture agents disclosed herein to identify, detect, quantify, and/or separate IL-17A or IL-17F in a biological sample. In certain embodiments, these methods utilize an immunoassay, with the capture agent replacing an antibody or its equivalent. In certain embodiments, the immunoassay may be a Western blot, pull-down assay, dot blot, or ELISA.

A biological sample for use in the methods provided herein may be selected from the group consisting of organs, tissue, bodily fluids, and cells. Where the biological sample is a bodily fluid, the fluid may be selected from the group consisting of blood, serum, plasma, urine, sputum, saliva, stool, spinal fluid, cerebral spinal fluid, lymph fluid, skin secretions, respiratory secretions, intestinal secretions, genitourinary tract secretions, tears, and milk. The organs include, e.g., the adrenal glands, bladder, bones, brain, breasts, cervix, esophagus, eyes, gall bladder, genitals, heart, kidneys, large intestine, liver, lungs, lymph nodes, ovaries, pancreas, pituitary gland, prostate, salivary glands, skeletal muscles, skin, small intestine, spinal cord, spleen, stomach, thymus gland, trachea, thyroid, testes, ureters, and urethra. Tissues include, e.g., epithelial, connective, nervous, and muscle tissues.

Provided herein in certain embodiments are methods of using the IL-17A or IL-17F capture agents disclosed herein to diagnose and/or classify (e.g., stage) a condition associated with IL-17A or IL-17F expression. In certain of these embodiments, the methods comprise (a) obtaining a biological sample from a subject; (b) measuring the presence or absence of IL-17A or IL-17F in the sample with the IL-17A or IL-17F capture agent; (c) comparing the levels of IL-17A or IL-17F to a predetermined control range for IL-17A or IL-17F; and (d) diagnosing a condition associated with IL-17A or IL-17F expression based on the difference between IL-17A or IL-17F levels in the biological sample and the predetermined control.

In other embodiments, the IL-17A or IL-17F capture agents disclosed herein are used as a mutant specific targeted therapeutic. In certain aspects of this embodiment, the IL-17A or IL-17F capture agent is administered alone without delivering DNA, a radiopharmaceutical or another active agent.

The IL-17A or IL-17F capture agents of the invention also can be used to target genetic material to IL-17A or IL-17F expressing cells. The genetic material can include nucleic acids, such as RNA or DNA, of either natural or synthetic origin, including recombinant RNA and DNA and antisense RNA and DNA. Types of genetic material that can be used include, for example, genes carried on expression vectors such as plasmids, phagemids, cosmids, yeast artificial chromosomes (YACs) and defective or "helper" viruses, antigene nucleic acids, both single and double stranded RNA and DNA and analogs thereof, such as phosphorothioate and phosphorodithioate oligodeoxynucleotides. Additionally, the genetic material can be combined, for example, with lipids, proteins or other polymers. Delivery vehicles for genetic material can include, for example, a virus particle, a retroviral or other gene therapy vector, a liposome, a complex of lipids (especially cationic lipids) and genetic material, a complex of dextran derivatives and genetic material, etc.

In an embodiment the capture agents of the invention are utilized in gene therapy. In this embodiment, genetic material, or one or more delivery vehicles containing genetic material can be conjugated to one or more IL-17A or IL-17F capture agents of this disclosure and administered to a patient.

Therapeutic agents and the IL-17A or IL-17F capture agents disclosed herein can be linked or fused in known ways, optionally using the same type of linkers discussed elsewhere in this application. Preferred linkers will be substituted or unsubstituted alkyl chains, amino acid chains, polyethylene glycol chains, and other simple polymeric linkers known in the art. More preferably, if the therapeutic agent is itself a protein, for which the encoding DNA sequence is known, the therapeutic protein and IL-17A or IL-17F binding polypeptide can be coexpressed from the same synthetic gene, created using recombinant DNA techniques, as described above. The coding sequence for the IL-17A or IL-17F binding polypeptide can be fused in frame with that of the therapeutic protein, such that the peptide is expressed at the amino- or carboxy-terminus of the therapeutic protein, or at a place between the termini, if it is determined that such placement would not destroy the required biological function of either the therapeutic protein or the IL-17A or IL-17F binding polypeptide. A particular advantage of this general approach is that concatamerization of multiple, tandemly arranged IL-17A or IL-17F capture agents is possible, thereby increasing the number and concentration of IL-17A or IL-17F binding sites associated with each therapeutic protein. In this manner, IL-17A or IL-17F binding avidity is increased, which would be expected to improve the efficacy of the recombinant therapeutic fusion protein.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

The disclosed compositions and methods can be further understood through the following numbered paragraphs.

1. A capture agent for a target, the capture agent comprising two or more ligands covalently linked to each other, wherein the ligands specifically bind to one of two or more distinct epitopes of a target that are in different locations on the target.

2. The capture agent of paragraph 1, wherein the capture agent comprises a first of the ligands has affinity for a first of the epitopes, a second of the ligands has affinity for a second of the epitopes, and a linker covalently connecting the first ligand to the second ligand.

3. The capture agent of paragraph 1 or 2, wherein the capture agent binds IL-17A, IL-17F, or both IL-17A and IL-17F.

4. The capture agent of any one of paragraphs 1-3, wherein the first epitope is an epitope on IL-17A, wherein the first ligand has affinity for the epitope on IL-17A.

5. The capture agent of any one of paragraphs 1-4, wherein the second epitope is an epitope on IL-17A, wherein the second ligand has affinity for the epitope on IL-17A.

6. The capture agent of any one of paragraphs 1-5, wherein the capture agent specifically binds IL-17A.

7. The capture agent of any one of paragraphs 1-5, wherein the capture agent is selective for IL-17A over IL-17F.

8. The capture agent of any one of paragraphs 4-7, wherein the first epitope comprises the amino acid sequence PNSEDKNFPRTVMVNL (SEQ ID NO:43).

9. The capture agent of any one of paragraphs 4-8, wherein the first ligand comprises an amino acid sequence 80-100% identical to an amino acid sequence selected from the group consisting of: (a) rhfrl (SEQ ID NO:44); (b) nrfff (SEQ ID NO:45); and (c) rkhyh (SEQ ID NO:46).

10. The capture agent of any one of paragraphs 4-10, wherein the first ligand has structure

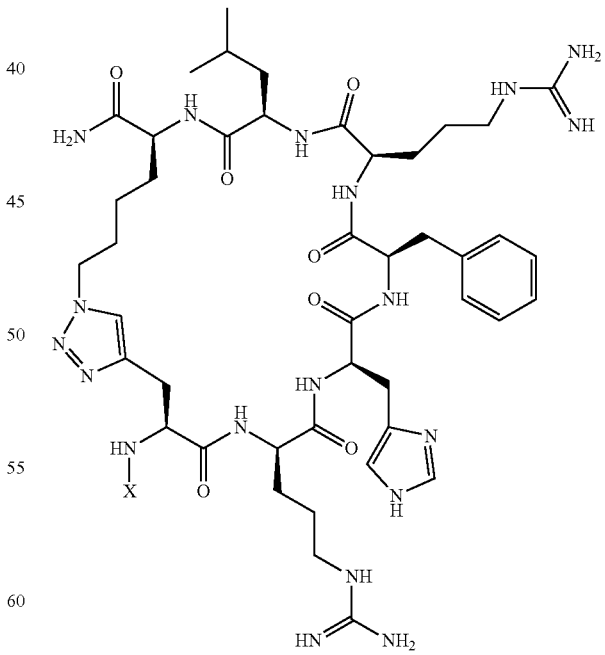

wherein X represents the rest of the capture agent.

11. The capture agent of any one of paragraphs 1-3, wherein the first epitope is an epitope on IL-17F, wherein the first ligand has affinity for the epitope on IL-17F.

12. The capture agent of any one of paragraphs 1-3 or 11, wherein the second epitope is an epitope on IL-17F, wherein the second ligand has affinity for the epitope on IL-17F.

13. The capture agent of any one of paragraphs 1-3, 11, or 12, wherein the capture agent specifically binds IL-17F.

14. The capture agent of any one of paragraphs 1-3 or 11-13, wherein the capture agent is selective for IL-17F over IL-17A.

15. The capture agent of any one of paragraphs 11-14, wherein the first epitope comprises the amino acid sequence FFQKPES (SEQ ID NO:1).

16. The capture agent of any one of paragraphs 11-15, wherein the first epitope comprises the amino acid sequence FFQKPESCPPVPGG (SEQ ID NO:2).

17. The capture agent of any one of paragraphs 11-16, wherein the second epitope comprises the amino acid sequence NENQRVS (SEQ ID NO:3).

18. The capture agent of any one of paragraphs 11-17, wherein the second epitope comprises the amino acid sequence GIINENQRVS (SEQ ID NO:4).

19. The capture agent of any one of paragraphs 11-18, wherein the first ligand comprises an amino acid sequence 80-100% identical to an amino acid sequence selected from the group consisting of: (a) FYKTH (SEQ ID NO:5); (b) FYKQH (SEQ ID NO:6); (c) FYLTH (SEQ ID NO:7); (d) FYLQH (SEQ ID NO:8); (e) RRATS (SEQ ID NO:9); (f) RRAQS (SEQ ID NO:10); (g) rrATS (SEQ ID NO:47); (h) rrAQS (SEQ ID NO:48); (i) rrats (SEQ ID NO:49); and (j) rraqs (SEQ ID NO:50).

20. The capture agent of any one of paragraphs 11-19, wherein the second ligand comprises an amino acid sequence 80-100% identical to an amino acid sequence selected from the group consisting of: (a) KYGEV (SEQ ID NO:11); (b) LYGEV (SEQ ID NO:12); (c) VHKSG (SEQ ID NO:13); (d) VHLSG (SEQ ID NO:14); (e) QKHGP (SEQ ID NO:15); (f) TKHGP (SEQ ID NO:16); (g) QLHGP (SEQ ID NO:17); (h) TLHGP (SEQ ID NO:18); (i) YDLQR (SEQ ID NO:19); (j) YDLTR (SEQ ID NO:20); (k) YDKQR (SEQ ID NO:21); (1) YDKTR (SEQ ID NO:22); (m) KKGWP (SEQ ID NO:23); (n) KLGWP (SEQ ID NO:24); (o) LKGWP (SEQ ID NO:25); (p) LLGWP (SEQ ID NO:26); (q) RSYNL (SEQ ID NO:27); (r) RSYNK (SEQ ID NO:28); (s) kYGEV (SEQ ID NO:51); (t) VHkSG (SEQ ID NO:52); (u) QkHGP (SEQ ID NO:53); (v) TkHGP (SEQ ID NO:54); (w) YDLQr (SEQ ID NO:55); (x) YDLTr (SEQ ID NO:56); (y) YDkQr (SEQ ID NO:57); (z) YDkTr (SEQ ID NO:58); (aa) kkGWP (SEQ ID NO:59); (bb) kLGWP (SEQ ID NO:60); (cc) LkGWP (SEQ ID NO:61); (dd) rSYNL (SEQ ID NO:62); (ee) rSYNk (SEQ ID NO:63); (ff) kygev (SEQ ID NO:64) (gg) vhksg (SEQ ID NO:65); (hh) qkhgp (SEQ ID NO:66); (ii) tkhgp (SEQ ID NO:67); (jj) ydlqr (SEQ ID NO:68); (kk) ydltr (SEQ ID NO:69); (ll) ydkqr (SEQ ID NO:70); (mm) ydktr (SEQ ID NO:71); (nn) kkgwp (SEQ ID NO:72); (oo) klgwp (SEQ ID NO:73); (pp) lkgwp (SEQ ID NO:74); (qq) rsynl (SEQ ID NO:75); and (rr) rsynk (SEQ ID NO:76).

21. The capture agent of any one of paragraphs 11-20, wherein the first ligand comprises the sequence RRATS (SEQ ID NO:9) and the second ligand comprises the sequence QKHGP (SEQ ID NO:15).

22. The capture agent of any one of paragraphs 11-20, wherein the first ligand comprises the sequence RRATS (SEQ ID NO:9) and the second ligand comprises the sequence RSYNK (SEQ ID NO:28).

23. The capture agent of any one of paragraphs 11-20, wherein the first ligand comprises the sequence rrATS (SEQ ID NO:47) and the second ligand comprises the sequence rSYNK (SEQ ID NO: 63).

24. The capture agent of any one of paragraphs 11-20, wherein the first ligand comprises the sequence rrats (SEQ ID NO:49) and the second ligand comprises the sequence rsynk (SEQ ID NO:76).

25. The capture agent of any one of paragraphs 11-20, having a structure selected from the group consisting of:

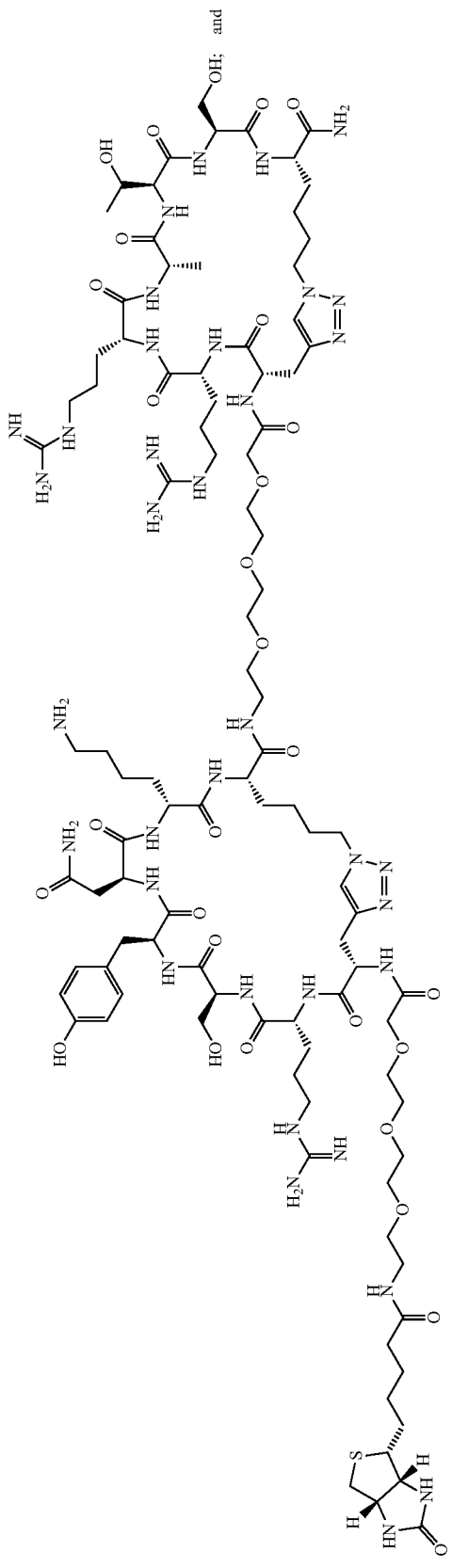
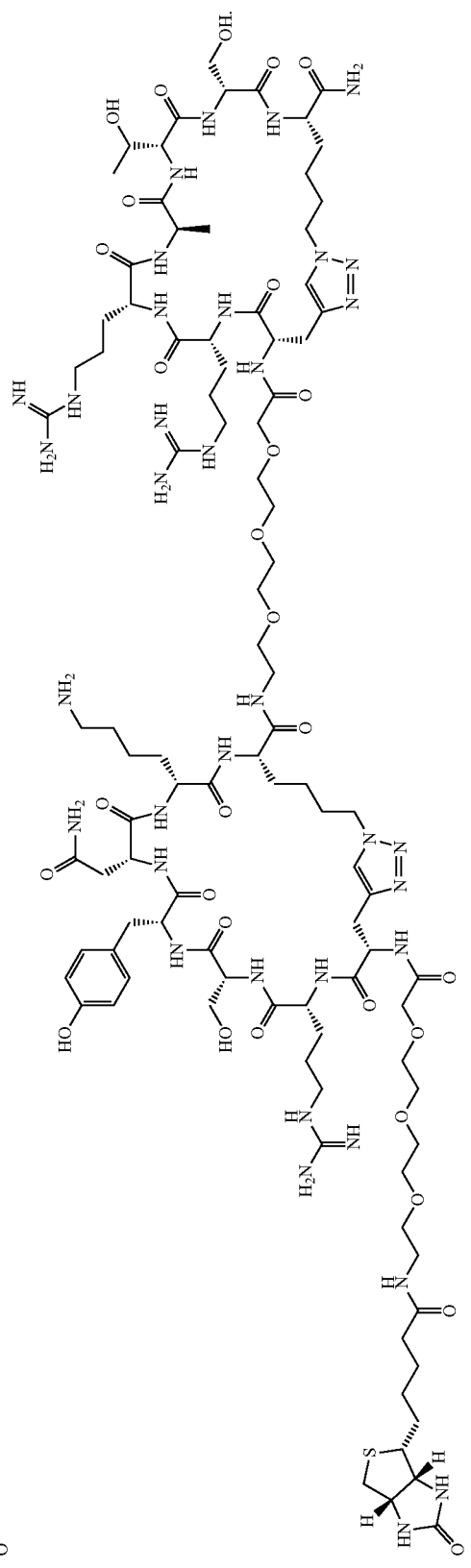

26. The capture agent of any one of paragraphs 1-3, wherein the first epitope is an epitope on IL-17A, wherein the first ligand has affinity for the epitope on IL-17A, wherein the second epitope is an epitope on IL-17F, wherein the second ligand has affinity for the epitope on IL-17F.

27. The capture agent of any one of paragraphs 1-3 or 26, wherein the capture agent specifically binds IL-17A/F heterodimer.

28. The capture agent of any one of paragraphs 1-3, 26, or 27, wherein the capture agent is selective for IL-17A/F heterodimer over IL-17F and over IL-17A.

29. The capture agent of any one of paragraphs 26-28, wherein the first epitope comprises the amino acid sequence PNSEDKNFPRTVMVNL (SEQ ID NO:43).

30. The capture agent of any one of paragraphs 26-29, wherein the first ligand comprises an amino acid sequence 80-100% identical to an amino acid sequence selected from the group consisting of: (a) rhfrl (SEQ ID NO:44); (b) nrfff (SEQ ID NO:45); and (c) rkhyh (SEQ ID NO:46).

31. The capture agent of any one of paragraphs 26-30, wherein the first ligand has structure

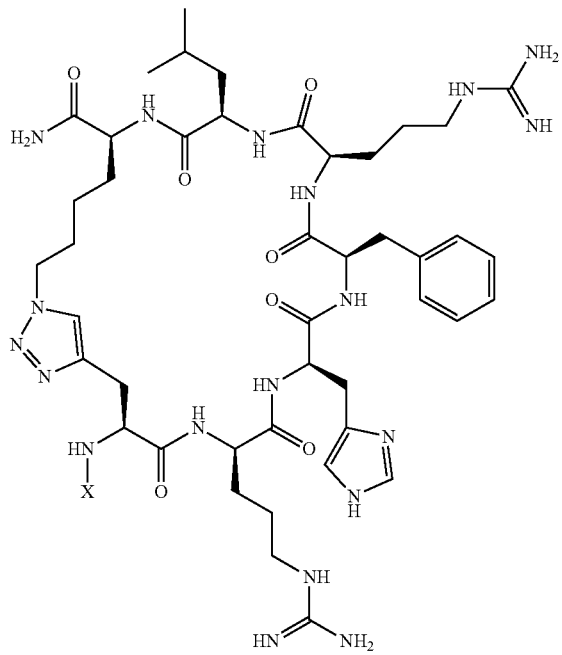

wherein X represents the rest of the capture agent.

32. The capture agent of any one of paragraphs 26-31, wherein the second epitope comprises the amino acid sequence NENQRVS (SEQ ID NO:3).

33. The capture agent of any one of paragraphs 26-32, wherein the second epitope comprises the amino acid sequence GIINENQRVS (SEQ ID NO:4).

34. The capture agent of any one of paragraphs 26-33, wherein the second ligand comprises an amino acid sequence 80-100% identical to an amino acid sequence selected from the group consisting of: (a) KYGEV (SEQ ID NO:11); (b) LYGEV (SEQ ID NO:12); (c) VHKSG (SEQ ID NO:13); (d) VHLSG (SEQ ID NO:14); (e) QKHGP (SEQ ID NO:15); (f) TKHGP (SEQ ID NO:16); (g) QLHGP (SEQ ID NO:17); (h) TLHGP (SEQ ID NO:18); (i) YDLQR (SEQ ID NO:19); (j) YDLTR (SEQ ID NO:20); (k) YDKQR (SEQ ID NO:21); (l) YDKTR (SEQ ID NO:22); (m) KKGWP (SEQ ID NO:23); (n) KLGWP (SEQ ID NO:24); (o) LKGWP (SEQ ID NO:25); (p) LLGWP (SEQ ID NO:26); (q) RSYNL (SEQ ID NO:27); (r) RSYNK (SEQ ID NO:28); (s) kYGEV (SEQ ID NO:51); (t) VHkSG (SEQ ID NO:52); (u) QkHGP (SEQ ID NO:53); (v) TkHGP (SEQ ID NO:54); (w) YDLQr (SEQ ID NO:55); (x) YDLTr (SEQ ID NO:56); (y) YDkQr (SEQ ID NO:57); (z) YDkTr (SEQ ID NO:58); (aa) kkGWP (SEQ ID NO:59); (bb) kLGWP (SEQ ID NO:60); (cc) LkGWP (SEQ ID NO:61); (dd) rSYNL (SEQ ID NO:62); (ee) rSYNk (SEQ ID NO:63); (ff) kygev (SEQ ID NO:64) (gg) vhksg (SEQ ID NO:65); (hh) qkhgp (SEQ ID NO:66); (ii) tkhgp (SEQ ID NO:67); (jj) ydlqr (SEQ ID NO:68); (kk) ydltr (SEQ ID NO:69); (ll) ydkqr (SEQ ID NO:70); (mm) ydktr (SEQ ID NO:71); (nn) kkgwp (SEQ ID NO:72); (oo) klgwp (SEQ ID NO:73); (pp) lkgwp (SEQ ID NO:74); (qq) rsynl (SEQ ID NO:75); and (rr) rsynk (SEQ ID NO:76).

35. The capture agent of any one of paragraphs 26-34, wherein the first ligand comprises the sequence rhfrl (SEQ ID NO:44) and the second ligand comprises the sequence QKHGP (SEQ ID NO:15).

36. The capture agent of any one of paragraphs 26-34, wherein the first ligand comprises the sequence rhfrl (SEQ ID NO:44) and the second ligand comprises the sequence RSYNK (SEQ ID NO:28).

37. The capture agent of any one of paragraphs 26-34, wherein the first ligand comprises the sequence rhfrl (SEQ ID NO:44) and the second ligand comprises the sequence rSYNK (SEQ ID NO: 63).

38. The capture agent of any one of paragraphs 26-34, wherein the first ligand comprises the sequence rhfrl (SEQ ID NO:44) and the second ligand comprises the sequence rsynk (SEQ ID NO:76).

39. The capture agent of any one of paragraphs 2-9, 11-24, 26-30, and 32-38, wherein the first ligand is cyclic.

40. The capture agent of any one of paragraphs 2-9, 11-24, 26-30, and 32-39, wherein the first ligand comprises a 1,4-substituted-1,2,3-triazole residue (Tz4) or a 1,5-substituted-1,2,3-triazole residue (Tz5).

41. The capture agent of paragraph 40, wherein the first ligand comprises a 1,4-substituted-1,2,3-triazole residue (Tz4).

42. The capture agent of paragraph 40, wherein the first ligand comprises a 1,5-substituted-1,2,3-triazole residue (Tz5).

43. The capture agent of any one of paragraphs 2-9, 11-24, 26-30, and 32-42, wherein the second ligand is cyclic.

44. The capture agent of any one of paragraphs 2-9, 11-24, 26-30, and 32-43, wherein the second ligand comprises a 1,4-substituted-1,2,3-triazole residue (Tz4) or a 1,5-substituted-1,2,3-triazole residue (Tz5).

45. The capture agent of paragraph 44, wherein the second ligand comprises a 1,4-substituted-1,2,3-triazole residue (Tz4).

46. The capture agent of paragraph 44, wherein the second ligand comprises a 1,5-substituted-1,2,3-triazole residue (Tz5).

47. The capture agent of any one of paragraphs 1-24 and 26-46, wherein the capture agent is labeled with a detectable moiety.

48. The capture agent of paragraph 47, wherein the detectable moiety is selected from the group consisting of biotin, copper-DOTA, biotin-PEG$_3$, aminooxyacetate, $^{19}$FB, $^{18}$FB and FITC-PEG$_3$.

49. The capture agent of paragraph 47, wherein the detectable moiety is selected from the group consisting of $^{64}$Cu DOTA, $^{68}$Ga DOTA, $^{68}$Ga NOTA, $^{18}$F, Al$^{18}$F NOTA, $^{68}$Ga, $^{89}$Zr, $^{124}$I, $^{94m}$Tc, $^{110m}$In, $^{11}$C and $^{76}$Br.

50. The capture agent of any one of paragraphs 2-9, 11-24, 26-30, and 32-49, wherein the linker is divalent.

51. The capture agent of any one of paragraphs 2-9, 11-24, 26-30, and 32-50, wherein the length of the linker corresponds to distance between the first epitope and the second epitope.

52. The capture agent of any one of paragraphs 2-9, 11-24, 26-30, and 32-51, wherein the length of the linker is from ~4.4 Å to ~26.4 Å, from ~8.8 Å to ~26.4 Å or from ~7 Å to ~15 Å.

53. The capture agent of any one of paragraphs 2-9, 11-24, 26-30, and 32-52, wherein the length of the linker is ~15 Å.

54. The capture agent of any one of paragraphs 2-9, 11-24, 26-30, and 32-53, wherein the linker comprises one or more repeat units of ethylene glycol.

55. The capture agent of paragraph 54, wherein the linker is selected from the group consisting of $PEG_1$, $PEG_2$, $PEG_3$, $PEG_4$ and $PEG_5$.

56. The capture agent of any one of paragraphs 2-9, 11-24, 26-30, and 32-53, wherein the linker comprises a peptide.

57. The capture agent of paragraph 56, wherein the linker is glycine.

58. A method for detecting IL-17A, IL-17F, or both IL-17A and IL-17F in a biological sample, the method comprising the step of contacting the biological sample with one or more capture agents of any one of paragraphs 1-57.

59. The method of paragraph 58, wherein at least one of the capture agents specifically binds IL-17A.

60. The method of paragraph 58 or 59, wherein IL-17A is detected.

61. The method of any one of paragraphs 58-60, wherein at least one of the capture agents specifically binds IL-17F.

62. The method of any one of paragraphs 58-61, wherein IL-17F is detected.

63. The method of any one of paragraphs 58-62, wherein at least one of the capture agents specifically binds IL-17A/F heterodimer.

64. The method of any one of paragraphs 58-62, wherein IL-17A/F heterodimer is detected.

65. The method of any one of paragraphs 58-64, wherein one or more of the capture agents are labeled with a detectable moiety.

66. The method of any one of paragraphs 58-65 further comprising the steps of binding IL-17A, IL-17F, or both IL-17A and IL-17F to the one or more capture agents, and detecting the detectable moiety linked to the one or more capture agents.

67. The method of paragraph 66, wherein the IL-17A is in the form of a homodimer or a heterodimer with IL-17F.

68. The method of paragraph 66, wherein the IL-17F is in the form of a homodimer or a heterodimer with IL-17A.

69. The method of any one of paragraphs 65-68 further comprising the steps of binding IL-17A, IL-17F, or both IL-17A and IL-17F to the one or more capture agents, and detecting the detectable moiety linked to the one or more capture agents.

101. A capture agent for a target, comprising, two or more ligands covalently linked to each other, wherein the ligands specifically bind to two distinct, epitopes of a target that are in different locations on said target.

102. The capture agent of paragraph 102, wherein said capture agent binds IL-17A.

103. A stable, synthetic capture agent that specifically binds IL-17A, wherein the capture agent comprises a ligand having affinity for an epitope on IL-17A.

104. The capture agent of paragraph 101, wherein the capture agent is selective for IL-17A over IL-17F.

105. The capture agent of paragraph 101, wherein the epitope comprises the amino acid sequence PNSEDKNF-PRTVMVNL[Az4] (SEQ ID NO:43).

106. The capture agent of paragraph 101, wherein the ligand comprises an amino acid sequence 80-100% identical to an amino acid sequence selected from the group consisting of: (a) rhfrl (SEQ ID NO:44); (b) nrfff (SEQ ID NO:45); and (c) rkhyh (SEQ ID NO:46).

107. The capture agent of paragraph 104, wherein the ligand is cyclic.

108. The capture agent of paragraph 105, wherein the ligand comprises a 1,4-substituted-1,2,3-triazole residue (Tz4) or a 1,5-substituted-1,2,3-triazole residue (Tz5).

109. The capture agent of paragraph 106, wherein the triazole residue is a 1,4-substituted-1,2,3-triazole (Tz4) residue.

110. The capture agent of paragraph 101, wherein the capture agent is labeled with a detectable moiety.

111. The capture agent of paragraph 108, wherein the detectable moiety is selected from the group consisting of biotin, copper-DOTA, biotin-$PEG_3$, aminooxyacetate, $^{19}FB$, $^{18}FB$ and FITC-$PEG_3$.

112. The capture agent of paragraph 108, wherein the detectable moiety is selected from the group consisting of $^{64}Cu$ DOTA, $^{68}Ga$ DOTA, $^{68}Ga$ NOTA, $^{18}F$, $Al^{18}F$ NOTA, $^{64}Cu$, $^{68}Ga$, $^{89}Zr$, $^{124}I$, $^{86}Y$, $^{94m}Tc$, $^{110m}In$, $^{11}C$ and $^{76}Br$.

113. The capture agent of paragraph 101, having structure

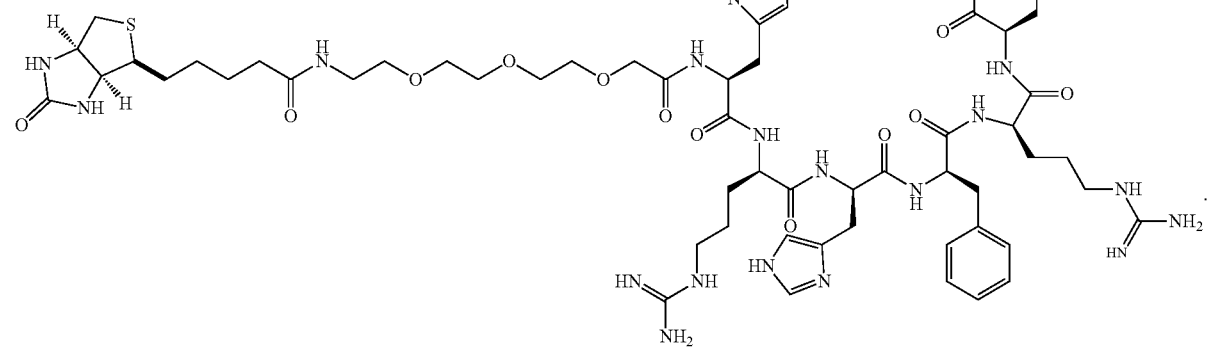

114. A method for detecting IL-17A in a biological sample, comprising the step of contacting the biological sample with one or more capture agents of any one of paragraphs 101-111.

115. The method of paragraph 112, wherein the capture agent is labeled with a detectable moiety.

116. The method of paragraph 113, further comprising the steps of binding IL-17A to said one or more capture agents, and detecting the detectable moiety linked to said one or more capture agents.

117. The method of paragraph 112, wherein the IL-17A is in the form of a homodimer, or a heterodimer with IL-17F.

118. A stable, synthetic capture agent that specifically binds IL-17A, wherein the capture agent comprises a first ligand having affinity for a first epitope on IL-17A, a second ligand having affinity for a second epitope on IL-17A, and a linker covalently connecting the first ligand to the second ligand.

119. The capture agent of paragraph 116, wherein the capture agent is selective for IL-17A over IL-17F.

120. The capture agent of paragraph 116, wherein the first epitope comprises the amino acid sequence PNSEDKNF-PRTVMVNL[Az4] (SEQ ID NO:43).

121. The capture agent of paragraph 116, wherein the first ligand comprises an amino acid sequence 80-100% identical to an amino acid sequence selected from the group consisting of: (a) rhfrl (SEQ ID NO:44); (b) nrfff (SEQ ID NO:45); and (c) rkhyh (SEQ ID NO:46).

122. The capture agent of any one of paragraphs 116-119, wherein the first ligand is cyclic.

123. The capture agent of any one of paragraphs 116-120, wherein the first ligand comprises a 1,4-substituted-1,2,3-triazole residue (Tz4) or a 1,5-substituted-1,2,3-triazole residue (Tz5).

124. The capture agent of paragraph 121, wherein the triazole residue is a 1,4-substituted-1,2,3-triazole (Tz4) residue.

125. The capture agent of any one of paragraphs 101-124, wherein the linker is divalent.

126. The capture agent of any one of paragraphs 101-125, wherein the length of the linker corresponds to distance between the first epitope and the second epitope.

127. The capture agent of paragraph 124, wherein the length of the linker is from ~4.4 Å to ~26.4 Å from ~8.8 Å to ~26.4 Å or from ~7 Å to ~15 Å.

128. The capture agent of paragraph 124, wherein the length of the linker is ~15 Å.

129. The capture agent of any one of paragraphs 116-126, wherein the linker comprises one or more repeat units of ethylene glycol.

130. The capture agent of any one of paragraphs 116-127, wherein the linker comprises a peptide. 131. The capture agent of paragraph 127, wherein the linker is glycine.

132. The capture agent of paragraph 127, wherein the linker is selected from the group consisting of $PEG_1$, $PEG_2$, $PEG_3$, $PEG_4$ and $PEG_5$.

133. The capture agent of paragraph 101, wherein the capture agent is labeled with a detectable moiety.

134. The capture agent of paragraph 133, wherein the detectable moiety is selected from the group consisting of biotin, copper-DOTA, biotin-PEG3, aminooxyacetate, $^{19}$FB, $^{18}$FB and $FITC-PEG_3$.

135. The capture agent of paragraph 133, wherein the detectable moiety is selected from the group consisting of $^{64}$Cu DOTA, $^{68}$Ga DOTA, $^{68}$Ga NOTA, $^{18}$F, Al$^{18}$F NOTA, $^{64}$Cu, $^{68}$Ga, $^{89}$Zr, $^{124}$I, $^{94m}$Tc, $^{110m}$In, $^{11}$C and $^{76}$Br.

136. A method for detecting IL-17A in a biological sample, comprising the step of contacting the biological sample with one or more capture agents of paragraph 116.

137. The method of paragraph 112, wherein the capture agent is labeled with a detectable moiety.

138. The method of paragraph 113, further comprising the steps of binding IL-17A to said one or more capture agents, and detecting the detectable moiety linked to said one or more capture agents.

139. The method of paragraph 112, wherein the IL-17A is in the form of a homodimer, or a heterodimer with IL-17F.

140. A stable, synthetic capture agent that specifically binds IL-17F, wherein the capture agent comprises a first ligand having affinity for a first epitope on IL-17F, a second ligand having affinity for a second epitope on IL-17F, and a linker covalently connecting the first ligand to the second ligand.

141. The capture agent of paragraph 140, wherein the capture agent is selective for IL-17F over IL-17A.

142. The capture agent of paragraph 140, wherein the first epitope comprises the amino acid sequence FFQKPES (SEQ ID NO:1).

143. The capture agent of paragraph 142, wherein the first epitope comprises the amino acid sequence FFQKPESCPPVPGG (SEQ ID NO:2).

144. The capture agent of paragraph 140, wherein the second epitope comprises the amino acid sequence NENQRVS (SEQ ID NO:3).

145. The capture agent of paragraph 144, wherein the second epitope comprises the amino acid sequence GII-NENQRVS (SEQ ID NO:4).

146. The capture agent of paragraph 140, wherein the first ligand comprises an amino acid sequence 80-100% identical to an amino acid sequence selected from the group consisting of: (a) FYKTH (SEQ ID NO:5); (b) FYKQH (SEQ ID NO:6); (c) FYLTH (SEQ ID NO:7); (d) FYLQH (SEQ ID NO:8); (e) RRATS (SEQ ID NO:9); (f) RRAQS (SEQ ID NO:10); (g) rrATS (SEQ ID NO:47); (h) rrAQS (SEQ ID NO:48); (i) rrats (SEQ ID NO:49); and (j) rraqs (SEQ ID NO:50).

147. The capture agent of any one of paragraphs 140-146, wherein the first ligand is cyclic.

148. The capture agent of any one of paragraphs 140-147, wherein the first ligand comprises a 1,4-substituted-1,2,3-triazole residue (Tz4) or a 1,5-substituted-1,2,3-triazole residue (Tz5).

149. The capture agent of paragraph 148, wherein the triazole residue is a 1,4-substituted-1,2,3-triazole (Tz4) residue.

150. The capture agent of paragraph 140, wherein the second ligand comprises an amino acid sequence 80-100% identical to an amino acid sequence selected from the group consisting of: (a) KYGEV (SEQ ID NO:11); (b) LYGEV (SEQ ID NO:12); (c) VHKSG (SEQ ID NO:13); (d) VHLSG (SEQ ID NO:14); (e) QKHGP (SEQ ID NO:15); (f) TKHGP (SEQ ID NO:16); (g) QLHGP (SEQ ID NO:17); (h) TLHGP (SEQ ID NO:18); (i) YDLQR (SEQ ID NO:19); (j) YDLTR (SEQ ID NO:20); (k) YDKQR (SEQ ID NO:21); (l) YDKTR (SEQ ID NO:22); (m) KKGWP (SEQ ID NO:23); (n) KLGWP (SEQ ID NO:24); (o) LKGWP (SEQ ID NO:25); (p) LLGWP (SEQ ID NO:26); (q) RSYNL (SEQ ID NO:27); (r) RSYNK (SEQ ID NO:28); (s) kYGEV (SEQ ID NO:51); (t) VHkSG (SEQ ID NO:52); (u) QkHGP (SEQ ID NO:53); (v) TkHGP (SEQ ID NO:54); (w) YDLQr (SEQ ID NO:55); (x) YDLTr (SEQ ID NO:56); (y) YDkQr (SEQ ID NO:57); (z) YDkTr (SEQ ID NO:58); (aa) kkGWP (SEQ ID NO:59); (bb) kLGWP (SEQ ID NO:60); (cc) LkGWP (SEQ ID NO:61); (dd) rSYNL (SEQ ID NO:62); (ee) rSYNk (SEQ ID NO:63); (ff) kygev (SEQ ID NO:64); (gg) vhksg (SEQ ID NO:65); (hh) qkhgp (SEQ ID NO:66); (ii) tkhgp (SEQ ID NO:67); (jj) ydlqr (SEQ ID NO:68); (kk) ydltr (SEQ ID NO:69); (ll) ydkqr (SEQ ID NO:70); (mm) ydktr (SEQ ID NO:71); (nn) kkgwp (SEQ ID NO:72); (oo) klgwp (SEQ ID NO:73); (pp) lkgwp (SEQ ID NO:74); (qq) rsynl (SEQ ID NO:75); and (rr) rsynk (SEQ ID NO:76).

151. The capture agent of paragraph 150, wherein the second ligand is cyclic.

152. The capture agent of any one of paragraphs 150 or 151, wherein the second ligand comprises a 1,4-substituted-1,2,3-triazole residue (Tz4) or a 1,5-substituted-1,2,3-triazole residue (Tz5).

153. The capture agent of paragraph 152, wherein the triazole residue is a 1,4-substituted-1,2,3-triazole residue (Tz4).

154. The capture agent of any one of paragraphs 140-143, wherein the linker is divalent.

155. The capture agent of any one of paragraphs 140-154, wherein the length of the linker corresponds to distance between the first epitope and the second epitope.

156. The capture agent of paragraph 155, wherein the length of the linker is from ~4.4 Å to ~26.4 Å, from ~8.8 Å to ~26.4 Å or from ~7 Å to ~15 Å.

157. The capture agent of paragraph 156, wherein the length of the linker is ~15 Å.

158. The capture agent of any one of paragraphs 140-157, wherein the linker comprises one or more repeat units of ethylene glycol.

159. The capture agent of any one of paragraphs 140-158, wherein the linker comprises a peptide.

160. The capture agent of paragraph 140, wherein the first ligand comprises the sequence RRATS (SEQ ID NO:9) and the second ligand comprises the sequence QKHGP (SEQ ID NO:15).

161. The capture agent of paragraph 140, wherein the first ligand comprises the sequence RRATS (SEQ ID NO:9) and the second ligand comprises the sequence RSYNK (SEQ ID NO:28).

162. The capture agent of paragraph 140, wherein the first ligand comprises the sequence rrATS (SEQ ID NO:47) and the second ligand comprises the sequence rSYNK (SEQ ID NO: 63).

163. The capture agent of paragraph 140, wherein the first ligand comprises the sequence rrats (SEQ ID NO:49) and the second ligand comprises the sequence rsynk (SEQ ID NO:76).

164. The capture agent of any one of paragraphs 160-163, wherein the first and second ligands are cyclic and comprise a Tz4 residue.

165. The capture agent of paragraph 164, wherein the linker is glycine.

166. The capture agent of paragraph 166, wherein the linker is selected from the group consisting of $PEG_1$, $PEG_2$, $PEG_3$, $PEG_4$ and $PEG_5$.

167. The capture agent of paragraph 140, wherein the capture agent is labeled with a detectable moiety.

168. The capture agent of paragraph 167, wherein the detectable moiety is selected from the group consisting of biotin, copper-DOTA, biotin-PEG3, aminooxyacetate, $^{19}FB$, $^{18}FB$ and FITC-$PEG_3$.

169. The capture agent of paragraph 167, wherein the detectable moiety is selected from the group consisting of $^{64}Cu$ DOTA, $^{68}Ga$ DOTA, $^{68}Ga$ NOTA, $^{18}F$, $Al^{18}F$ NOTA, $^{64}Cu$, $^{68}Ga$, $^{89}Zr$, $^{124}I$, $^{94m}Tc$, $^{110m}In$, $^{11}C$ and $^{76}Br$.

170. The capture agent of paragraph 140, having a structure selected from the group consisting of:

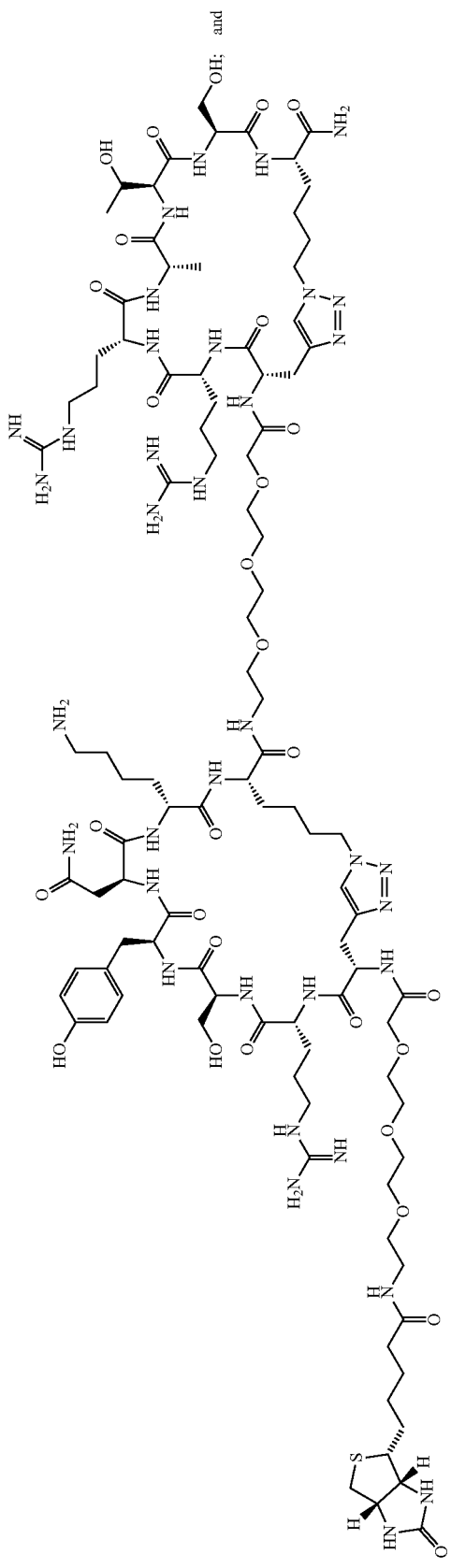
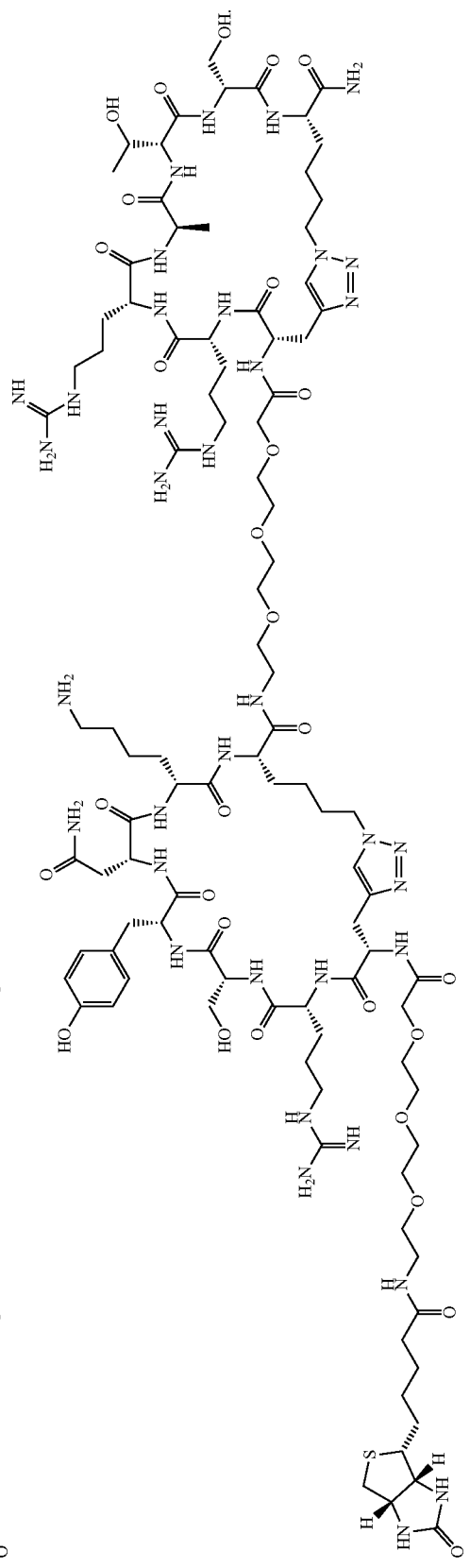

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

EXAMPLES

As described in detail below, examples of the disclosed biligands were produced using a one-bead-one-compound (OBOC) library of alkyne-appended macrocycle peptides screened against the target SynEp appending an azide and a biotin detection label. In this system, those peptides that bind to the SynEp in just the right orientation are covalently coupled through a click reaction between azide and alkyne. After thoroughly washing to remove non-covalently bound copies of the SynEp, the beads are treated with alkaline phosphatase (AP)-conjugated streptavidin. Hit beads are visualized using BCIP/NBT and picked for sequencing. Hits are scaled up and tested against the full-length protein to identify the best binders.

Example 1

IL-17A and IL-17F Epitope Design

The primary sequences of IL-17F and IL-17A were examined to understand where there are regions of identity or similarity, and where there are differences. To create macrocyclic peptide ligands that can effectively discriminate IL-17F (amino acids 1 to 52 of SEQ ID NO:38; shown below) from IL-17A (amino acids 1 to 49 of SEQ ID NO:37; shown below), attention was placed on those sequences that are unique to the two proteins. Sequence differences that discriminate IL-17F from IL-17A were found to occur in the N-terminal region of the mature proteins. In IL-17F, this region of uniqueness corresponds to Arg-31 to Thr-79. In particular, Phe-40 to Ser-70 was studied. Epitope1: amino acids 10 to 24 of SEQ ID NO:38. Epitope2: amino acids 30 to 39 of SEQ ID NO:38.

```
IL-17A:    IVKAGITIPRNP.GCPNSEDKNFPRIVMVNLNIHNRNTNTN..PKRSSDYYNRST

IL-17F:    RKIPKVGHTFFQKPESCPPVPGG........SMKLDIGIINENQRVSMSRNIESRST

Epitope1:           FFQKPESXPPVPGG........S

Epitope2:                                         GIXNENQRVS
X = Az4 substitution (click handle)
```

Sequence alignment of IL-17F (amino acids 3 to 132 of SEQ ID NO:38) and IL-17A (amino acids 1 to 135 of SEQ ID NO:38). SynEps were designed to span regions containing significantly different residues between IL-17F and IL-17A (shaded sequences).

```
                40        50        60         70
IL17F    IPKVGHTFFQKPESCPP-----VPGGSM-KLDIGIINENQRVSMSR
         : :.: :.  ..:        :   : .:.:   :  :    . :
IL17A    IVKAGITIPRNP-GCPNSEDKNFPRTVMVNLNIHNRNTNTNPKRSS
          20        30        40        50         60

80        90       100       110
IL17F    NIESRSTSPWNYTVTWDPNRYPSEVVQAQCRNLGCINAQGKEDISM
          . .::::::    . ::.::::  . .:::.::::::.:.  :   :
IL17A    DYYNRSTSPWNLHRNEDPERYPSVIWEAKCRHLGCINADGNVDYHM
              70        80        90       100       110

120       130       140       150       160
IL17F    NSVPIQQETLVVRRKHQGCSVSFQLEKVLVTVGCTCVTPVIHHV
         :::::::: ::.::.    :  ::.::.::.::::::::..:::
IL17A    NSVPIQQEILVLRREPPHCPNSFRLEKILVSVGCTCVTPIVHHV
              120       130       140       150
```

Two polypeptide epitopes were chemically synthesized and exploited as the targets for generating specific macrocyclic peptide ligands against IL-17F. Epitopes were designed with a biotin-$PEG_3$ assay handle and a strategically substituted azide click handle (Az4=L-azidolysine). The site of click handle substitution in each epitope was determined by examining the protein structure and identifying an amino acid (a) whose side chain is surface-exposed and does not interact with other atoms in the protein, and (b) that is chemically similar to Az4. IL-17F Epitope1 (Phe-40 to Ser-54) is located very close to the N-terminus of IL-17F, and is substituted with Az4 at a central location (Cys-48). IL-17F Epitope2 (Gly-60 to Ser-69) is found after Epitope1 in the primary sequence, and is substituted with Az4 at Ile-62. The sequence of Epitope1 is Biotin-$PEG_3$-FFQKPES [Az4]PPVPGGS, where FFQKPES is SEQ ID NO:1 and PPVPGGS is SEQ ID NO:32. The sequence of Epitope2 is Biotin-$PEG_3$-GI[Az4]NENQRVS (SEQ ID NO:33). Epitope1 MALDI-TOF MS (m/z): calcd. for $C_{99}H_{151}N_{25}O_{27}S$ (M+H) 2155.09; found (M+H+O)=2171.23.

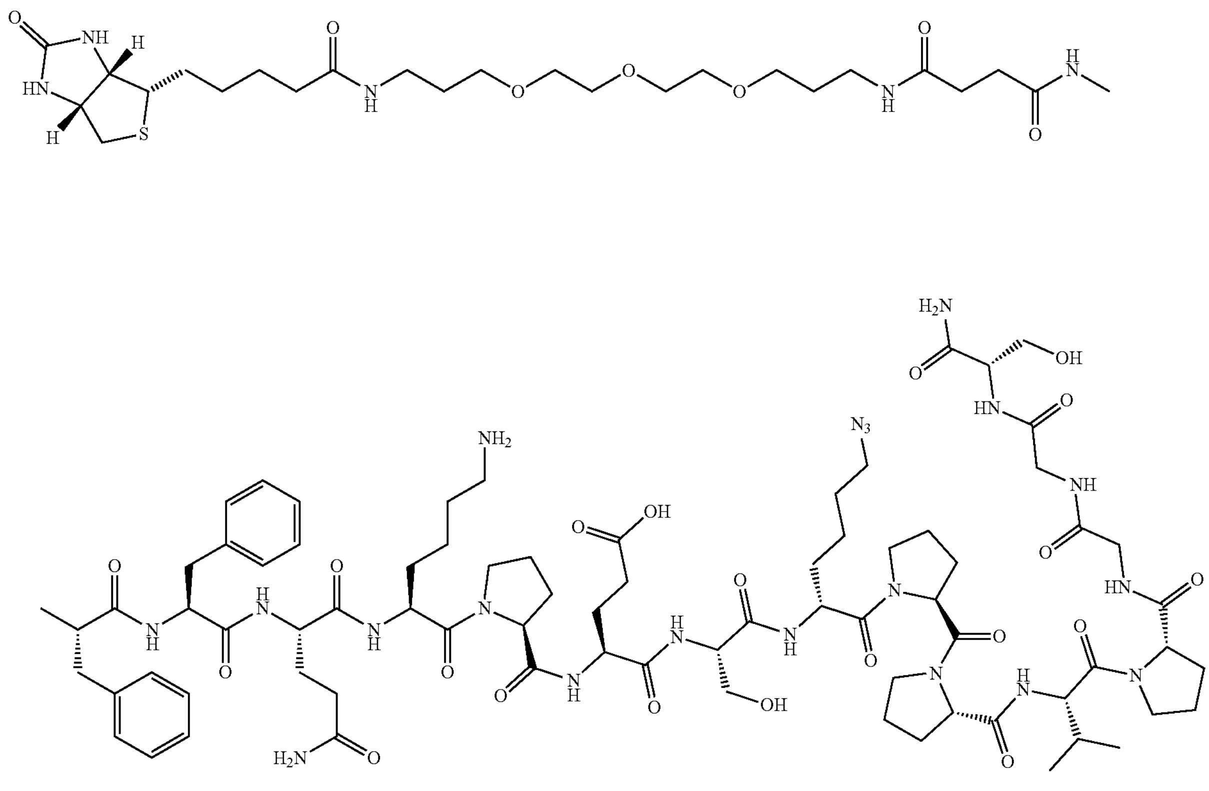

Epitope2 MALDI-TOF MS (m/z): calcd. for $C_{64}H_{109}N_{23}O_{22}S$ (M+H) 1584.78; found (M+H+O)=1600.69.

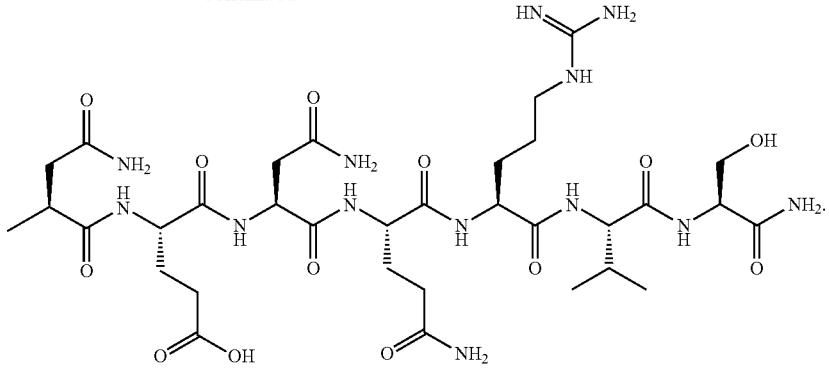

A similar strategy was employed to identify IL-17A Epitope3 (Ile-27 to Lys-61, or more specifically, Pro-33 to Leu-49). The sequence of Epitope3 is Biotin-PEG$_3$-PNSEDKNFPRTVMVNL[Az4] (SEQ ID NO:43). MALDI-TOF MS (m/z): calcd. for $C_{104}H_{169}N_{31}O_{32}S_2$(M+H) 2429.20; found 2429.73.

drate and 5% (v/v) N,N-diisopropylethylamine for 5 min. These monocyclic peptides were then cleaved from the resin for 2 h with 92.5% trifluoroacetic acid (TFA), 2.5% H2O, 2.5% triisopropylsilane (TIS), and 2.5% DODT (3,6-dioxa-1,8-octanedithiol), and then purified by reversed phase HPLC using a C18 column. The synthesis of anti-IL-17F

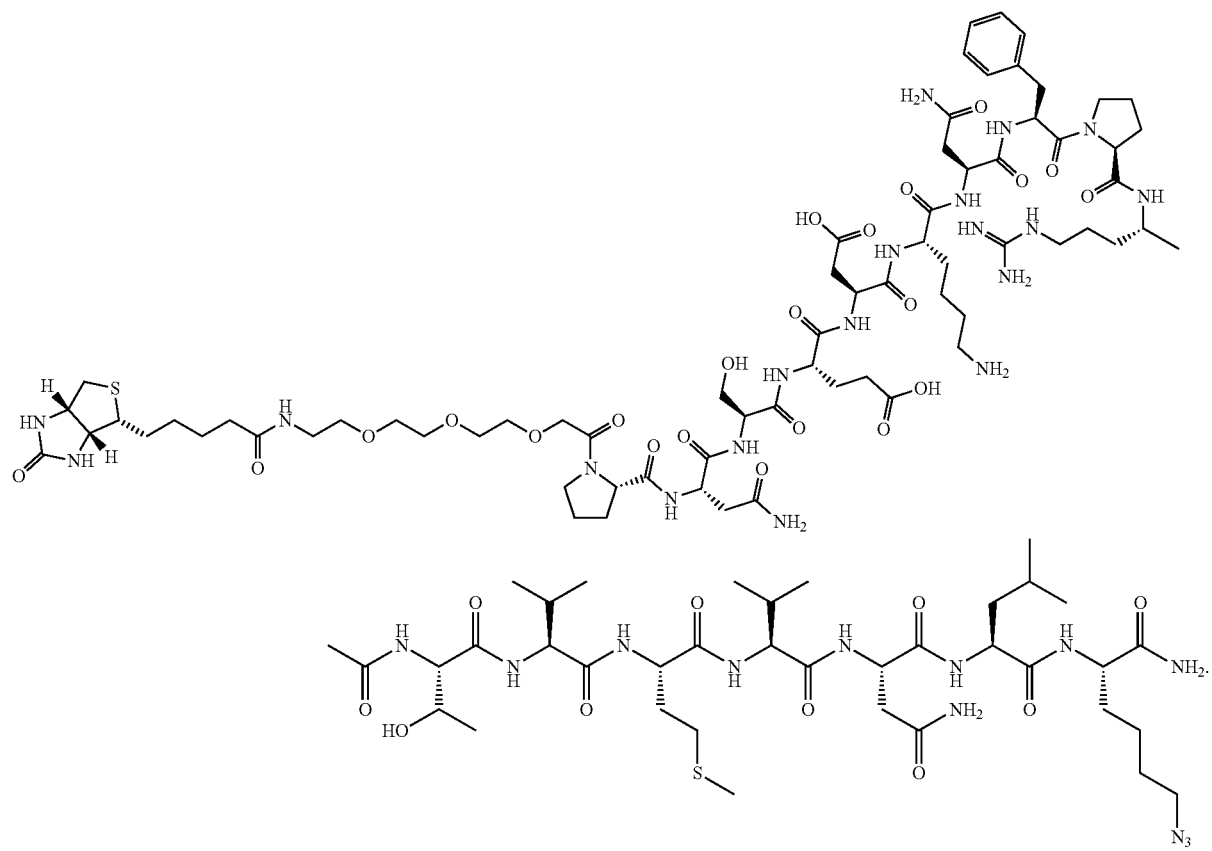

To synthesize monocyclic peptides, first the linear peptide was synthesized on Rink amide resin using conventional Fmoc-based solid-phase synthesis. The peptide was cyclized between the N-terminal Pra and C-terminal Az4 using copper(I) iodide (1.5 eq.) and ascorbic acid (5 eq.) in 4:1 NMP:piperidine. On the next day, the residual copper bound to the resin was removed by shaking the resin with NMP containing 5% (w/v) sodium diethyldithiocarbamate trihybiligands began with synthesizing, cyclizing and chelating LF1. Fmoc-protected polyethylene glycol (PEG) linkers of various lengths (PEG1, PEG2, PEG3, PEG4, and PEG5) were then coupled. LF2 was then synthesized and cyclized, the residual copper was removed by chelation, and the biligand was cleaved from the resin and purified by reversed phase HPLC.

Example 2

Screening for Macrocycle Anchors Against IL-17F Epitope1

Screens were performed using a triazole-cyclized OBOC library of the form $H_2N$-Pra-Cy(XXXXX)-Met-TG, where TG=TentaGel® S $NH_2$ resin (S 30 902, Rapp Polymere), X=one of seventeen L-amino acids (lacking Cys, Met, and Ile), Pra=L-propargylglycine, and Cy( )=triazole cyclization via flanking Pra and Az4 (=L-azidolysine) residues. Macrocycles were identified against the IL-17F Epitope1 fragment using a four-step screening process: 1) a pre-clear to eliminate non-specific binders, 2) a product screen to identify hits resulting from epitope-templated in situ click chemistry, 3) a target screen against His-tagged IL-17F protein, and 4) another target screen against His-tagged IL-17F protein in 2% (v/v) human serum to identify peptides whose binding to IL-17F is unperturbed by serum proteins. In particular, synthetic epitopes were designed (based on protein sequence and structure analysis) to span regions containing significantly different residues between IL-17F and IL-17A (red, green). A one-bead-one-compound (OBOC) library of alkyne-appended macrocycle peptides was screened against the target SynEp appending an azide and a biotin detection label. Those peptides that bind to the SynEp in just the right orientation are covalently coupled via a click reaction between azide and alkyne. After thoroughly washing to remove non-covalently bound copies of the SynEp, the beads are treated with alkaline phosphatase (AP)-conjugated streptavidin. Hit beads are visualized using BCIP/NBT and picked for sequencing. Hits are scaled up and tested against the full-length protein to identify the best binders.

Pre-clear. Swelled library beads (500 mg) were blocked overnight with Blocking Buffer (25 mM Tris-HCl, 150 mM NaCl, 1% (w/v) BSA, and 0.05% (v/v) Tween-20, pH 7.6) at 4° C., then washed with Blocking Buffer three times. A 1:10,000 dilution of Streptavidin-Alkaline Phosphatase (V559C, Promega) in 5 mL Blocking Buffer was added to the beads and incubated with gentle shaking at room temperature for 1 h. The beads were subsequently washed with 3×3 mL TBS (25 mM Tris-HCl, 150 mM NaCl, pH 7.6) (1 min ea), 3×3 mL 0.1 M glycine pH 2.8 wash buffer, 3×3 mL TBS, then 3×3 mL Alkaline Phosphatase buffer (100 mM Tris-HCl, 150 mM NaCl, 1 mM $MgCl_2$, pH 9) (5 min ea). Binding was visualized by incubating the beads in the presence of 5-bromo-4-chloro-3-indolyl phosphate/nitro blue tetrazolium (BCIP/NBT) substrate (53771, Promega) for 25 mM. Purple beads indicated background binders and were removed by pipet and discarded. The remaining clear beads were collected and stripped with 7.5 M guanidine hydrochloride pH 2.0 for 30 min, washed ten times with water, and incubated in 1-methyl-2-pyrrolidinone (NMP) overnight to decolorize.

Product Screen with IL-17F Epitope1. Beads remaining from the pre-clear were washed with water ten times and TBS three times. Beads were then incubated with 3 mL of 100 μM IL-17F Epitope1 fragment (Biotin-PEG$_3$-FFQKPES (SEQ ID NO:1)[Az4]PPVPGGS(SEQ ID NO:32)) in TBS for 1.5 h at room temperature to allow for an in situ click reaction to occur. The beads were washed with TBS ten times and then incubated with 7.5 M guanidine hydrochloride pH 2.0 for 1 h to remove all IL-17F epitope not attached covalently to the beads. These beads were washed with TBS ten times and re-blocked with Blocking Buffer for 2 h. A 1:10,000 dilution of Streptavidin-Alkaline Phosphatase in 5 mL Blocking Buffer was added for 1 h to detect the presence of IL-17F epitope clicked to beads. The beads were subsequently washed with 3×3 mL TBS (1 min ea), 3×3 mL 0.1 M glycine pH 2.8 wash buffer, 3×3 mL TBS, then 3×3 mL Alkaline Phosphatase (pH 9) buffer (5 min ea). After this, the beads were developed with BCIP/NBT for 25 min as outlined in the pre-clear. Purple epitope-conjugated hit beads were selected by pipet and saved. These hits (25 total: 5 dark purple, 20 medium to light purple) were treated with 7.5 M guanidine hydrochloride pH 2.0 for 30 min to remove attached streptavidin, washed ten times with water, and incubated in NMP overnight to decolorize.

Target Screen with His-tagged IL-17F Protein. Product hits were washed with water ten times and stored in TBS at 4° C. These 25 beads were transferred to a Corning® 8162 Costar® Spin-X® centrifuge tube filter (cellulose acetate membrane) and incubated with Blocking Buffer for 3 h at room temperature. The beads were rinsed three times with Blocking Buffer and then incubated with 150 nM of full-length His-tagged IL-17F protein (ab167911, Abcam) in Blocking Buffer (preparation: 0.5 μL His-tagged IL-17F protein in 200 μL Blocking Buffer) for 1 h at room temperature. The beads were washed three times with Blocking Buffer and then incubated with 500 μL of 1:10,000 Anti-6X His tag® antibody [HIS-1] (Alkaline Phosphatase-conjugated) (ab49746, Abcam) in Blocking Buffer for 1 h at room temperature. The beads were subsequently washed with 3×500 μL Blocking Buffer, 3×500 μL TBS, then 3×500 μL Alkaline Phosphatase (pH 9) buffer (centrifuging at 7000 rpm for 30 sec after each wash). After this, the beads were developed with BCIP/NBT for 10 min. Purple hit beads bound to IL-17F protein were selected by pipet and saved. 20 beads were purple indicating binding to both the IL-17 epitope and protein, while 5 were clear indicating no binding to IL-17F protein. The 20 target hits were treated with 7.5 M guanidine hydrochloride pH 2.0 for 30 min to remove bound proteins, washed ten times with water, and incubated in NMP overnight to decolorize.

Target Screen with His-tagged IL-17F Protein in 2% (v/v) Human Serum. Target hits were washed with water ten times. These 20 beads were incubated with Blocking Buffer for 7 h in a Corning® 8162 Costar® Spin-X® centrifuge tube filter (cellulose acetate membrane). The beads were rinsed three times with Blocking Buffer and then incubated with 150 nM of full-length His-tagged IL-17F protein (ab167911, Abcam) in Blocking Buffer containing 2% (v/v) human serum (HS-30, Omega Scientific) for 1 h at room temperature (preparation: 1.25 μL His-tagged IL-17F protein+10 μL filtered serum +490 μL Blocking Buffer). Note: Before the screen, particulate matter was removed from serum by centrifugation (7000 rpm, 30 sec) using a Corning® 8162 Costar® Spin-X® tube filter. The beads were washed three times with Blocking Buffer and then incubated with 500 μL of 1:10,000 Anti-6X His tag® antibody [HIS-1] (Alkaline Phosphatase-conjugated) (ab49746, Abcam) in Blocking Buffer for 1 h at room temperature. The beads were subsequently washed with 3×500 μL Blocking Buffer, 3×500 μL TBS, then 3×500 μL Alkaline Phosphatase (pH 9) buffer (centrifuging at 7000 rpm for 30 sec after each wash). After this, the beads were developed with BCIP/NBT for 10 min. Purple hit beads were selected by pipet and saved. The 2 hits whose binding to IL-17F protein was unperturbed by serum proteins were treated with 7.5 M guanidine hydrochloride pH 2.0 for 30 min to remove bound proteins, washed ten times with water, and incubated in NMP overnight to decolorize. The 2 hits were finally washed with water ten times to prepare for sequencing analysis.

Sequencing was performed via Edman degradation on an Applied Biosystems Procise® cLC 2-cartridge system in the Protein/Peptide Micro Analytical Laboratory at Caltech. The Edman sequencer was unable to distinguish between 1) residues K (lysine) and L (leucine), and 2) residues Q (glutamine) and T (threonine). Sequencing results are shown in Table 1 including the K/L and Q/T variants. In parentheses, o=orange, r=red, g=green, -=white.

TABLE 1

Sequences of macrocyclic peptide hits identified against IL-17F Epitope1

|  | x2 | x3 | x4 | x5 | x6 |
|---|---|---|---|---|---|
| hit 1 | F (g) | Y (g) | K (r) | T (o) | H (r) |
|  | F (g) | Y (g) | K (r) | Q (o) | H (r) |
|  | F (g) | Y (g) | L (—) | T (o) | H (r) |
|  | F (g) | Y (g) | L (—) | Q (o) | H (r) |
| hit 2 | R (r) | R (r) | A (—) | T (o) | S (o) |
|  | R (r) | R (r) | A (—) | Q (o) | S (o) |

Synthesis Data for IL-17F Epitope1 Hits
Cy(FYKTH)(SEQ ID NO:5)-PEG$_3$-biotin. MALDI-MS (m/z): calcd. for $C_{65}H_{97}N_{17}O_{14}S$ (M+H) 1372.71; found 1374.24.

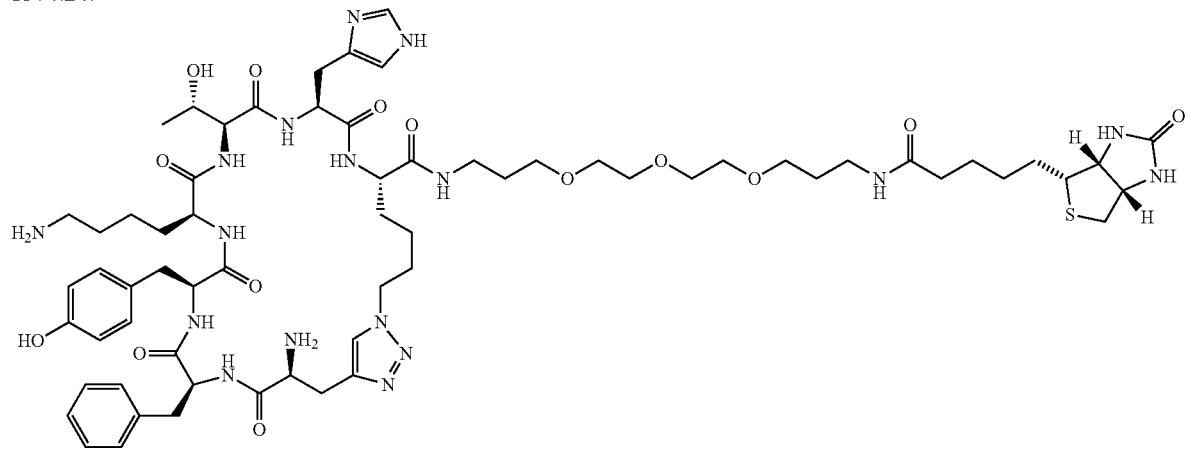

Cy(FYKQH)(SEQ ID NO:6)-PEG$_3$-biotin. MALDI-MS (m/z): calcd. for $C_{66}H_{97}N_{18}O_{14}S$ (M+H) 1399.72; found 1401.36.

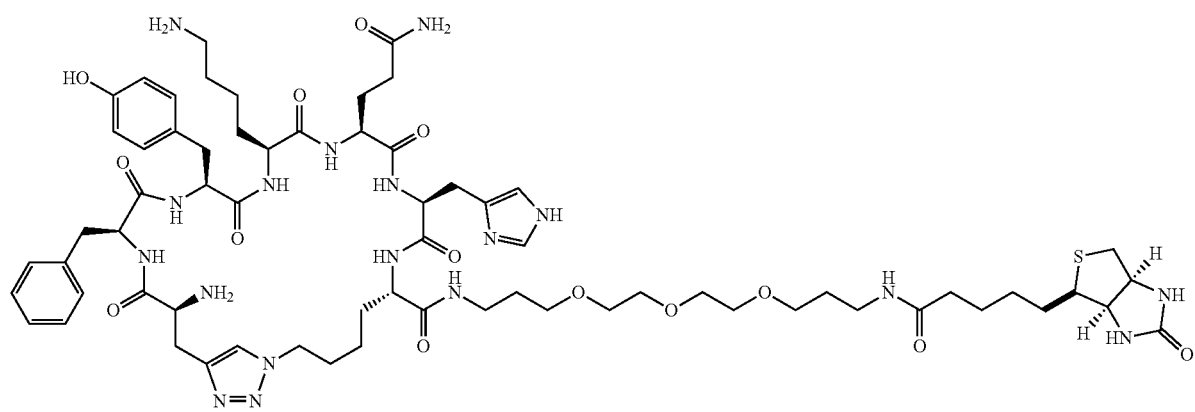

Cy(FYLTH)(SEQ ID NO:7)-PEG$_3$-biotin. MALDI-MS (m/z): calcd. for $C_{65}H_{96}N_{16}O_{14}S$ (M+H) 1357.70; found 1360.15.

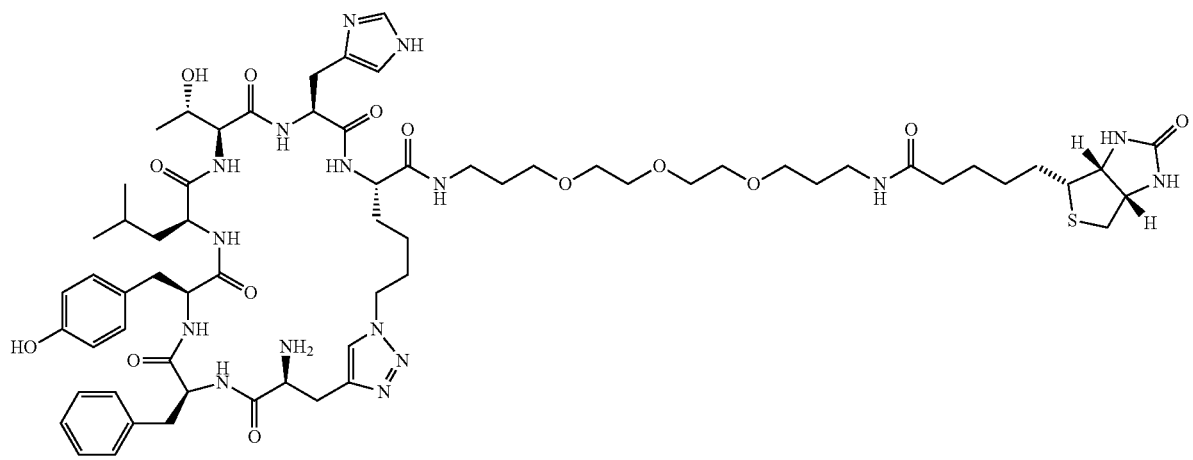
Cy(FYLQH)(SEQ ID NO:8)-PEG$_3$-biotin. MALDI-MS (m/z): calcd. for C$_{66}$H$_{97}$N$_{17}$O$_{14}$S (M+H) 1384.71; found 1386.24.
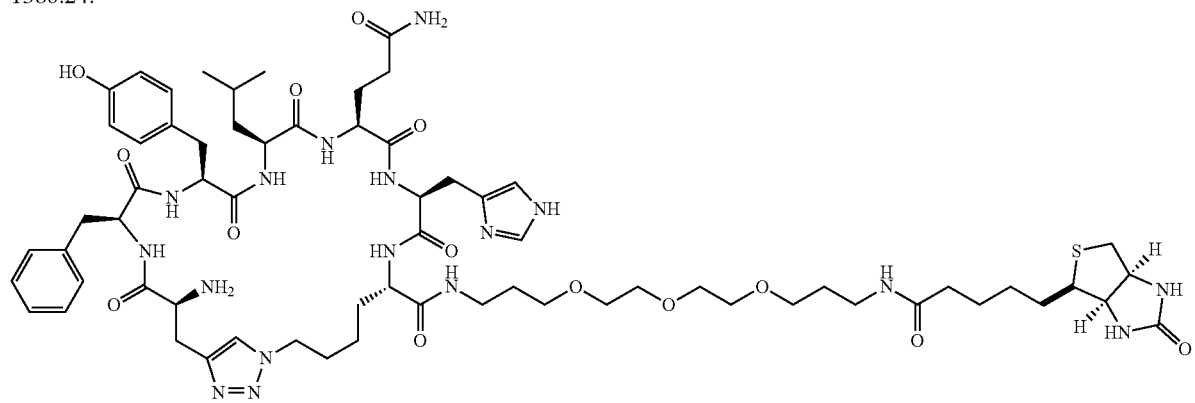
Cy(RRATS)(SEQ ID NO:9)-PEG$_3$-biotin. MALDI-MS (m/z): calcd. for C$_{53}$H$_{94}$N$_{20}$O$_{14}$S (M+H) 1269.70; found 1269.91.
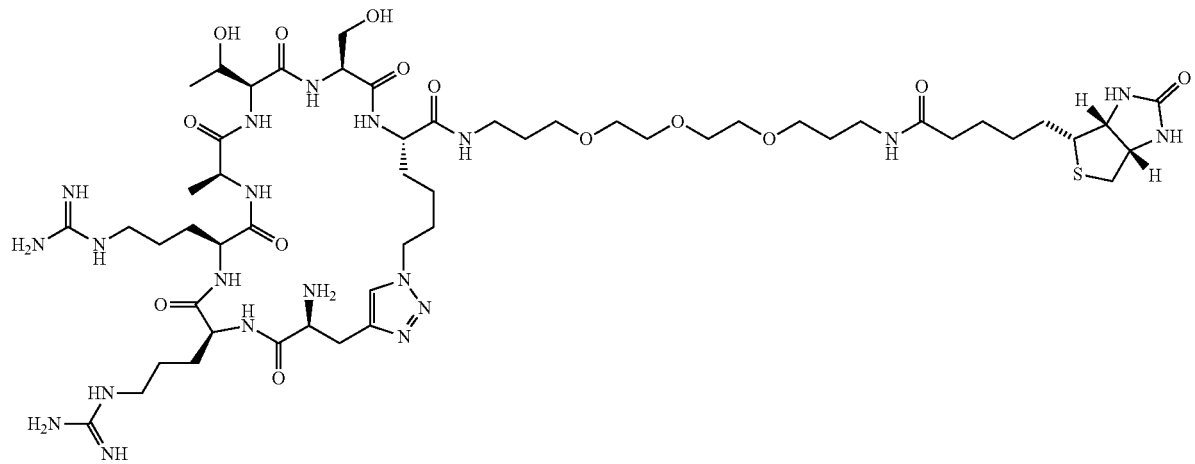
Cy(RRAQS)(SEQ ID NO:10)-PEG$_3$-biotin. MALDI-MS (m/z): calcd. for C$_{54}$H$_{95}$N$_{21}$O$_{14}$S (M+H) 1295.71; found 1296.19.

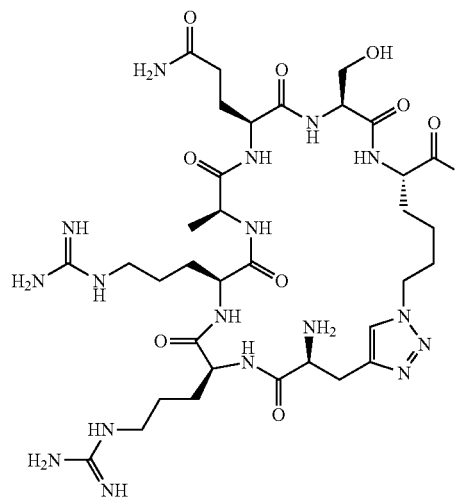 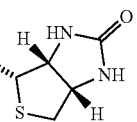
Example 3
In Vitro Assays with IL-17F Epitope1 Targeted Ligands
Sandwich ELISA. A Using an excitation wavelength of 430 nm, fluorescent emission at 535 nm was recorded by Beckman Coulter DTX880 photometer. Data are shown after subtraction of the no-epitope background.

For this experiment, the IL-17F Epitope1 was re-synthesized with a $His_6$ assay handle and C48S substitution instead of a click handle. Two additional His-tagged IL-17F epitopes were synthesized to contain strategic scrambling of the sequences either N-terminal or C-terminal to C48S (scrambled residues are shown in italics):

1) $His_6$-$PEG_3$-FFQKPESSPPVPGGS; (SEQ ID NO: 39)

2) $His_6$-$PEG_3$-FFQKPESS*PVSPGPG*; (scrambled C-terminal to click handle; SEQ ID NO: 40)

3) $His_6$-$PEG_3$-*SQFEKFP*SPPVPGGS. (scrambled N-terminal to click handle; SEQ ID NO: 41)

Point ELISAs for the three His-tagged IL-17F epitopes were conducted against the immobilized macrocyclic peptide ligands. For $PEG_3$-biotin-modified Cy(RRATS) (SEQ ID NO:9) and Cy(RRAQS) (SEQ ID NO:10), positive ELISA signals were obtained for the His-tagged IL-17F Epitope1 (C48S) and the epitope scrambled C-terminal to click handle. Binding was destroyed when the epitope was scrambled N-terminal to the click handle. Therefore, the macrocyclic peptide ligands show preferential binding to the sequence FFQKPES (SEQ ID NO:1) within IL-17F Epitope1 (C48S). On the other hand, biotinylated monoclonal anti-IL17F showed no appreciable binding to the His-tagged IL-17F epitopes as it was raised against a protein immunogen.

In summary, these results confirm that the epitope-targeting strategy produced sub-100 nM affinity macrocyclic peptide ligands that selectively recognize IL-17F epitopes as well as the full-length protein.

Example 4

Screening for Macrocycle Anchor Against IL-17F Epitope2

Screens were similarly performed to target the IL-17F Epitope2 fragment (Biotin-$PEG_3$-GI[Az4]NENQRVS) (SEQ ID NO:33) using the triazole-cyclized OBOC library of the form $H_2N$-Pra-Cy(XXXXX)-Met-TG. Macrocycles were identified against the IL-17F Epitope2 fragment using the aforementioned four-step screening process: 1) a pre-clear to eliminate non-specific binders, 2) a product screen to identify hits resulting from epitope-templated in situ click chemistry, 3) a target screen against His-tagged IL-17F protein, and 4) additional target screens against His-tagged IL-17F protein in 1% to 5% (v/v) human serum to identify peptides whose binding to IL-17F is unperturbed by serum proteins.

Product Screen with IL-17F Epitope2. The product screen was conducted with 3 mL of 100 μM IL-17F Epitope2 fragment (Biotin-$PEG_3$-GI[Az4]NENQRVS) (SEQ ID NO:33) in TBS for 1.5 h at room temperature to allow for an in situ click reaction to occur. The beads were washed with TBS ten times and then incubated with 7.5 M guanidine hydrochloride pH 2.0 for 1 h to remove all IL-17F epitope not attached covalently to the beads. These beads were washed with TBS ten times and re-blocked with Blocking Buffer for 2 h. A 1:10,000 dilution of Streptavidin-Alkaline Phosphatase in 5 mL Blocking Buffer was added for 1 h to detect the presence of IL-17F epitope clicked to beads. The beads were subsequently washed with 3×3 mL TBS (1 min ea), 3×3 mL 0.1 M glycine pH 2.8 wash buffer, 3×3 mL TBS, then 3×3 mL Alkaline Phosphatase (pH 9) buffer (5 min ea). After this, the beads were developed with BCIP/NBT for 25 min as outlined in the pre-clear. Purple epitope-conjugated hit beads were selected by pipet and saved. These hits (98 total: 50 dark purple, 48 medium to light purple) were treated with 7.5 M guanidine hydrochloride pH 2.0 for 30 min to remove attached streptavidin, washed ten times with water, and incubated in NMP overnight to decolorize.

Target Screen with His-tagged IL-17F Protein. Product hits were washed with water ten times and stored in TBS at 4° C. These 98 beads were transferred to a Corning® 8162 Costar® Spin-X® centrifuge tube filter (cellulose acetate membrane) and incubated with Blocking Buffer for 3 h at room temperature. The beads were rinsed three times with Blocking Buffer and then incubated with 150 nM of full-length His-tagged IL-17F protein (ab167911, Abcam) in Blocking Buffer (preparation: 0.5 μL His-tagged IL-17F protein in 200 μL Blocking Buffer) for 1 h at room temperature. The beads were washed three times with Blocking Buffer and then incubated with 500 μL of 1:10,000 Anti-6X His tag® antibody [HIS-1] (Alkaline Phosphatase-conjugated) (ab49746, Abcam) in Blocking Buffer for 1 h at room temperature. The beads were subsequently washed with 3×500 μL Blocking Buffer, 3×500 μL TBS, then 3×500 μL Alkaline Phosphatase (pH 9) buffer (centrifuging at 7000 rpm for 30 sec after each wash). After this, the beads were developed with BCIP/NBT for 10 min. Purple hit beads bound to IL-17F protein were selected by pipet and saved. 53 beads were purple indicating binding to both the IL-17 epitope and protein, while 40 were clear indicating no binding to IL-17F protein. The 53 target hits were treated with 7.5 M guanidine hydrochloride pH 2.0 for 30 min to remove bound proteins, washed ten times with water, and incubated in NMP overnight to decolorize.

Target Screen with His-tagged IL-17F Protein in 1% (v/v) Human Serum. Target hits were washed with water ten times. These 53 beads were incubated with Blocking Buffer for 7 h in a Corning® 8162 Costar® Spin-X® centrifuge tube filter (cellulose acetate membrane). The beads were rinsed three times with Blocking Buffer and then incubated with 150 nM of full-length His-tagged IL-17F protein (ab167911, Abcam) in Blocking Buffer containing 1% (v/v) human serum (HS-30, Omega Scientific) for 1 h at room temperature (preparation: 1.25 μL His-tagged IL-17F protein+5 μL filtered serum+495 μL Blocking Buffer). Note: Before the screen, particulate matter was removed from serum by centrifugation (7000 rpm, 30 sec) using a Corning® 8162 Costar® Spin-X® tube filter. The beads were washed three times with Blocking Buffer and then incubated with 500 μL of 1:10,000 Anti-6X His tag® antibody [HIS-1] (Alkaline Phosphatase-conjugated) (ab49746, Abcam) in Blocking Buffer for 1 h at room temperature. The beads were subsequently washed with 3×500 μL Blocking Buffer, 3×500 μL TBS, then 3×500 μL Alkaline Phosphatase (pH 9) buffer (centrifuging at 7000 rpm for 30 sec after each wash). After this, the beads were developed with BCIP/NBT for 10 min. Purple hit beads were selected by pipet and saved. The 23 hits whose binding to IL-17F protein was unperturbed by serum proteins were treated with 7.5 M guanidine hydrochloride pH 2.0 for 30 min to remove bound proteins, washed ten times with water, and incubated in NMP overnight to decolorize.

Target Screen with His-tagged IL-17F Protein in 5% (v/v) Human Serum to Refine the Number of Hits. The 23 beads were washed with water ten times and then incubated with Blocking Buffer for 7 h in a Corning® 8162 Costar® Spin-X® centrifuge tube filter (cellulose acetate membrane). The beads were rinsed three times with Blocking Buffer and then incubated with 150 nM of full-length His-tagged IL-17F protein (ab167911, Abcam) in Blocking Buffer containing 5% (v/v) human serum (HS-30, Omega Scientific) for 1 h at room temperature (preparation: 1.25 μL His-tagged IL-17F protein+25 μL filtered serum+475 μL Blocking Buffer). Note: Before the screen, particulate matter was removed from serum by centrifugation (7000 rpm, 30 sec) using a Corning® 8162 Costar® Spin-X® tube filter. The beads were washed three times with Blocking Buffer and then incubated with 500 μL of 1:10,000 Anti-6X His tag® antibody [HIS-1] (Alkaline Phosphatase-conjugated) (ab49746, Abcam) in Blocking Buffer for 1 h at room temperature. The beads were subsequently washed with 3×500 μL Blocking Buffer, 3×500 μL TBS, then 3×500 μL Alkaline Phosphatase (pH 9) buffer (centrifuging at 7000 rpm for 30 sec after each wash). After this, the beads were developed with BCIP/NBT for 10 min. Purple hit beads were selected by pipet and saved. The 6 hits whose binding to IL-17F protein was unperturbed by the increased background of serum proteins were treated with 7.5 M guanidine hydrochloride pH 2.0 for 30 min to remove bound proteins, washed ten times with water, and incubated in NMP overnight to decolorize. The 6 hits were finally washed with water ten times to prepare for sequencing analysis.

Sequencing was performed via Edman degradation. The Edman sequencer was unable to distinguish between 1) residues K (lysine) and L (leucine), and 2) residues Q (glutamine) and T (threonine). Sequencing results are shown in Table 2 including the K/L and Q/T variants. In parentheses, o=orange, r=red, g=green, b=blue, −=white.

TABLE 2

Sequences of macrocyclic peptide hits identified against IL-17F Epitope2

| | x2 | x3 | x4 | x5 | x6 |
|---|---|---|---|---|---|
| hit 3 | Q (o) | K (r) | H (r) | G (—) | P (—) |
| | T (o) | K (r) | H (r) | G (—) | P (—) |
| | Q (o) | L (—) | H (r) | G (—) | P (—) |
| | T (o) | L (—) | H (r) | G (—) | P (—) |
| hit 1 | K (r) | Y (g) | G (—) | E (b) | V (—) |
| | L (—) | Y (g) | G (—) | E (b) | V (—) |
| hit 4 | Y (g) | D (b) | L (—) | Q (o) | R (r) |
| | Y (g) | D (b) | L (—) | T (o) | R (r) |
| | Y (g) | D (b) | K (r) | Q (o) | R (r) |
| | Y (g) | D (b) | K (r) | T (o) | R (r) |
| hit 2 | V (—) | H (r) | K (r) | S (o) | G (—) |
| | V (—) | H (r) | L (—) | S (o) | G (—) |
| hit 5 | K (r) | K (r) | G (—) | W (g) | P (—) |
| | K (r) | L (—) | G (—) | W (g) | P (—) |
| | L (—) | K (r) | G (—) | W (g) | P (—) |
| | L (—) | L (—) | G (—) | W (g) | P (—) |
| hit 6 | R (r) | S (o) | Y (g) | N (o) | L (—) |
| | R (r) | S (o) | Y (g) | N (o) | K (r) |

These candidate peptides were re-synthesized on a cleavable resin, purified by reversed phase HPLC using a C18 column, and tested against the IL-17F protein by ELISA.

Synthesis Data for IL-17F Epitope2 Hits

Cy(KYGEV)(SEQ ID NO:11)-PEG$_3$-biotin. MALDI-MS (m/z): calcd. for $C_{58}H_{93}N_{15}O_{15}S$ (M+H) 1272.67; found 1274.02.

Cy(LYGEV)(SEQ ID NO:12)-PEG$_3$-biotin. MALDI-MS (m/z): calcd. for $C_{58}H_{92}N_{14}O_{15}S$ (M+H) 1257.66; found 1259.13.

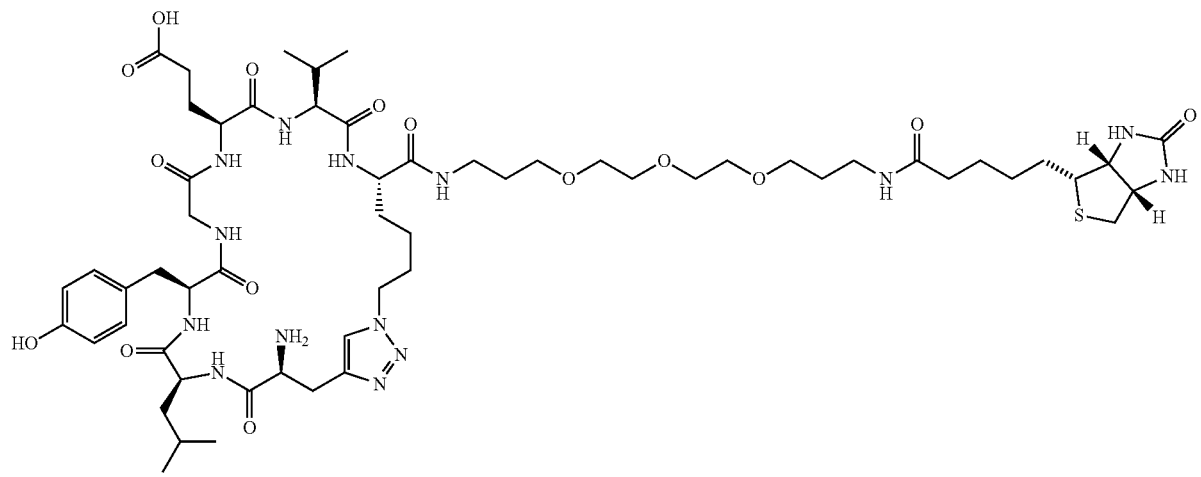
Cy(VHKSG)(SEQ ID NO:13)-PEG$_3$-biotin. MALDI-MS (m/z): calcd. for $C_{53}H_{89}N_{17}O_{13}S$ (M+H) 1204.65; found 1206.20.
Cy(VHLSG)(SEQ ID NO:14)-PEG$_3$-biotin. MALDI-MS (m/z): calcd. for $C_{53}H_{88}N_{16}O_{13}S$ (M+H) 1189.64; found 1191.11.
Cy(QKHGP)(SEQ ID NO:15)-PEG$_3$-biotin. MALDI-MS (m/z): calcd. for $C_{55}H_{90}N_{18}O_{13}S$ (M+H) 1243.67; found 1245.18.

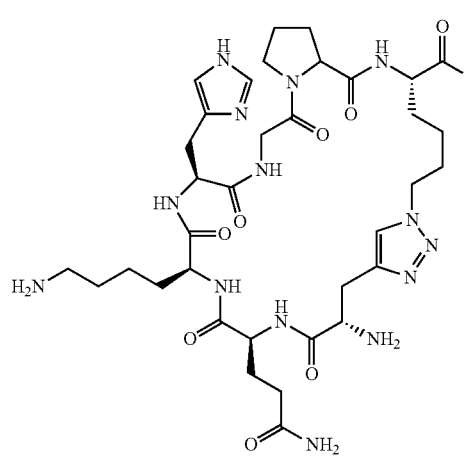
Cy(TKHGP)(SEQ ID NO:16)-PEG$_3$-biotin. MALDI-MS (m/z): calcd. for $C_{54}H_{89}N_{17}O_{13}S$ (M+H) 1216.65; found 1218.25.
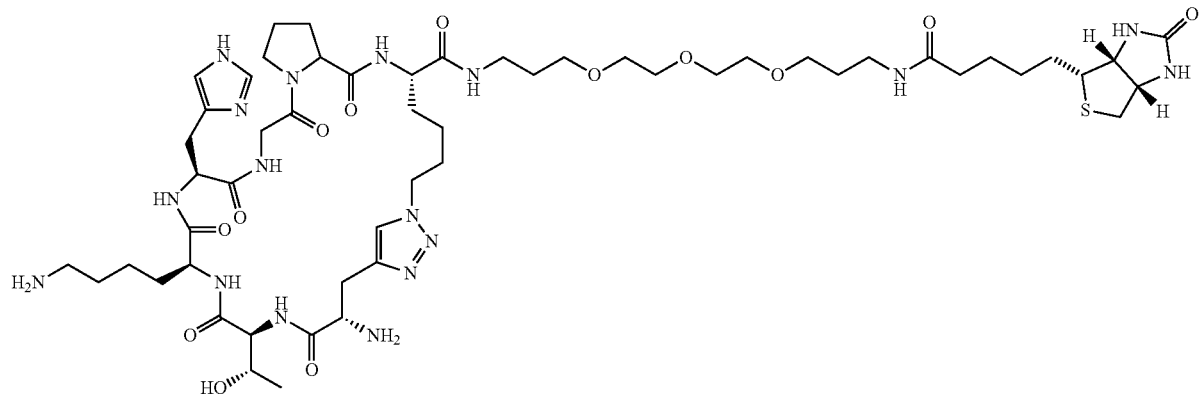
Cy(QLHGP)(SEQ ID NO:17)-PEG$_3$-biotin. MALDI-MS (m/z): calcd. for $C_{55}H_{89}N_{17}O_{13}S$ (M+H) 1228.65; found 1228.84.
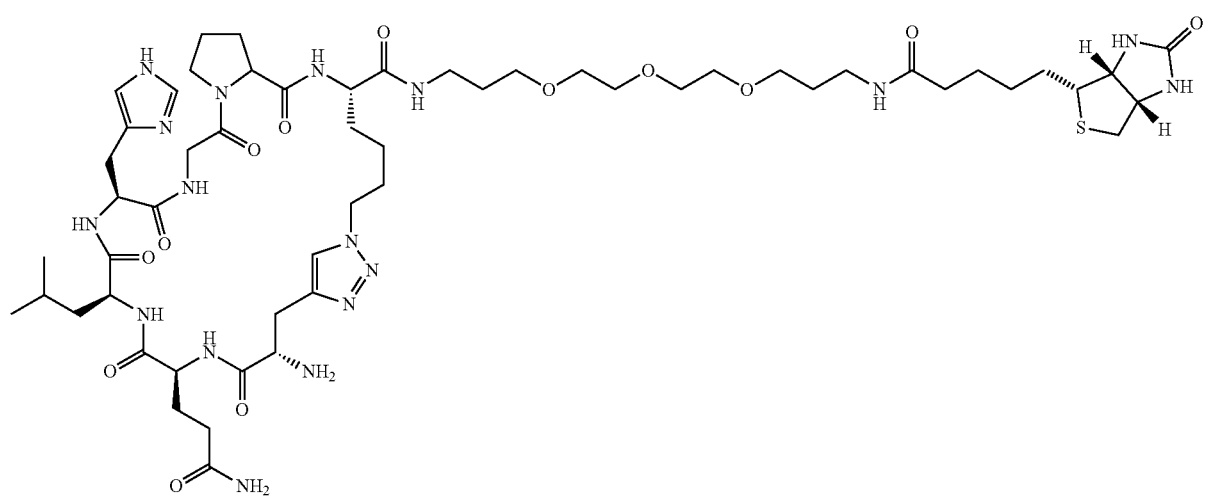
Cy(TLHGP)(SEQ ID NO:18)-PEG$_3$-biotin. MALDI-MS (m/z): calcd. for $C_{54}H_{88}N_{16}O_{13}S$ (M+H) 1201.64; found 1201.73.

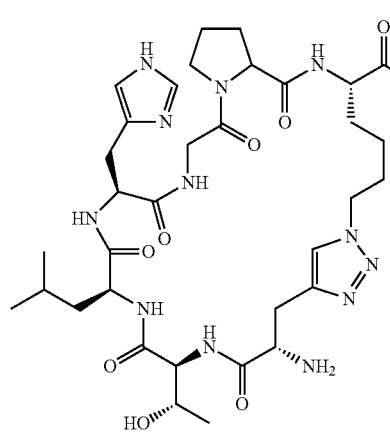
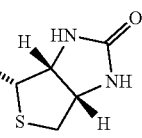
Cy(YDLQR)(SEQ ID NO:19)-PEG$_3$-biotin. MALDI-MS (m/z): calcd. for $C_{61}H_{98}N_{18}O_{16}S$ (M+H) 1371.71; found 1372.16.
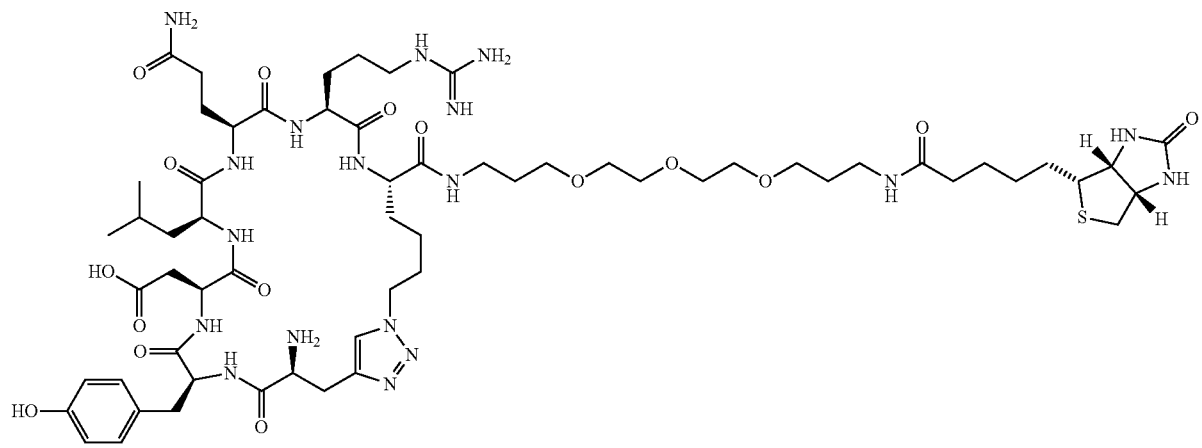
Cy(YDLTR)(SEQ ID NO:20)-PEG$_3$-biotin. MALDI-MS (m/z): calcd. for $C_{60}H_{97}N_{17}O_{16}S$ (M+H) 1344.70; found 1345.13.
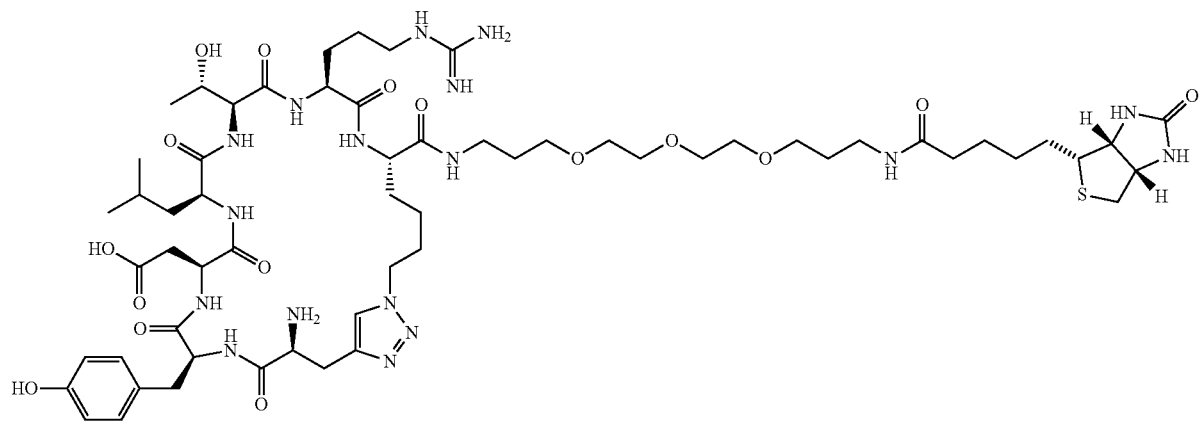
Cy(YDKQR)(SEQ ID NO:21)-PEG$_3$-biotin. MALDI-MS (m/z): calcd. for $C_{61}H_{99}N_{19}O_{16}S$ (M+H) 1386.72; found 1387.00.

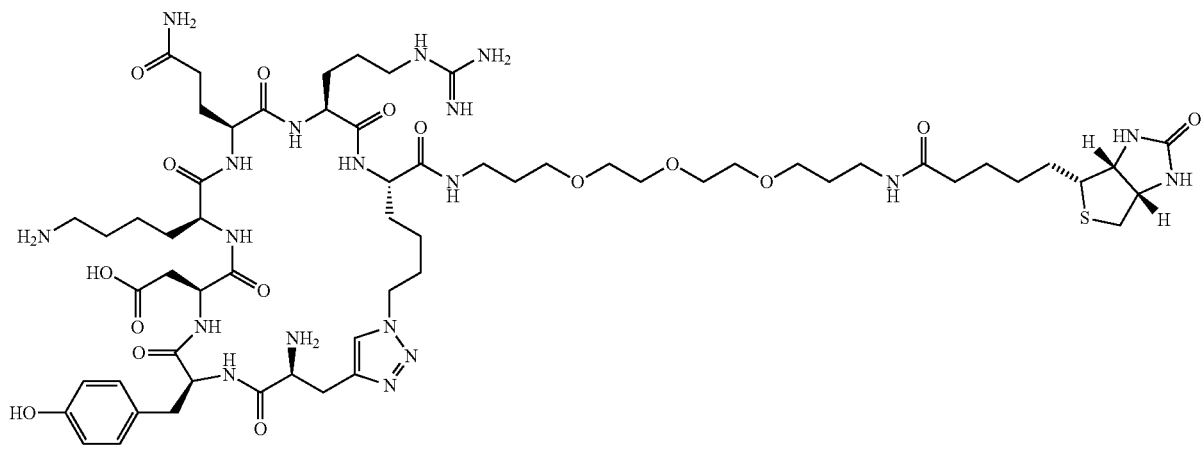
Cy(YDKTR)(SEQ ID NO:22)-PEG$_3$-biotin. MALDI-MS (m/z): calcd. for $C_{60}H_{98}N_{18}O_{16}S$ (M+H) 1359.71; found 1359.94.
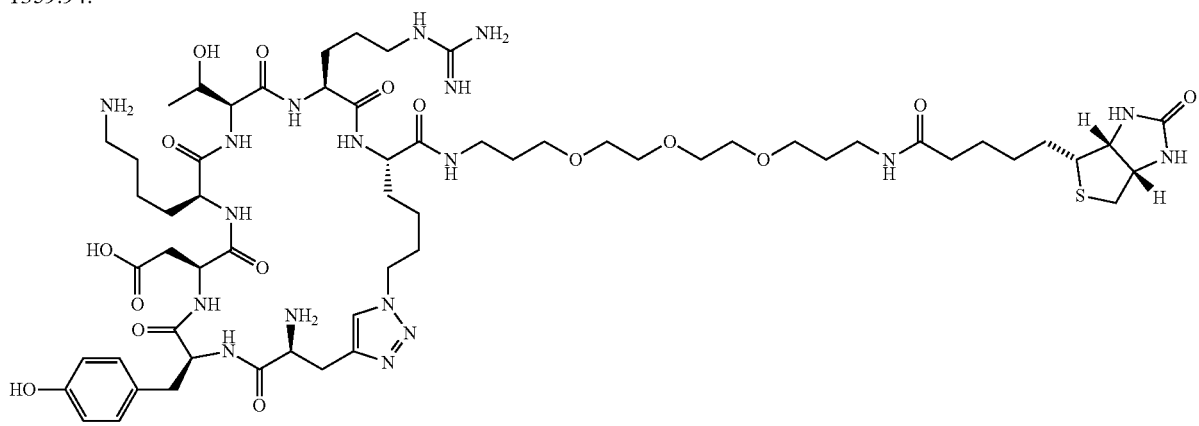
Biotin-PEG$_3$-Cy(KKGWP) (SEQ ID NO:23). MALDI-MS (m/z): calcd. for $C_{59}H_{91}N_{17}O_{13}S$ (M+H) 1278.67; found 1278.83.
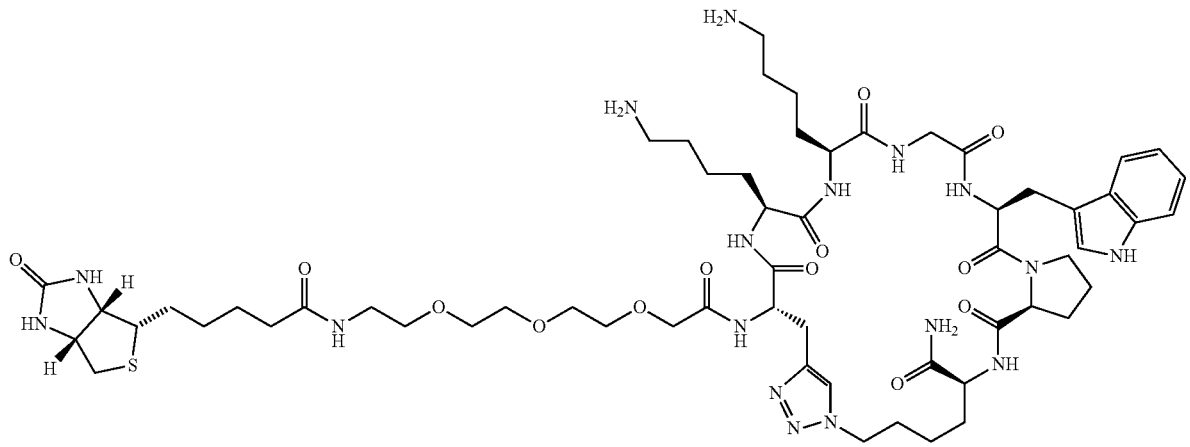 [SMILES: NCCCC[C@@H]1NC(=O)[C@H](CCCCN)NC(=O)[C@@H](NC(=O)COCCOCCOCCNC(=O)CCCC[C@@H]2SC[C@@H]3NC(=O)N[C@@H]32)Cc2cn(nn2)CCCC[C@@H](C(N)=O)NC(=O)[C@@H]2CCCN2C(=O)[C@H](Cc2c[nH]c3ccccc23)NC(=O)CNC1=O]
Biotin-PEG$_3$-Cy(KLGWP) (SEQ ID NO:24). MALDI-MS (m/z): calcd. for $C_{59}H_{90}N_{16}O_{13}S$ (M+H) 1263.66; found 1263.92.

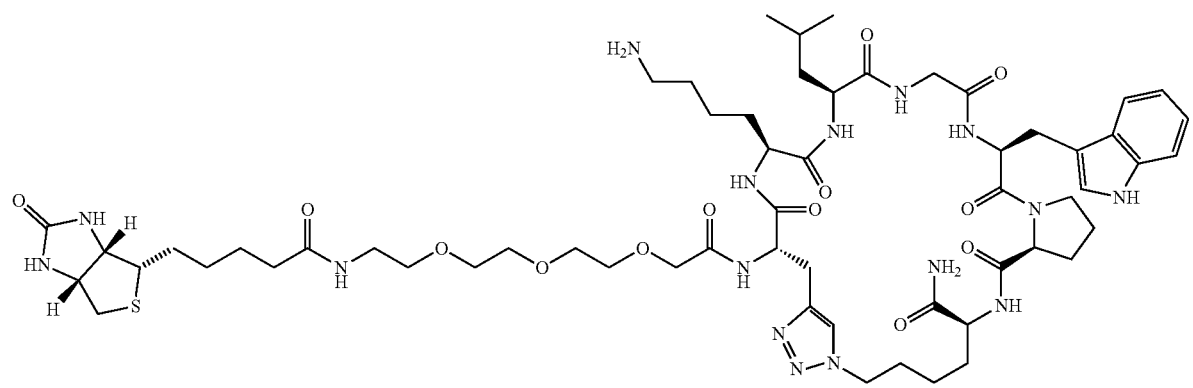 [SMILES: CC(C)C[C@@H]1NC(=O)[C@H](CCCCN)NC(=O)[C@@H](NC(=O)COCCOCCOCCNC(=O)CCCC[C@@H]2SC[C@@H]3NC(=O)N[C@@H]32)Cc2cn(nn2)CCCC[C@@H](C(N)=O)NC(=O)[C@@H]2CCCN2C(=O)[C@H](Cc2c[nH]c3ccccc23)NC(=O)CNC1=O]
Biotin-PEG$_3$-Cy(LKGWP) (SEQ ID NO:25). MALDI-MS (m/z): calcd. for C$_{59}$H$_{90}$N$_{16}$O$_{13}$S (M+H) 1263.66; found 1263.86.
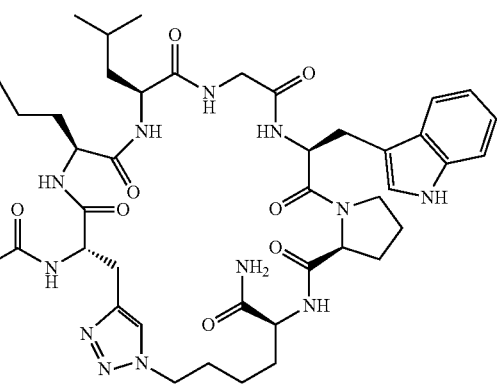
Biotin-PEG$_3$-Cy(LLGWP) (SEQ ID NO:26). MALDI-MS (m/z): calcd. for C$_{59}$H$_{89}$N$_{15}$O$_{13}$S (M+H) 1248.65; found 1248.89.
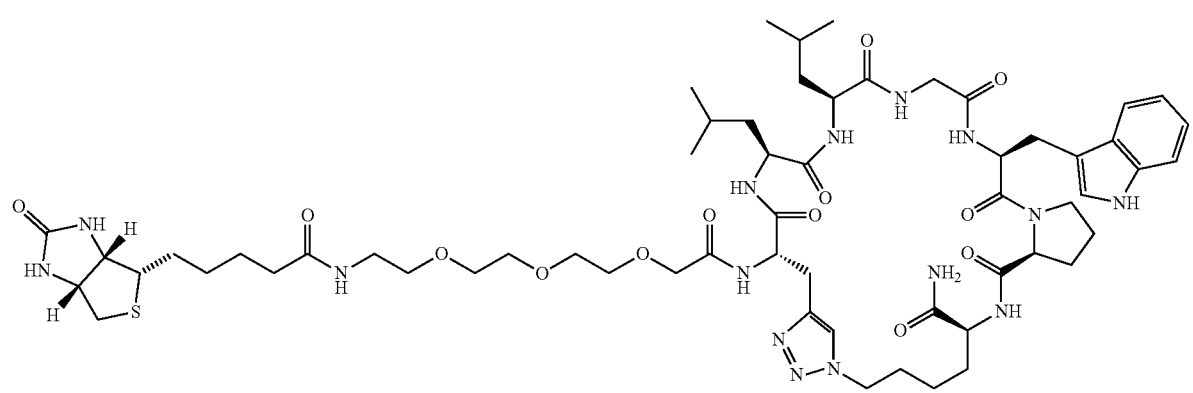 [SMILES: CC(C)C[C@@H]1NC(=O)[C@H](CC(C)C)NC(=O)[C@@H](NC(=O)COCCOCCOCCNC(=O)CCCC[C@@H]2SC[C@@H]3NC(=O)N[C@@H]32)Cc2cn(nn2)CCCC[C@@H](C(N)=O)NC(=O)[C@@H]2CCCN2C(=O)[C@H](Cc2c[nH]c3ccccc23)NC(=O)CNC1=O]
Biotin-PEG$_3$-Cy(RSYNL) (SEQ ID NO:27). MALDI-MS (m/z): calcd. for C$_{57}$H$_{90}$N$_{18}$O$_{16}$S (M+H) 1315.65; found 1315.95.

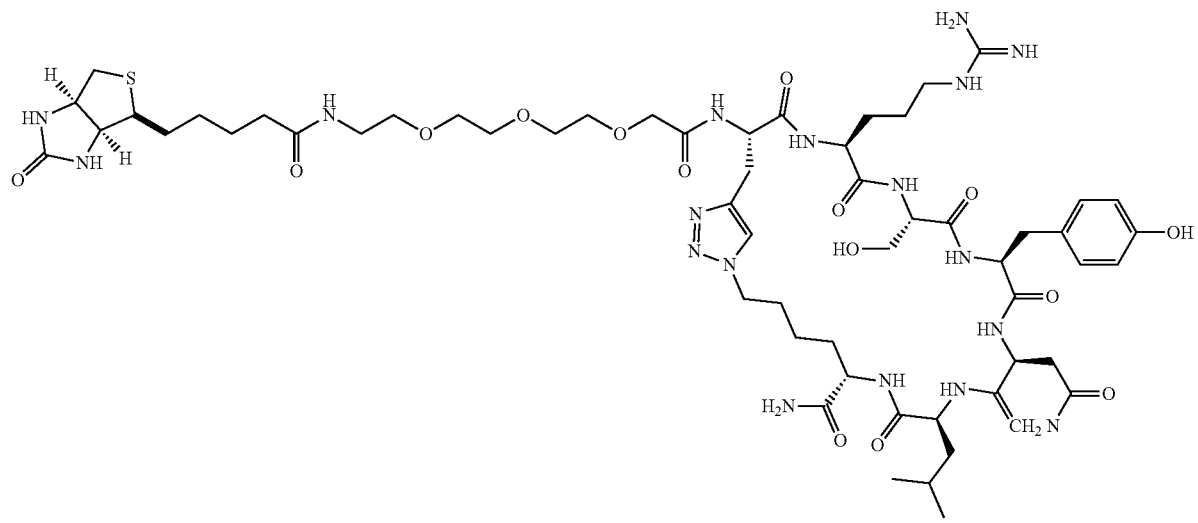 [SMILES: C=C1N[C@@H](CC(C)C)C(=O)N[C@H](C(N)=O)CCCCn2cc(nn2)C[C@H](NC(=O)COCCOCCOCCNC(=O)CCCC[C@@H]2SC[C@@H]3NC(=O)N[C@@H]32)C(=O)N[C@@H](CCCNC(=N)N)C(=O)N[C@@H](CO)C(=O)N[C@@H](Cc2ccc(O)cc2)C(=O)N[C@H]1CC(N)=O]

Biotin-PEG$_3$-Cy(RSYNK) (SEQ ID NO:28). MALDI-MS (m/z): calcd. for $C_{57}H_{91}N_{19}O_{16}S$ (M+H) 1330.66; found 1331.06.

(SEQ ID NO:15) and Cy(TKHGP) (SEQ ID NO:16) exhibited EC$_{50}$ values of 64±10 nM and 72±16 nM, respectively, for human IL-17F protein. Cy(KKGWP) (SEQ ID NO:23)

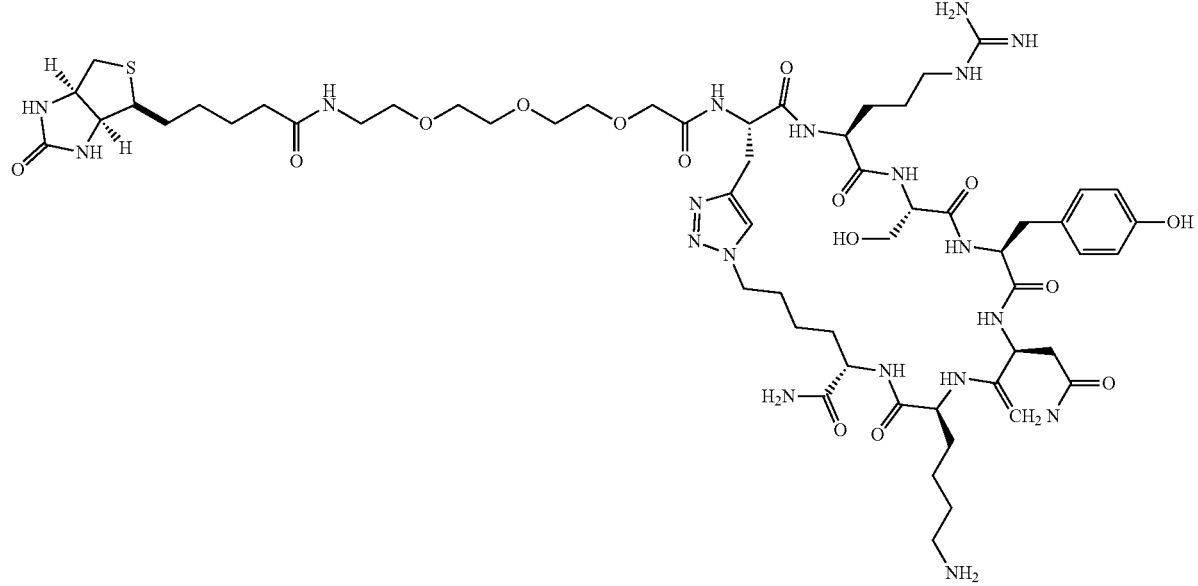 [SMILES: C=C1N[C@@H](CCCCN)C(=O)N[C@H](C(N)=O)CCCCn2cc(nn2)C[C@H](NC(=O)COCCOCCOCCNC(=O)CCCC[C@@H]2SC[C@@H]3NC(=O)N[C@@H]32)C(=O)N[C@@H](CCCNC(=N)N)C(=O)N[C@@H](CO)C(=O)N[C@@H](Cc2ccc(O)cc2)C(=O)N[C@H]1CC(N)=O]

Example 5

In Vitro Assays with IL-17F Epitope2 Targeted Ligands

Sandwich ELISA. These assays were performed using the same protocol that was used to evaluate the IL-17F Epitope1 targeted ligands.

The binding affinity of PEG$_3$-biotin-modified Cy(QKHGP) (SEQ ID NO:15), Cy(TKHGP) (SEQ ID NO:16), Cy(KKGWP) (SEQ ID NO:23), and Cy(RSYNK) (SEQ ID NO:28) was tested in an ELISA format. For these assays, a dilution series of full-length His-tagged IL-17F protein was captured using the macrocyclic peptide ligands immobilized on a NeutrAvidin-coated plate. Cy(QKHGP) and Cy(RSYNK) (SEQ ID NO:28) exhibited EC$_{50}$ values of 24±3 nM and 15±5 nM, respectively, for human IL-17F protein. Interestingly, Cy(RSYNK) (SEQ ID NO:28) exceeds the binding affinity of the similarly assayed biotinylated monoclonal anti-IL17F.

Point ELISA (IL-17F vs. IL-17A selectivity assay). A black 96-well NeutrAvidin Coated High Binding Capacity plate (15510, Pierce) was coated with 2 µM macrocyclic peptide ligand in TBS (pH 7.6) for 2 h at room temperature. Biotinylated monoclonal anti-IL17F (TA319597, Origene) was coated at 4 µg/mL in TBS as a control. The plate was aspirated and then washed with TBS (5×) and Wash Buffer (0.05% (v/v) Tween-20 in PBS, 1×). Full-length His-tagged IL-17F (ab167911, Abcam) and IL-17A (ab166882, Abcam) proteins were prepared at 100 nM and 10 nM in Wash Buffer and incubated in the designated microwells for 90 min at room temperature. Microwells were aspirated and subsequently washed with Wash Buffer (10×). To detect the bound IL-17F and IL-17A proteins, Alkaline Phosphatase (AP)-conjugated Anti-6X His tag® antibody [HIS-1] (ab49746, Abcam) was prepared at 1:10,000 dilution and added to the microwells for 1 h at room temperature. The plate was aspirated and washed with Wash Buffer (11×). AttoPhos® AP Fluorescent Substrate System (S1000, Promega) was employed to develop the microwells. Using an excitation wavelength of 430 nm, fluorescent emission at 535 nm was recorded by Beckman Coulter DTX880 photometer.

The selectivity of PEG$_3$-biotin-modified Cy(QKHGP) (SEQ ID NO:15), Cy(TKHGP) (SEQ ID NO:16), Cy(KKGWP) (SEQ ID NO:23), and Cy(RSYNK) (SEQ ID NO:28) was tested in an ELISA format. For these assays, the full-length His-tagged IL-17F and IL-17A proteins were captured using the macrocyclic peptide ligands immobilized on a NeutrAvidin-coated plate. Both Cy(KKGWP) (SEQ ID NO:23) and Cy(RSYNK) (SEQ ID NO:28) exhibited 4:1 selectivity for IL-17F at 100 nM. Other ligands, including Cy(QKHGP) (SEQ ID NO:15) and Cy(TKHGP) (SEQ ID NO:16), and biotinylated monoclonal anti-IL17F show even higher (almost absolute) selectivity for IL-17F. Again, these results confirm the selective nature of the epitope-targeting strategy. Point ELISAs for human IL-17F and IL-17A proteins against macrocyclic peptide ligands RRATS (SEQ ID NO:9), RSYNK (SEQ ID NO:28), (QKHGP) (SEQ ID NO:15), demonstrate preferential binding to IL-17F or IL-17A.

Example 6

Screening for Macrocycle Anchor Against IL-17A Epitope3

A similar screening protocol was performed to target the IL-17A Epitope3 fragment (Biotin-$PEG_3$-PNSEDKNFPRTVMVNL[Az4]), (SEQ ID NO:43) using the triazole-cyclized OBOC library of D-amino acids.

Product Screen with IL-17A Epitope3. The product screen was conducted with 3 mL of 100 μM IL-17A Epitope3 fragment (Biotin-$PEG_3$-PNSEDKNFPRTVMVNL[Az4]), (SEQ ID NO:43) in TBS for 1.5 h at room temperature to allow for an in situ click reaction to occur. The beads were washed with TBS ten times and then incubated with 7.5 M guanidine hydrochloride pH 2.0 for 1 h to remove all IL-17A epitope not attached covalently to the beads. These beads were washed with TBS ten times and re-blocked with Blocking Buffer for 2 h. A 1:10,000 dilution of Streptavidin-Alkaline Phosphatase in 5 mL Blocking Buffer was added for 1 h to detect the presence of IL-17A epitope clicked to beads. The beads were subsequently washed with 3×3 mL TBS (1 min ea), 3×3 mL 0.1 M glycine pH 2.8 wash buffer, 3×3 mL TBS, then 3×3 mL Alkaline Phosphatase (pH 9) buffer (5 min ea). After this, the beads were developed with BCIP/NBT for 25 min as outlined in the pre-clear. Purple epitope-conjugated hit beads were selected by pipet and saved. These hits were treated with 7.5 M guanidine hydrochloride pH 2.0 for 30 min to remove attached streptavidin, washed ten times with water, and incubated in NMP overnight to decolorize. Due to the small number of hit beads identified, no further IL-17A screens were performed.

Sequencing was performed via Edman degradation. Sequencing results are shown in Table 3. In parentheses, o=orange, r=red, g=green, −=white.

TABLE 3

Sequences of macrocyclic peptide hits identified against IL-17A Epitope3

| | x2 | x3 | x4 | x5 | x6 |
|---|---|---|---|---|---|
| hit 1 | r (r) | h (r) | f (g) | r (r) | l (—) |
| hit 2 | n (o) | r (r) | f (g) | f (g) | f (g) |
| hit 3 | r (r) | k (r) | h (r) | y (g) | h (r) |

Example 7

Designing a Linker to Covalently Join Two Macrocyclic Ligands

The tertiary structure of the IL-17F protein was subsequently exploited as a scaffold for developing a biligand PCC agent that exhibits true cooperative binding ($K_D$ range of <1 nM). Combinations of two macrocycles were covalently joined together to create a biligand PCC agent that displays high avidity for the two epitopes.

Important to this process is the design of suitable linker to bridge the distance between the two epitopes of the protein. The 3-D crystal structure of IL-17F (PDB ID: 1JPY) was analyzed in PyMOL (DeLano Scientific) to identify the distances between IL-17F Epitope1 and IL-17F Epitope2. In IL-17F Epitope1, focus was placed on the sequence FFQKPES (SEQ ID NO:1) because the macrocycles Cy(RRATS) (SEQ ID NO:9) and Cy(RRAQS) (SEQ ID NO:10) were determined to interact with this region preferentially. The sequence NENQRVS (SEQ ID NO:3) within IL-17F Epitope2 was the assumed binding region for macrocycles Cy(QKHGP) (SEQ ID NO:15), Cy(TKHGP) (SEQ ID NO:16), Cy(KKGWP) (SEQ ID NO:23), and Cy(RSYNK) (SEQ ID NO:28) because of the N-terminal location of the click handle. Because IL-17F natively exists as a homodimer, distances were measured between the two epitopes within one and across both monomers. In the monomeric IL-17F protein, the sequence FFQKPES (SEQ ID NO:1) (in IL-17F Epitope1) and IL-17F Epitope2 NENQRVS (SEQ ID NO:3) are separated by ~15 Å. Thus, a chemical linker of ~15 Å would be useful for covalently joining one macrocycle targeted to IL-17F Epitope1 and one macrocycle targeted to IL-17F Epitope2. The resultant cooperative biligands would be useful for detection or treatment of IL-17F and the IL-17A/F heterodimer. In the homodimeric IL-17F protein, the sequence FFQKPES (SEQ ID NO:1) (in IL-17F Epitope1) from one monomer and IL-17F Epitope2 NENQRVS (SEQ ID NO:3) from the other monomer are separated by ~7 Å. Thus, a chemical linker of ~7 Å would be useful for covalently joining one macrocycle targeted to IL-17F Epitope1 and one macrocycle targeted to IL-17F Epitope2. The resultant cooperative biligands would be useful for detection or treatment of IL-17F. Using a linker whose length is similar to the distance between the two binding sites bridging the protein dimer, another biligand can be synthesized containing macrocycles targeted to each of the two IL-17F epitopes. PDB ID: 1JPY.

Similarly, IL-17A natively exists as a homodimer and distances can be measured between the two epitopes within one and across both monomers. In the monomeric IL-17A protein, the sequence PNSEDKNFPRTVMVNL (SEQ ID NO:43) (in IL-17A Epitope3) and another IL-17A epitope are separated by the approximate distance between the epitopes. The resultant cooperative biligands would be useful for detection or treatment of IL-17A and the IL-17A/F heterodimer. Using a linker whose length is similar to the distance between the two binding sites bridging the protein dimer, another biligand can be synthesized containing macrocycles targeted to each of the two IL-17A epitopes. PDB ID: 4HSA.

For IL-17A/F heterodimers, distances can be measured between the two epitopes across both monomers. A chemical linker of approximately the distance between the epitopes would be useful for covalently joining one macrocycle targeted to the IL-17F epitope and one macrocycle targeted to IL-17A epitope. The resultant cooperative biligands would be useful for detection or treatment of IL-17A/F heterodimer. Using a linker whose length is similar to the distance between the two binding sites bridging the protein dimer, another biligand can be synthesized containing macrocycles targeted to each of the two IL-17A/F epitopes. IL-17A/F heterodimer structure reported by Goepfert et al., Scientific Reports 7:8906 (2017).

Example 8

Synthesis of Cooperative Biligand Candidates

Cooperative biligand candidates were synthesized with a variable length linker covalently joining one macrocycle from IL-17F Epitope1 with one macrocycle from IL-17F Epitope2. The linker connecting the two macrocycles was a single PEGylated amino acid (Fmoc-NH-$PEG_x$-Propionic Acid; x=1 to 5) or glycine (Gly). A PEG linker was chosen because it is available in various lengths that would bridge the 7-15 Å distance between the two epitopes of the protein. PEG also is expected to display anti-biofouling properties.

Cooperative biligand candidates were first generated from Cy(RRATS) (SEQ ID NO:9) (targeted to IL-17F Epitope1) and Cy(QKHGP) (SEQ ID NO:15) (targeted to IL-17F Epitope2). Cy(QKHGP) (SEQ ID NO:15) was prioritized based on its high selectivity for IL-17F. Structures of the cooperative biligand candidates Biotin-$PEG_3$-Cy(RRATS) (SEQ ID NO:9)-$PEG_x$-Cy(QKHGP)(SEQ ID NO:15) are shown below. The biligand candidates have linkers ranging from 4.4 to 26.4 Å joining the two macrocycles. Cooperative biligand candidates were also generated from Cy(RRATS) (SEQ ID NO:9) (targeted to IL-17F Epitope1) and Cy(RSYNK) (SEQ ID NO:28) (targeted to IL-17F Epitope2). Cy(RSYNK) (SEQ ID NO:28) was prioritized based on its high affinity for IL-17F.

Biotin-$PEG_3$-Cy(RRATS)(SEQ ID NO:9)-Gly-Cy(QKHGP) (SEQ ID NO:15) (Gly=4.4 Å).

Chemical Formula: $C_{88}H_{143}N_{35}O_{24}S$
Exact Mass: 2106.08
Molecular Weight: 2107.36

Biotin-$PEG_3$-Cy(RRATS)(SEQ ID NO:9)-$PEG_1$-Cy(QKHGP) (SEQ ID NO:15) ($PEG_1$=8.8 Å).

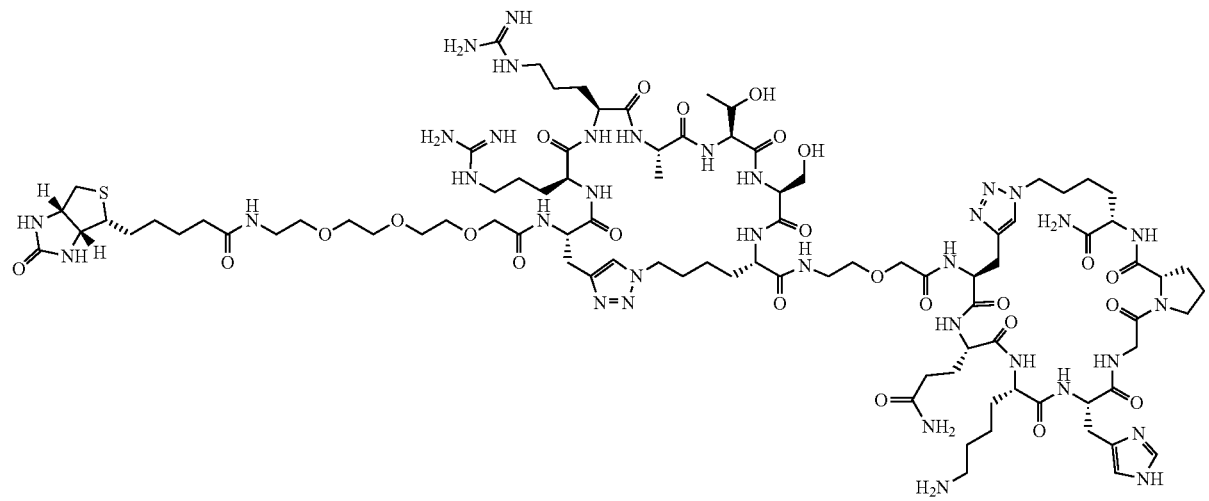
Chemical Formula: $C_{90}H_{147}N_{35}O_{25}S$
Exact Mass: 2150.10
Molecular Weight: 2151.41
Biotin-PEG$_3$-Cy(RRATS)(SEQ ID NO:9)-PEG$_2$-Cy(QKHGP) (SEQ ID NO:15) (PEG$_2$=13.2 Å).
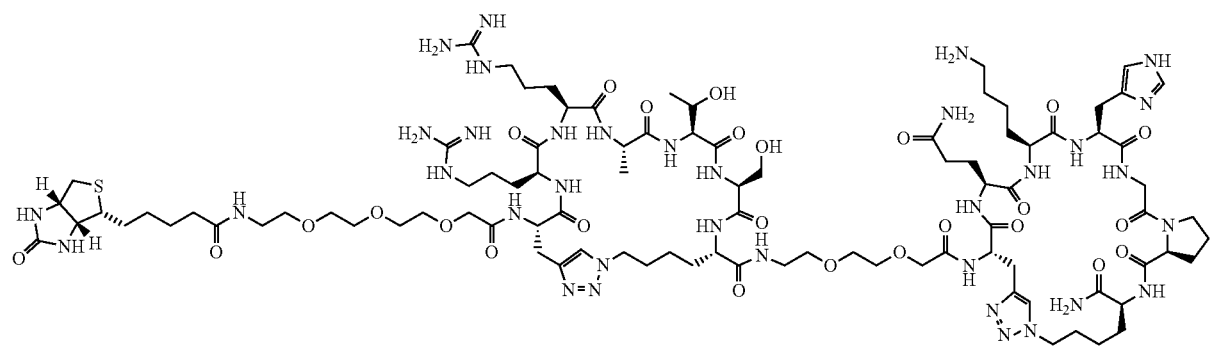
Chemical Formula: $C_{92}H_{151}N_{35}O_{26}S$
Exact Mass: 2194.13
Molecular Weight: 2195.47
Biotin-PEG$_3$-Cy(RRATS)(SEQ ID NO:9)-PEG$_3$-Cy(QKHGP) (SEQ ID NO:15) (PEG$_3$=17.6 Å).

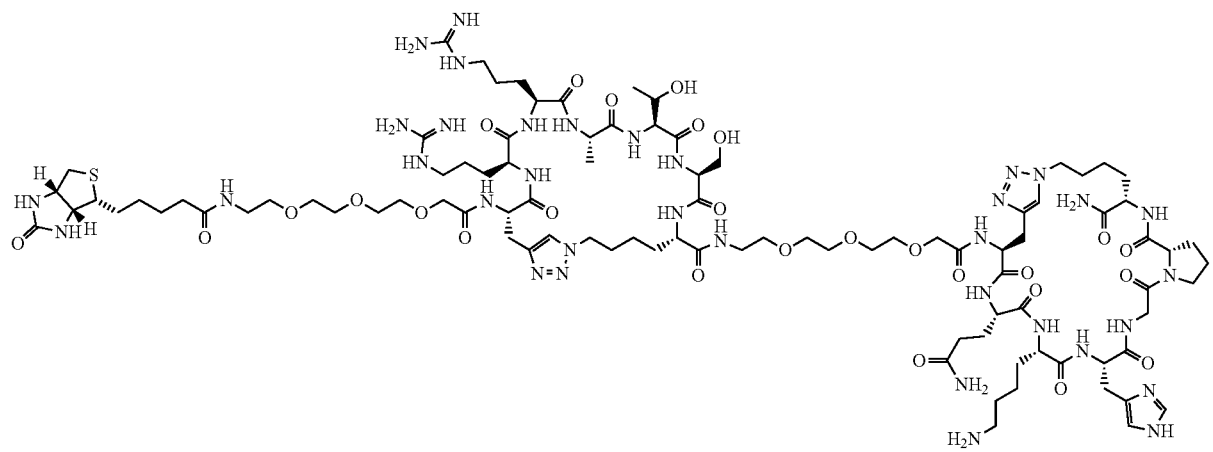
Chemical Formula: $C_{94}H_{155}N_{35}O_{27}S$
Exact Mass: 2238.16
Molecular Weight: 2239.52
Biotin-PEG$_3$-Cy(RRATS)(SEQ ID NO:9)-PEG$_4$-Cy(QKHGP) (SEQ ID NO:15) (PEG$_4$=22 Å).
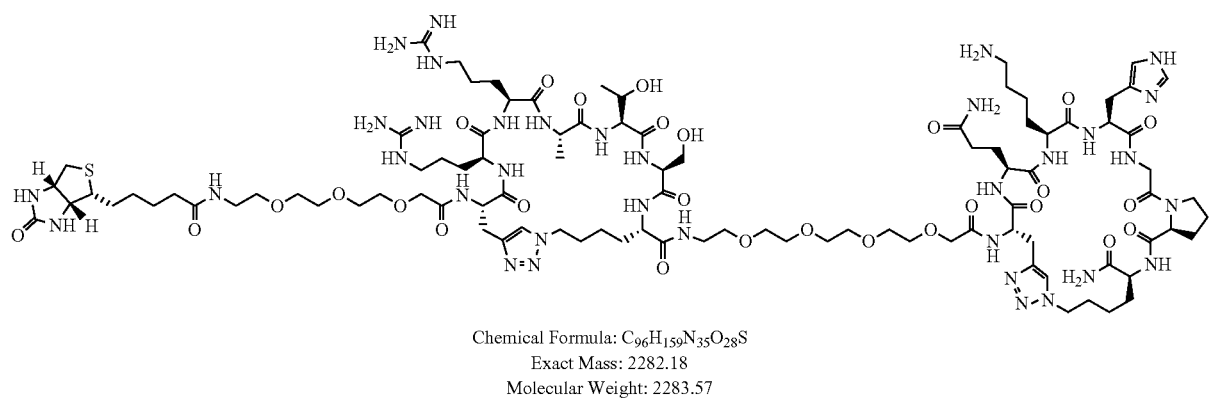
Chemical Formula: $C_{96}H_{159}N_{35}O_{28}S$
Exact Mass: 2282.18
Molecular Weight: 2283.57
Biotin-PEG$_3$-Cy(RRATS)(SEQ ID NO:9)-PEG$_5$-Cy(QKHGP) (SEQ ID NO:15) (PEG$_5$=26.4 Å).
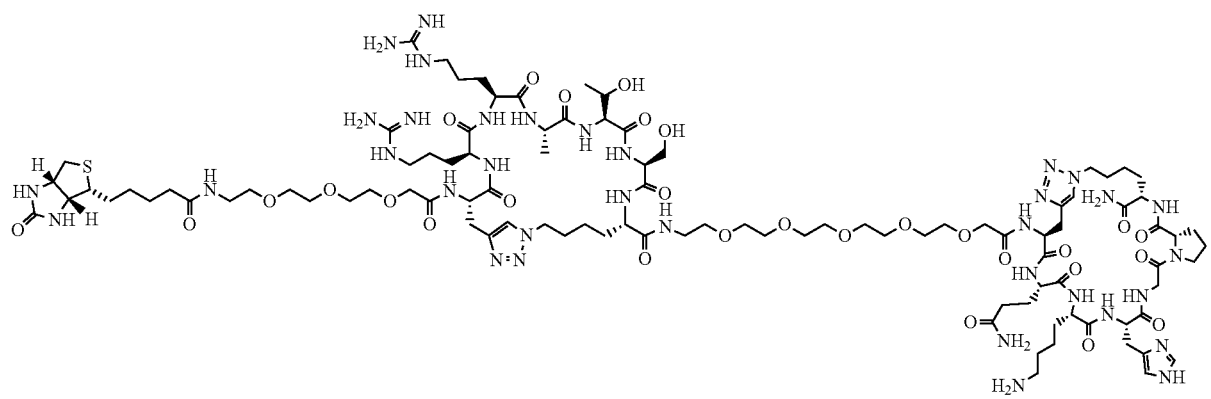
Chemical Formula: $C_{98}H_{163}N_{35}O_{29}S$
Exact Mass: 2326.21
Molecular Weight: 2327.62

Example 9

Interleukin 17F (IL17F): Use the Crystal Structure and PCC Assay Data to Estimate the Distance Between the Two Ligands, and Select a Best Linker from that Information IL-17F and IL-17A are close homologs, as shown by the alignment of IL-17F (SEQ ID NO:38) and IL-17A (SEQ ID NO:37) below. Residues with double dots are identical, single dots are homologous and no dots are unique.

```
                                                            *
IL-17F   .......... .......... .......... ...RKIPKVG HTFFQKPESC   17
                                               : :.:  :. ..: .:
IL-17A   .......... .......... .......... .....IVKAG ITIPRNP.GC   14

IL-17F   PPVPGG.... ....SMKLDI GIINENQRVS MSRNIESRST SPWNYTVTWD   59
         :               .        : :       :     ::: ::::     :
IL-17A   PNSEDKNFPR TVMVNLNIHN RNTNTN..PK RSSDYYNRST SPWNLHRNED   62

IL-17F   PNRYPSEVVQ AQCRNLGCIN A..QGKEDIS MNSVPI.QQE TLVVRRKHQG  106
         : ::::     : :: ::::: :    :   :  :::::: :::  :: ::
IL-17A   PERYPSVIWE AKCRHLGCIN A..DGNVDYH MNSVPI.QQE ILVLRREPPH  109

*
IL-17F   CSV....... ....SFQLEK VL..VTVGCT CVTPVIHHVG ...         133
         :              :: :::  :   : :::: ::::   :::
IL-17A   CPN....... ....SFRLEK IL..VSVGCT CVTPIVHHVA ...         136
```

Biligand PCCs were made for IL-17F that bound at two distinct epitopes while monoligand PCs were made for IL-17A. The PCC-targeted epitopes L1 and L2 are two epitopes that distinguish IL-17F from IL-17A. These epitopes are not sequence-adjacent, but are proximal within the folded protein structure. The distance between the chemically accessible spots on the PCCs is estimated to be 15 Å. Each of the PCCs exhibit $K_D$ values in the range of 15-70 nM.

Previous efforts have demonstrated that binding affinity enhancement through cooperativity can be achieved by conjoining two binders against a target protein via a chemical linker. (B. Farrow, M. Wong, J. Malette, B. Lai, K. M. Deyle, S. Das, A. Nag, H. D. Agnew, J. R. Heath, Angew. Chem. 2015, 127, 7220-7225; Angew. Chem. Int. Ed. 2015, 54, 7114-7119). The length of the linker should correspond to distance between the first and second epitopes. To generate a superior capture agent against IL-17F, linkers comprising one or more repeat units of ethylene glycol were utilized to conjoin the two monocyclic peptides, one against the N-terminal portion of Epitope1 and one against Epitope2. This series of biligands was then tested to determine the ideal linker length between the two epitopes.

To adequately investigate the estimated distance between the two epitopes, biligand candidates were synthesized with PEG linkers ranging from ~4.4 to ~26.4 Å in length to covalently join two macrocycles. The linker connecting the two macrocycles was a single PEGylated amino acid. The general structure of biligands comprising $L_F1$ (SEQ ID NO:9) and $L_F2$ (SEQ ID NO:28) (X=biotin-PEG3) is shown below.

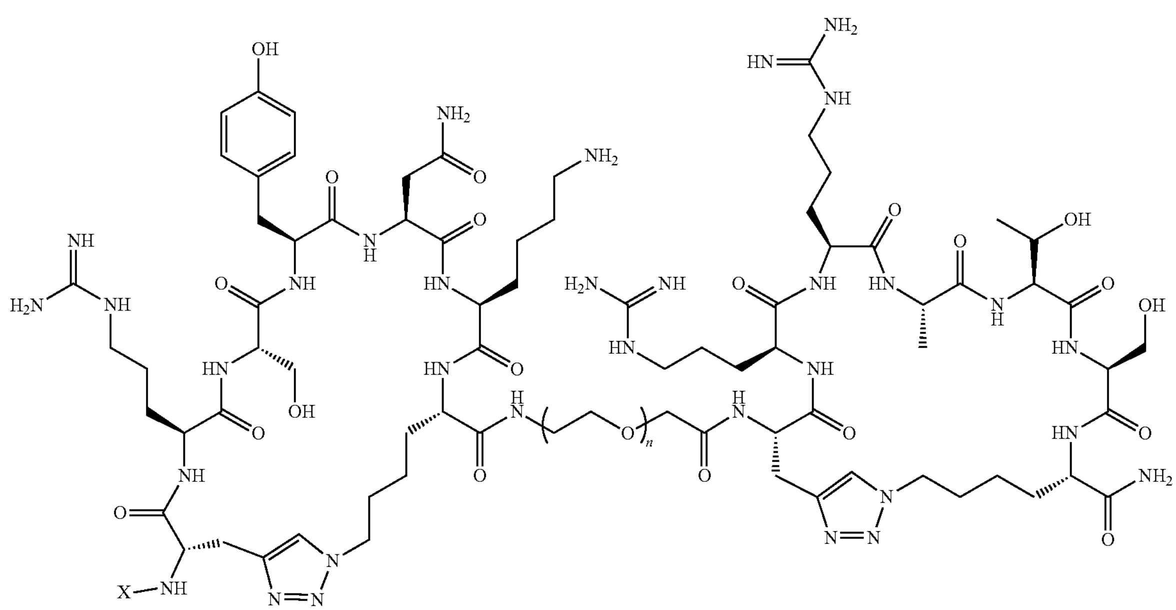

n = 1, 2, 3, 4, 5

The PCCs Cy(RRATS) (SEQ ID NO:9) (targeted to IL-17F Epitope1) and Cy(RSYNK) (SEQ ID NO:28) (targeted to IL-17F Epitope2) were built with chemical handles for further elaboration. Cy(RSYNK) (SEQ ID NO:28) was prioritized based on its high affinity for IL-17F ($K_D$=15 nM). The distance between those chemical handles, when the PCCs are bound to IL-17F, is an estimated 15 Å. This predicts that an optimized linker connecting the two PCCs will have a length near 15 Å. That prediction was validated by testing polyethylene glycol (PEG) oligomer-based linkers of varying lengths for binding to His-tagged IL-17F human recombinant protein. Specifically, biligands of the form Biotin-$PEG_3$-Cy(RSYNK)(SEQ ID NO:28)-$PEG_x$-Cy(RRATS) (SEQ ID NO:9) (x=1 to 5) were tested. When the two PCCs are covalently linked to each other by using the PEG oligomer of length closest to 15 Å, the resultant biligand Cy(RSYNK)(SEQ ID NO:28)-$PEG_3$-Cy(RRATS) (SEQ ID NO:9) exhibits a $K_D$ value of 246 pM against IL-17F. This represents a>100-fold improvement in affinity relative to the individual PCC macrocyclic ligands. Shorter or longer linkers yield biligand affinities ($EC_{50}$=4-8 nM) that, while improved over either of the monoligands, are about ~10-fold below that of the optimal linker. Specifically, a linker of length closest to 15 Å ($PEG_3$) yields the best binder (by ~10-fold). The bivalent interaction of Biotin-$PEG_3$-Cy(RSYNK)(SEQ ID NO:28)-$PEG_3$-Cy(RRATS) (SEQ ID NO:9) is at least 16 times stronger than the other biligands. A similar binding affinity for Biotin-$PEG_3$-Cy(RSYNK)(SEQ ID NO:28)-$PEG_3$-Cy(RRATS) (SEQ ID NO:9) ($K_D$=252±13 pM) was achieved in solution by fluorescence polarization.

Binding specificity experiments (point ELISAs) of Biotin-$PEG_3$-Cy(RSYNK) (SEQ ID NO:28)-$PEG_3$-Cy(RRATS) (SEQ ID NO:9) against recombinant human IL-17F and IL-17A proteins showed 4:1 selectivity for IL-17F. Contacting surface-immobilized Biotin-$PEG_3$-Cy(RSYNK)(SEQ ID NO:28)-$PEG_3$-Cy(RRATS) (SEQ ID NO:9) with IL-17F protein in a background of human serum showed no reduction in binding efficiency in 10% (v/v) serum. Binding to IL-17F in 25% (v/v) serum is also detectable. These results suggest that the selectivity of the biligand is directly related to the selectivity of the constituent macrocycles.

Structures of the biligand candidates Biotin-$PEG_3$-Cy(RSYNK)(SEQ ID NO:28)-$PEG_x$-Cy(RRATS) (SEQ ID NO:9) with PEG linkers ranging from 8.8 to 26.4 Å (x=1 to 5) to join the two macrocycles are shown below.

Biotin-$PEG_3$-Cy(RSYNK)(SEQ ID NO:28)-$PEG_1$-Cy(RRATS)(SEQ ID NO:9) ($PEG_1$=8.8 Å). This ligand is appended with an N-terminal Biotin-$PEG_3$ label. MALDI-TOF MS (m/z): calcd. for $C_{94}H_{154}N_{36}O_{27}S$ (M+H) 2252.15; found 2252.53.

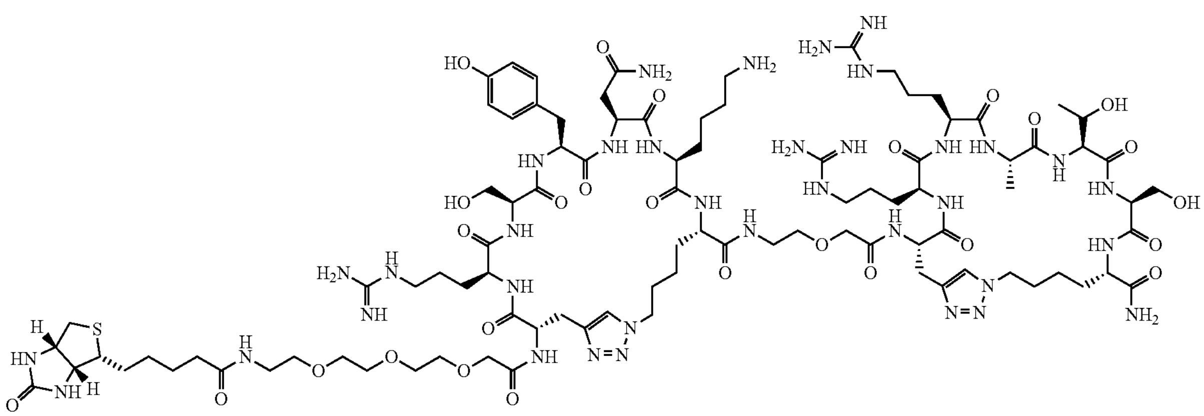

Chemical Formula: $C_{94}H_{154}N_{36}O_{27}S$
Exact Mass: 2251.15
Molecular Weight: 2252.52

Biotin-$PEG_3$-Cy(RSYNK)(SEQ ID NO:28)-$PEG_2$-Cy(RRATS) (SEQ ID NO:9) ($PEG_2$=13.2 Å). This ligand is appended with an N-terminal Biotin-$PEG_3$ label. MALDI-TOF MS (m/z): calcd. for $C_{96}H_{158}N_{36}O_{28}S$ (M+H) 2296.18; found 2296.61.

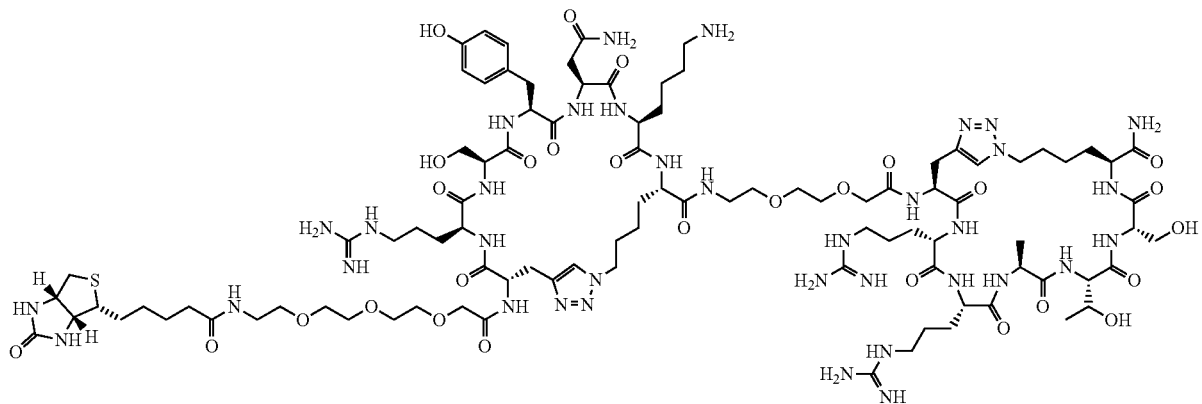

Chemical Formula: $C_{96}H_{158}N_{36}O_{28}S$
Exact Mass: 2295.18
Molecular Weight: 2296.57

Biotin-PEG$_3$-Cy(RSYNK)(SEQ ID NO:28)-PEG$_3$-Cy(RRATS) (SEQ ID NO:9) (PEG$_3$=17.6 Å). This ligand is appended with an N-terminal Biotin-PEG$_3$ label. MALDI-TOF MS (m/z): calcd. for $C_{98}H^{162}N_{36}O_{29}S$ (M+H) 2340.20; found 2340.26.

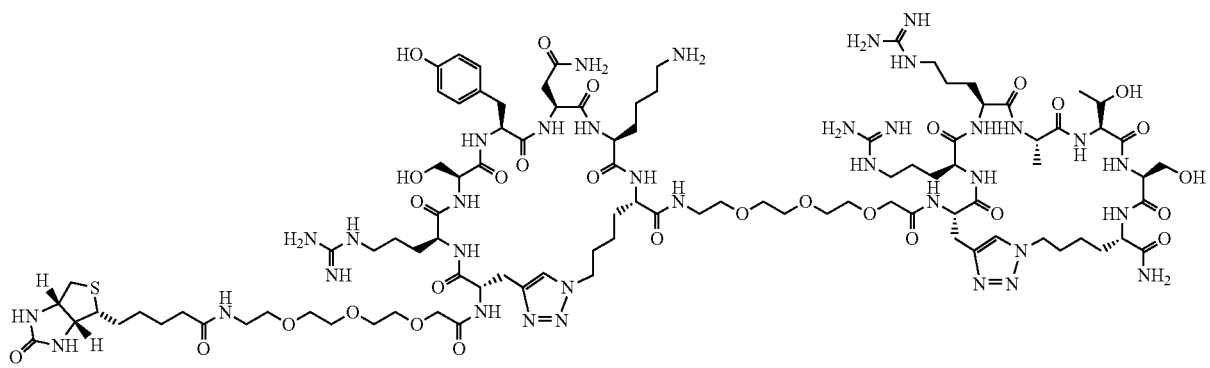

Chemical Formula: $C_{98}H_{162}N_{36}O_{29}S$
Exact Mass: 2339.20
Molecular Weight: 2340.62

Biotin-PEG$_3$-Cy(RSYNK)(SEQ ID NO:28)-PEG$_4$-Cy(RRATS) (SEQ ID NO:9) (PEG$_4$=22 Å). This ligand is appended with an N-terminal Biotin-PEG$_3$ label. MALDI-TOF MS (m/z): calcd. for $C_{100}H_{166}N_{36}O_{30}S$ (M+H) 2384.23; found 2384.24.

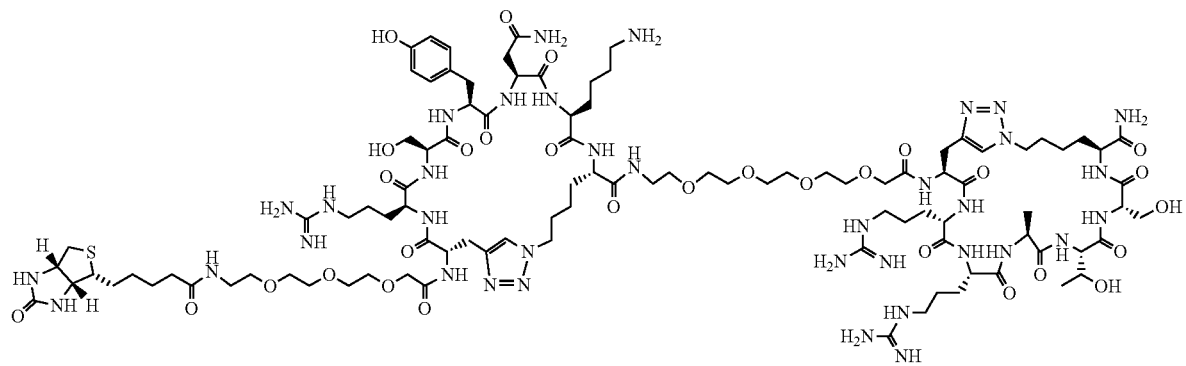

Chemical Formula: $C_{100}H_{166}N_{36}O_{30}S$
Exact Mass: 2383.23
Molecular Weight: 2384.68

Biotin-PEG$_3$-Cy(RSYNK)(SEQ ID NO:28)-PEG$_3$-Cy(RRATS) (SEQ ID NO:9) (PEG$_3$=26.4 Å). This ligand is appended with an N-terminal Biotin-PEG$_3$ label. MALDI-TOF MS (m/z): calcd. for $C_{102}H_{170}N_{36}O_{31}S$ (M+H) 2428.26; found 2428.98.

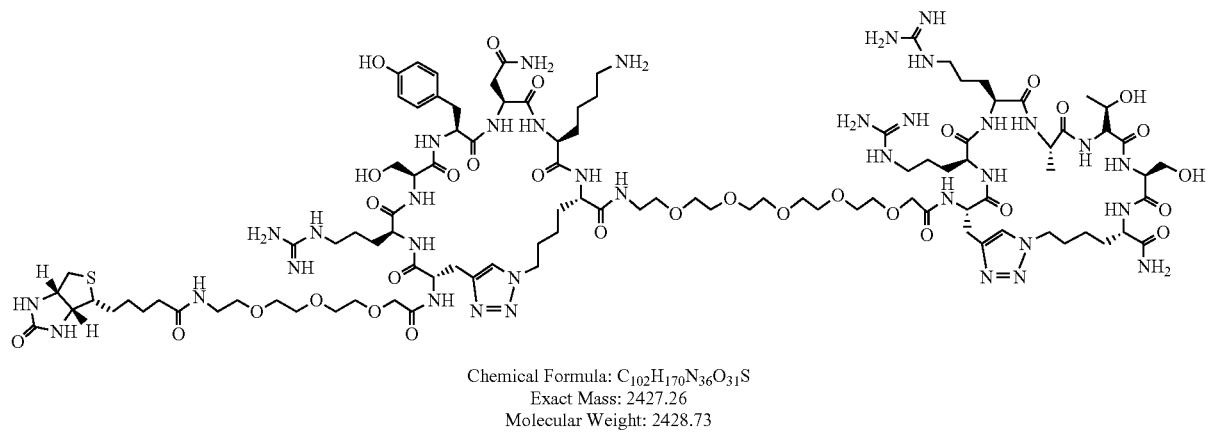 [SMILES: C[C@@H]1NC(=O)[C@H](CCCNC(=N)N)NC(=O)[C@H](CCCNC(=N)N)NC(=O)[C@@H](NC(=O)COCCOCCOCCOCCOCCNC(=O)[C@@H]2CCCCn3cc(nn3)C[C@H](NC(=O)COCCOCCOCCNC(=O)CCCC[C@H]3SC[C@H]4NC(=O)N[C@H]43)C(=O)N[C@@H](CCCNC(=N)N)C(=O)N[C@@H](CO)C(=O)N[C@@H](Cc3ccc(O)cc3)C(=O)N[C@@H](CC(N)=O)C(=O)N[C@@H](CCCCN)C(=O)N2)Cc2cn(nn2)CCCC[C@@H](C(N)=O)NC(=O)[C@H](CO)NC(=O)C([C@@H](C)O)NC1=O]

Chemical Formula: $C_{102}H_{170}N_{36}O_{31}S$
Exact Mass: 2427.26
Molecular Weight: 2428.73

The steps that were used in the synthesis of biligands are illustrated below, illustrated by the solid-phase synthesis of Biotin-PEG$_3$-Cy(RSYNK)(SEQ ID NO:28)-PEG$_3$-Cy(RRATS) (SEQ ID NO:9). Amino acids are shown in one-letter code, with L-amino acids in uppercase and D-amino acids in lowercase. Reagents and conditions: (a) standard Fmoc/HBTU chemistry; (b) copper(I) iodide (1.5 eq.) and L-ascorbic acid (5 eq.) in 4:1 NMP:piperidine, overnight; (c) 5% (w/v) sodium diethyldithiocarbamate trihydrate and 5% (v/v) DIEA in NMP for 5 min, followed by thorough washes with NMP; (d) Fmoc-NH-PEG3-CH2COOH (2 eq.), HATU (1.9 eq.), DIEA (5 eq.), 2 h; (e) standard Fmoc/HBTU chemistry; (f) copper(I) iodide (1.5 eq.) and L-ascorbic acid (5 eq.) in 4:1 NMP:piperidine, overnight; (g) 5% (w/v) sodium diethyldithiocarbamate trihydrate and 5% (v/v) DIEA in NMP for 5 min, followed by thorough washes with NMP; (h) TFA/H2O/TIS/DODT (92.5/2.5/2.5/2.5) for 2 h, followed by ether precipitation.

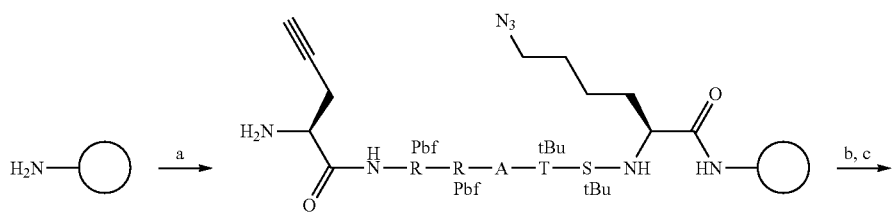

-continued
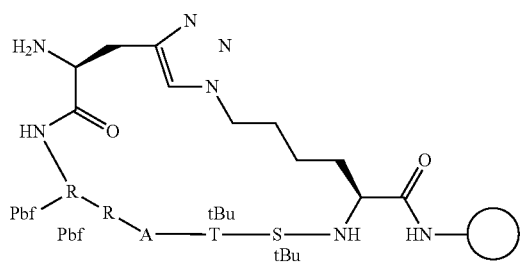
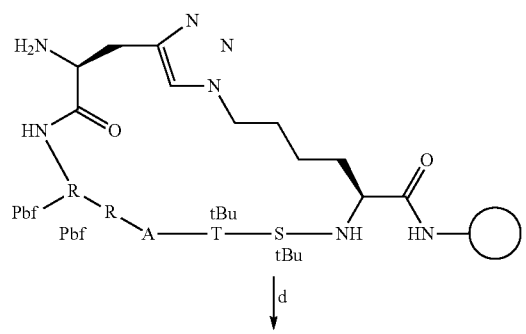
↓d
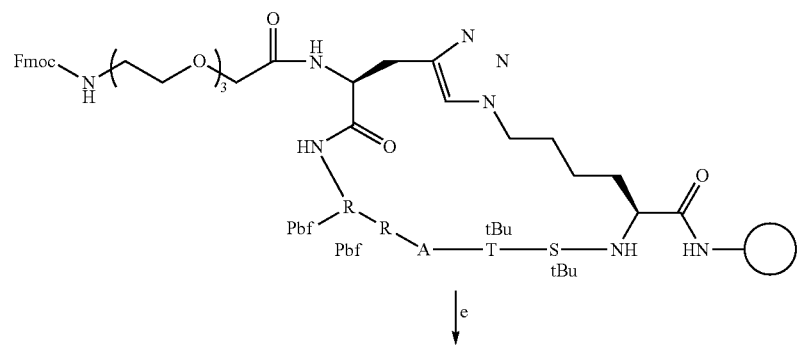
↓e
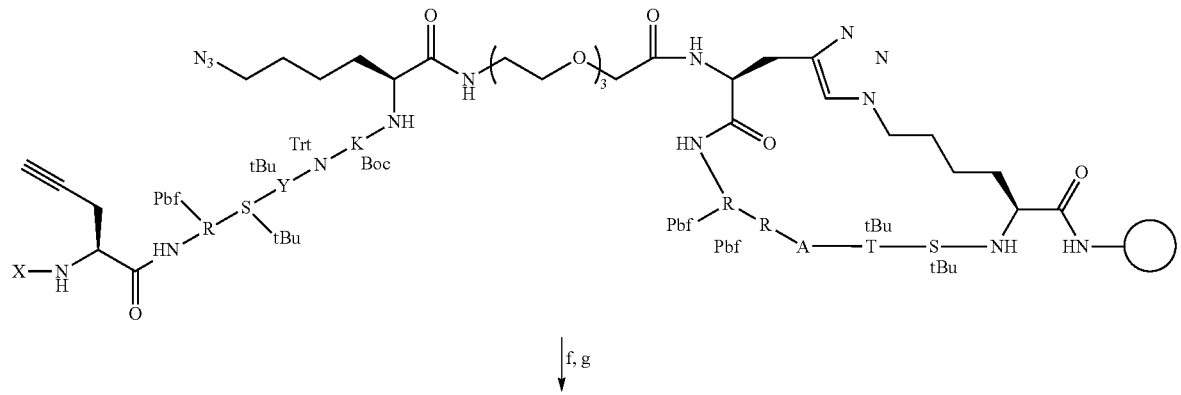
↓f, g

-continued

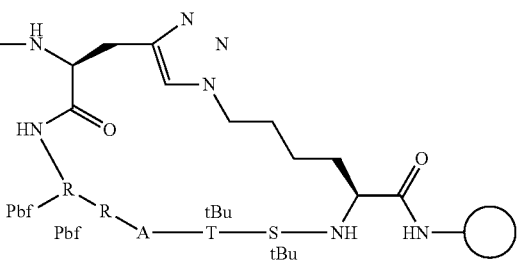

↓ h

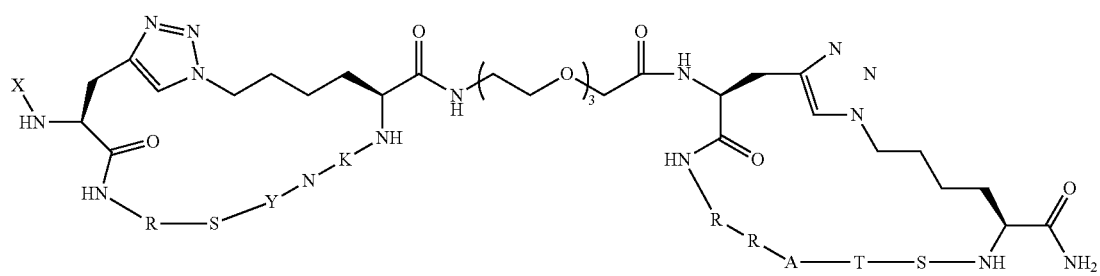

In in vitro assays, X is

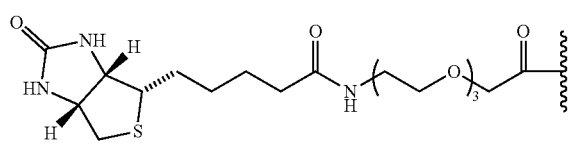

Example 10

Linkage of the Two Ligands Using Best Available Knowledge, Resulting in a Biligand with Improved Affinity Over the Individual Ligands Biligand binders to IL-17F with linkers that are shorter ($PEG_1$, $PEG_2$) or longer ($PEG_4$, $PEG_5$) than 15 Å exhibit $K_D$ values of 1-4 nM against IL-17F. These values represent a 5- to 25-fold improvement in affinity relative to the individual PCC macrocyclic ligands.

Plasmodium falciparum Histidine Rich Protein-2 (Pf.HRP-2) is an unstructured protein, but has many epitopes that repeat throughout the structure. A series of PCCs were developed against various Pf.HRP-2 epitopes. The sequence map of Pf.HRP-2 (SEQ ID NO:42) is shown below with repeats highlighted.

MVSFSKNKVLSAAVFASVLLLDNNNSAFNNNLCSKNAKGLNLNKRLLHET
QAHVDDAHHAHHVADAHHAHHAADAHHAHHAADAHHAHHAADAHHAHHAAD
AHHAHHAAYAHHAHHAADAHHAHHASDAHHAADAHHAAYAHHAHHAADAHH
AHHASDAHHAADAHHAAYAHHAHHAADAHHAADAHHATDAHHAHHAADAHH
ATDAHHAADAHHATDAHHAADAHHAADAHHATDAHHAADAHHATDAHHAAD
AHHAADAHHATDAHHAHHAADAHHAAAHHATDAHHATDAHHAAAHHEAATH
CLRH

The cyclic peptide, Cy(YKYYR) (SEQ ID NO:29) was developed against the AHHAHHAAD (SEQ ID NO:35) epitope. Cy(YKYYR) (SEQ ID NO:29) exhibits a $EC_{50}$ of 220 nM. Because of the number of epitope repeats, a cooperative binder was sought by simply linking two Cy(YKYYR) (SEQ ID NO:29) PCCs together with about a 1.5 nm long linker. The resultant linked biligand exhibited an $EC_{50}$ of 20 nM (20.8±1.3 nM). Chemical formula: $C_{130}H_{188}N_{34}O_{30}S$. Exact mass: 2737.40. Molecular weight: 2739.20.

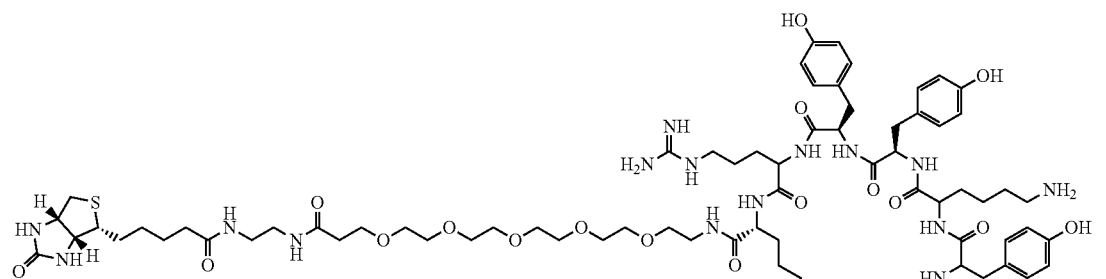

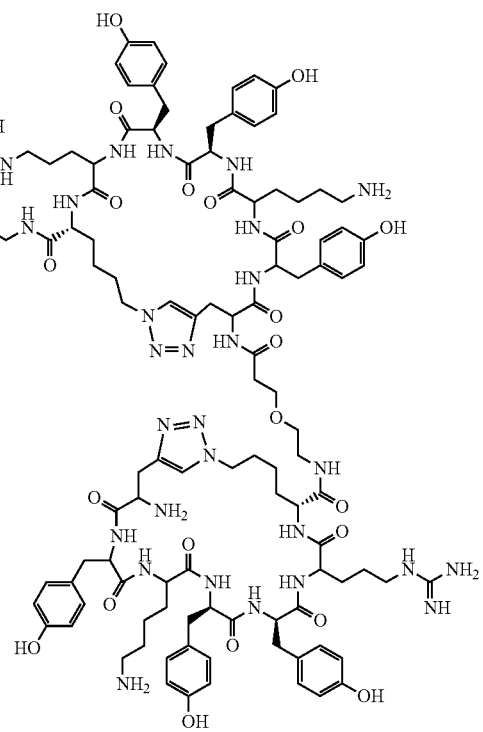

The cyclic PCC with variable sequence GWNVDL (SEQ ID NO:30) was developed against the C-terminal sequence of Pf.HRP-2 (AHHATDAHHAAAHHEAATHCL) (SEQ ID NO:36) ($EC_{50}$=50 nM). A linker between this PCC and cyclic YKYYR (SEQ ID NO:29) (see above; $EC_{50}$=220 nM) was developed by screening a 10,000 element library of variable length linker molecules. The resultant biligand exhibited an $EC_{50}$ of 540 pM, which is a 100-fold improvement over the better of the two ligand components. The structure of this biligand (cy(YKYYR)(SEQ ID NO:29)-linker-cy(GWNVDL) (SEQ ID NO:30)) is shown below. Chemical formula: $C_{150}H_{226}N_{44}O_{32}S$. Exact mass: 3187.71. Molecular weight: 3189.74.

Example 11

Affinity and Specificity of Anti-IL-17F and Anti-IL-17A Macrocycles

The macrocycles of Tables 1-3 were re-synthesized and then tested for affinity against recombinant His-tagged IL-17F or IL-17A protein. The structure of $L_F1$ (SEQ ID NO:9), the lead macrocycle for IL-17F Epitope 1 is shown below (X=$PEG_3$-biotin). MALDI-TOF MS (m/z): calcd. for $C_{53}H_{94}N_{20}O_{14}S$ (M+H) 1269.70; found 1269.95.

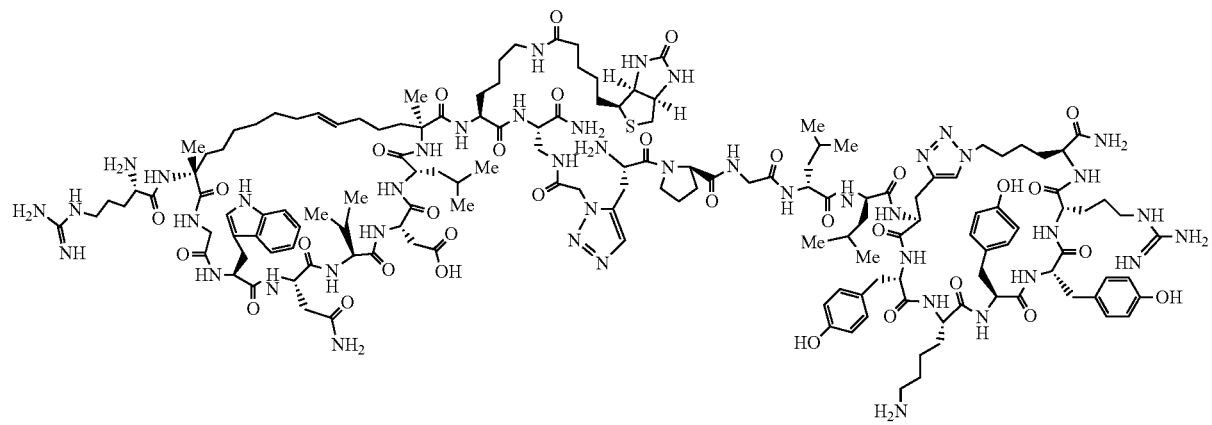

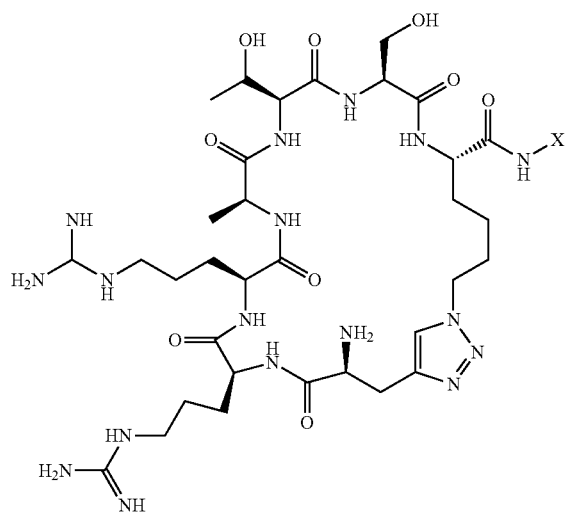

The structure of $L_F2$ (SEQ ID NO: 28), the lead macrocycle Epitope2, is shown below (X=PEG$_3$-biotin). MALDI-TOF MS (m/z): calcd. for $C_{57}H_{91}N_{19}O_{16}S$ (M+H) 1330.66; found 1331.06.

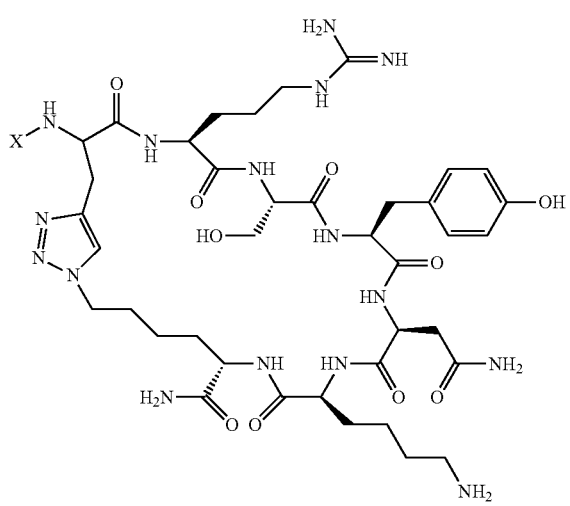

The bonding affinities of the macrocycles were tested in solution by titrating the recombinant human IL-17F protein against fluorescein 5-isothiocyanate (5-FITC)-tagged macrocycles by fluorescence polarization. These assays yielded $K_D=50\pm15$ nM for $L_F1$ and $K_D=28\pm9$ nM for $L_F2$. Similar binding affinities for surface-immobilized $L_F1$ ($EC_{50}=66\pm9$ nM) and $L_F2$ (EC50=15±5 nM) were achieved by enzyme-linked immunosorbent assay (ELISA). $L_F2$ (SEQ ID NO: 28) demonstrated similar binding affinity ($EC_{50}=15\pm5$ nM) to an anti-IL-17F monoclonal antibody ($EC_{50}=20.8\pm0.2$ nM), while $L_F1$ (SEQ ID NO:9) showed $EC_{50}=66\pm9$ nM. The structure of $L_A3$ (SEQ ID NO:44), the lead macrocycle developed against IL-17A Epitope3, is shown below (X=PEG$_3$-biotin). MALDI-TOF MS (m/z): calcd. for $C_{62}H_{98}N_{22}O_{13}S$ (M+H) 1391.74; found 1392.36.

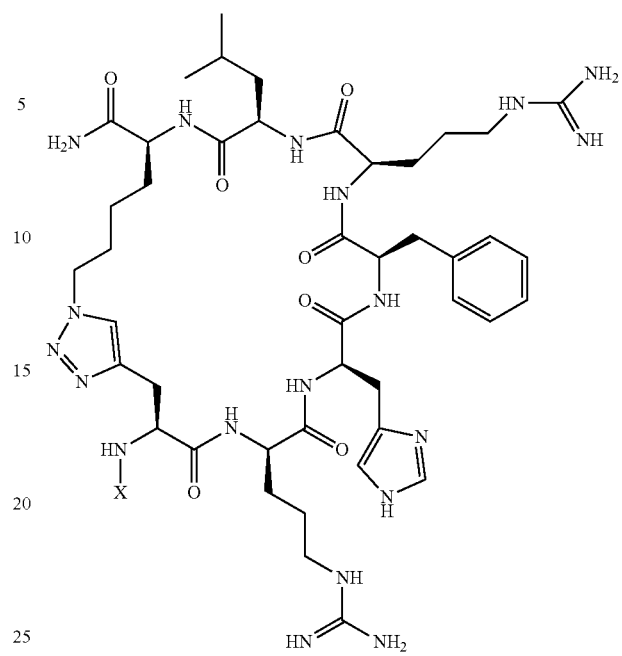

The affinity of macrocycle $L_A3$ (SEQ ID NO:44) against recombinant human IL-17A protein was determined by ELISA. Its binding curve demonstrates an $EC_{50}$ (4.5±0.4 nM) similar to that of the anti-IL-17A monoclonal antibody (4.3±1.6 nM).

Binding specificity experiments were performed with recombinant human IL-17F and IL-17A proteins. Surface-immobilized macrocycles were contacted with IL-17F, IL-17A, or no protein. Despite the high sequence identity between the IL-17F and IL-17A proteins, $L_F1$ (SEQ ID NO:9) and $L_F2$ (SEQ ID NO: 28) preferentially bound to IL-17F. $L_F1$ (SEQ ID NO:9) showed 10:1 selectivity for IL-17F, while $L_F2$ (SEQ ID NO: 28) showed 4:1 selectivity. On the other hand, $L_A3$ (SEQ ID NO:44) preferentially bound to IL-17A, with 3:1 selectivity for IL-17A. These results confirm the selective nature of the epitope-targeting strategy, and demonstrate that the ligands bind to the full-length protein. Similarly assayed anti-IL-17F and anti-IL-17A monoclonal antibodies showed greater than 100:1 selectivity.

Target binding in biologically complex samples was interrogated by contacting surface-immobilized macrocycles with IL-17F protein in a background of human serum. For $L_F1$, this assay showed no reduction in IL-17F binding efficiency in increasing amounts of serum up to 10% (v/v). $L_F2$ demonstrated binding to IL-17F in 10% (v/v) serum with reduced intensity suggesting comparatively more off-target interactions with human serum proteins.

Example 12

Alanine Scanning of Anti-IL-17F Macrocycles

To thoroughly address the specificity of the developed macrocycles, derivatives of $L_F1$ and $L_F2$ were synthesized by systematically replacing each amino acid with alanine. The resulting nine single-alanine mutants of $L_F1$ and $L_F2$ were assayed for binding to recombinant human IL-17F protein by ELISA. Results are presented as the ratio of binding affinity ($EC_{50}$) of the mutant to that of the unmodified peptide. Of the four single-alanine variants of $L_F1$, two (R1A, R2A) caused a significant impairment of IL-17F binding, indicating that the Arg1 and Arg2 are critical for binding. The binding affinities of the other two mutants (T4A, S5A) were perturbed to a smaller extent. Of the five single-alanine variants of $L_F2$, Ser2 is the most critical for IL-17F binding, followed by Arg1, Lys5, and Asn4. Only the alanine substitution for Tyr3 caused minimal change to the binding affinity. These results show that most amino acids in $L_F1$ and $L_F2$ are important for IL-17F binding. Double-alanine substitutions of $L_F1$ and $L_F2$ were also constructed and assayed, and showed equivalent or larger perturbation of binding, independently validating the results of the single-alanine mutants. The standard Gibbs free energy change ($\Delta G° = RT\ln K_D$) calculated for the binding of macrocycles $L_F1$ and $L_F2$ to IL-17F at 25° C. is −9.9 and −10.3 kcal/mol, respectively. Each amino acid substitution to alanine accounts for −1 kcal/mol or less in this calculation or, in other words, the binding of each single macrocycle to IL-17F has significant specific and non-specific contributions.

Example 13

Orientation of Macrocycle Binding to IL-17F

In anticipation of forming a biligand with $L_F2$ (SEQ ID NO: 28), it was important to gain insight on whether $L_F1$ (SEQ ID NO:9) preferentially binds to the N- or C-terminus of Epitope1. Therefore, two His-tagged IL-17F epitopes were generated, scrambling the sequence either N-terminal or C-terminal to the location of the azide click handle. His6 assay handle and C48S substitution instead of a click handle. The scrambled amino acids are shown in italics. MALDI-TOF MS (m/z): calculated for $C_{116}H_{163}N_{37}O_{31}$ (M+H) 2571.23; found 2571.57.

NO:9) (SynEp1 (N-terminus)) and $L_F2$ (SEQ ID NO: 28) (SynEp2) were located with guidance from the IL-17F crystal structure (S. G. Hymowitz, E. H. Filvaroff, J. Yin, J. Lee, L. Cai, P. Risser, M. Maruoka, W. Mao, J. Foster, R. F. Kelley, G. Pan, A. L. Gurney, A. M. de Vos, M. A. Starovasnik, EMBO J. 2001, 20, 5332-5341). The distance bridging $L_F1$ (SEQ ID NO:9) and $L_F2$ (SEQ ID NO: 28) in a monomeric IL-17F is estimated to be 18 Å, as determined in PyMOL (version 1.5, Schrödinger, LLC).

Example 14

Stability of Anti-IL-17F Biligand

Bi-$L_F$ Biotin-PEG$_3$-Cy(RSYNK)(SEQ ID NO:28)-PEG$_3$-Cy(RRATS) (SEQ ID NO:9) was incubated with trypsin to study its susceptibility to protease digestion. Trypsin can cleave peptides and proteins on the C-terminal side of lysine and arginine L-amino acids. For this assay, test compounds were treated with trypsin protease (1 h at 37° C.) or left untreated as a control. In an Eppendorf tube, 4 µL of trypsin solution (10 µg/mL in 1 mM HCl) and 80 pmol of biligand were added to TBS for a final volume of 20 µL. The solution was incubated for 1 h at 37° C., and then further diluted with 80 µL TBS. 50 µL of each sample was injected into a Dionex Ultimate 3000 series analytical HPLC fitted with a Phenomenex Luna-C18 column, and eluted with a gradient of 10%-62% acetonitrile in 0.1% TFA (v/v) in water over 45 min. The samples were monitored at 215 nm.

The analytical HPLC data for Bi-$L_F$ Biotin-PEG$_3$-Cy (RSYNK)(SEQ ID NO:28)-PEG$_3$-Cy(RRATS) (SEQ ID NO:9) before and after treatment with trypsin was compared. The biligand peak disappeared and three new peaks were observed with earlier retention times. The smaller fragments suggested trypsin digestion indeed occurred, possibly as trypsin cleaves the C-terminal side of L-lysine and L-arginine.

Sequence: His$_6$-PEG$_3$-*SQFEKFP*SPPVPGGS (SEQ ID NO: 41)

Sequence: His$_6$-PEG$_3$-FFQKPESS*PVSPGPG* (SEQ ID NO: 40)

Point ELISAs were then conducted to determine the binding between $L_F1$ (SEQ ID NO:9) and the His-tagged peptides with the scrambled N- or C-terminus. $L_F1$ (SEQ ID NO:9) was shown to preferentially bind to the N-terminal portion of Epitope1. The binding epitopes of $L_F1$ (SEQ ID To improve the resistance to trypsin activity, two biligand variants were synthesized. Bi-$L_S$ Biotin-PEG$_3$-Cy(rSYNk) (SEQ ID NO:63)-PEG$_3$-Cy(rrATS) (SEQ ID NO:47) contains strategic substitution of the trypsin-sensitive amino acids with D-arginine (D-Arg) and D-lysine (D-Lys). The structure of Bi-L$_S$ Biotin-PEG$_3$-Cy(rSYNk) (SEQ ID NO:63)-PEG$_3$-Cy(rrATS) (SEQ ID NO:47) is shown below. Analytical HPLC showed their susceptibility to trypsin digestion. X=biotin-PEG$_3$.

A sandwich ELISA was performed to compare the binding affinities of the biligand variants (EC$_{50}$=750-770 pM). The slightly weaker binding of Bi-L$_S$ Biotin-PEG$_3$-Cy(rSYNk)(SEQ ID NO:63)-PEG$_3$-Cy(rrATS)(SEQ ID

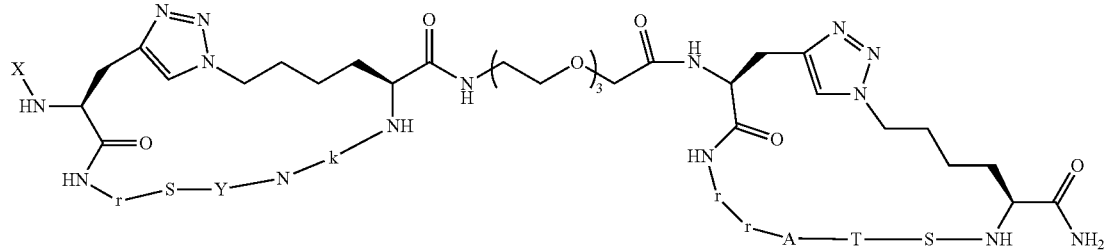

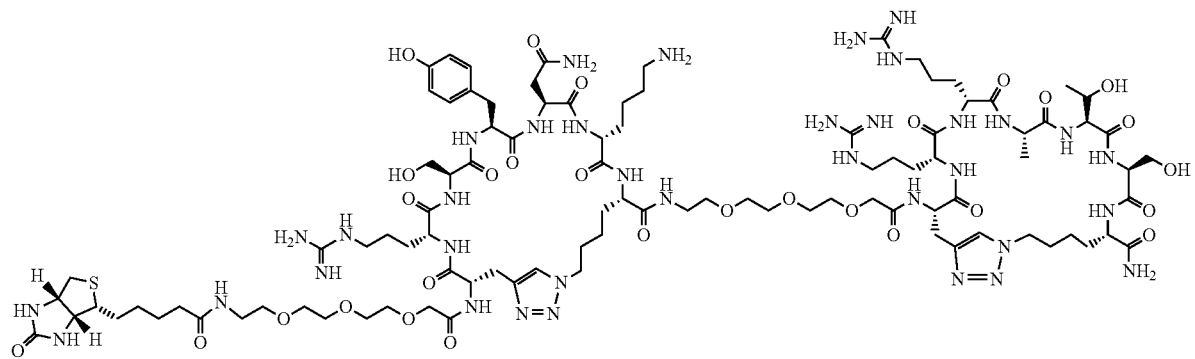

The structure of Bi-L$_G$ Biotin-PEG$_3$-Cy(rsynk)(SEQ ID NO:76)-PEG$_3$-Cy(rrats) (SEQ ID NO:49) is shown below. Bi-L$_G$ Biotin-PEG$_3$-Cy(rsynk)(SEQ ID NO:76)-PEG$_3$-Cy(rrats) (SEQ ID NO:49) modifies all the L-amino acids into their D-amino acid counterparts. Analytical HPLC showed their resistance to trypsin digestion. X=biotin-PEG$_3$.

NO:47) and Bi-L$_G$ Biotin-PEG$_3$-Cy(rsynk)(SEQ ID NO:76)-PEG$_3$-Cy(rrats)(SEQ ID NO:49) to IL-17F is compensated by a significantly improved biological stability. The analytical HPLC data show that Bi-L$_S$ Biotin-PEG$_3$-Cy(rSYNk)(SEQ ID NO:63)-PEG$_3$-Cy(rrATS)(SEQ ID NO:47) and Bi-L$_G$ Biotin-PEG$_3$-Cy(rsynk)(SEQ ID

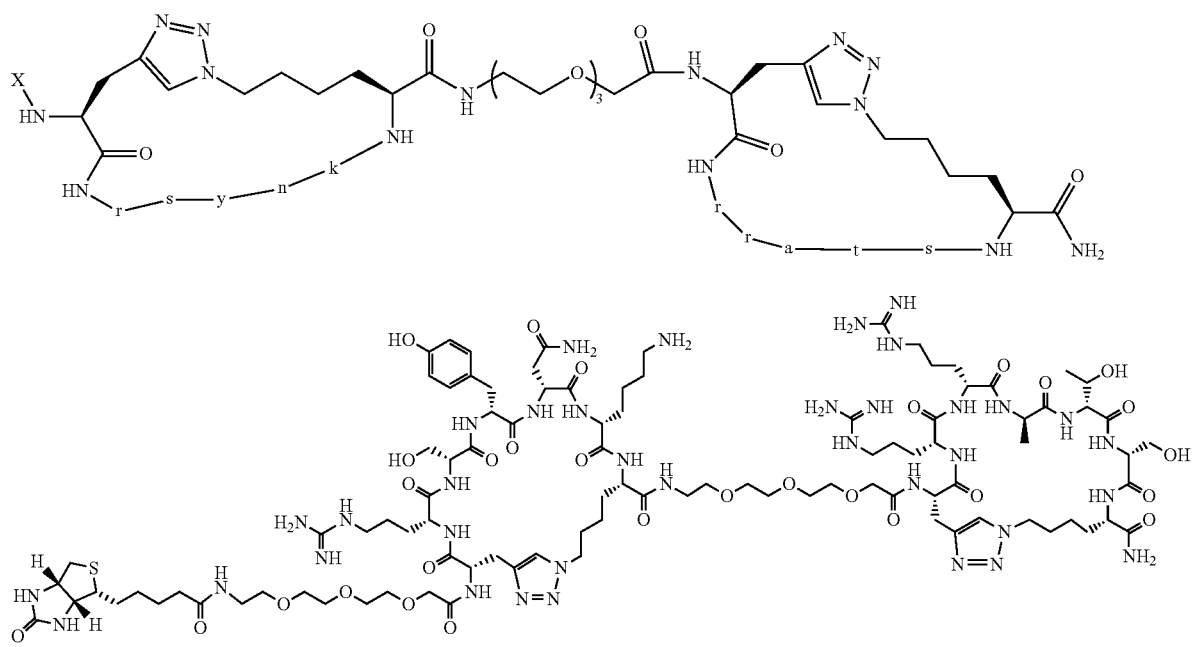

NO:76)-PEG$_3$-Cy(rrats)(SEQ ID NO:49) are resistant to trypsin digestion. This suggests that trypsin stability can be engineered by replacing L-Arg and L-Lys with their D-amino acid counterparts.

Example 15

Alanine Scanning of Anti-IL-17F Macrocycles

To thoroughly address the specificity of the developed macrocycles, derivatives of $L_F1$ and $L_F2$ were synthesized by systematically replacing each amino acid with alanine. The resulting nine single-alanine mutants of $L_F1$ and $L_F2$ were assayed for binding to recombinant human IL-17F protein by ELISA. Results calculated as the ratio of binding affinity ($EC_{50}$) of the mutant to that of the unmodified peptide. Of the four single-alanine variants of $L_F1$, two (R1A, R2A) caused a significant impairment of IL-17F binding, indicating that the Arg1 and Arg2 are critical for binding. The binding affinities of the other two mutants (T4A, S5A) were perturbed to a smaller extent. Of the five single-alanine variants of $L_F2$, Ser2 is the most critical for IL-17F binding, followed by Arg1, Lys5, and Asn4. Only the alanine substitution for Tyr3 caused minimal change to the binding affinity. These results show that most amino acids in $L_F1$ and $L_F2$ are important for IL-17F binding. Double-alanine substitutions of $L_F1$ and $L_F2$ were also constructed and assayed, and showed equivalent or larger perturbation of binding, independently validating the results of the single-alanine mutants.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

Throughout this specification the word "comprise," or variations such as "comprises" or "comprising," will be understood to imply the inclusion of a stated element, integer or step, or group of elements, integers or steps, but not the exclusion of any other element, integer or step, or group of elements, integers or steps.

It must be noted that as used herein and in the appended claims, the singular forms "a", "an", and "the" include plural reference unless the context clearly dictates otherwise. Thus, for example, reference to "a capture agent" includes a plurality of such capture agents, reference to "the capture agents" is a reference to one or more capture agents and equivalents thereof known to those skilled in the art, and so forth.

Throughout the description and claims of this specification, the word "comprise" and variations of the word, such as "comprising" and "comprises," means "including but not limited to," and is not intended to exclude, for example, other additives, components, integers or steps.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. It should be understood that all of the individual values and sub-ranges of values contained within an explicitly disclosed range are also specifically contemplated and should be considered disclosed unless the context specifically indicates otherwise. Finally, it should be understood that all ranges refer both to the recited range as a range and as a collection of individual numbers from and including the first endpoint to and including the second endpoint. In the latter case, it should be understood that any of the individual numbers can be selected as one form of the quantity, value, or feature to which the range refers. In this way, a range describes a set of numbers or values from and including the first endpoint to and including the second endpoint from which a single member of the set (i.e. a single number) can be selected as the quantity, value, or feature to which the range refers. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Although the description of materials, compositions, components, steps, techniques, etc. may include numerous options and alternatives, this should not be construed as, and is not an admission that, such options and alternatives are equivalent to each other or, in particular, are obvious alternatives. Thus, for example, a list of different ligands does not indicate that the listed ligands are obvious one to the other, nor is it an admission of equivalence or obviousness.

Every ligand or capture agent disclosed herein is intended to be and should be considered to be specifically disclosed herein. Further, every subgroup that can be identified within this disclosure is intended to be and should be considered to be specifically disclosed herein. As a result, it is specifically contemplated that any ligand or capture agent, or subgroup of ligands or capture agents can be either specifically included for or excluded from use or included in or excluded from a list of ligands or capture agents.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a capture agent is disclosed and discussed and a number of modifications that can be made to a number of molecules including the capture agent are discussed, each and every combination and permutation of capture agent and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. Further, each of the materials, compositions, components, etc. contemplated and disclosed as above can also be specifically and independently included or excluded from any group, subgroup, list, set, etc. of such materials. These concepts apply to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Those skilled in the art will recognize, or be able to ascertain using no more than routine experimentation, many equivalents to the specific embodiments of the method and compositions described herein. Such equivalents are intended to be encompassed by the following claims.

We claim:

1. A capture agent for a target, the capture agent comprising two or more ligands covalently linked to each other, wherein the ligands each specifically bind to one of two or more distinct epitopes of the target that are in different locations on the target,
wherein the capture agent comprises a first of the ligands having specific affinity for a first of the epitopes, a second of the ligands having specific affinity for a second of the epitopes, and a linker covalently connecting the first ligand to the second ligand,
wherein the target is IL-17A, IL-17F, or both IL-17A and IL-17F,
wherein the first epitope comprises the amino acid sequence FFQKPES (SEQ ID NO:1) or the amino acid sequence PNSEDKNFPRTVMVNL (SEQ ID NO:43),
wherein the second epitope comprises the amino acid sequence NENQRVS (SEQ ID NO:3) or the amino acid sequence PNSEDKNFPRTVMVNL (SEQ ID NO:43),
wherein the first ligand comprises a first peptide having an amino acid sequence 80-100% identical to an amino acid sequence selected from the group consisting of rhfrl (SEQ ID NO:44), nrfff (SEQ ID NO:45), rkhyh (SEQ ID NO:46), rrATS (SEQ ID NO:47), rrAQS (SEQ ID NO:48), rrats (SEQ ID NO:49), and rraqs (SEQ ID NO:50),
wherein the second ligand comprises a second peptide having an amino acid sequence 80-100% identical to an amino acid sequence selected from the group consisting of KYGEV (SEQ ID NO:11), LYGEV (SEQ ID NO:12), VHKSG (SEQ ID NO:13), VHLSG (SEQ ID NO:14), QKHGP (SEQ ID NO:15), TKHGP (SEQ ID NO:16), QLHGP (SEQ ID NO:17), TLHGP (SEQ ID NO:18), YDLQR (SEQ ID NO:19), YDLTR (SEQ ID NO:20), YDKQR (SEQ ID NO:21), YDKTR (SEQ ID NO:22), KKGWP (SEQ ID NO:23), KLGWP (SEQ ID NO:24), LKGWP (SEQ ID NO:25), LLGWP (SEQ ID NO:26), RSYNL (SEQ ID NO:27), RSYNK (SEQ ID NO:28), kYGEV (SEQ ID NO:51), VHkSG (SEQ ID NO:52), QkHGP (SEQ ID NO:53), TkHGP (SEQ ID NO:54), YDLQr (SEQ ID NO:55), YDLTr (SEQ ID NO:56), YDkQr (SEQ ID NO:57), YDkTr (SEQ ID NO:58), kkGWP (SEQ ID NO:59), kLGWP (SEQ ID NO:60), LkGWP (SEQ ID NO:61), rSYNL (SEQ ID NO:62), rSYNk (SEQ ID NO:63), kygev (SEQ ID NO:64), vhksg (SEQ ID NO:65), qkhgp (SEQ ID NO:66), tkhgp (SEQ ID NO:67), ydlqr (SEQ ID NO:68), ydltr (SEQ ID NO:69), ydkqr (SEQ ID NO:70), ydktr (SEQ ID NO:71), kkgwp (SEQ ID NO:72), klgwp (SEQ ID NO:73), lkgwp (SEQ ID NO:74), rsynl (SEQ ID NO:75), rsynk (SEQ ID NO:76), rhfrl (SEQ ID NO:44), nrfff (SEQ ID NO:45), and rkhyh (SEQ ID NO:46),
wherein the first ligand is cyclic, and wherein the second ligand is cyclic.

2. The capture agent of claim 1, wherein the capture agent specifically binds IL-17F.

3. The capture agent of claim 1, wherein the capture agent is selective for IL-17F over IL-17A.

4. The capture agent of claim 1, wherein the first epitope comprises the amino acid sequence FFQKPESCPPVPGG (SEQ ID NO:2).

5. The capture agent of claim 1, wherein the second epitope comprises the amino acid sequence GIINENQRVS (SEQ ID NO:4).

6. The capture agent of claim 1, wherein the first ligand comprises an amino acid sequence 80-100% identical to an amino acid sequence selected from the group consisting of rrATS (SEQ ID NO:47), rrAQS (SEQ ID NO:48), rrats (SEQ ID NO:49), and rraqs (SEQ ID NO:50).

7. The capture agent of claim 1, wherein the second ligand comprises an amino acid sequence 80-100% identical to an amino acid sequence selected from the group consisting of kYGEV (SEQ ID NO:51), VHkSG (SEQ ID NO:52), QkHGP (SEQ ID NO:53), TkHGP (SEQ ID NO:54), YDLQr (SEQ ID NO:55), YDLTr (SEQ ID NO:56), YDkQr (SEQ ID NO:57), YDkTr (SEQ ID NO:58), kkGWP (SEQ ID NO:59), kLGWP (SEQ ID NO:60), LkGWP (SEQ ID NO:61), rSYNL (SEQ ID NO:62), rSYNk (SEQ ID NO:63), kygev (SEQ ID NO:64)vhksg (SEQ ID NO:65), qkhgp (SEQ ID NO:66), tkhgp (SEQ ID NO:67), ydlqr (SEQ ID NO:68), ydltr (SEQ ID NO:69), ydkqr (SEQ ID NO:70), ydktr (SEQ ID NO:71), kkgwp (SEQ ID NO:72), klgwp (SEQ ID NO:73), lkgwp (SEQ ID NO:74), rsynl (SEQ ID NO:75), and rsynk (SEQ ID NO:76).

8. The capture agent of claim 1, wherein the first ligand comprises the sequence rrats (SEQ ID NO:49) and the second ligand comprises the sequence rsynk (SEQ ID NO:76).

9. The capture agent of claim 1, having a structure selected from the group consisting of:

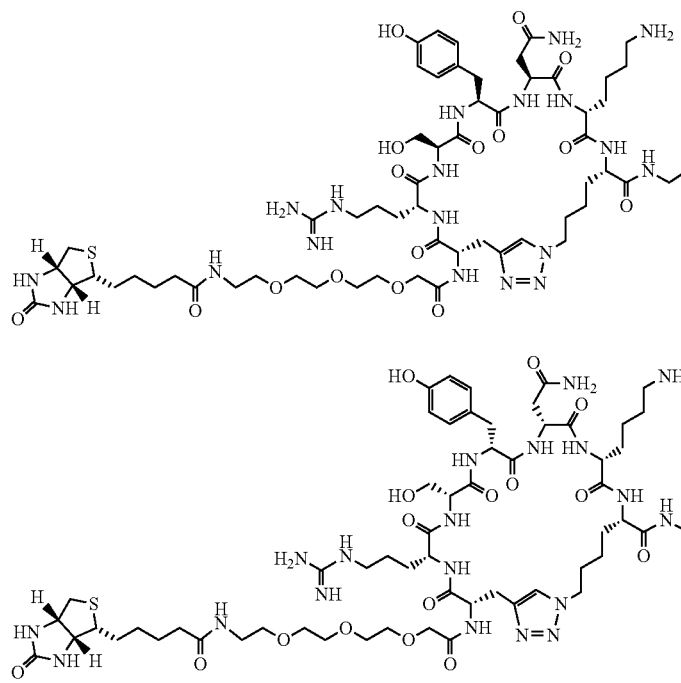
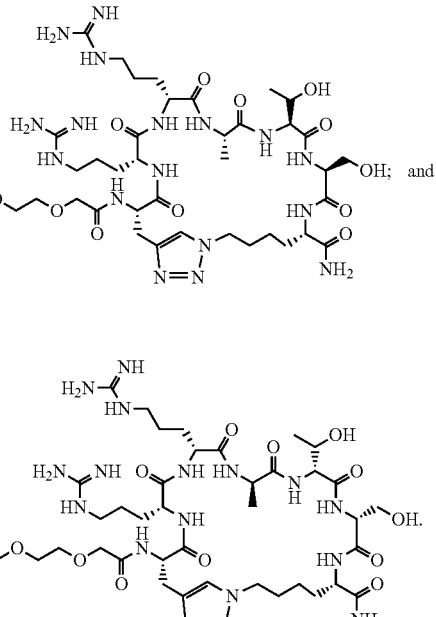

10. The capture agent of claim 1, wherein the first ligand comprises a 1,4-substituted-1,2,3-triazole residue (Tz4) or a 1,5-substituted-1,2,3-triazole residue (Tz5).

11. The capture agent of claim 10, wherein the first ligand comprises a 1,4-substituted-1,2,3-triazole residue (Tz4).

12. The capture agent of claim 10, wherein the first ligand comprises a 1,5-substituted-1,2,3-triazole residue (Tz5).

13. The capture agent of claim 1, wherein the second ligand comprises a 1,4-substituted-1,2,3-triazole residue (Tz4) or a 1,5-substituted-1,2,3-triazole residue (Tz5).

14. The capture agent of claim 13, wherein the second ligand comprises a 1,4-substituted-1,2,3-triazole residue (Tz4).

15. The capture agent of claim 13, wherein the second ligand comprises a 1,5-substituted-1,2,3-triazole residue (Tz5).

16. The capture agent of claim 1, wherein the capture agent is labeled with a detectable moiety.

17. The capture agent of claim 16, wherein the detectable moiety is selected from the group consisting of biotin, copper-DOTA, biotin-PEG3, aminooxyacetate, $^{19}$FB, $^{18}$FB and FITC-PEG3.

18. The capture agent of claim 16, wherein the detectable moiety is selected from the group consisting of $^{64}$Cu DOTA, $^{68}$Ga DOTA, $^{68}$Ga NOTA, $^{18}$F, Al$^{18}$F NOTA, $^{64}$Cu, $^{68}$Ga, $^{89}$Zr, $^{124}$I, $^{86}$Y, $^{94m}$Tc, $^{110m}$In, $^{11}$C and $^{76}$Br.

19. The capture agent of claim 1, wherein the linker is divalent.

20. The capture agent of claim 1, wherein the length of the linker corresponds to distance between the first epitope and the second epitope.

21. The capture agent of claim 1, wherein the length of the linker is ~15 Å.

22. The capture agent of claim 1, wherein the linker comprises PEG$_3$.

23. The capture agent of claim 1, wherein the linker comprises a peptide.

24. The capture agent of claim 23, wherein the peptide comprises glycine.

25. A method for detecting IL-17A, IL-17F, or both IL-17A and IL-17F in a biological sample, the method comprising the steps of:
contacting the biological sample with one or more of the capture agents of claim 16;
allowing the capture agents to bind to the IL-17A, IL-17F or both IL-17A and IL-17F; and
detecting the bound capture agents via the detectable moiety.

26. The capture agent of claim 1, wherein the first epitope comprises the amino acid sequence PNSEDKNF-PRTVMVNL (SEQ ID NO:43).

27. The capture agent of claim 1, wherein the first ligand has structure

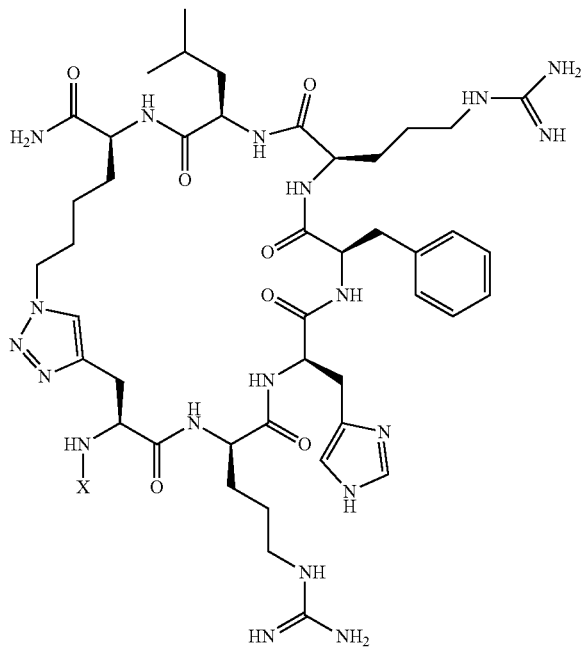

wherein X represents the rest of the capture agent.

28. The capture agent of claim 6, wherein the second ligand comprises an amino acid sequence 80-100% identical to an amino acid sequence selected from the group consisting of kYGEV (SEQ ID NO:51), VHkSG (SEQ ID NO:52), QkHGP (SEQ ID NO:53), TkHGP (SEQ ID NO:54), YDLQr (SEQ ID NO:55), YDLTr (SEQ ID NO:56), YDkQr (SEQ ID NO:57), YDkTr (SEQ ID NO:58), kkGWP (SEQ ID NO:59), kLGWP (SEQ ID NO:60), LkGWP (SEQ ID NO:61), rSYNL (SEQ ID NO:62), rSYNk (SEQ ID NO:63), kygev (SEQ ID NO:64)vhksg (SEQ ID NO:65), qkhgp (SEQ ID NO:66), tkhgp (SEQ ID NO:67), ydlqr (SEQ ID NO:68), ydltr (SEQ ID NO:69), ydkqr (SEQ ID NO:70), ydktr (SEQ ID NO:71), kkgwp (SEQ ID NO:72), klgwp (SEQ ID NO:73), lkgwp (SEQ ID NO:74), rsynl (SEQ ID NO:75), and rsynk (SEQ ID NO:76).

29. The capture agent of claim 6, wherein the second ligand comprises an amino acid sequence 80-100% identical to an amino acid sequence selected from the group consisting of rhfrl (SEQ ID NO:44), nrfff (SEQ ID NO:45), and rkhyh (SEQ ID NO:46).

30. The capture agent of claim 7, wherein the first ligand comprises an amino acid sequence 80-100% identical to an amino acid sequence selected from the group consisting of rhfrl (SEQ ID NO:44), nrfff (SEQ ID NO:45), and rkhyh (SEQ ID NO:46).

31. The capture agent of claim 1, wherein the first ligand comprises a first peptide having an amino acid sequence selected from the group consisting of rhfrl (SEQ ID NO:44), nrfff (SEQ ID NO:45), rkhyh (SEQ ID NO:46), rrATS (SEQ ID NO:47), rrAQS (SEQ ID NO:48), rrats (SEQ ID NO:49), and rraqs (SEQ ID NO:50),
wherein the second ligand comprises a second peptide having an amino acid sequence selected from the group consisting of KYGEV (SEQ ID NO:11), LYGEV (SEQ ID NO:12), VHKSG (SEQ ID NO:13), VHLSG (SEQ ID NO:14), QKHGP (SEQ ID NO:15), TKHGP (SEQ ID NO:16), QLHGP (SEQ ID NO:17), TLHGP (SEQ ID NO:18), YDLQR (SEQ ID NO:19), YDLTR (SEQ ID NO:20), YDKQR (SEQ ID NO:21), YDKTR (SEQ ID NO:22), KKGWP (SEQ ID NO:23), KLGWP (SEQ ID NO:24), LKGWP (SEQ ID NO:25), LLGWP (SEQ ID NO:26), RSYNL (SEQ ID NO:27), RSYNK (SEQ ID NO:28), kYGEV (SEQ ID NO:51), VHkSG (SEQ ID NO:52), QkHGP (SEQ ID NO:53), TkHGP (SEQ ID NO:54), YDLQr (SEQ ID NO:55), YDLTr (SEQ ID NO:56), YDkQr (SEQ ID NO:57), YDkTr (SEQ ID NO:58), kkGWP (SEQ ID NO:59), kLGWP (SEQ ID NO:60), LkGWP (SEQ ID NO:61), rSYNL (SEQ ID NO:62), rSYNk (SEQ ID NO:63), kygev (SEQ ID NO:64), vhksg (SEQ ID NO:65), qkhgp (SEQ ID NO:66), tkhgp (SEQ ID NO:67), ydlqr (SEQ ID NO:68), ydltr (SEQ ID NO:69), ydkqr (SEQ ID NO:70), ydktr (SEQ ID NO:71), kkgwp (SEQ ID NO:72), klgwp (SEQ ID NO:73), lkgwp (SEQ ID NO:74), rsynl (SEQ ID NO:75), rsynk (SEQ ID NO:76), rhfrl (SEQ ID NO:44), nrfff (SEQ ID NO:45), and rkhyh (SEQ ID NO:46).

32. The capture agent of claim 31, wherein the first ligand comprises an amino acid sequence selected from the group consisting of rrATS (SEQ ID NO:47), rrAQS (SEQ ID NO:48), rrats (SEQ ID NO:49), and rraqs (SEQ ID NO:50).

33. The capture agent of claim 32, wherein the second ligand comprises an amino acid sequence selected from the group consisting of kYGEV (SEQ ID NO:51), VHkSG (SEQ ID NO:52), QkHGP (SEQ ID NO:53), TkHGP (SEQ ID NO:54), YDLQr (SEQ ID NO:55), YDLTr (SEQ ID NO:56), YDkQr (SEQ ID NO:57), YDkTr (SEQ ID NO:58), kkGWP (SEQ ID NO:59), kLGWP (SEQ ID NO:60), LkGWP (SEQ ID NO:61), rSYNL (SEQ ID NO:62), rSYNk (SEQ ID NO:63), kygev (SEQ ID NO:64)vhksg (SEQ ID NO:65), qkhgp (SEQ ID NO:66), tkhgp (SEQ ID NO:67), ydlqr (SEQ ID NO:68), ydltr (SEQ ID NO:69), ydkqr (SEQ ID NO:70), ydktr (SEQ ID NO:71), kkgwp (SEQ ID NO:72), klgwp (SEQ ID NO:73), lkgwp (SEQ ID NO:74), rsynl (SEQ ID NO:75), and rsynk (SEQ ID NO:76).

34. The capture agent of claim 32, wherein the second ligand comprises an amino acid sequence 80-100% identical to an amino acid sequence selected from the group consisting of rhfrl (SEQ ID NO:44), nrfff (SEQ ID NO:45), and rkhyh (SEQ ID NO:46).

35. The capture agent of claim 31, wherein the second ligand comprises an amino acid sequence selected from the group consisting of kYGEV (SEQ ID NO:51), VHkSG (SEQ ID NO:52), QkHGP (SEQ ID NO:53), TkHGP (SEQ ID NO:54), YDLQr (SEQ ID NO:55), YDLTr (SEQ ID NO:56), YDkQr (SEQ ID NO:57), YDkTr (SEQ ID NO:58), kkGWP (SEQ ID NO:59), kLGWP (SEQ ID NO:60), LkGWP (SEQ ID NO:61), rSYNL (SEQ ID NO:62), rSYNk (SEQ ID NO:63), kygev (SEQ ID NO:64)vhksg (SEQ ID NO:65), qkhgp (SEQ ID NO:66), tkhgp (SEQ ID NO:67), ydlqr (SEQ ID NO:68), ydltr (SEQ ID NO:69), ydkqr (SEQ ID NO:70), ydktr (SEQ ID NO:71), kkgwp (SEQ ID NO:72), klgwp (SEQ ID NO:73), lkgwp (SEQ ID NO:74), rsynl (SEQ ID NO:75), and rsynk (SEQ ID NO:76).

36. The capture agent of claim 35, wherein the first ligand comprises an amino acid sequence selected from the group consisting of rhfrl (SEQ ID NO:44), nrfff (SEQ ID NO:45), and rkhyh (SEQ ID NO:46).

37. A capture agent for a target, the capture agent comprising two or more ligands covalently linked to each other, wherein the ligands each specifically bind to one of two or more distinct epitopes of the target that are in different locations on the target,
wherein the capture agent comprises a first of the ligands having specific affinity for a first of the epitopes, a second of the ligands having specific affinity for a second of the epitopes, and a linker covalently connecting the first ligand to the second ligand, wherein the target is IL-17A, IL-17F, or both IL-17A and IL-17F, wherein the first epitope comprises the amino acid sequence FFQKPES (SEQ ID NO:1) or the amino acid sequence PNSEDKNFPRTVMVNL (SEQ ID NO:43), wherein the second epitope comprises the amino acid sequence NENQRVS (SEQ ID NO:3) or the amino acid sequence PNSEDKNFPRTVMVNL (SEQ ID NO:43), wherein the first ligand comprises a first peptide having an amino acid sequence 80-100% identical to an amino acid sequence selected from the group consisting of rhfrl (SEQ ID NO:44), nrfff (SEQ ID NO:45), rkhyh (SEQ ID NO:46), FYKTH (SEQ ID NO:5), FYKQH (SEQ ID NO:6), FYLTH (SEQ ID NO:7), FYLQH (SEQ ID NO:8), RRATS (SEQ ID NO:9), RRAQS (SEQ ID NO:10), rrATS (SEQ ID NO:47), rrAQS (SEQ ID NO:48), rrats (SEQ ID NO:49), and rraqs (SEQ ID NO:50), wherein the second ligand comprises a second peptide having an amino acid sequence 80-100% identical to an amino acid sequence selected from the group consisting of kYGEV (SEQ ID NO:51), VHkSG (SEQ ID NO:52), QkHGP (SEQ ID NO:53), TkHGP (SEQ ID NO:54), YDLQr (SEQ ID NO:55), YDLTr (SEQ ID NO:56), YDkQr (SEQ ID NO:57), YDkTr (SEQ ID NO:58), kkGWP (SEQ ID NO:59), kLGWP (SEQ ID NO:60), LkGWP (SEQ ID NO:61), rSYNL (SEQ ID NO:62), rSYNk (SEQ ID NO:63), kygev (SEQ ID NO:64), vhksg (SEQ ID NO:65), qkhgp (SEQ ID NO:66), tkhgp (SEQ ID NO:67), ydlqr (SEQ ID NO:68), ydltr (SEQ ID NO:69), ydkqr (SEQ ID NO:70), ydktr (SEQ ID NO:71), kkgwp (SEQ ID NO:72), klgwp (SEQ ID NO:73), lkgwp (SEQ ID NO:74), rsynl (SEQ ID NO:75), rsynk (SEQ ID NO:76), rhfrl (SEQ ID NO:44), nrfff (SEQ ID NO:45), and rkhyh (SEQ ID NO:46), wherein the first ligand is cyclic, and wherein the second ligand is cyclic.

38. The capture agent of claim 37, wherein the second ligand comprises an amino acid sequence 80-100% identical to an amino acid sequence selected from the group consisting of rhfrl (SEQ ID NO:44), nrfff (SEQ ID NO:45), and rkhyh (SEQ ID NO:46).

39. The capture agent of claim 37, wherein the first ligand comprises a first peptide having an amino acid sequence selected from the group consisting of rhfrl (SEQ ID NO:44), nrfff (SEQ ID NO:45), rkhyh (SEQ ID NO:46), FYKTH (SEQ ID NO:5), FYKQH (SEQ ID NO:6), FYLTH (SEQ ID NO:7), FYLQH (SEQ ID NO:8), RRATS (SEQ ID NO:9), RRAQS (SEQ ID NO:10), rrATS (SEQ ID NO:47), rrAQS (SEQ ID NO:48), rrats (SEQ ID NO:49), and rraqs (SEQ ID NO:50), wherein the second ligand comprises a second peptide having an amino acid sequence selected from the group consisting of kYGEV (SEQ ID NO:51), VHkSG (SEQ ID NO:52), QkHGP (SEQ ID NO:53), TkHGP (SEQ ID NO:54), YDLQr (SEQ ID NO:55), YDLTr (SEQ ID NO:56), YDkQr (SEQ ID NO:57), YDkTr (SEQ ID NO:58), kkGWP (SEQ ID NO:59), kLGWP (SEQ ID NO:60), LkGWP (SEQ ID NO:61), rSYNL (SEQ ID NO:62), rSYNk (SEQ ID NO:63), kygev (SEQ ID NO:64), vhksg (SEQ ID NO:65), qkhgp (SEQ ID NO:66), tkhgp (SEQ ID NO:67), ydlqr (SEQ ID NO:68), ydltr (SEQ ID NO:69), ydkqr (SEQ ID NO:70), ydktr (SEQ ID NO:71), kkgwp (SEQ ID NO:72), klgwp (SEQ ID NO:73), lkgwp (SEQ ID NO:74), rsynl (SEQ ID NO:75), rsynk (SEQ ID NO:76), rhfrl (SEQ ID NO:44), nrfff (SEQ ID NO:45), and rkhyh (SEQ ID NO:46), wherein the first ligand is cyclic, and wherein the second ligand is cyclic.

40. The capture agent of claim 39, wherein the second ligand comprises an amino acid sequence selected from the group consisting of rhfrl (SEQ ID NO:44), nrfff (SEQ ID NO:45), and rkhyh (SEQ ID NO:46).

* * * * *

SEQUENCE LISTING

```
<160> NUMBER OF SEQ ID NOS: 76

<210> SEQ ID NO 1
<211> LENGTH: 7
<212> TYPE: PRT
<213> ORGANISM: Homo sapiens

<400> SEQUENCE: 1

Phe Phe Gln Lys Pro Glu Ser
1               5

<210> SEQ ID NO 2
<211> LENGTH: 14
<212> TYPE: PRT
<213> ORGANISM: Homo sapiens

<400> SEQUENCE: 2

Phe Phe Gln Lys Pro Glu Ser Cys Pro Pro Val Pro Gly Gly
1               5                   10

<210> SEQ ID NO 3
<211> LENGTH: 7
<212> TYPE: PRT
<213> ORGANISM: Homo sapiens

<400> SEQUENCE: 3

Asn Glu Asn Gln Arg Val Ser
1               5

<210> SEQ ID NO 4
<211> LENGTH: 10
<212> TYPE: PRT
<213> ORGANISM: Homo sapiens

<400> SEQUENCE: 4

Gly Ile Ile Asn Glu Asn Gln Arg Val Ser
1               5                   10
```

```
<210> SEQ ID NO 5
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 5

Phe Tyr Lys Thr His
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 6

Phe Tyr Lys Gln His
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 7

Phe Tyr Leu Thr His
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 8

Phe Tyr Leu Gln His
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 9

Arg Arg Ala Thr Ser
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 10

Arg Arg Ala Gln Ser
1               5
```

```
<210> SEQ ID NO 11
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 11

Lys Tyr Gly Glu Val
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 12

Leu Tyr Gly Glu Val
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 13

Val His Lys Ser Gly
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 14

Val His Leu Ser Gly
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 15

Gln Lys His Gly Pro
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 16

Thr Lys His Gly Pro
1               5

<210> SEQ ID NO 17
```

```
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 17

Gln Leu His Gly Pro
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 18

Thr Leu His Gly Pro
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 19

Tyr Asp Leu Gln Arg
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 20

Tyr Asp Leu Thr Arg
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 21

Tyr Asp Lys Gln Arg
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 22

Tyr Asp Lys Thr Arg
1               5

<210> SEQ ID NO 23
<211> LENGTH: 5
```

```
<212> TYPE: PRT
<213> ORGANISM: Artificial Sequence
<220> FEATURE:
<223> OTHER INFORMATION: Synthetic Peptide

<400> SEQUENCE: 23

Lys Lys Gly Trp Pro
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 24

Lys Leu Gly Trp Pro
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 25

Leu Lys Gly Trp Pro
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 26

Leu Leu Gly Trp Pro
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 27

Arg Ser Tyr Asn Leu
1               5

<210> SEQ ID NO 28
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 28

Arg Ser Tyr Asn Lys
1               5

<210> SEQ ID NO 29
<211> LENGTH: 5
<212> TYPE: PRT
```

```
<213> ORGANISM: Artificial Sequence
<220> FEATURE:
<223> OTHER INFORMATION: Synthetic Peptide

<400> SEQUENCE: 29

Tyr Lys Tyr Tyr Arg
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 30

Gly Trp Asn Val Asp Leu
1               5

<210> SEQ ID NO 31
<211> LENGTH: 163
<212> TYPE: PRT
<213> ORGANISM: Homo sapiens

<400> SEQUENCE: 31

Met Thr Val Lys Thr Leu His Gly Pro Ala Met Val Lys Tyr Leu Leu
1               5                   10                  15

Leu Ser Ile Leu Gly Leu Ala Phe Leu Ser Glu Ala Ala Arg Lys
                20                  25                  30

Ile Pro Lys Val Gly His Thr Phe Phe Gln Lys Pro Glu Ser Cys Pro
            35                  40                  45

Pro Val Pro Gly Gly Ser Met Lys Leu Asp Ile Gly Ile Ile Asn Glu
        50                  55                  60

Asn Gln Arg Val Ser Met Ser Arg Asn Ile Glu Ser Arg Ser Thr Ser
65                  70                  75                  80

Pro Trp Asn Tyr Thr Val Thr Trp Asp Pro Asn Arg Tyr Pro Ser Glu
                85                  90                  95

Val Val Gln Ala Gln Cys Arg Asn Leu Gly Cys Ile Asn Ala Gln Gly
            100                 105                 110

Lys Glu Asp Ile Ser Met Asn Ser Val Pro Ile Gln Gln Glu Thr Leu
        115                 120                 125

Val Val Arg Arg Lys His Gln Gly Cys Ser Val Ser Phe Gln Leu Glu
    130                 135                 140

Lys Val Leu Val Thr Val Gly Cys Thr Cys Val Thr Pro Val Ile His
145                 150                 155                 160

Arg Val Gln

<210> SEQ ID NO 32
<211> LENGTH: 7
<212> TYPE: PRT
<213> ORGANISM: Homo sapiens

<400> SEQUENCE: 32

Pro Pro Val Pro Gly Gly Ser
1               5

<210> SEQ ID NO 33
<211> LENGTH: 7
<212> TYPE: PRT
<213> ORGANISM: Homo sapiens
```

<400> SEQUENCE: 33

Asn Glu Asn Gln Arg Val Ser
1               5

<210> SEQ ID NO 34
<211> LENGTH: 155
<212> TYPE: PRT
<213> ORGANISM: Homo sapiens

<400> SEQUENCE: 34

Met Thr Pro Gly Lys Thr Ser Leu Val Ser Leu Leu Leu Leu Leu Ser
1               5                   10                  15

Leu Glu Ala Ile Val Lys Ala Gly Ile Thr Ile Pro Arg Asn Pro Gly
            20                  25                  30

Cys Pro Asn Ser Glu Asp Lys Asn Phe Pro Arg Thr Val Met Val Asn
        35                  40                  45

Leu Asn Ile His Asn Arg Asn Thr Asn Thr Asn Pro Lys Arg Ser Ser
    50                  55                  60

Asp Tyr Tyr Asn Arg Ser Thr Ser Pro Trp Asn Leu His Arg Asn Glu
65                  70                  75                  80

Asp Pro Glu Arg Tyr Pro Ser Val Ile Trp Glu Ala Lys Cys Arg His
                85                  90                  95

Leu Gly Cys Ile Asn Ala Asp Gly Asn Val Asp Tyr His Met Asn Ser
            100                 105                 110

Val Pro Ile Gln Gln Glu Ile Leu Val Leu Arg Arg Glu Pro Pro His
        115                 120                 125

Cys Pro Asn Ser Phe Arg Leu Glu Lys Ile Leu Val Ser Val Gly Cys
    130                 135                 140

Thr Cys Val Thr Pro Ile Val His His Val Ala
145                 150                 155

<210> SEQ ID NO 35
<211> LENGTH: 9
<212> TYPE: PRT
<213> ORGANISM: Plasmodium falciparum

<400> SEQUENCE: 35

Ala His His Ala His His Ala Ala Asp
1               5

<210> SEQ ID NO 36
<211> LENGTH: 21
<212> TYPE: PRT
<213> ORGANISM: Plasmodium falciparum

<400> SEQUENCE: 36

Ala His His Ala Thr Asp Ala His His Ala Ala His His Glu Ala
1               5                   10                  15

Ala Thr His Cys Leu
            20

<210> SEQ ID NO 37
<211> LENGTH: 136
<212> TYPE: PRT
<213> ORGANISM: Homo sapiens

<400> SEQUENCE: 37

Ile Val Lys Ala Gly Ile Thr Ile Pro Arg Asn Pro Gly Cys Pro Asn
1               5                   10                  15

```
Ser Glu Asp Lys Asn Phe Pro Arg Thr Val Met Val Asn Leu Asn Ile
             20                  25                  30

His Asn Arg Asn Thr Asn Thr Asn Pro Lys Arg Ser Ser Asp Tyr Tyr
         35                  40                  45

Asn Arg Ser Thr Ser Pro Trp Asn Leu His Arg Asn Glu Asp Pro Glu
 50                  55                  60

Arg Tyr Pro Ser Val Ile Trp Glu Ala Lys Cys Arg His Leu Gly Cys
 65                  70                  75                  80

Ile Asn Ala Asp Gly Asn Val Asp Tyr His Met Asn Ser Val Pro Ile
             85                  90                  95

Gln Gln Glu Ile Leu Val Leu Arg Arg Glu Pro Pro His Cys Pro Asn
            100                 105                 110

Ser Phe Arg Leu Glu Lys Ile Leu Val Ser Val Gly Cys Thr Cys Val
            115                 120                 125

Thr Pro Ile Val His His Val Ala
            130                 135

<210> SEQ ID NO 38
<211> LENGTH: 133
<212> TYPE: PRT
<213> ORGANISM: Homo sapiens

<400> SEQUENCE: 38

Arg Lys Ile Pro Lys Val Gly His Thr Phe Phe Gln Lys Pro Glu Ser
1               5                  10                  15

Cys Pro Pro Val Pro Gly Gly Ser Met Lys Leu Asp Ile Gly Ile Ile
             20                  25                  30

Asn Glu Asn Gln Arg Val Ser Met Ser Arg Asn Ile Glu Ser Arg Ser
         35                  40                  45

Thr Ser Pro Trp Asn Tyr Thr Val Thr Trp Asp Pro Asn Arg Tyr Pro
 50                  55                  60

Ser Glu Val Val Gln Ala Gln Cys Arg Asn Leu Gly Cys Ile Asn Ala
 65                  70                  75                  80

Gln Gly Lys Glu Asp Ile Ser Met Asn Ser Val Pro Ile Gln Gln Glu
             85                  90                  95

Thr Leu Val Val Arg Arg Lys His Gln Gly Cys Ser Val Ser Phe Gln
            100                 105                 110

Leu Glu Lys Val Leu Val Thr Val Gly Cys Thr Cys Val Thr Pro Val
            115                 120                 125

Ile His His Val Gln
            130

<210> SEQ ID NO 39
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 39

Phe Phe Gln Lys Pro Glu Ser Ser Pro Val Pro Gly Gly Ser
1               5                  10                  15

<210> SEQ ID NO 40
<211> LENGTH: 15
<212> TYPE: PRT
<213> ORGANISM: Artificial Sequence
<220> FEATURE:
<223> OTHER INFORMATION: Synthetic Peptide
```

-continued

```
<400> SEQUENCE: 40

Phe Phe Gln Lys Pro Glu Ser Ser Pro Val Ser Pro Gly Pro Gly
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 41

Ser Gln Phe Glu Lys Phe Pro Ser Pro Pro Val Pro Gly Gly Ser
1               5                   10                  15

<210> SEQ ID NO 42
<211> LENGTH: 309
<212> TYPE: PRT
<213> ORGANISM: Plasmodium falciparum

<400> SEQUENCE: 42

Met Val Ser Phe Ser Lys Asn Lys Val Leu Ser Ala Ala Val Phe Ala
1               5                   10                  15

Ser Val Leu Leu Leu Asp Asn Asn Ser Ala Phe Asn Asn Asn Leu
            20                  25                  30

Cys Ser Lys Asn Ala Lys Gly Leu Asn Leu Asn Lys Arg Leu Leu His
            35                  40                  45

Glu Thr Gln Ala His Val Asp Asp Ala His His Ala His His Val Ala
        50                  55                  60

Asp Ala His His Ala His His Ala Ala Asp Ala His His Ala His His
65                  70                  75                  80

Ala Ala Asp Ala His His Ala His His Ala Ala Asp Ala His His Ala
                85                  90                  95

His His Ala Ala Asp Ala His His Ala His His Ala Ala Tyr Ala His
            100                 105                 110

His Ala His His Ala Ala Asp Ala His His Ala His His Ala Ser Asp
            115                 120                 125

Ala His His Ala Ala Asp Ala His His Ala Ala Tyr Ala His His Ala
        130                 135                 140

His His Ala Ala Asp Ala His His Ala His His Ala Ser Asp Ala His
145                 150                 155                 160

His Ala Ala Asp Ala His His Ala Ala Tyr Ala His His Ala His His
                165                 170                 175

Ala Ala Asp Ala His His Ala Ala Asp Ala His His Ala Thr Asp Ala
            180                 185                 190

His His Ala His His Ala Ala Asp Ala Arg His Ala Thr Asp Ala His
            195                 200                 205

His Ala Ala Asp Ala His His Ala Thr Asp Ala His His Ala Ala Asp
        210                 215                 220

Ala His His Ala Ala Asp Ala His His Ala Thr Asp Ala His His Ala
225                 230                 235                 240

Ala Asp Ala His His Ala Thr Asp Ala His His Ala Ala Asp Ala His
                245                 250                 255

His Ala Ala Asp Ala His His Ala Thr Asp Ala His His Ala His His
            260                 265                 270

Ala Ala Asp Ala His His Ala Ala Ala His His Ala Thr Asp Ala His
```

```
                    275                 280                 285
His Ala Thr Asp Ala His His Ala Ala Ala His His Glu Ala Ala Thr
        290                 295                 300

His Cys Leu Arg His
305

<210> SEQ ID NO 43
<211> LENGTH: 16
<212> TYPE: PRT
<213> ORGANISM: Homo sapiens

<400> SEQUENCE: 43

Pro Asn Ser Glu Asp Lys Asn Phe Pro Arg Thr Val Met Val Asn Leu
1               5                   10                  15

<210> SEQ ID NO 44
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D enantiomer

<400> SEQUENCE: 44

Arg His Phe Arg Leu
1               5

<210> SEQ ID NO 45
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D enantiomer

<400> SEQUENCE: 45

Asn Arg Phe Phe Phe
1               5

<210> SEQ ID NO 46
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D enantiomer

<400> SEQUENCE: 46

Arg Lys His Tyr His
1               5

<210> SEQ ID NO 47
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
```

```
<222> LOCATION: (1)..(2)
<223> OTHER INFORMATION: D enantiomer

<400> SEQUENCE: 47

Arg Arg Ala Thr Ser
1               5

<210> SEQ ID NO 48
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(2)
<223> OTHER INFORMATION: D enantiomer

<400> SEQUENCE: 48

Arg Arg Ala Gln Ser
1               5

<210> SEQ ID NO 49
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D enantiomer

<400> SEQUENCE: 49

Arg Arg Ala Thr Ser
1               5

<210> SEQ ID NO 50
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D enantiomer

<400> SEQUENCE: 50

Arg Arg Ala Gln Ser
1               5

<210> SEQ ID NO 51
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)

<400> SEQUENCE: 51

Lys Tyr Gly Glu Val
1               5

<210> SEQ ID NO 52
<211> LENGTH: 5
<212> TYPE: PRT
```

```
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: D enantiomer

<400> SEQUENCE: 52

Val His Lys Ser Gly
1               5

<210> SEQ ID NO 53
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)

<400> SEQUENCE: 53

Gln Lys His Gly Pro
1               5

<210> SEQ ID NO 54
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: D enantiomer

<400> SEQUENCE: 54

Thr Lys His Gly Pro
1               5

<210> SEQ ID NO 55
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: D enantiomer

<400> SEQUENCE: 55

Tyr Asp Leu Gln Arg
1               5

<210> SEQ ID NO 56
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: D enantiomer

<400> SEQUENCE: 56

Tyr Asp Leu Thr Arg
1               5
```

```
<210> SEQ ID NO 57
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: D enantiomer
<220> FEATURE:
<221> NAME/KEY: MISC_FEATURE
<222> LOCATION: (5)..(5)
<223> OTHER INFORMATION: D enantiomer

<400> SEQUENCE: 57

Tyr Asp Lys Gln Arg
1               5

<210> SEQ ID NO 58
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: D enantiomer
<220> FEATURE:
<221> NAME/KEY: MISC_FEATURE
<222> LOCATION: (5)..(5)
<223> OTHER INFORMATION: D enantiomer

<400> SEQUENCE: 58

Tyr Asp Lys Thr Arg
1               5

<210> SEQ ID NO 59
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(2)
<223> OTHER INFORMATION: D enantiomer

<400> SEQUENCE: 59

Lys Lys Gly Trp Pro
1               5

<210> SEQ ID NO 60
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: D enantiomer

<400> SEQUENCE: 60

Lys Leu Gly Trp Pro
1               5

<210> SEQ ID NO 61
```

```
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: D enantiomer

<400> SEQUENCE: 61

Leu Lys Gly Trp Pro
1               5

<210> SEQ ID NO 62
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: D enantiomer

<400> SEQUENCE: 62

Arg Ser Tyr Asn Leu
1               5

<210> SEQ ID NO 63
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: D enantiomer

<400> SEQUENCE: 63

Arg Ser Tyr Asn Lys
1               5

<210> SEQ ID NO 64
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D enantiomer

<400> SEQUENCE: 64

Lys Tyr Gly Glu Val
1               5

<210> SEQ ID NO 65
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D enantiomer

<400> SEQUENCE: 65
```

```
Val His Lys Ser Gly
1               5

<210> SEQ ID NO 66
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D enantiomer

<400> SEQUENCE: 66

Gln Lys His Gly Pro
1               5

<210> SEQ ID NO 67
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D enantiomer

<400> SEQUENCE: 67

Thr Lys His Gly Pro
1               5

<210> SEQ ID NO 68
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D enantiomer

<400> SEQUENCE: 68

Tyr Asp Leu Gln Arg
1               5

<210> SEQ ID NO 69
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D enantiomer

<400> SEQUENCE: 69

Tyr Asp Leu Thr Arg
1               5

<210> SEQ ID NO 70
<211> LENGTH: 5
<212> TYPE: PRT
<213> ORGANISM: Artificial Sequence
<220> FEATURE:
<223> OTHER INFORMATION: Synthetic Peptide
```

```
<220> FEATURE:
<221> NAME/KEY: MISC_FEATURE
<222> LOCATION: (1)..(5)
<223> OTHER INFORMATION: D enantiomer

<400> SEQUENCE: 70

Tyr Asp Lys Gln Arg
1               5

<210> SEQ ID NO 71
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D enantiomer

<400> SEQUENCE: 71

Tyr Asp Lys Thr Arg
1               5

<210> SEQ ID NO 72
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D enantiomer

<400> SEQUENCE: 72

Lys Lys Gly Trp Pro
1               5

<210> SEQ ID NO 73
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D enantiomer

<400> SEQUENCE: 73

Lys Leu Gly Trp Pro
1               5

<210> SEQ ID NO 74
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D enantiomer

<400> SEQUENCE: 74

Leu Lys Gly Trp Pro
1               5
```

```
<210> SEQ ID NO 75
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D enantiomer

<400> SEQUENCE: 75

Arg Ser Tyr Asn Leu
1               5

<210> SEQ ID NO 76
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D enantiomer

<400> SEQUENCE: 76

Arg Ser Tyr Asn Lys
1               5
```